US012031143B2

(12) United States Patent
Lu et al.

(10) Patent No.: US 12,031,143 B2
(45) Date of Patent: Jul. 9, 2024

(54) COMBINATIONS OF INSECTICIDAL POLYPEPTIDES HAVING IMPROVED ACTIVITY SPECTRUM AND USES THEREOF

(71) Applicant: PIONEER HI-BRED INTERNATIONAL, INC., Johnston, IA (US)

(72) Inventors: Albert L Lu, West Des Moines, IA (US); Knut Meyer, Des Moines, IA (US); Gilda Rauscher, Johnston, IA (US); Gusui Wu, Foster City, CA (US)

(73) Assignee: PIONEER HI-BRED INTERNATIONAL, INC., Johnston, IA (US)

( * ) Notice: Subject to any disclaimer, the term of this patent is extended or adjusted under 35 U.S.C. 154(b) by 0 days.

(21) Appl. No.: 18/161,939

(22) Filed: Jan. 31, 2023

(65) Prior Publication Data

US 2023/0227843 A1 Jul. 20, 2023

Related U.S. Application Data

(62) Division of application No. 16/956,182, filed as application No. PCT/US2018/062968 on Nov. 29, 2018, now abandoned.

(60) Provisional application No. 62/609,879, filed on Dec. 22, 2017.

(51) Int. Cl.

| | |
|---|---|
| ***C12N 15/82*** | (2006.01) |
| ***A01N 63/00*** | (2020.01) |
| ***A01N 63/50*** | (2020.01) |
| ***C07K 14/325*** | (2006.01) |
| ***C07K 14/415*** | (2006.01) |

(52) U.S. Cl.

CPC ......... *C12N 15/8286* (2013.01); *A01N 63/00* (2013.01); *A01N 63/50* (2020.01); *C07K 14/325* (2013.01); *C07K 14/415* (2013.01)

(58) Field of Classification Search

None

See application file for complete search history.

(56) References Cited

U.S. PATENT DOCUMENTS

| | | | | |
|---|---|---|---|---|
| 11,155,829 | B2 * | 10/2021 | Barry | A01N 63/50 |
| 2016/0201044 | A1 | 7/2016 | Singh et al. | |
| 2016/0339078 | A1 | 11/2016 | Hamill et al. | |
| 2017/0233440 | A1 | 8/2017 | Barry et al. | |
| 2020/0332314 | A1 | 10/2020 | Lu et al. | |

FOREIGN PATENT DOCUMENTS

| | | | |
|---|---|---|---|
| WO | 2015023846 | A2 | 2/2015 |
| WO | 2015120270 | A1 | 8/2015 |
| WO | 2015120276 | A1 | 8/2015 |
| WO | 2017/023486 | A1 | 2/2017 |
| WO | 2017/184673 | A1 | 10/2017 |
| WO | 2018/005411 | A1 | 1/2018 |

OTHER PUBLICATIONS

International Search Report and Written Opinion for International Application PCT/US18/62968, dated Apr. 30, 2019.
Extended European Search Report for European Application No. 18892239.7, mailed Jan. 24, 2022, 10 Pages.
International Preliminary Report on Patentability for International Application No. PCT/US2018/062968, mailed Jul. 2, 2020, 9 Pages.
Partial Supplementary European Search Report for European Application No. 18892239.7, mailed Oct. 22, 2021, 10 Pages.

* cited by examiner

*Primary Examiner* — Weihua Fan
*Assistant Examiner* — Brian James Sullivan

(57) ABSTRACT

Compositions and methods for controlling pests are provided. The methods involve transforming organisms with a nucleic acid sequence encoding an insecticidal protein. In particular, the nucleic acid sequences are useful for preparing plants and microorganisms that possess insecticidal activity. Thus, transformed bacteria, plants, plant cells, plant tissues and seeds are provided. Compositions are insecticidal nucleic acids and proteins of bacterial species. The sequences find use in the construction of expression vectors for subsequent transformation into organisms of interest including plants, as probes for the isolation of other homologous (or partially homologous) genes. The pesticidal proteins find use in controlling, inhibiting growth or killing Lepidopteran, Coleopteran, Dipteran, fungal, Hemipteran and nematode pest populations and for producing compositions with insecticidal activity.

7 Claims, 5 Drawing Sheets

Specification includes a Sequence Listing.

Fig. 1A

```
                1                                                  50
IPD103Aa   (1)  -----------MADKAAAAAREAEEEVETTMDETEAVGTHLDFLGADVKL
IPD103Ab   (1)  ------------MADQAAAAREAEEEVETTMDETEAVGTHLDFLGADVKL
IPD103Ac   (1)  ------------MAEPAAAAREAEEEVETTMDETEAVGTHLDFLGADVKL
IPD103Ad   (1)  ------------MADQGAAAREAEEEVETTMDETEAVGTHLDFL-ADVKV
IPD103Ae   (1)  ------------MADQ-AAAREAEEEVETTMDETEAVGTHLDFL-ADVKV
IPD103Bd   (1)  ------------MADQVAAARGAEEEVETTMDETEAVGTHLDFL-ADVKV
IPD103Ba   (1)  MRERERERERERMAEPAAAAAKKAEEEVEIFMDDTEAVGTHLDFL-AGLKV
IPD103Bb   (1)  -----------MAEPAAAAAKKAEEEVEIFMDDTEAVGTHLDFL-AGLKV
IPD103Ca   (1)  MRERERERERERMAEPAAAAAKKAEEEVEIFMDDTEAVGTHLDFL-AGLKV
IPD103Be   (1)  -----------MADPATAAREAEEEVQETLMDETEAVGTHLDFV-AGLEV
IPD103Bf   (1)  ---MQRERERERMADQAAAAAREAEEEVEVFMDETEAVGTHLDFL-AGLNV
IPD103Bk   (1)  -----------MADQAAAAAREAEEEVEVFMDETEAVGTHLDFL-AGLNV
IPD103Bi   (1)  ----------MADKVAAASRAQGAEEVEDLMDETEAVGTHLDCMGGDVKV
IPD103Da   (1)  ---------MADEVAGHHGPACEEEEEEMLMDETEAVGVHAIDG---LFV
IPD103Bc   (1)  -----------MADKAPPPAREAEEEVEETMDETEAVGTHLDLIAHLSVQ
IPD103Bj   (1)  -----------MADKAPPPAREAEEEVEETMDETEAVGTHLDLIAHLSVQ
IPD103Bg   (1)  --------MADKVAAAPPPAREAEEEVEETMDETEAVGTHLDLIATL---
IPD103Bh   (1)  --------MADKVAAAPPPAREAEEEVEETMDETEAVGTHLDLIATL---

                51                                                100
IPD103Aa  (40)  QPRNIITVEVDAAAVIQQIREIFQTMARHFNSTRVVRDEAIKGIRDHFRA
IPD103Ab  (39)  QPRNIITVEVDAAAVIQQIREIFQTMARHFNSTRVVRDEAIKGIRDHFRA
IPD103Ac  (39)  QPRNIITVEVDAAAVIQQIREIFQTMARHFNSTRVVRDEAIKGIRDHFRA
IPD103Ad  (38)  QPRNIITVEVDAAAVIQQIREIFQTMARHFNSTRVVRDEAIKGIRDHFRA
IPD103Ae  (37)  QPRNIITVEVDAAAVIQQIREIFQTMARHFNSTRVVRDEAIKGIRDHFRA
IPD103Bd  (38)  QPRSIITVEVDAAAVIQQIREIFQTMARHFNSTRVVRDEAIKGIRDHFRA
IPD103Ba  (50)  QPRKIITVEVDPAAVIQQIREIFQTMARHFNSTTVVRDEAIKGIRDHFRA
IPD103Bb  (39)  QPRKIITVEVDPAAVIQQIREIFQTLARHFNSTTVVRDEAIKGIRDHFRA
IPD103Ca  (50)  QPRKIITVEVDPAAVIQQIREIFQTLARHFNSTTVVRDEAIKGIRDHFRA
IPD103Be  (39)  QPRKVITVEVDAAAVIQQIREIFRTMASHFNSTRVVRDEAIKGIRDHFRA
IPD103Bf  (47)  QPRKVITVEVDAAAVIQQIREIFQTMARHFNSTRVVRDEAIKGIRDHFRA
IPD103Bk  (39)  QPRKVITVEVDAAAVIQQIREIFQTMARHFNSTRVVRDEAIKGIRDHFRA
IPD103Bi  (41)  QARGIITVEVDPAAVIQQIREIFQTLARHYNSTRVVRDAAIKAIRDHFRA
IPD103Da  (39)  QNRSIITVEVDAAAVIQQIREIFASMIKHYNSTRVVRDEAIKSIRDHFRL
IPD103Bc  (40)  -PRGIITVEVDPAAVIQQIREIFQTMARHFNSTRVVRDEAIKGIRDHFRA
IPD103Bj  (40)  -PRGIITVEVDPAAVIQQIREIFQTMARHFNSTRVVRDEAIKGIRDHFRA
IPD103Bg  (40)  -PRGIITVEVDSAAVIQQIREIFQTMARHFNSTRVVRDEAIKGIRDHFRA
IPD103Bh  (40)  -PRGIITVEVDGAAVIQQIREIFQTMARHFNSTRVVRDEAIKGIRDHFRA
```

Fig. 1B

```
                   101                                               150
IPD103Aa    (90)   AVPTRNVVVIHTQHVHT-LVGLEHTHLVLQTGIFKKVPVDIYVFKSGVFT
IPD103Ab    (89)   AVPTRNVVVIHTQHVHT-LVGLEHTHLVLQTGIFKKVPVDIYVFKSGVFT
IPD103Ac    (89)   AVPTRNVVVIHTQHVHT-LVGLEHTHLVLQTGIFKKVPVDIYVFKSGVFT
IPD103Ad    (88)   AVPTRNVVVIHTQHVQT-LVAVEHSHIVLQTGIFKKVPVDIYVFKSGVFT
IPD103Ae    (87)   AVPTRNVVVIHTQHVQT-LVAVEHSHIVLQTGIFKKVPVDIYVFKSGVFT
IPD103Bd    (88)   AVPTRNVVVVHTQHVHT-LVGLEHTNIVLQTGLFKKVPVDIYVFKSGVFT
IPD103Ba   (100)   AVPTRNVVVVHTQHIHT-LEGLEHTNLVLQTGLFRKVPVDIYVFKSGVFT
IPD103Bb    (89)   AVPTRNVVVVHTQHIHT-LEGLEHTNLVLQTGRFRKVPVDIYVFKSGVFT
IPD103Ca   (100)   AVPTRNVVVVHTQHIHT-LEGLEHTNLVLQTGRFRKVPVDIYVFKSGVFT
IPD103Be    (89)   AVPTRNVVVVHTQHIHT-LEGLEHTNLVLQTGLFKKVPVDIYVFKSGVFT
IPD103Bf    (97)   AVPTRNVVVVHTQHIHT-LVDVEHTNLVLQTGIFKKVPVDIYVFKSGVFT
IPD103Bk    (89)   AVPTRNVVVVHTQHIHT-LVDVEHTNLVLQTGIFKKVPVDIYVFKSGVFT
IPD103Bi    (91)   AVPTRNVVVIHTQHVHT-LADVEHSHLVLQTGIFKKVPVDIYVFKSGVFT
IPD103Da    (89)   AVPTRNVVVIHTQHVHT-LDAVESSHLVLRTGLFKKVPVDIFVFKSGVFT
IPD103Bc    (89)   AVPTRNVVVIHTQHVHT-LVGLEHTHLVLQTGIFRTVPVDIYVFKSGVFT
IPD103Bj    (89)   AVPTRNVVVIHTQHVHT-LVGLEHTHLVLQTGIFRTVPVDIYVFKSGVLT
IPD103Bg    (89)   AIPTRNVVVIHTQHVHT-LVGLEHTHLVLQTGIFKKVPVDVYVFKSGVLT
IPD103Bh    (89)   AIPTRNVVVIHTQHVHT-LVGLEHTHLVLQTGIFKKVPVDVYVFKSGVLT

                   151                              184
IPD103Aa   (139)   NLGDGGFINWAWGGFVDQVVGKRIHFRLPPGALP
IPD103Ab   (138)   NLGDGGFINWAWGGFVDQVVGKRIHFRLPPGALP
IPD103Ac   (138)   NLGDGGFINWAWGGFVDQVVGKRIHFRLPPGALP
IPD103Ad   (137)   NLGDGGYINWAWGGFVDQVVGKRIHFRLPPGALP
IPD103Ae   (136)   NLGDGGYINWAWGGFVDQVVGKRIHFRLPPGALP
IPD103Bd   (137)   LLGDGGFINWAWGGFVDQVVGKRIHFRLPPGALP
IPD103Ba   (149)   LLGDGGFINWAWGGFVEQVVGKRIHFRLPPGALP
IPD103Bb   (138)   LLGDGGFINWAWGGFVEQVVGKRIHFRLPPGALP
IPD103Ca   (149)   LLGDGGFINWAWGGFVEQVVGKRIHFRLPPGALP
IPD103Be   (138)   LLGDGGFINWAWGGFVQEVAGKRIXFRLPPGALP
IPD103Bf   (146)   LLGDGGFINWAWGGFVDQVDGKRIHFRLPPGALP
IPD103Bk   (138)   LLGDGGFINWAWGGFVDQVDGKRIHFRLPPGALP
IPD103Bi   (140)   NLGDGGFINWAWGGYVTEVVGKRIHFRLPPGALP
IPD103Da   (138)   NLGDGGFINWAWGGYGVNHTAKRVVFSRPPGALP
IPD103Bc   (138)   NLGDGGFINWAWGGFVTEVVGKRVHFRLPPGALP
IPD103Bj   (138)   NLGDGGFINWAWGGFVTEVVGKRVHFRLPPGALP
IPD103Bg   (138)   NLGDGGFINWAWGGFVTEVVGKRVHFRLPPGALP
IPD103Bh   (138)   NLGDGGFINWAWGGFVTEVVGKRVHFRLPPGALP
```

COMBINATIONS OF INSECTICIDAL POLYPEPTIDES HAVING IMPROVED ACTIVITY SPECTRUM AND USES THEREOF

CROSS REFERENCE

This application claims the benefit of U.S. patent application Ser. No. 16/956,182, filed on Jun. 19, 2020, which claims the benefit of International Patent Application No. PCT/US2018/062968 filed on Nov. 29, 2018, which claims the benefit of U.S. Provisional Application No. 62/609,879 filed Dec. 22, 2017, which is incorporated herein by reference in their entireties.

REFERENCE TO SEQUENCE LISTING SUBMITTED ELECTRONICALLY

The official copy of the sequence listing is submitted electronically via Patent Center as an XML formatted sequence listing with a file named 7497USPCDXMLST26SeqListing.XML created on 25 Jan. 2023 and having a size of 514 KB and is filed concurrently with the specification. The sequence listing contained in this XML formatted document is part of the specification and is herein incorporated by reference in its entirety.

FIELD

This disclosure relates to the field of molecular biology. Provided are transgenic plants comprising molecular or breeding stacks of genes that encode pesticidal proteins. These stacks of nucleic acid sequences that encode pesticidal proteins are useful in the production of transgenic pest-resistant plants.

BACKGROUND

Biological control of insect pests of agricultural significance using a microbial agent, such as fungi, bacteria or another species of insect affords an environmentally friendly and commercially attractive alternative to synthetic chemical pesticides. Generally speaking, the use of biopesticides presents a lower risk of pollution and environmental hazards and biopesticides provide greater target specificity than is characteristic of traditional broad-spectrum chemical insecticides. In addition, biopesticides often cost less to produce and thus improve economic yield for a wide variety of crops.

Certain species of microorganisms of the genus *Bacillus* posses pesticidal activity against a range of insect pests including Lepidoptera, Diptera, Coleoptera, Hemiptera and others. *Bacillus thuringiensis* (Bt) and *Bacillus popilliae* are among the most successful biocontrol agents discovered to date. Insect pathogenicity has also been attributed to strains of *B. larvae, B. lentimorbus, B. sphaericus* and *B. cereus*. Microbial insecticides, particularly those obtained from *Bacillus* strains, have played an important role in agriculture as alternatives to chemical pest control.

Crop plants have been developed with enhanced insect resistance by genetically engineering crop plants to produce pesticidal proteins from *Bacillus*. For example, corn and cotton plants have been genetically engineered to produce pesticidal proteins isolated from strains of *Bacillus thuringiensis*. These genetically engineered crops are now widely used in agriculture and have provided the farmer with an environmentally friendly alternative to traditional insect-control methods. While they have proven to be very successful commercially, these genetically engineered, insect-resistant crop plants provide resistance to only a narrow range of the economically important insect pests. In some cases, insects can develop resistance to different insecticidal compounds, which raises the need to identify alternative biological control agents for pest control.

Accordingly, there remains a need for new pesticidal proteins and combinations of pesticidal proteins with different ranges of insecticidal activity against insect pests, e.g., insecticidal proteins which are active against a variety of insects in the order Lepidoptera and the order Coleoptera including but not limited to insect pests that have developed resistance to existing insecticides.

SUMMARY

In one aspect, transgene stacks and methods for conferring pesticidal activity to bacteria, plants, plant cells, tissues and seeds are provided. Transgene stacks include nucleic acid molecules encoding sequences for pesticidal and insecticidal polypeptides, vectors comprising those nucleic acid molecules, and host cells comprising the vectors. Compositions, which comprise transformed bacteria, plants, plant cells, tissues and seeds are also provided. Methods of controlling an insect pest population are also provided.

In one aspect, transgene stacks comprising an IPD103 polypeptide are encompassed. Provided are transgene stacks that comprise an IPD103 polypeptides of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, and SEQ ID NO: 38, as well as amino acid substitutions, deletions, insertions, fragments thereof and combinations thereof. Also provided are transgene stacks that comprise an IPD103 polypeptide and at least one other gene encoding another insecticidal polypeptide. Provided are transgene stacks comprising an IPD103 polypeptide and at least one pesticidal polypeptide selected from a Cry1B polypeptide, a variant Cry1B polypeptide, a Cry1C polypeptide, a Cry1D polypeptide, and a Cry1J polypeptide.

In another aspect methods are provided for producing the transgene stacks and for using those polypeptides for controlling or killing a Lepidopteran, Coleopteran, nematode, fungi, and/or Dipteran pests. The transgenic plants of the embodiments express one or more of the pesticidal sequences disclosed herein. In various embodiments, the transgenic plant further comprises one or more additional genes for insect resistance, for example, one or more additional genes for controlling Coleopteran, Lepidopteran, Hemipteran or nematode pests. The transgenic plant may comprise any gene imparting an agronomic trait of interest.

In another aspect, methods for detecting the nucleic acids and polypeptides of the embodiments in a sample are also included. A kit for detecting the presence of the transgene stack in a sample is provided. The kit may be provided along with all reagents and control samples necessary for carrying out a method for detecting the intended agent, as well as instructions for use.

In another aspect, the compositions and methods of the embodiments are useful to produce organisms with enhanced pest resistance or tolerance. These organisms and compositions comprising the organisms are desirable for agricultural purposes.

BRIEF DESCRIPTION OF THE FIGURES

FIG. 1A-1B shows an amino acid sequence alignment, using the ALIGNX® module of the Vector NTI® suite, of the IPD103Aa polypeptide (SEQ ID NO: 2), IPD103Ab polypeptide (SEQ ID NO: 4), IPD103Ac polypeptide (SEQ ID NO: 6), IPD103Ad polypeptide (SEQ ID NO: 8), IPD103Ae polypeptide (SEQ ID NO: 10), IPD103Ba polypeptide (SEQ ID NO: 12), IPD103Bb polypeptide (SEQ ID NO: 14), IPD103Bc polypeptide (SEQ ID NO: 16), IPD103Bd polypeptide (SEQ ID NO: 18), IPD103Be polypeptide (SEQ ID NO: 20), IPD103Bf polypeptide (SEQ ID NO: 22), IPD103Bg polypeptide (SEQ ID NO: 24), IPD103Bh polypeptide (SEQ ID NO: 26), IPD103Ca polypeptide (SEQ ID NO: 34), and IPD103 Da polypeptide (SEQ ID NO: 38). The amino acid sequence diversity between the amino acid sequences is highlighted. Conservative amino acid differences are indicated by ( ) shading and non-conservative amino acid difference by ( ) shading.

DETAILED DESCRIPTION

Figure 2:
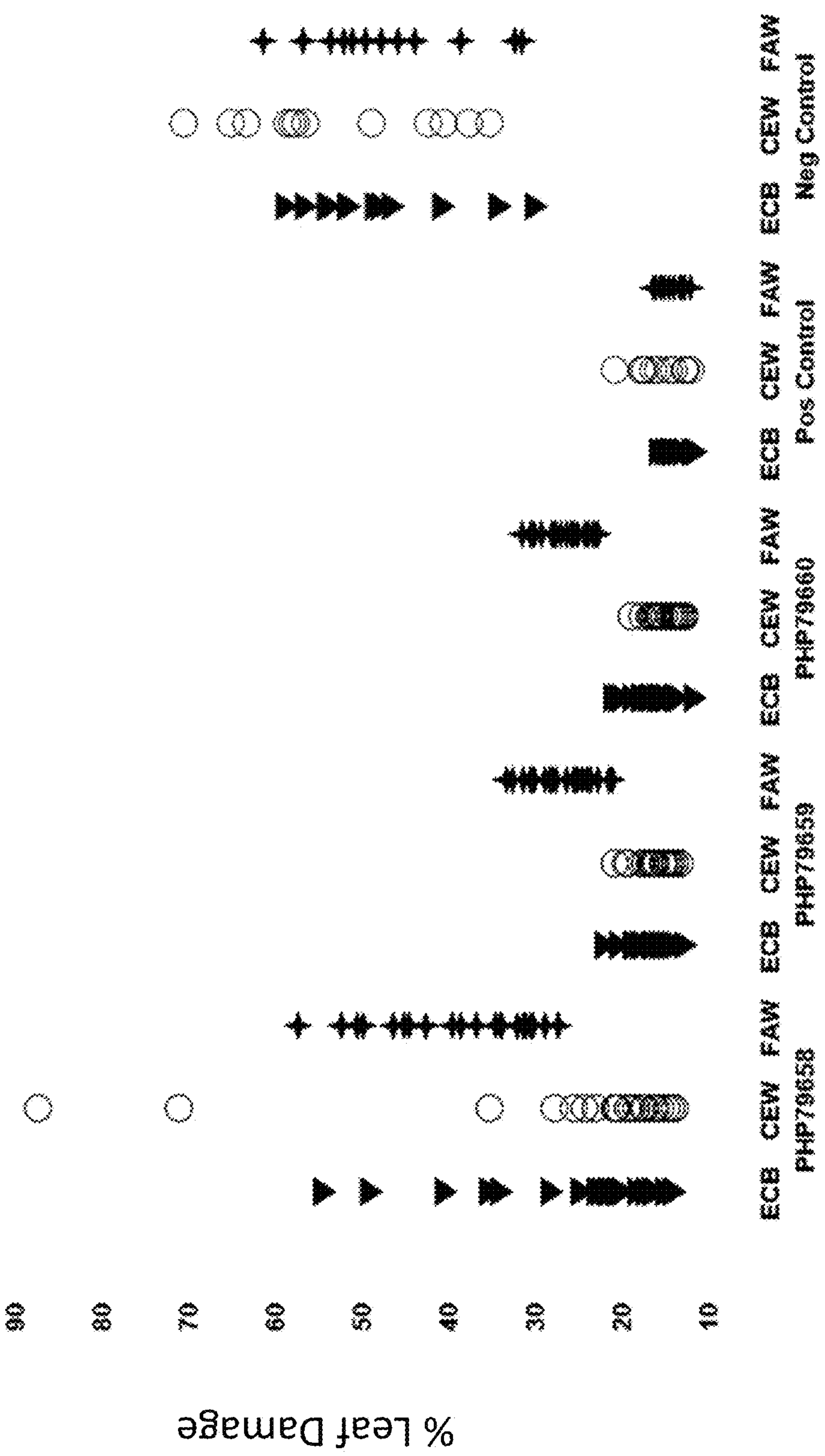
FIG. 2 shows the % leaf damage by CEW, ECB and FAW of individual transgenic T0 maize events from constructs PHP79658, PHP79559 and PHP79660 expressing the IPD103Aa polypeptide (SEQ ID NO: 2).
Figure 3:
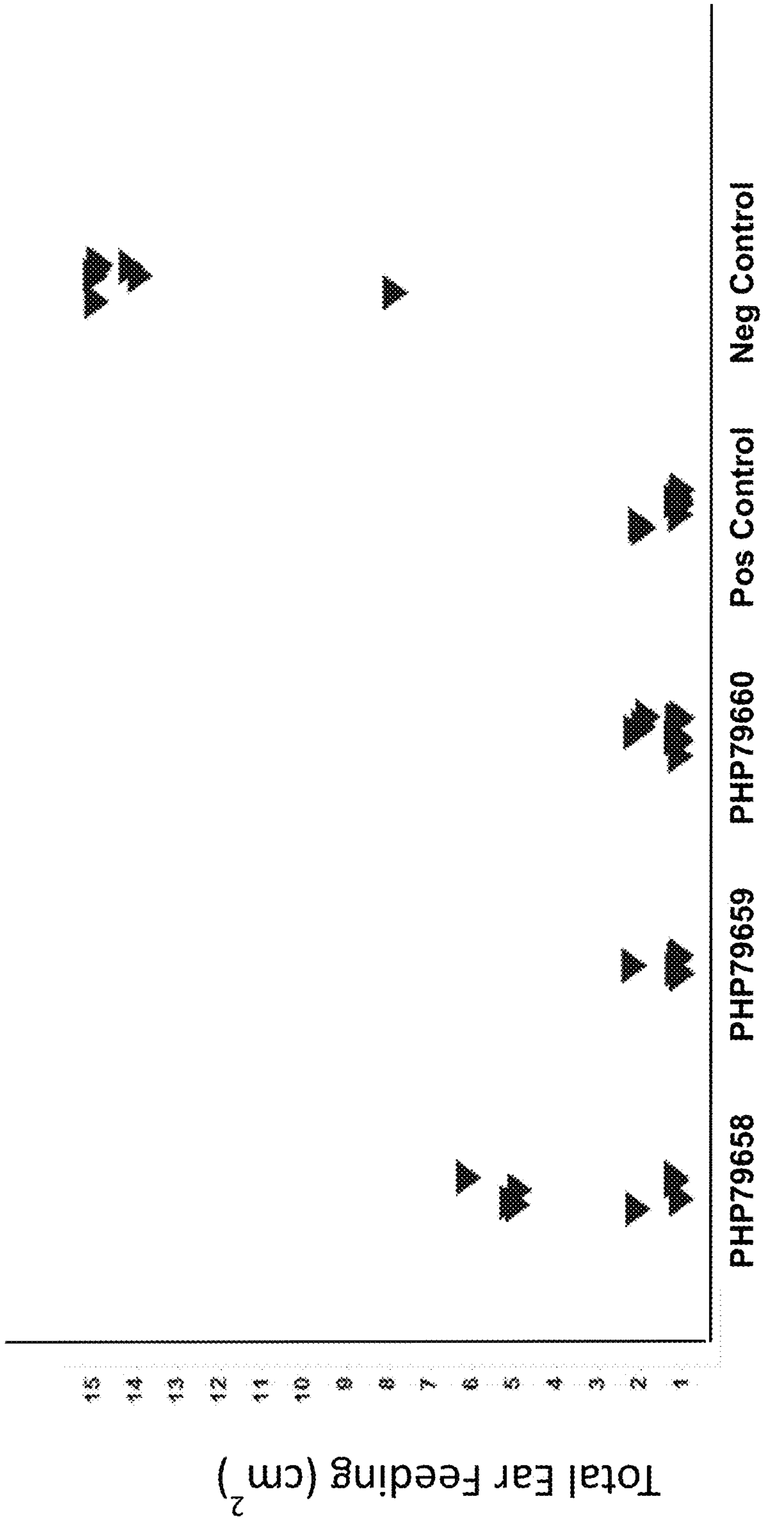
FIG. 3 shows the Total Corn Ear Feeding ($cm^2$) by CEW of individual transgenic T0 maize events from constructs PHP79658, PHP79559 and PHP79660 expressing the IPD103Aa polypeptide (SEQ ID NO: 2).

It is to be understood that this disclosure is not limited to the particular methodology, protocols, cell lines, genera, and reagents described, as such may vary. It is also to be understood that the terminology used herein is for the purpose of describing particular embodiments only, and is not intended to limit the scope of the present disclosure.

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents. All technical and scientific terms used herein have the same meaning as commonly understood to one of ordinary skill in the art to which this disclosure belongs unless clearly indicated otherwise.

The present disclosure is drawn to molecular stacks and breeding stacks and methods for controlling pests. As used herein, a "molecular stack" is defined as multiple trait genes delivered in one or more pieces of recombinant DNA simultaneously or consecutively into a single transgenic locus. As used herein, a "breeding stack" is defined as multiple trait genes that are delivered by conventional breeding, by the crossing of a transgenic plant containing individual transgene(s) in a first transgenic locus, with another transgenic plant containing other single or multiple transgenes in a second transgenic locus. The methods involve transforming organisms with a molecular nucleic acid sequences encoding an IPD103 polypeptide and at least one other pesticidal polypeptide. Thus, transformed bacteria, plants, plant cells, plant tissues and seeds are provided. The compositions include pesticidal nucleic acids and proteins of bacterial species. The transgene stacks find use in controlling or killing Lepidopteran, Coleopteran, Dipteran, fungal, Hemipteran and/or nematode pest populations and for producing transgenic plants with pesticidal activity. Insect pests of interest include, but are not limited to, Lepidoptera species including but not limited to: Corn Earworm, (CEW) (*Helicoverpa zea*), European Corn Borer (ECB) (*Ostrinia nubialis*), diamond-back moth, e.g., *Helicoverpa zea* Boddie; soybean looper, e.g., *Pseudoplusia includens* Walker; and velvet bean caterpillar e.g., *Anticarsia gemmatalis* Hübner and Coleoptera species including but not limited to Western corn rootworm (*Diabrotica virgifera*)—WCRW, Southern corn rootworm (*Diabrotica undecimpunctata howardi*)—SCRW, and Northern corn rootworm (*Diabrotica barberi*)—NCRW.

By "pesticidal toxin" or "pesticidal protein" is used herein to refer to a toxin that has toxic activity against one or more pests, including, but not limited to, members of the Lepidoptera, Diptera, Hemiptera and Coleoptera orders or the Nematoda phylum or a protein that has homology to such a protein. Pesticidal proteins have been isolated from organisms including, for example, *Bacillus* sp., *Pseudomonas* sp., *Photorhabdus* sp., *Xenorhabdus* sp., *Clostridium bifermentans* and *Paenibacillus popilliae*. Pesticidal proteins include but are not limited to: insecticidal proteins from *Pseudomonas* sp. such as PSEEN3174 (Monalysin; (2011) *PLoS Pathogens* 7:1-13); from *Pseudomonas protegens* strain CHA0 and Pf-5 (previously *fluorescens*) (Pechy-Tarr, (2008) *Environmental Microbiology* 10:2368-2386; GenBank Accession No. EU400157); from *Pseudomonas taiwanensis* (Liu, et al., (2010) *J. Agric. Food Chem.*, 58:12343-12349) and from *Pseudomonas pseudoalcaligenes* (Zhang, et al., (2009) *Annals of Microbiology* 59:45-50 and Li, et al., (2007) *Plant Cell Tiss. Organ Cult.* 89:159-168); insecticidal proteins from *Photorhabdus* sp. and *Xenorhabdus* sp. (Hinchliffe, et al., (2010) *The Open Toxicology Journal*, 3:101-118 and Morgan, et al., (2001) *Applied and Envir. Micro.* 67:2062-2069); U.S. Pat. Nos. 6,048,838, and 6,379,946; a PIP-1 polypeptide of US Patent Publication US20140007292; an AfIP-1A and/or AfIP-1B polypeptide of US Patent Publication US20140033361; a PHI-4 polypeptide of US Patent Publication US20140274885 and US20160040184; a PIP-47 polypeptide of PCT Publication Number WO2015/023846, a PIP-72 polypeptide of PCT Publication Number WO2015/038734; a PtIP-50 polypeptide and a PtIP-65 polypeptide of PCT Publication Number WO2015/120270; a PtIP-83 polypeptide of PCT Publication Number WO2015/120276; a PtIP-96 polypeptide of US Publication No. 2017-0233440; an IPD079 polypeptide of US Publication No. 2018-0222947; an IPD082 polypeptide of PCT WO 2017/105987, and δ-endotoxins including, but not limited to, the Cry1, Cry2, Cry3, Cry4, Cry5, Cry6, Cry7, Cry8, Cry9, Cry10, Cry11, Cry12, Cry13, Cry14, Cry15, Cry16, Cry17, Cry18, Cry19, Cry20, Cry21, Cry22, Cry23, Cry24, Cry25, Cry26, Cry27, Cry28, Cry29, Cry30, Cry31, Cry32, Cry33, Cry34, Cry35,Cry36, Cry37, Cry38, Cry39, Cry40, Cry41, Cry42, Cry43, Cry44, Cry45, Cry46, Cry47, Cry49, Cry50, Cry51, Cry52, Cry53, Cry54, Cry55, Cry56, Cry57, Cry58, Cry59, Cry60, Cry61, Cry62, Cry63, Cry64, Cry65, Cry66, Cry67, Cry68, Cry69, Cry70, Cry71, and Cry 72 classes of δ-endotoxin genes and the *B. thuringiensis* cytolytic cyt1 and cyt2 genes. Members of these classes of *B. thuringiensis* insecticidal proteins (see, Crickmore, et al., "*Bacillus thuringiensis* toxin nomenclature" (2011), at lifesci.sussex.ac.uk/home/Neil_Crickmore/Bt/ which can be accessed on the world-wide web using the "www" prefix).

Examples of δ-endotoxins also include but are not limited to Cry1A proteins of U.S. Pat. Nos. 5,880,275 and 7,858,849; a DIG-3 or DIG-11 toxin (N-terminal deletion of α-helix 1 and/or α-helix 2 variants of cry proteins such as Cry1A, Cry3A) of U.S. Pat. Nos. 8,304,604, 8,304,605 and 8,476,226; Cry1B of PCT WO 2004/020636; Cry1C of U.S. Pat. No. 6,033,874; Cry1F of U.S. Pat. Nos. 5,188,960 and 6,218,188; Cry1A/F chimeras of U.S. Pat. Nos. 7,070,982; 6,962,705 and 6,713,063); a Cry2 protein such as Cry2Ab protein of U.S. Pat. No. 7,064,249); a Cry3A protein including but not limited to an engineered hybrid insecticidal protein (eHIP) created by fusing unique combinations of variable regions and conserved blocks of at least two different Cry proteins (US Patent Application Publication Number 2010/0017914); a Cry4 protein; a Cry5 protein; a Cry6 protein; Cry8 proteins of U.S. Pat. Nos. 7,329,736, 7,449,552, 7,803,943, 7,476,781, 7,105,332, 7,378,499 and 7,462,760; a Cry9 protein such as such as members of the Cry9A, Cry9B, Cry9C, Cry9D, Cry9E and Cry9F families; a Cry15 protein of Naimov, et al., (2008) *Applied and Environmental Microbiology,* 74:7145-7151; a Cry22, a Cry34Ab1 protein of U.S. Pat. Nos. 6,127,180, 6,624,145 and 6,340,593; a CryET33 and cryET34 protein of U.S. Pat. Nos. 6,248,535, 6,326,351, 6,399,330, 6,949,626, 7,385,107 and 7,504,229; a CryET33 and CryET34 homologs of US Patent Publication Number 2006/0191034, 2012/0278954, and PCT Publication Number WO 2012/139004; a Cry35Ab1 protein of U.S. Pat. Nos. 6,083,499, 6,548,291 and 6,340,593; a Cry46 protein, a Cry 51 protein, a Cry binary toxin; a TIC901 or related toxin; TIC807 of US Patent Application Publication Number 2008/0295207; ET29, ET37, TIC809, TIC810, TIC812, TIC127, TIC128 of PCT US 2006/033867; AXMI-027, AXMI-036, and AXMI-038 of U.S. Pat. No. 8,236,757; AXMI-031, AXMI-039, AXMI-040, AXMI-049 of U.S. Pat. No. 7,923,602; AXMI-018, AXMI-020 and AXMI-021 of WO 2006/083891; AXMI-010 of WO 2005/038032; AXMI-003 of WO 2005/021585; AXMI-008 of US Patent Application Publication Number 2004/0250311; AXMI-006 of US Patent Application Publication Number 2004/0216186; AXMI-007 of US Patent Application Publication Number 2004/0210965; AXMI-009 of US Patent Application Number 2004/0210964; AXMI-014 of US Patent Application Publication Number 2004/0197917; AXMI-004 of US Patent Application Publication Number 2004/0197916; AXMI-028 and AXMI-029 of WO 2006/119457; AXMI-007, AXMI-008, AXMI-0080rf2, AXMI-009, AXMI-014 and AXMI-004 of WO 2004/074462; AXMI-150 of U.S. Pat. No. 8,084,416; AXMI-205 of US Patent Application Publication Number 2011/0023184; AXMI-011, AXMI-012, AXMI-013, AXMI-015, AXMI-019, AXMI-044, AXMI-037, AXMI-043, AXMI-033, AXMI-034, AXMI-022, AXMI-023, AXMI-041, AXMI-063 and AXMI-064 of US Patent Application Publication Number 2011/0263488; AXMI-R1 and related proteins of US Patent Application Publication Number 2010/0197592; AXMI221Z, AXMI222z, AXMI223z, AXMI224z and AXMI225z of WO 2011/103248; AXMI218, AXMI219, AXMI220, AXMI226, AXMI227, AXMI228, AXMI229, AXMI230 and AXMI231 of WO 2011/103247; AXMI-115, AXMI-113, AXMI-005, AXMI-163 and AXMI-184 of U.S. Pat. No. 8,334,431; AXMI-001, AXMI-002, AXMI-030, AXMI-035 and AXMI-045 of US Patent Application Publication Number 2010/0298211; AXMI-066 and AXMI-076 of US Patent Application Publication Number 2009/0144852; AXMI128, AXMI130, AXMI131, AXMI133, AXMI140, AXMI141, AXMI142, AXMI143, AXMI144, AXMI146, AXMI148, AXMI149, AXMI152, AXMI153, AXMI154, AXMI155, AXMI156, AXMI157, AXMI158, AXMI162, AXMI165, AXMI166, AXMI167, AXMI168, AXMI169, AXMI170, AXMI171, AXMI172, AXMI173, AXMI174, AXMI175, AXMI176, AXMI177, AXMI178, AXMI179, AXMI180, AXMI181, AXMI182, AXMI185, AXMI186, AXMI187, AXMI188, AXMI189 of U.S. Pat. No. 8,318,900; AXMI079, AXMI080, AXMI081, AXMI082, AXMI091, AXMI092, AXMI096, AXMI097, AXMI098, AXMI099, AXMI100, AXMI101, AXMI102, AXMI103, AXMI104, AXMI107, AXMI108, AXMI109, AXMI110, AXMI111, AXMI112, AXMI114, AXMI116, AXMI117, AXMI118, AXMI119, AXMI120, AXMI121, AXMI122, AXMI123, AXMI124, AXMI1257, AXMI1268, AXMI127, AXMI129, AXMI164, AXMI151, AXMI161, AXMI183, AXMI132, AXMI138, AXMI137 of US Patent Application Publication Number 2010/0005543, cry proteins such as Cry1A and Cry3A having modified proteolytic sites of U.S. Pat. No. 8,319,019; a Cry1Ac, Cry2Aa and Cry1Ca toxin protein from *Bacillus thuringiensis* strain VBTS 2528 of US Patent Application Publication Number 2011/0064710. The insecticidal activity of Cry proteins is known to one skilled in the art (for review, see, van Frannkenhuyzen, (2009) *J. Invert. Path.* 101:1-16). The use of Cry proteins as transgenic plant traits and Cry-transgenic plants including but not limited to plants expressing Cry1Ac, Cry1Ac+Cry2Ab, Cry1Ab, Cry1A.105, Cry1F, Cry1Fa2, Cry1F+Cry1Ac, Cry2Ab, Cry3A, mCry3A, Cry3Bb1, Cry34Ab1, Cry35Ab1, Vip3A, mCry3A, Cry9c and CBI-Bt have received regulatory approval (see, Sanahuja, (2011) *Plant Biotech Journal* 9:283-300 and the CERA. (2010) GM Crop Database Center for Environmental Risk Assessment (CERA), ILSI Research Foundation, Washington D.C. at cera-gmc.org/index.php?action=gm_crop_database which can be accessed on the world-wide web using the "www" prefix). More than one pesticidal proteins can also be expressed in plants such as Vip3Ab & Cry1Fa (US2012/0317682); Cry1BE & Cry1F (US2012/0311746); Cry1CA & Cry1AB (US2012/0311745); Cry1F & CryCa (US2012/0317681); Cry1Da & Cry1Be (US2012/0331590); Cry1Da & Cry1Fa (US2012/0331589); Cry1AB & Cry1BE (US2012/0324606); Cry1Fa & Cry2Aa and Cry1I & Cry1E (US2012/0324605); Cry34Ab/35Ab and Cry6Aa (US20130167269); Cry34Ab/VCry35Ab & Cry3Aa (US20130167268); and Cry3A and Cry1Ab or Vip3Aa (US20130116170). Pesticidal proteins also include insecticidal lipases including lipid acyl hydrolases of U.S. Pat. No. 7,491,869, and cholesterol oxidases such as from *Streptomyces* (Purcell et al. (1993) *Biochem Biophys Res Commun* 15:1406-1413). Pesticidal proteins also include VIP (vegetative insecticidal proteins) toxins of U.S. Pat. Nos. 5,877,012, 6,107,279 6,137,033, 7,244,820, 7,615,686, and 8,237,020 and the like (see, lifesci.sussex-.ac.uk/home/Neil_Crickmore/Bt/vip.html which can be accessed on the world-wide web using the "www" prefix). Pesticidal proteins also include toxin complex (TC) proteins, obtainable from organisms such as *Xenorhabdus, Photorhabdus* and *Paenibacillus* (see, U.S. Pat. Nos. 7,491,698 and 8,084,418). Some TC proteins have "stand alone" insecticidal activity and other TC proteins enhance the activity of the stand-alone toxins produced by the same given organism. The toxicity of a "stand-alone" TC protein (from *Photorhabdus, Xenorhabdus* or *Paenibacillus*, for example) can be enhanced by one or more TC protein "potentiators" derived from a source organism of a different genus. There are three main types of TC proteins. As referred to herein, Class A proteins ("Protein A") are stand-alone toxins. Class B proteins ("Protein B") and Class C proteins ("Protein C") enhance the toxicity of Class A proteins. Examples of Class A proteins are TcbA, TcdA, XptA1 and XptA2. Examples of Class B proteins are TcaC, TcdB, XptB1Xb and XptC1Wi. Examples of Class C proteins are TccC, XptC1Xb and XptB1Wi. Pesticidal proteins also include spider, snake and scorpion venom proteins. Examples of spider venom peptides include but not limited to lycotoxin-1 peptides and mutants thereof (U.S. Pat. No. 8,334,366).

In some embodiments, an "IPD103 polypeptide" or "IPD103 protein" is defined as a polypeptide having insecticidal activity, as disclosed in PCT WO 2018/005411, which is herein incorporated by reference.

In some embodiments, the IPD103 polypeptide has at least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36 or SEQ ID NO: 38. The term "about" when used herein in context with percent sequence identity means+/−0.5%.

In some embodiments, the IPD103 polypeptide has at least 95% identity to the amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36 or SEQ ID NO: 38.

In some embodiments, the IPD103 polypeptide comprises the amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36 or SEQ ID NO: 38.

In some embodiments, the IPD103 polypeptide has at least 95% identity to the amino acid sequence of SEQ ID NO: 252, SEQ ID NO: 253, SEQ ID NO: 254, SEQ ID NO: 255, SEQ ID NO: 256, SEQ ID NO: 257, SEQ ID NO: 258, SEQ ID NO: 259, SEQ ID NO:260 or SEQ ID NO: 261.

In some embodiments, the IPD103 polypeptide comprises the amino acid sequence of SEQ ID NO: 252, SEQ ID NO: 253, SEQ ID NO: 254, SEQ ID NO: 255, SEQ ID NO: 256, SEQ ID NO: 257, SEQ ID NO: 258, SEQ ID NO: 259, SEQ ID NO:260 or SEQ ID NO: 261.

In some embodiments, a "PtIP-83 polypeptide" or "PtIP-83 protein" is defined as a polypeptide having insecticidal activity, as disclosed in US Publication US 21060347799, which is herein incorporated by reference.

In some embodiments, the PtIP-83 polypeptide has at least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, and SEQ ID NO: 61.

In some embodiments, the PtIP-83 polypeptide comprises an amino acid sequence having at least 95% sequence identity to an amino acid sequence of SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, and SEQ ID NO: 61.

In some embodiments, the PtIP-83 polypeptide comprises an amino acid sequence of SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59, and SEQ ID NO: 61.

In some embodiments, the Cry1B polypeptide is selected from Cry1Ba1 (Accession CAA29898, Cry1Ba2 (Accession CAA65003), Cry1Ba3 (Accession AAK63251), Cry1Ba4 (Accession AAK51084, Cry1Ba5 (Accession ABO20894), Cry1Ba6 (Accession ABL60921), Cry1Ba7 (Accession HQ439781), Cry1Bb1 (AAA22344), Cry1Bb2 (Accession HQ439782), Cry1Bc1 (Accession CAA86568), Cry1Bd1 (Accession AAD10292), Cry1Bd2 (Accession AAM93496), Cry1Be1 (Accession AAC32850), Cry1Be2 (Accession AAQ52387), Cry1Be3 (Accession ACV96720), Cry1Be4 (Accession HM070026), Cry1Bf1 (Accession CAC50778), Cry1Bf2 (Accession AAQ52380), Cry1Bg1 (Accession AAO39720), Cry1Bh1 (Accession HQ589331), and Cry1Bi1 (Accession KC156700).

In some embodiments, the Cry1B polypeptide is selected from a Cry1B of U.S. Pat. Nos. 8,772,577, 9,404,121, US Publication US 20160194364, and U.S. Ser. No. 62/607,372, which are incorporated herein.

In some embodiments, the Cry1B polypeptide is selected from the amino acid sequence of SEQ ID NO: 63, SEQ ID NO: 109, SEQ ID NO: 111, SEQ ID NO: 221, SEQ ID NO: 223, SEQ ID NO: 224, SEQ ID NO: 225, SEQ ID NO: 226, SEQ ID NO: 227, SEQ ID NO: 228, and SEQ ID NO: 229.

In some embodiments, the Cry1B polypeptide is a variant Cry1B polypeptide of US Publication US 20170226164 and WO Publication WO2017/180715, which are incorporated herein.

In some embodiments, the variant Cry1B polypeptide comprises the amino acid sequence of SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 84, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210 or SEQ ID NO: 211.

In some embodiments, the variant Cry1B polypeptide is selected from SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 84, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, and SEQ ID NO: 211.

In some embodiments, the Cry1C polypeptide is selected from Cry1Ca1 (Accession CAA30396), Cry1Ca2 (Accession CAA31951), Cry1Ca3 (Accession AAA22343), Cry1Ca4 (Accession CAA01886), Cry1Ca5 (Accession CAA65457), Cry1Ca6 (Accession AAF37224), Cry1Ca7 (Accession AAG50438), Cry1Ca8 (Accession AAM00264), Cry1Ca9 (Accession AAL79362), Cry1Ca10 (Accession AAN16462), Cry1Ca11 (Accession AAX53094), Cry1Ca12 (Accession HM070027), Cry1Ca13 (Accession HQ412621), Cry1Ca14 (Accession JN651493), Cry1Cb1 (Accession M97880), Cry1Cb2 (Accession AAG35409), Cry1Cb3 (Accession ACD50894), Cry1Cb-like (Accession AAX63901), Cry1Da1 (Accession CAA38099), Cry1Da2 (Accession I76415), and Cry1Da3 (Accession HQ43978).

In some embodiments, the Cry1C polypeptide comprises an amino acid sequence having at least 95% sequence identity to the Cry1Ca polypeptide of SEQ ID NO: 230.

In some embodiments, the Cry1C polypeptide comprises the amino acid sequence of SEQ ID NO: 230.

In some embodiments, the Cry1D polypeptide is selected from Cry1Da1 (Accession CAA38099), Cry1Da2 (Accession I76415), Cry1Da3 (Accession HQ439784), Cry1db1 (Accession CAA80234), Cry1db2 (Accession AAK48937), Cry1Dc1 (Accession ABK35074), and a Cry1D polypeptide of US 2017 0233759, which is herein incorporated by reference in its entirety.

In some embodiments, the Cry1D polypeptide comprises an amino acid sequence having at least 95% sequence identity to the Cry1Da polypeptide of US 2017 0233759.

In some embodiments, the Cry1D polypeptide comprises an amino acid sequence having at least 95% sequence identity to the Cry1Da polypeptide of SEQ ID NO: 231, SEQ ID NO: 233, SEQ ID NO: 235, SEQ ID NO: 237, SEQ ID NO: 239 or SEQ ID NO: 241.

In some embodiments, the Cry1D polypeptide comprises the amino acid sequence of SEQ ID NO: 231, SEQ ID NO: 233, SEQ ID NO: 235, SEQ ID NO: 237, SEQ ID NO: 239 or SEQ ID NO: 241.

In some embodiments, the Cry1J polypeptide is selected from Cry1Ja1 (Accession AAA22341), Cry1Ja2 (Accession HM070030), Cry1Ja3 (Accession JQ228425), Cry1Jb1 (Accession AAA98959), Cry1Jc1 (Accession AAC31092), Cry1Jc2 (Accession AAQ52372), Cry1Jd1 (Accession CAC50779).

In some embodiments, the Cry1J polypeptide is selected from a variant Cry1J of US Publication Number US20170240603.

In some embodiments, the Cry1J variant polypeptide comprises an amino acid sequence having at least 95% identity to SEQ ID NO: 213, SEQ ID NO: 215, SEQ ID NO: 217 or SEQ ID NO: 219.

In some embodiments, the Cry1J variant polypeptide comprises the amino acid sequence of SEQ ID NO: 213, SEQ ID NO: 215, SEQ ID NO: 217 or SEQ ID NO: 219.

In some embodiments, the variant Cry1J polypeptide is selected from SEQ ID NO: 213, SEQ ID NO: 215, SEQ ID NO: 217 or SEQ ID NO: 219.

Nucleic Acid Molecules, and Variants and Fragments Thereof

Isolated or recombinant nucleic acid molecules comprising nucleic acid sequences encoding IPD103 polypeptides, PtIP-83 polypeptides, Cry1B polypeptides, variant Cry1B polypeptides, Cry1C polypeptides, Cry1D polypeptide, and Cry1J polypeptides As used herein, the term “nucleic acid molecule” refers to DNA molecules (e.g., recombinant DNA, cDNA, genomic DNA, plastid DNA, mitochondrial DNA) and RNA molecules (e.g., mRNA) and analogs of the DNA or RNA generated using nucleotide analogs. The nucleic acid molecule can be single-stranded or double-stranded, but preferably is double-stranded DNA.

An “isolated” nucleic acid molecule (or DNA) is used herein to refer to a nucleic acid sequence (or DNA) that is no longer in its natural environment, for example in vitro. A “recombinant” nucleic acid molecule (or DNA) is used herein to refer to a nucleic acid sequence (or DNA) that is in a recombinant bacterial or plant host cell. In some embodiments, an “isolated” or “recombinant” nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the disclosure, "isolated" or "recombinant" when used to refer to nucleic acid molecules excludes isolated chromosomes.

In some embodiments, an isolated nucleic acid molecule encoding polypeptides of the disclosure has one or more change in the nucleic acid sequence compared to the native or genomic nucleic acid sequence. In some embodiments the change in the native or genomic nucleic acid sequence includes but is not limited to: changes in the nucleic acid sequence due to the degeneracy of the genetic code; changes in the nucleic acid sequence due to the amino acid substitution, insertion, deletion and/or addition compared to the native or genomic sequence; removal of one or more intron; deletion of one or more upstream or downstream regulatory regions; and deletion of the 5' and/or 3' untranslated region associated with the genomic nucleic acid sequence. In some embodiments, the nucleic acid molecule encoding an IPD103 polypeptide is a non-genomic sequence.

A variety of polynucleotides that encode polypeptides of the disclosure or related proteins are contemplated. Such polynucleotides are useful for production of polypeptides of the disclosure in host cells when operably linked to a suitable promoter, transcription termination and/or polyadenylation sequences. Such polynucleotides are useful in DNA constructs, molecular stack, and breeding stacks of the disclosure.

Polynucleotides Encoding Polypeptides

One source of polynucleotides that encode IPD103 polypeptides or related proteins is a fern or other primitive plant species selected from but not limited to *Athyrium* species, *Platycerium* species, *Pteris* species, *Colysis* species, *Nephrolepis* species, *Polystichium* species, *Thelypteris* species, *Tectaria* species, and *Davallia* species, which contains an IPD103 polynucleotide of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35 or SEQ ID NO: 37, encoding an IPD103 polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36, and SEQ ID NO: 38, respectively. The polynucleotides of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35 or SEQ ID NO: 37 can be used to express IPD103 polypeptides in recombinant bacterial hosts that include but are not limited to *Agrobacterium, Bacillus, Escherichia, Salmonella, Pseudomonas* and *Rhizobium* bacterial host cells.

Polynucleotides that encode polypeptides of the disclosure can also be synthesized de novo from a polypeptide sequence of the disclosure. The sequence of the polynucleotide gene can be deduced from a polypeptide sequence of the disclosure through use of the genetic code. Computer programs such as "BackTranslate" (GCG™ Package, Acclerys, Inc. San Diego, Calif.) can be used to convert a peptide sequence to the corresponding nucleotide sequence encoding the peptide. Furthermore, synthetic polynucleotide sequences of the disclosure can be designed so that they will be expressed in plants.

In some embodiments, an "IPD103 polynucleotide" is defined as a polynucleotide, disclosed in PCT WO 2018/005411, which is incorporated herein by reference, encoding an IPD103 polypeptide having insecticidal activity.

In some embodiments, the IPD103 polynucleotide encodes an IPD103 polypeptide having at least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36 or SEQ ID NO: 38.

In some embodiments, the IPD103 polynucleotide encodes an IPD103 polypeptide having at least 95% identity to the amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36 or SEQ ID NO: 38.

In some embodiments, the IPD103 polynucleotide encodes an IPD103 polypeptide comprises the amino acid sequence of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36 or SEQ ID NO: 38.

In some embodiments, the polynucleotide encoding an IPD103 polypeptide is the sequence set forth in SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35 or SEQ ID NO: 37.

In some embodiments, the IPD103 polynucleotide encodes an IPD103 polypeptide comprises the amino acid sequence of SEQ ID NO: 252, SEQ ID NO: 253, SEQ ID NO: 254, SEQ ID NO: 255, SEQ ID NO: 256, SEQ ID NO: 257, SEQ ID NO: 258, SEQ ID NO: 259, SEQ ID NO:260 or SEQ ID NO: 261.

In some embodiments, the polynucleotide encoding an IPD103 polypeptide is the sequence set forth in SEQ ID NO: 242, SEQ ID NO: 243, SEQ ID NO: 244, SEQ ID NO: 245, SEQ ID NO: 246, SEQ ID NO: 247, SEQ ID NO: 248, SEQ ID NO: 249, SEQ ID NO:250 or SEQ ID NO: 251.

In some embodiments, a "PtIP-83 polynucleotide" is defined as a polynucleotide disclosed in US Publication US 21060347799 (incorporated herein by reference) encoding a PtIP-83 polypeptide having insecticidal activity.

In some embodiments, the PtIP-83 polynucleotide encodes a PtIP-83 polypeptide having at least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59 or SEQ ID NO: 61.

In some embodiments, the PtIP-83 polynucleotide encodes a PtIP-83 polypeptide comprising an amino acid sequence having at least 95% sequence identity to an amino acid sequence of SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59 or SEQ ID NO: 61.

In some embodiments, the PtIP-83 polynucleotide encodes a PtIP-83 polypeptide comprising the amino acid sequence of SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59 or SEQ ID NO: 61.

In some embodiments, polynucleotides are provided that encode a Cry1B polypeptide selected from Cry1Ba1 (Accession CAA29898, Cry1Ba2 (Accession CAA65003), Cry1Ba3 (Accession AAK63251), Cry1Ba4 (Accession AAK51084, Cry1Ba5 (Accession ABO20894), Cry1Ba6 (Accession ABL60921), Cry1Ba7 (Accession HQ439781), Cry1Bb1 (AAA22344), Cry1Bb2 (Accession HQ439782), Cry1Bc1 (Accession CAA86568), Cry1Bd1 (Accession AAD10292), Cry1Bd2 (Accession AAM93496), Cry1Be1 (Accession AAC32850), Cry1Be2 (Accession AAQ52387), Cry1Be3 (Accession ACV96720), Cry1Be4 (Accession HM070026), Cry1Bf1 (Accession CAC50778), Cry1Bf2 (Accession AAQ52380), Cry1Bg1 (Accession AAO39720), Cry1Bh1 (Accession HQ589331), and Cry1Bi1 (Accession KC156700).

In some embodiments, polynucleotides are provided that encode a Cry1B polypeptide selected from a Cry1B of U.S. Pat. Nos. 8,772,577, 9,404,121, US Publication US 2016 0194364, and U.S. Ser. No. 62/607,372, which are incorporated herein by reference.

In some embodiments, polynucleotides are provided that encode a Cry1B polypeptide selected from the amino acid sequence of SEQ ID NO: 63, SEQ ID NO: 109, SEQ ID NO: 111, SEQ ID NO: 221, SEQ ID NO: 223, SEQ ID NO: 224, SEQ ID NO: 225, SEQ ID NO: 226, SEQ ID NO: 227, SEQ ID NO: 228, and SEQ ID NO: 229.

In some embodiments, polynucleotides are provided that encode a variant Cry1B polypeptide of US Publication US 20170226164 and WO Publication WO2017/180715, which are incorporated herein by reference.

In some embodiments, polynucleotides are provided that encode a variant Cry1B polypeptide comprising the amino acid sequence of SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 84, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210 or SEQ ID NO: 211.

In some embodiments, polynucleotides are provided that encode a variant Cry1B polypeptide selected from SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 84, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, and SEQ ID NO: 211.

In some embodiments, polynucleotides are provided that encode a Cry1C polypeptide selected from Cry1Ca1 (Accession CAA30396), Cry1Ca2 (Accession CAA31951), Cry1Ca3 (Accession AAA22343), Cry1Ca4 (Accession CAA01886), Cry1Ca5 (Accession CAA65457), Cry1Ca6 (Accession AAF37224), Cry1Ca7 (Accession AAG50438), Cry1Ca8 (Accession AAM00264), Cry1Ca9 (Accession AAL79362), Cry1Ca10 (Accession AAN16462), Cry1Ca11 (Accession AAX53094), Cry1Ca12 (Accession HM070027), Cry1Ca13 (Accession HQ412621), Cry1Ca14 (Accession JN651493), Cry1Cb1 (Accession M97880), Cry1Cb2 (Accession AAG35409), Cry1Cb3 (Accession ACD50894), Cry1Cb-like (Accession AAX63901), Cry1Da1 (Accession CAA38099), Cry1Da2 (Accession I76415), and Cry1Da3 (Accession HQ43978).

In some embodiments, polynucleotides are provided that encode a Cry1C polypeptide comprises an amino acid sequence having at least 95% sequence identity to the Cry1Ca polypeptide of SEQ ID NO: 230.

In some embodiments, polynucleotides are provided that encode a Cry1C polypeptide comprises the amino acid sequence of SEQ ID NO: 230.

In some embodiments, polynucleotides are provided that encode a Cry1D polypeptide selected from Cry1Da1 (Accession CAA38099), Cry1Da2 (Accession I76415), Cry1Da3 (Accession HQ439784), Cry1db1 (Accession CAA80234), Cry1db2 (Accession AAK48937), and Cry1Dc1 (Accession ABK35074).

In some embodiments, polynucleotides are provided that encode a Cry1D polypeptide comprises an amino acid sequence having at least 95% sequence identity to the Cry1Da polypeptide of SEQ ID NO: 231, SEQ ID NO: 233, SEQ ID NO: 235, SEQ ID NO: 237, SEQ ID NO: 239 or SEQ ID NO: 241.

In some embodiments, polynucleotides are provided that encode a Cry1D polypeptide comprises the amino acid sequence of a Cry1Da polypeptide of SEQ ID NO: 231, SEQ ID NO: 233, SEQ ID NO: 235, SEQ ID NO: 237, SEQ ID NO: 239 or SEQ ID NO: 241.

In some embodiments, polynucleotides are provided that encode a Cry1J polypeptide selected from Cry1Ja1 (Accession AAA22341), Cry1Ja2 (Accession HM070030), Cry1Ja3 (Accession JQ228425), Cry1Jb1 (Accession AAA98959), Cry1Jc1 (Accession AAC31092), Cry1Jc2 (Accession AAQ52372), and Cry1Jd1 (Accession CAC50779).

In some embodiments, polynucleotides are provided that encode a variant Cry1J polypeptide of US Publication Number US20170240603.

In some embodiments, polynucleotides are provided that encode a Cry1J variant polypeptide comprising an amino acid sequence having at least 95% identity to SEQ ID NO: 213, SEQ ID NO: 215, SEQ ID NO: 217 or SEQ ID NO: 219.

In some embodiments, polynucleotides are provided that encode a Cry1J variant polypeptide comprising the amino acid sequence of SEQ ID NO: 213, SEQ ID NO: 215, SEQ ID NO: 217 or SEQ ID NO: 219.

In some embodiments, polynucleotides are provided that encode a variant Cry1J polypeptide selected from SEQ ID NO: 213, SEQ ID NO: 215, SEQ ID NO: 217 or SEQ ID NO: 219.

In some embodiments, the nucleic acid molecule encoding a polypeptide of the disclosure is a non-genomic nucleic acid sequence. As used herein a "non-genomic nucleic acid sequence" or "non-genomic nucleic acid molecule" or "non-genomic polynucleotide" refers to a nucleic acid molecule that has one or more change in the nucleic acid sequence compared to a native or genomic nucleic acid sequence. In some embodiments the change to a native or genomic nucleic acid molecule includes but is not limited to: changes in the nucleic acid sequence due to the degeneracy of the genetic code; optimization of the nucleic acid sequence for expression in plants; changes in the nucleic acid sequence to introduce at least one amino acid substitution, insertion, deletion and/or addition compared to the native or genomic sequence; removal of one or more intron associated with the genomic nucleic acid sequence; insertion of one or more heterologous introns; deletion of one or more upstream or downstream regulatory regions associated with the genomic nucleic acid sequence; insertion of one or more heterologous upstream or downstream regulatory regions; deletion of the 5' and/or 3' untranslated region associated with the genomic nucleic acid sequence; insertion of a heterologous 5' and/or 3' untranslated region; and modification of a polyadenylation site. In some embodiments, the non-genomic nucleic acid molecule is a synthetic nucleic acid sequence.

In some embodiments, the nucleic acid molecule encoding an IPD103 polypeptide is a non-genomic polynucleotide having a nucleotide sequence having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater identity, to the nucleic acid sequence of SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35 or SEQ ID NO: 37, wherein the IPD103 polypeptide has insecticidal activity.

In some embodiments, the IPD103 polynucleotide encodes an IPD103 polypeptide comprising an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or greater identity across the entire length of the amino acid sequence of SEQ ID NO: 2.

Compositions

Compositions comprising a molecular stack or breeding stack comprising an IPD103 polypeptide and at least one other pesticidal protein are also embraced.

Nucleotide Constructs, Expression Cassettes and Vectors

The use of the term "nucleotide constructs" or "DNA construct" as used herein is not intended to limit the embodiments to nucleotide constructs comprising DNA. Nucleotide constructs particularly polynucleotides and oligonucleotides composed of ribonucleotides and combinations of ribonucleotides and deoxyribonucleotides may also be employed in the methods disclosed herein. The nucleotide constructs, nucleic acids, and nucleotide sequences of the embodiments additionally encompass all complementary forms of such constructs, molecules, and sequences. Further, the nucleotide constructs, nucleotide molecules, and nucleotide sequences of the embodiments encompass all nucleotide constructs, molecules, and sequences which can be employed in the methods of the embodiments for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs, nucleic acids, and nucleotide sequences of the embodiments also encompass all forms of nucleotide constructs including, but not limited to, single-stranded forms, double-stranded forms, hairpins, stem-and-loop structures and the like.

A further embodiment relates to a transformed organism such as an organism selected from plant and insect cells, bacteria, yeast, baculovirus, protozoa, nematodes and algae. The transformed organism comprises a DNA molecule of the embodiments, an expression cassette comprising the DNA molecule or a vector comprising the expression cassette, which may be stably incorporated into the genome of the transformed organism.

The sequences of the embodiments are provided in DNA constructs for expression in the organism of interest. The construct will include 5' and 3' regulatory sequences operably linked to a sequence of the embodiments. The term "operably linked" as used herein refers to a functional linkage between a promoter and a second sequence, wherein the promoter sequence initiates and mediates transcription of the DNA sequence corresponding to the second sequence. Generally, operably linked means that the nucleic acid sequences being linked are contiguous and where necessary to join two protein coding regions in the same reading frame. The construct may additionally contain at least one additional gene to be cotransformed into the organism. Alternatively, the additional gene(s) can be provided on multiple DNA constructs.

Such a DNA construct is provided with a plurality of restriction sites for insertion of the IPD103 polypeptide gene sequence of the disclosure to be under the transcriptional regulation of the regulatory regions. The DNA construct may additionally contain selectable marker genes.

The DNA construct will generally include in the 5' to 3' direction of transcription: a transcriptional and translational initiation region (i.e., a promoter), a DNA sequence of the embodiments, and a transcriptional and translational termination region (i.e., termination region) functional in the organism serving as a host. The transcriptional initiation region (i.e., the promoter) may be native, analogous, foreign or heterologous to the host organism and/or to the sequence of the embodiments. Additionally, the promoter may be the natural sequence or alternatively a synthetic sequence. The term "foreign" as used herein indicates that the promoter is not found in the native organism into which the promoter is introduced. Where the promoter is "foreign" or "heterologous" to the sequence of the embodiments, it is intended that the promoter is not the native or naturally occurring promoter for the operably linked sequence of the embodiments. As used herein, a chimeric gene comprises a coding sequence operably linked to a transcription initiation region that is heterologous to the coding sequence. Where the promoter is a native or natural sequence, the expression of the operably linked sequence is altered from the wild-type expression, which results in an alteration in phenotype.

In some embodiments, DNA constructs are provided comprising: a polynucleotide encoding an IPD103 polypeptide having insecticidal activity; and one or more polynucleotide selected from: a polynucleotide encoding a PtIP-83 polypeptide having insecticidal activity; a polynucleotide encoding a Cry1B polypeptide having insecticidal activity; a polynucleotide encoding a variant Cry1B polypeptide having insecticidal activity; a polynucleotide encoding a Cry1C polypeptide having insecticidal activity; a polynucleotide encoding a Cry1D polypeptide having insecticidal activity; and a polynucleotide encoding a Cry1J polypeptide having insecticidal activity.

In some embodiments, DNA constructs are provided wherein the polynucleotide encoding the polypeptides are each operably linked to a heterologous regulatory element.

In some embodiments, the DNA construct comprises a polynucleotide disclosed in PCT WO 2018/005411, which is incorporated herein by reference, encoding an IPD103 polypeptide having insecticidal activity.

In some embodiments, the DNA construct comprises a polynucleotide encoding an IPD103 polypeptide having at least 95% identity to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36 or SEQ ID NO: 38.

In some embodiments, the DNA comprises a polynucleotide encoding an IPD103 polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36 or SEQ ID NO: 38.

In some embodiments, the DNA construct comprises a PtIP-83 polynucleotide disclosed in US Publication US 21060347799 encoding a PtIP-83 polypeptide having insecticidal activity.

In some embodiments, the DNA construct comprises a PtIP-83 polynucleotide encoding a PtIP-83 polypeptide having at least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59 or SEQ ID NO: 61.

In some embodiments, the DNA construct comprises a PtIP-83 polynucleotide encoding a PtIP-83 polypeptide comprising an amino acid sequence having at least 95% sequence identity to an amino acid sequence of SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59 or SEQ ID NO: 61.

In some embodiments, the DNA construct comprises a PtIP-83 polynucleotide encoding a PtIP-83 polypeptide comprising the amino acid sequence of SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59 or SEQ ID NO: 61.

In some embodiments, the DNA construct comprises a polynucleotides encode a Cry1B polypeptide selected from Cry1Ba1 (Accession CAA29898, Cry1Ba2 (Accession CAA65003), Cry1Ba3 (Accession AAK63251), Cry1Ba4 (Accession AAK51084, Cry1Ba5 (Accession ABO20894), Cry1Ba6 (Accession ABL60921), Cry1Ba7 (Accession HQ439781), Cry1Bb1 (AAA22344), Cry1Bb2 (Accession HQ439782), Cry1Bc1 (Accession CAA86568), Cry1Bd1 (Accession AAD10292), Cry1Bd2 (Accession AAM93496), Cry1Be1 (Accession AAC32850), Cry1Be2 (Accession AAQ52387), Cry1Be3 (Accession ACV96720), Cry1Be4 (Accession HM070026), Cry1Bf1 (Accession CAC50778), Cry1Bf2 (Accession AAQ52380), Cry1Bg1 (Accession AAO39720), Cry1Bh1 (Accession HQ589331), and Cry1Bi1 (Accession KC156700).

In some embodiments, the DNA construct comprises a polynucleotide encoding a Cry1B polypeptide selected from a Cry1B of U.S. Pat. Nos. 8,772,577, 9,404,121, US Publication US 20160194364, and U.S. Ser. No. 62/607,372, which are incorporated herein by reference.

In some embodiments, the DNA construct comprises a polynucleotide encoding a Cry1B polypeptide selected from the amino acid sequence of SEQ ID NO: 63, SEQ ID NO: 109, SEQ ID NO: 111, SEQ ID NO: 221, SEQ ID NO: 223, SEQ ID NO: 224, SEQ ID NO: 225, SEQ ID NO: 226, SEQ ID NO: 227, SEQ ID NO: 228, and SEQ ID NO: 229.

In some embodiments, the DNA construct comprises a polynucleotide encoding a variant Cry1B polypeptide of US Publication US 20170226164 and WO Publication WO2017/180715, which are incorporated herein by reference.

In some embodiments, the DNA construct comprises a polynucleotide encoding a variant Cry1B polypeptide comprising the amino acid sequence of SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 84, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210 or SEQ ID NO: 211.

In some embodiments, the DNA construct comprises a polynucleotide encoding a variant Cry1B polypeptide selected from SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 84, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, and SEQ ID NO: 211.

In some embodiments, the DNA construct comprises a polynucleotide encoding a Cry1C polypeptide selected from Cry1Ca1 (Accession CAA30396), Cry1Ca2 (Accession CAA31951), Cry1Ca3 (Accession AAA22343), Cry1Ca4 (Accession CAA01886), Cry1Ca5 (Accession CAA65457), Cry1Ca6 (Accession AAF37224), Cry1Ca7 (Accession AAG50438), Cry1Ca8 (Accession AAM00264), Cry1Ca9 (Accession AAL79362), Cry1Ca10 (Accession AAN16462), Cry1Ca11 (Accession AAX53094), Cry1Ca12 (Accession HM070027), Cry1Ca13 (Accession HQ412621), Cry1Ca14 (Accession JN651493), Cry1Cb1 (Accession M97880), Cry1Cb2 (Accession AAG35409), Cry1Cb3 (Accession ACD50894), Cry1Cb-like (Accession AAX63901), Cry1Da1 (Accession CAA38099), Cry1Da2 (Accession I76415), and Cry1Da3 (Accession HQ43978).

In some embodiments, the Cry1C polypeptide comprises an amino acid sequence having at least 95% sequence identity to Cry1Ca polypeptide.

In some embodiments, the Cry1C polypeptide comprises the amino acid sequence of a Cry1Ca polypeptide.

In some embodiments, the DNA construct comprises a polynucleotide encoding a Cry1D polypeptide selected from Cry1Da1 (Accession CAA38099), Cry1Da2 (Accession I76415), Cry1Da3 (Accession HQ439784), Cry1db1 (Accession CAA80234), Cry1db2 (Accession AAK48937), and Cry1Dc1 (Accession ABK35074).

In some embodiments, the Cry1D polypeptide comprises an amino acid sequence having at least 95% sequence identity to Cry1Da polypeptide.

In some embodiments, the Cry1D polypeptide comprises the amino acid sequence of a Cry1Da polypeptide.

In some embodiments, the DNA construct comprises a polynucleotide encoding a Cry1J polypeptide selected from Cry1Ja1 (Accession AAA22341), Cry1Ja2 (Accession HM070030), Cry1Ja3 (Accession JQ228425), Cry1Jb1 (Accession AAA98959), Cry1Jc1 (Accession AAC31092), Cry1Jc2 (Accession AAQ52372), and Cry1Jd1 (Accession CAC50779).

In some embodiments, the DNA construct comprises a polynucleotide encoding a variant Cry1J polypeptide of US Publication Number US20170240603.

In some embodiments, the DNA construct comprises a polynucleotide encoding a Cry1J variant polypeptide comprising an amino acid sequence having at least 95% identity to SEQ ID NO: 213, SEQ ID NO: 215, SEQ ID NO: 217 or SEQ ID NO: 219.

In some embodiments, the DNA construct comprises a polynucleotide encoding a Cry1J variant polypeptide comprising the amino acid sequence of SEQ ID NO: 213, SEQ ID NO: 215, SEQ ID NO: 217 or SEQ ID NO: 219.

In some embodiments, the DNA construct comprises a polynucleotide encoding a variant Cry1J polypeptide selected from SEQ ID NO: 213, SEQ ID NO: 215, SEQ ID NO: 217 or SEQ ID NO: 219.

In some embodiments, the DNA construct may also include a transcriptional enhancer sequence. As used herein, the term an "enhancer" refers to a DNA sequence which can stimulate promoter activity, and may be an innate element of the promoter or a heterologous element inserted to enhance the level or tissue-specificity of a promoter. Various enhancers, including for example, introns with gene expression enhancing properties in plants (US Patent Application Publication Number 2009/0144863, the ubiquitin intron (i.e., the maize ubiquitin intron 1 (see, for example, NCBI sequence S94464)), the omega enhancer or the omega prime enhancer (Gallie, et al., (1989) *Molecular Biology of RNA* ed. Cech (Liss, New York) 237-256 and Gallie, et al., (1987) *Gene* 60:217-25), the CaMV 35S enhancer (see, e.g., Benfey, et al., (1990) *EMBO J.* 9:1685-96) and the enhancers of U.S. Pat. No. 7,803,992 may also be used, each of which is incorporated by reference. The above list of transcriptional enhancers is not meant to be limiting. Any appropriate transcriptional enhancer can be used in the embodiments.

The termination region may be native with the transcriptional initiation region, may be native with the operably linked DNA sequence of interest, may be native with the plant host or may be derived from another source (i.e., foreign or heterologous to the promoter, the sequence of interest, the plant host or any combination thereof).

Convenient termination regions are available from the Ti-plasmid of *A. tumefaciens*, such as the octopine synthase and nopaline synthase termination regions. See also, Guerineau, et al., (1991) *Mol. Gen. Genet.* 262:141-144; Proudfoot, (1991) *Cell* 64:671-674; Sanfacon, et al., (1991) *Genes Dev.* 5: 1 41-1 49; Mogen, et al., (1990) *Plant Cell* 2:1261-1272; Munroe, et al., (1990) *Gene* 91:151-158; Ballas, et al., (1989) *Nucleic Acids Res.* 17:7891-7903 and Joshi, et al., (1987) *Nucleic Acid Res.* 15:9627-9639.

Where appropriate, a nucleic acid may be optimized for increased expression in the host organism. Thus, where the host organism is a plant, the synthetic nucleic acids can be synthesized using plant-preferred codons for improved expression. See, for example, Campbell and Gowri, (1990) *Plant Physiol.* 92:1-11 for a discussion of host-preferred usage. For example, although nucleic acid sequences of the embodiments may be expressed in both monocotyledonous and dicotyledonous plant species, sequences can be modified to account for the specific preferences and GC content preferences of monocotyledons or dicotyledons as these preferences have been shown to differ (Murray et al. (1989) *Nucleic Acids Res.* 17:477-498). Thus, the maize-preferred for a particular amino acid may be derived from known gene sequences from maize. Maize usage for 28 genes from maize plants is listed in Table 4 of Murray, et al., supra. Methods are available for synthesizing plant-preferred genes, for example, Murray, et al., (1989) *Nucleic Acids Res.* 17:477-498, and Liu H et al. *Mol Bio Rep* 37:677-684, 2010, herein incorporated by reference. A *Zea* maize usage table can be also found at kazusa.or.jp//cgi-bin/show.cgi?species=4577, which can be accessed using the www prefix.

A *Glycine max* usage table can be found at kazusa.or.jp//cgi-bin/show.cgi?species=3847&aa=1&style=N, which can be accessed using the www prefix.

In some embodiments, the recombinant nucleic acid molecule encoding a polypeptide of the disclosure has maize optimized codons.

Additional sequence modifications are known to enhance gene expression in a cellular host. These include elimination of sequences encoding spurious polyadenylation signals, exon-intron splice site signals, transposon-like repeats, and other well-characterized sequences that may be deleterious to gene expression. The GC content of the sequence may be adjusted to levels average for a given cellular host, as calculated by reference to known genes expressed in the host cell. The term "host cell" as used herein refers to a cell which contains a vector and supports the replication and/or expression of the expression vector is intended. Host cells may be prokaryotic cells such as *E. coli* or eukaryotic cells such as yeast, insect, amphibian or mammalian cells or monocotyledonous or dicotyledonous plant cells. An example of a monocotyledonous host cell is a maize host cell. When possible, the sequence is modified to avoid predicted hairpin secondary mRNA structures.

The expression cassettes may additionally contain 5' leader sequences. Such leader sequences can act to enhance translation. Translation leaders include: picornavirus leaders, for example, EMCV leader (Encephalomyocarditis 5' noncoding region) (Elroy-Stein, et al., (1989) *Proc. Natl. Acad. Sci. USA* 86:6126-6130); potyvirus leaders, for example, TEV leader (Tobacco Etch Virus) (Gallie, et al., (1995) *Gene* 165(2):233-238), MDMV leader (Maize Dwarf Mosaic Virus), human immunoglobulin heavy-chain binding protein (BiP) (Macejak, et al., (1991) *Nature* 353:90-94); untranslated leader from the coat protein mRNA of alfalfa mosaic virus (AMV RNA 4) (Jobling, et al., (1987) *Nature* 325:622-625); tobacco mosaic virus leader (TMV) (Gallie, et al., (1989) in *Molecular Biology of RNA*, ed. Cech (Liss, New York), pp. 237-256) and maize chlorotic mottle virus leader (MCMV) (Lommel, et al., (1991) *Virology* 81:382-385). See also, Della-Cioppa, et al., (1987) *Plant Physiol.* 84:965-968. Such constructs may also contain a "signal sequence" or "leader sequence" to facilitate co-translational or post-translational transport of the peptide to certain intracellular structures such as the chloroplast (or other plastid), endoplasmic reticulum or Golgi apparatus.

"Signal sequence" as used herein refers to a sequence that results in cotranslational or post-translational peptide transport across the cell membrane. In eukaryotes, this typically involves secretion into the Golgi apparatus, with some resulting glycosylation. Insecticidal toxins of bacteria are often synthesized as protoxins, which are proteolytically activated in the gut of the target pest (Chang, (1987) *Methods Enzymol.* 153:507-516). In some embodiments, the signal sequence is located in the native sequence or may be derived from a sequence of the embodiments. "Leader sequence" as used herein refers to any sequence that when translated, results in an amino acid sequence sufficient to trigger co-translational transport of the peptide chain to a subcellular organelle. Thus, this includes leader sequences targeting transport and/or glycosylation by passage into the endoplasmic reticulum, passage to vacuoles, plastids including chloroplasts, mitochondria, and the like. Nuclear-encoded proteins targeted to the chloroplast thylakoid lumen compartment have a characteristic bipartite transit peptide, composed of a stromal targeting signal peptide and a lumen targeting signal peptide. The stromal targeting information is in the amino-proximal portion of the transit peptide. The lumen targeting signal peptide is in the carboxyl-proximal portion of the transit peptide, and contains all the information for targeting to the lumen. Recent research in proteomics of the higher plant chloroplast has achieved in the identification of numerous nuclear-encoded lumen proteins (Kieselbach et al. *FEBS LETT* 480:271-276, 2000; Peltier et al. Plant Cell 12:319-341, 2000; Bricker et al. *Biochim. Biophys Acta* 1503:350-356, 2001), the lumen targeting signal peptide of which can potentially be used in accordance with the present disclosure. About 80 proteins from *Arabidopsis*, as well as homologous proteins from spinach and garden pea, are reported by Kieselbach et al., *Photosynthesis Research,* 78:249-264, 2003. In particular, Table 2 of this publication, which is incorporated into the description herewith by reference, discloses 85 proteins from the chloroplast lumen, identified by their accession number (see also US Patent Application Publication 2009/09044298). In addition, the recently published draft version of the rice genome (Goff et al, *Science* 296:92-100, 2002) is a suitable source for lumen targeting signal peptide which may be used in accordance with the present disclosure.

Suitable chloroplast transit peptides (CTP) include chimeric CT's comprising but not limited to, an N-terminal domain, a central domain or a C-terminal domain from a CTP from *Oryza sativa* 1-decoy-D xylose-5-Phosphate Synthase *Oryza sativa*-Superoxide dismutase *Oryza sativa*-soluble starch synthase *Oryza sativa*-NADP-dependent Malic acid enzyme *Oryza sativa*-Phospho-2-dehydro-3-deoxyheptonate Aldolase 2 *Oryza sativa*-L-Ascorbate peroxidase 5 *Oryza sativa*-Phosphoglucan water dikinase, *Zea Mays* ssRUBISCO, *Zea Mays*-beta-glucosidase, *Zea Mays*-Malate dehydrogenase, *Zea Mays* Thioredoxin M-type US Patent Application Publication 2012/0304336).

The genes encoding polypeptides of the disclosure to be targeted to the chloroplast may be optimized for expression in the chloroplast to account for differences in usage between the plant nucleus and this organelle. In this manner, the nucleic acids of interest may be synthesized using chloroplast-preferred sequences.

In preparing the expression cassette, the various DNA fragments may be manipulated so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites or the like. For this purpose, in vitro mutagenesis, primer repair, restriction, annealing, resubstitutions, e.g., transitions and transversions, may be involved.

Many promoters can be used in the practice of the embodiments. The promoters can be selected based on the desired outcome. The nucleic acids can be combined with constitutive, tissue-preferred, inducible or other promoters for expression in the host organism. Suitable constitutive promoters for use in a plant host cell include, for example, the core promoter of the Rsyn7 promoter and other constitutive promoters disclosed in WO 1999/43838 and U.S. Pat. No. 6,072,050; the core CaMV 35S promoter (Odell, et al., (1985) *Nature* 313:810-812); rice actin (McElroy, et al., (1990) *Plant Cell* 2:163-171); ubiquitin (Christensen, et al., (1989) *Plant Mol. Biol.* 12:619-632 and Christensen, et al., (1992) *Plant Mol. Biol.* 18:675-689); pEMU (Last, et al., (1991) *Theor. Appl. Genet.* 81:581-588); MAS (Velten, et al., (1984) *EMBO J.* 3:2723-2730); ALS promoter (U.S. Pat. No. 5,659,026) and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142 and 6,177,611.

Depending on the desired outcome, it may be beneficial to express the gene from an inducible promoter. Of particular interest for regulating the expression of the nucleotide sequences of the embodiments in plants are wound-inducible promoters. Such wound-inducible promoters, may respond to damage caused by insect feeding, and include potato proteinase inhibitor (pin II) gene (Ryan, (1990) *Ann. Rev. Phytopath.* 28:425-449; Duan, et al., (1996) *Nature Biotechnology* 14:494-498); wun1 and wun2, U.S. Pat. No. 5,428,148; win1 and win2 (Stanford, et al., (1989) *Mol. Gen. Genet.* 215:200-208); systemin (McGurl, et al., (1992) *Science* 225:1570-1573); WIP1 (Rohmeier, et al., (1993) *Plant Mol. Biol.* 22:783-792; Eckelkamp, et al., (1993) *FEBS Letters* 323:73-76); MPI gene (Corderok, et al., (1994) *Plant J.* 6(2):141-150) and the like, herein incorporated by reference.

Additionally, pathogen-inducible promoters may be employed in the methods and nucleotide constructs of the embodiments. Such pathogen-inducible promoters include those from pathogenesis-related proteins (PR proteins), which are induced following infection by a pathogen; e.g., PR proteins, SAR proteins, beta-1,3-glucanase, chitinase, etc. See, for example, Redolfi, et al., (1983) *Neth. J. Plant Pathol.* 89:245-254; Uknes, et al., (1992) *Plant Cell* 4: 645-656 and Van Loon, (1985) *Plant Mol. Virol.* 4:111-116. See also, WO 1999/43819, herein incorporated by reference.

Of interest are promoters that are expressed locally at or near the site of pathogen infection. See, for example, Marineau, et al., (1987) *Plant Mol. Biol.* 9:335-342; Matton, et al., (1989) *Molecular Plant-Microbe Interactions* 2:325-331; Somsisch, et al., (1986) *Proc. Natl. Acad. Sci. USA* 83:2427-2430; Somsisch, et al., (1988) *Mol. Gen. Genet.* 2:93-98 and Yang, (1996) *Proc. Natl. Acad. Sci. USA* 93:14972-14977. See also, Chen, et al., (1996) *Plant J.* 10:955-966; Zhang, et al., (1994) *Proc. Natl. Acad. Sci. USA* 91:2507-2511; Warner, et al., (1993) *Plant J.* 3:191-201; Siebertz, et al., (1989) *Plant Cell* 1:961-968; U.S. Pat. No. 5,750,386 (nematode-inducible) and the references cited therein. Of particular interest is the inducible promoter for the maize PRms gene, whose expression is induced by the pathogen *Fusarium moniliforme* (see, for example, Cordero, et al., (1992) *Physiol. Mol. Plant Path.* 41:189-200).

Chemical-regulated promoters can be used to modulate the expression of a gene in a plant through the application of an exogenous chemical regulator. Depending upon the objective, the promoter may be a chemical-inducible promoter, where application of the chemical induces gene expression or a chemical-repressible promoter, where application of the chemical represses gene expression. Chemical-inducible promoters include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (see, for example, the glucocorticoid-inducible promoter in Schena, et al., (1991) *Proc. Natl. Acad. Sci. USA* 88:10421-10425 and McNellis, et al., (1998) *Plant J.* 14(2):247-257) and tetracycline-inducible and tetracycline-repressible promoters (see, for example, Gatz, et al., (1991) *Mol. Gen. Genet.* 227:229-237 and U.S. Pat. Nos. 5,814,618 and 5,789,156), herein incorporated by reference.

Tissue-preferred promoters can be utilized to target enhanced polypeptide expression within a particular plant tissue. Tissue-preferred promoters include those discussed in Yamamoto, et al., (1997) *Plant J.* 12(2)255-265; Kawamata, et al., (1997) *Plant Cell Physiol.* 38(7):792-803; Hansen, et al., (1997) *Mol. Gen Genet.* 254(3):337-343; Russell, et al., (1997) *Transgenic Res.* 6(2):157-168; Rinehart, et al., (1996) *Plant Physiol.* 112(3):1331-1341; Van Camp, et al., (1996) *Plant Physiol.* 112(2):525-535; Canevascini, et al., (1996) *Plant Physiol.* 112(2):513-524; Yamamoto, et al., (1994) *Plant Cell Physiol.* 35(5):773-778; Lam, (1994) *Results Probl. Cell Differ.* 20:181-196; Orozco, et al., (1993) *Plant Mol Biol.* 23(6):1129-1138; Matsuoka, et al., (1993) *Proc Natl. Acad. Sci. USA* 90(20):9586-9590 and Guevara-Garcia, et al., (1993) *Plant J.* 4(3):495-505. Such promoters can be modified, if necessary, for weak expression.

Leaf-preferred promoters include, for example, Yamamoto, et al., (1997) *Plant J.* 12(2):255-265; Kwon, et al., (1994) *Plant Physiol.* 105:357-67; Yamamoto, et al., (1994) *Plant Cell Physiol.* 35(5):773-778; Gotor, et al., (1993) *Plant J.* 3:509-18; Orozco, et al., (1993) *Plant Mol. Biol.* 23(6):1129-1138 and Matsuoka, et al., (1993) *Proc. Natl. Acad. Sci. USA* 90(20):9586-9590.

Root-preferred or root-specific promoters are known and can be selected from the many available from the literature or isolated de novo from various compatible species. See, for example, Hire, et al., (1992) *Plant Mol. Biol.* 20(2):207-218 (soybean root-specific glutamine synthetase gene); Keller and Baumgartner, (1991) *Plant Cell* 3(10):1051-1061 (root-specific control element in the GRP 1.8 gene of French bean); Sanger, et al., (1990) *Plant Mol. Biol.* 14(3):433-443 (root-specific promoter of the mannopine synthase (MAS) gene of *Agrobacterium tumefaciens*) and Miao, et al., (1991) *Plant Cell* 3(1):11-22 (full-length cDNA clone encoding cytosolic glutamine synthetase (GS), which is expressed in roots and root nodules of soybean). See also, Bogusz, et al., (1990) *Plant Cell* 2(7):633-641, where two root-specific promoters isolated from hemoglobin genes from the nitrogen-fixing nonlegume *Parasponia andersonii* and the related non-nitrogen-fixing nonlegume *Trema tomentosa* are described. The promoters of these genes were linked to a β-glucuronidase reporter gene and introduced into both the nonlegume *Nicotiana tabacum* and the legume *Lotus corniculatus*, and in both instances root-specific promoter activity was preserved. Leach and Aoyagi, (1991) describe their analysis of the promoters of the highly expressed roIC and roID root-inducing genes of *Agrobacterium rhizogenes* (see, *Plant Science* (Limerick) 79(1):69-76). They concluded that enhancer and tissue-preferred DNA determinants are dissociated in those promoters. Teeri, et al., (1989) used gene fusion to IacZ to show that the *Agrobacterium* T-DNA gene encoding octopine synthase is especially active in the epidermis of the root tip and that the TR2' gene is root specific in the intact plant and stimulated by wounding in leaf tissue, an especially desirable combination of characteristics for use with an insecticidal or larvicidal gene (see, *EMBO J.* 8(2):343-350). The TR1' gene fused to nptII (neomycin phosphotransferase II) showed similar characteristics. Additional root-preferred promoters include the VfENOD-GRP3 gene promoter (Kuster, et al., (1995) *Plant Mol. Biol.* 29(4):759-772) and roIB promoter (Capana, et al., (1994) *Plant Mol. Biol.* 25(4):681-691. See also, U.S. Pat. Nos. 5,837,876; 5,750,386; 5,633,363; 5,459,252; 5,401,836; 5,110,732 and 5,023,179. *Arabidopsis thaliana* root-preferred regulatory sequences are disclosed in US20130117883.

"Seed-preferred" promoters include both "seed-specific" promoters (those promoters active during seed development such as promoters of seed storage proteins) as well as "seed-germinating" promoters (those promoters active during seed germination). See, Thompson, et al., (1989) *BioEssays* 10:108, herein incorporated by reference. Such seed-preferred promoters include, but are not limited to, Cim1 (cytokinin-induced message); cZ19B1 (maize 19 kDa zein); and milps (myo-inositol-1-phosphate synthase) (see, U.S. Pat. No. 6,225,529, herein incorporated by reference). Gamma-zein and Glb-1 are endosperm-specific promoters. For dicots, seed-specific promoters include, but are not limited to, Kunitz trypsin inhibitor 3 (KTi3) (Jofuku and Goldberg, (1989) *Plant Cell* 1:1079-1093), bean β-phaseolin, napin, β-conglycinin, glycinin 1, soybean lectin, cruciferin, and the like. For monocots, seed-specific promoters include, but are not limited to, maize 15 kDa zein, 22 kDa zein, 27 kDa zein, g-zein, waxy, shrunken 1, shrunken 2, globulin 1, etc. See also, WO 2000/12733, where seed-preferred promoters from end1 and end2 genes are disclosed; herein incorporated by reference. In dicots, seed specific promoters include but are not limited to seed coat promoter from *Arabidopsis*, pBAN; and the early seed promoters from *Arabidopsis*, p26, p63, and p63tr (U.S. Pat. Nos. 7,294,760 and 7,847,153). A promoter that has "preferred" expression in a particular tissue is expressed in that tissue to a greater degree than in at least one other plant tissue. Some tissue-preferred promoters show expression almost exclusively in the particular tissue.

Where low level expression is desired, weak promoters will be used. Generally, the term "weak promoter" as used herein refers to a promoter that drives expression of a coding sequence at a low level. By low level expression at levels of between about 1/1000 transcripts to about 1/100,000 transcripts to about 1/500,000 transcripts is intended. Alternatively, it is recognized that the term "weak promoters" also encompasses promoters that drive expression in only a few cells and not in others to give a total low level of expression. Where a promoter drives expression at unacceptably high levels, portions of the promoter sequence can be deleted or modified to decrease expression levels.

Such weak constitutive promoters include, for example the core promoter of the Rsyn7 promoter (WO 1999/43838 and U.S. Pat. No. 6,072,050), the core 35S CaMV promoter, and the like. Other constitutive promoters include, for example, those disclosed in U.S. Pat. Nos. 5,608,149; 5,608,144; 5,604,121; 5,569,597; 5,466,785; 5,399,680; 5,268,463; 5,608,142 and 6,177,611, herein incorporated by reference.

The above list of promoters is not meant to be limiting. Any appropriate promoter can be used in the embodiments.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones and 2,4-dichlorophenoxyacetate (2,4-D). Additional examples of suitable selectable marker genes include, but are not limited to, genes encoding resistance to chloramphenicol (Herrera Estrella, et al., (1983) *EMBO J.* 2:987-992); methotrexate (Herrera Estrella, et al., (1983) *Nature* 303:209-213 and Meijer, et al., (1991) *Plant Mol. Biol.* 16:807-820); streptomycin (Jones, et al., (1987) *Mol. Gen. Genet.* 210:86-91); spectinomycin (Bretagne-Sagnard, et al., (1996) *Transgenic Res.* 5:131-137); bleomycin (Hille, et al., (1990) *Plant Mol. Biol.* 7:171-176); sulfonamide (Guerineau, et al., (1990) *Plant Mol. Biol.* 15:127-136); bromoxynil (Stalker, et al., (1988)

*Science* 242:419-423); glyphosate (Shaw, et al., (1986) *Science* 233:478-481 and U.S. patent application Ser. Nos. 10/004,357 and 10/427,692); phosphinothricin (DeBlock, et al., (1987) *EMBO J.* 6:2513-2518). See generally, Yarranton, (1992) *Curr. Opin. Biotech.* 3:506-511; Christopherson, et al., (1992) *Proc. Natl. Acad. Sci. USA* 89:6314-6318; Yao, et al., (1992) *Cell* 71:63-72; Reznikoff, (1992) *Mol. Microbiol.* 6:2419-2422; Barkley, et al., (1980) in *The Operon*, pp. 177-220; Hu, et al., (1987) *Cell* 48:555-566; Brown, et al., (1987) *Cell* 49:603-612; Figge, et al., (1988) *Cell* 52:713-722; Deuschle, et al., (1989) *Proc. Natl. Acad. Sci. USA* 86:5400-5404; Fuerst, et al., (1989) *Proc. Natl. Acad. Sci. USA* 86:2549-2553; Deuschle, et al., (1990) *Science* 248:480-483; Gossen, (1993) Ph.D. Thesis, University of Heidelberg; Reines, et al., (1993) *Proc. Natl. Acad. Sci. USA* 90:1917-1921; Labow, et al., (1990) *Mol. Cell. Biol.* 10:3343-3356; Zambretti, et al., (1992) *Proc. Natl. Acad. Sci. USA* 89:3952-3956; Baim, et al., (1991) *Proc. Natl. Acad. Sci. USA* 88:5072-5076; Wyborski, et al., (1991) *Nucleic Acids Res.* 19:4647-4653; Hillenand-Wissman, (1989) *Topics Mol. Struc. Biol.* 10:143-162; Degenkolb, et al., (1991) *Antimicrob. Agents Chemother.* 35:1591-1595; Kleinschnidt, et al., (1988) *Biochemistry* 27:1094-1104; Bonin, (1993) Ph.D. Thesis, University of Heidelberg; Gossen, et al., (1992) *Proc. Natl. Acad. Sci. USA* 89:5547-5551; Oliva, et al., (1992) *Antimicrob. Agents Chemother.* 36:913-919; Hlavka, et al., (1985) *Handbook of Experimental Pharmacology*, Vol. 78 (Springer-Verlag, Berlin) and Gill, et al., (1988) *Nature* 334:721-724. Such disclosures are herein incorporated by reference.

The above list of selectable marker genes is not meant to be limiting. Any selectable marker gene can be used in the embodiments.

Plant Transformation

The methods of the embodiments involve introducing a polypeptide or polynucleotide into a plant. "Introducing" is as used herein means presenting to the plant the polynucleotide or polypeptide in such a manner that the sequence gains access to the interior of a cell of the plant. The methods of the embodiments do not depend on a particular method for introducing a polynucleotide or polypeptide into a plant, only that the polynucleotide or polypeptides gains access to the interior of at least one cell of the plant. Methods for introducing polynucleotide or polypeptides into plants include, but not limited to, stable transformation methods, transient transformation methods, and virus-mediated methods.

"Stable transformation" is as used herein means that the nucleotide construct introduced into a plant integrates into the genome of the plant and is capable of being inherited by the progeny thereof. "Transient transformation" as used herein means that a polynucleotide is introduced into the plant and does not integrate into the genome of the plant or a polypeptide is introduced into a plant. "Plant" as used herein refers to whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells and pollen).

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway, et al., (1986) *Biotechniques* 4:320-334), electroporation (Riggs, et al., (1986) *Proc. Natl. Acad. Sci. USA* 83:5602-5606), *Agrobacterium*-mediated transformation (U.S. Pat. Nos. 5,563,055 and 5,981,840), direct gene transfer (Paszkowski, et al., (1984) *EMBO J.* 3:2717-2722) and ballistic particle acceleration (see, for example, U.S. Pat. Nos. 4,945,050; 5,879,918; 5,886,244 and 5,932,782; Tomes, et al., (1995) in *Plant Cell, Tissue, and Organ Culture: Fundamental Methods*, ed. Gamborg and Phillips, (Springer-Verlag, Berlin) and McCabe, et al., (1988) *Biotechnology* 6:923-926) and Lecl transformation (WO 00/28058). For potato transformation see, Tu, et al., (1998) *Plant Molecular Biology* 37:829-838 and Chong, et al., (2000) *Transgenic Research* 9:71-78. Additional transformation procedures can be found in Weissinger, et al., (1988) *Ann. Rev. Genet.* 22:421-477; Sanford, et al., (1987) *Particulate Science and Technology* 5:27-37 (onion); Christou, et al., (1988) *Plant Physiol.* 87:671-674 (soybean); McCabe, et al., (1988) *Bio/Technology* 6:923-926 (soybean); Finer and McMullen, (1991) *In Vitro Cell Dev. Biol.* 27P:175-182 (soybean); Singh, et al., (1998) *Theor. Appl. Genet.* 96:319-324 (soybean); Datta, et al., (1990) *Biotechnology* 8:736-740 (rice); Klein, et al., (1988) *Proc. Natl. Acad. Sci. USA* 85:4305-4309 (maize); Klein, et al., (1988) *Biotechnology* 6:559-563 (maize); U.S. Pat. Nos. 5,240,855; 5,322,783 and 5,324,646; Klein, et al., (1988) *Plant Physiol.* 91:440-444 (maize); Fromm, et al., (1990) *Biotechnology* 8:833-839 (maize); Hooykaas-Van Slogteren, et al., (1984) *Nature* (London) 311:763-764; U.S. Pat. No. 5,736,369 (cereals); Bytebier, et al., (1987) *Proc. Natl. Acad. Sci. USA* 84:5345-5349 (Liliaceae); De Wet, et al., (1985) in *The Experimental Manipulation of Ovule Tissues*, ed. Chapman, et al., (Longman, New York), pp. 197-209 (pollen); Kaeppler, et al., (1990) *Plant Cell Reports* 9:415-418 and Kaeppler, et al., (1992) *Theor. Appl. Genet.* 84:560-566 (whisker-mediated transformation); D'Halluin, et al., (1992) *Plant Cell* 4:1495-1505 (electroporation); Li, et al., (1993) *Plant Cell Reports* 12:250-255 and Christou and Ford, (1995) *Annals of Botany* 75:407-413 (rice); Osjoda, et al., (1996) *Nature Biotechnology* 14:745-750 (maize via *Agrobacterium tumefaciens*); all of which are herein incorporated by reference.

In specific embodiments, the sequences of the embodiments can be provided to a plant using a variety of transient transformation methods. Such transient transformation methods include, but are not limited to, the introduction of the polynucleotide or variants and fragments thereof directly into the plant or the introduction of the polypeptide transcript into the plant. Such methods include, for example, microinjection or particle bombardment. See, for example, Crossway, et al., (1986) *Mol Gen. Genet.* 202:179-185; Nomura, et al., (1986) *Plant Sci.* 44:53-58; Hepler, et al., (1994) *Proc. Natl. Acad. Sci.* 91:2176-2180 and Hush, et al., (1994) *The Journal of Cell Science* 107:775-784, all of which are herein incorporated by reference. Alternatively, the polynucleotide can be transiently transformed into the plant using techniques including viral vector system and the precipitation of the polynucleotide in a manner that precludes subsequent release of the DNA. Thus, transcription from the particle-bound DNA can occur, but the frequency with which it is released to become integrated into the genome is greatly reduced. Such methods include the use of particles coated with polyethylimine (PEI; Sigma #P3143).

Methods are known in the art for the targeted insertion of a polynucleotide at a specific location in the plant genome. In one embodiment, the insertion of the polynucleotide at a desired genomic location is achieved using a site-specific recombination system. See, for example, WO 1999/25821, WO 1999/25854, WO 1999/25840, WO 1999/25855 and WO 1999/25853, all of which are herein incorporated by reference. Briefly, the polynucleotide of the embodiments can be contained in transfer cassette flanked by two non-identical recombination sites. The transfer cassette is introduced into a plant have stably incorporated into its genome a target site which is flanked by two non-identical recombination sites that correspond to the sites of the transfer cassette. An appropriate recombinase is provided and the transfer cassette is integrated at the target site. The polynucleotide of interest is thereby integrated at a specific chromosomal position in the plant genome.

Plant transformation vectors may be comprised of one or more DNA vectors comprised of more than one contiguous DNA segment needed for achieving plant transformation. These vectors are often referred to as "binary vectors". Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the pesticidal gene are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer (Hellens and Mullineaux, (2000) *Trends in Plant Science* 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

In general, plant transformation methods involve transferring heterologous DNA into target plant cells (e.g., immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Following integration of heterologous foreign DNA into plant cells, one then applies a maximum threshold level of appropriate selection in the medium to kill the untransformed cells and separate and proliferate the putatively transformed cells that survive from this selection treatment by transferring regularly to a fresh medium. By continuous passage and challenge with appropriate selection, one can identify and proliferate the cells that are transformed with the plasmid vector. Molecular and biochemical methods can then be used to confirm the presence of the integrated heterologous gene of interest into the genome of the transgenic plant.

Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grows into a mature plant and produces fertile seeds (e.g., Hiei, et al., (1994) *The Plant Journal* 6:271-282; Ishida, et al., (1996) *Nature Biotechnology* 14:745-750). Explants are typically transferred to a fresh supply of the same medium and cultured routinely. A general description of the techniques and methods for generating transgenic plants are found in Ayres and Park, (1994) *Critical Reviews in Plant Science* 13:219-239 and Bommineni and Jauhar, (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

The cells that have been transformed may be grown into plants in accordance with conventional ways. See, for example, McCormick, et al., (1986) *Plant Cell Reports* 5:81-84. These plants may then be grown, and either pollinated with the same transformed strain or different strains, and the resulting hybrid having constitutive or inducible expression of the desired phenotypic characteristic identified. Two or more generations may be grown to ensure that expression of the desired phenotypic characteristic is stably maintained and inherited and then seeds harvested to ensure that expression of the desired phenotypic characteristic has been achieved.

The nucleotide sequences of the embodiments may be provided to the plant by contacting the plant with a virus or viral nucleic acids. Generally, such methods involve incorporating the nucleotide construct of interest within a viral DNA or RNA molecule. It is recognized that the recombinant proteins of the embodiments may be initially synthesized as part of a viral polyprotein, which later may be processed by proteolysis in vivo or in vitro to produce the desired polypeptide. It is also recognized that such a viral polyprotein, comprising at least a portion of the amino acid sequence of a polypeptide of the embodiments, may have the desired pesticidal activity. Such viral polyproteins and the nucleotide sequences that encode for them are encompassed by the embodiments. Methods for providing plants with nucleotide constructs and producing the encoded proteins in the plants, which involve viral DNA or RNA molecules, in, for example, U.S. Pat. Nos. 5,889,191; 5,889,190; 5,866,785; 5,589,367 and 5,316,931; herein incorporated by reference.

Methods for transformation of chloroplasts include, for example, Svab, et al., (1990) *Proc. Natl. Acad. Sci. USA* 87:8526-8530; Svab and Maliga, (1993) *Proc. Natl. Acad. Sci. USA* 90:913-917; Svab and Maliga, (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride, et al., (1994) *Proc. Natl. Acad. Sci. USA* 91:7301-7305.

The embodiments further relate to plant-propagating material of a transformed plant of the embodiments including, but not limited to, seeds, tubers, corms, bulbs, leaves and cuttings of roots and shoots.

The embodiments may be used for transformation of any plant species, including, but not limited to, monocots and dicots. Examples of plants of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (Carthamus tinctorius), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (Citrus spp.), cocoa (*Theobroma cacao*), tea (*Camellia sinensis*), banana (Musa spp.), avocado (*Persea americana*), fig (*Ficus casica*), guava (*Psidium guajava*), mango (*Mangifera indica*), olive (*Olea europaea*), *papaya* (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), *hydrangea* (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and *chrysanthemum*. Conifers that may be employed in practicing the embodiments include, for example, pines such as loblolly pine (*Pinus taeda*), slash pine (*Pinus elliotii*), *ponderosa* pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Plants of the embodiments include crop plants (for example, corn, alfalfa, sunflower, *Brassica*, soybean, cotton, safflower, peanut, sorghum, wheat, millet, tobacco, etc.), such as corn and soybean plants.

Turf grasses include, but are not limited to: annual bluegrass (*Poa annus*); annual ryegrass (*Lolium multiflorum*); Canada bluegrass (*Poa compressa*); Chewing's fescue (*Festuca rubra*); colonial bentgrass (*Agrostis tenuis*); creeping bentgrass (*Agrostis palustris*); crested wheatgrass (*Agropyron desertorum*); fairway wheatgrass (*Agropyron cristatum*); hard fescue (*Festuca longifolia*); Kentucky bluegrass (*Poa pratensis*); orchardgrass (*Dactylis glomerata*); perennial ryegrass (*Lolium perenne*); red fescue (*Festuca rubra*); redtop (*Agrostis alba*); rough bluegrass (*Poa trivialis*); sheep fescue (*Festuca ovina*); smooth bromegrass (*Bromus inermis*); tall fescue (*Festuca arundinacea*); timothy (*Phleum pratense*); velvet bentgrass (*Agrostis canina*); weeping alkaligrass (*Puccinellia distans*); western wheatgrass (*Agropyron smithi*;); Bermuda grass (*Cynodon* spp.); St. Augustine grass (*Stenotaphrum secundatum*); *zoysia* grass (*Zoysia* spp.); Bahia grass (*Paspalum notatum*); carpet grass (*Axonopus affinis*); centipede grass (*Eremochloa ophiuroides*); kikuyu grass (*Pennisetum clandesinum*); seashore *paspalum* (*Paspalum vaginatum*); blue gramma (*Bouteloua gracilis*); buffalo grass (*Buchloe dactyloids*); sideoats gramma (*Bouteloua curtipendula*).

Plants of interest include grain plants that provide seeds of interest, oil-seed plants, and leguminous plants. Seeds of interest include grain seeds, such as corn, wheat, barley, rice, sorghum, rye, millet, etc. Oil-seed plants include cotton, soybean, safflower, sunflower, *Brassica*, maize, alfalfa, palm, coconut, flax, castor, olive, etc. Leguminous plants include beans and peas. Beans include guar, locust bean, fenugreek, soybean, garden beans, cowpea, mung bean, lima bean, fava bean, lentils, chickpea, etc.

Evaluation of Plant Transformation

Following introduction of heterologous foreign DNA into plant cells, the transformation or integration of heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell, (2001) Molecular Cloning: A Laboratory Manual. Cold Spring Harbor Laboratory Press, Cold Spring Harbor, NY). PCR is carried out using oligonucleotide primers specific to the gene of interest or *Agrobacterium* vector background, etc.

Plant transformation may be confirmed by Southern blot analysis of genomic DNA (Sambrook and Russell, (2001) supra). In general, total DNA is extracted from the transformant, digested with appropriate restriction enzymes, fractionated in an agarose gel and transferred to a nitrocellulose or nylon membrane. The membrane or "blot" is then probed with, for example, radiolabeled 32P target DNA fragment to confirm the integration of introduced gene into the plant genome according to standard techniques (Sambrook and Russell, (2001) supra).

In Northern blot analysis, RNA is isolated from specific tissues of transformant, fractionated in a formaldehyde agarose gel, and blotted onto a nylon filter (Sambrook and Russell, (2001) supra). Expression of RNA encoded by the pesticidal gene is then tested by hybridizing the filter to a radioactive probe derived from a pesticidal gene (Sambrook and Russell, (2001) supra).

Western blot, biochemical assays and the like may be carried out on the transgenic plants to confirm the presence of protein encoded by the pesticidal gene by standard procedures (Sambrook and Russell, 2001, supra) using antibodies that bind to one or more epitopes present on the polypeptide.

Methods to Introduce Genome Editing Technologies into Plants

In some embodiments, the disclosed polynucleotide compositions can be introduced into the genome of a plant using genome editing technologies, or previously introduced polynucleotides in the genome of a plant may be edited using genome editing technologies. For example, the disclosed polynucleotides can be introduced into a desired location in the genome of a plant through the use of double-stranded break technologies such as TALENs, meganucleases, zinc finger nucleases, CRISPR-Cas, and the like. For example, the disclosed polynucleotides can be introduced into a desired location in a genome using a CRISPR-Cas system, for the purpose of site-specific insertion. The desired location in a plant genome can be any desired target site for insertion, such as a genomic region amenable for breeding or may be a target site located in a genomic window with an existing trait of interest. Existing traits of interest could be either an endogenous trait or a previously introduced trait.

In some embodiments, where the disclosed polynucleotide has previously been introduced into a genome, genome editing technologies may be used to alter or modify the introduced polynucleotide sequence. Site specific modifications that can be introduced into the disclosed polynucleotide compositions include those produced using any method for introducing site specific modification, including, but not limited to, through the use of gene repair oligonucleotides (e.g. US Publication 2013/0019349), or through the use of double-stranded break technologies such as TALENs, meganucleases, zinc finger nucleases, CRISPR-Cas, and the like. Such technologies can be used to modify the previously introduced polynucleotide through the insertion, deletion or substitution of nucleotides within the introduced polynucleotide. Alternatively, double-stranded break technologies can be used to add additional nucleotide sequences to the introduced polynucleotide. Additional sequences that may be added include, additional expression elements, such as enhancer and promoter sequences. In another embodiment, genome editing technologies may be used to position additional insecticidally-active proteins in close proximity to the disclosed polynucleotide compositions disclosed herein within the genome of a plant, in order to generate molecular stacks or breeding stacks of insecticidally-active proteins.

An "altered target site," "altered target sequence." "modified target site," and "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

Stacking of Traits in Transgenic Plant

Transgenic plants may comprise a stack of one or more insecticidal polynucleotides disclosed herein with one or more additional polynucleotides resulting in the production or suppression of multiple polypeptide sequences. Transgenic plants comprising stacks of polynucleotide sequences can be obtained by either or both of traditional breeding methods or through genetic engineering methods. These methods include, but are not limited to, breeding individual lines each comprising a polynucleotide of interest, transforming a transgenic plant comprising a gene disclosed herein with a subsequent gene and co-transformation of genes into a single plant cell. As used herein, the term "stacked" includes having the multiple traits present in the same plant (i.e., both traits are incorporated into the nuclear genome, one trait is incorporated into the nuclear genome and one trait is incorporated into the genome of a plastid or both traits are incorporated into the genome of a plastid). In one non-limiting example, "stacked traits" comprise a molecular stack or breeding stack where the sequences are physically adjacent to each other. A trait, as used herein, refers to the phenotype derived from a particular sequence or groups of sequences. Co-transformation of genes can be carried out using single transformation vectors comprising multiple genes or genes carried separately on multiple vectors. If the sequences are stacked by genetically transforming the plants, the polynucleotide sequences of interest can be combined at any time and in any order. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO 1999/25821, WO 1999/25854, WO 1999/25840, WO 1999/25855 and WO 1999/25853, all of which are herein incorporated by reference.

In some embodiments, provided are transgenic plants comprising a molecular stack comprising: a polynucleotide encoding an IPD103 polypeptide having insecticidal activity; and one or more polynucleotides selected from: a polynucleotide encoding a PtIP-83 polypeptide having insecticidal activity; a polynucleotide encoding a Cry1B polypeptide having insecticidal activity; a polynucleotide encoding a variant Cry1B polypeptide having insecticidal activity; a polynucleotide encoding a Cry1C polypeptide having insecticidal activity; a polynucleotide encoding a Cry1D polypeptide having insecticidal activity and a polynucleotide encoding a Cry1J polypeptide having insecticidal activity.

In some embodiments, the molecular stack provides insecticidal activity against *Heliothine* and/or *Spodoptera* pest species. In some embodiments, the *Heliothine* and/or *Spodoptera* pest is selected from velvetbean caterpillar (VBC) *Anticarsia gemmatalis*, soybean looper (SBL) *Pseudoplusia includens*, corn earworm (CEW) *Heliothis zea*, tobacco budworm (TBW) *Heliothis virescens*, cotton bollworm (CBW) *Helicoverpa zea*, fall armyworm (FAW) *Spodoptera frugiperda*, and southern armyworm (SAW) *Spodoptera eridania.*

In some embodiments, the molecular stack comprises a polynucleotide disclosed in PCT WO 2018/005411, which is incorporated herein by reference), encoding an IPD103 polypeptide having insecticidal activity.

In some embodiments, the molecular stack comprises a polynucleotide encoding an IPD103 polypeptide having at least 95% identity to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36 or SEQ ID NO: 38.

In some embodiments, the molecular stack comprises a polynucleotide encoding an IPD103 polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36 or SEQ ID NO: 38.

In some embodiments, the molecular stack comprises a PtIP-83 polynucleotide disclosed in US Publication US 21060347799 encoding a PtIP-83 polypeptide having insecticidal activity.

In some embodiments, the molecular stack comprises a PtIP-83 polynucleotide encoding a PtIP-83 polypeptide having at least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59 or SEQ ID NO: 61.

In some embodiments, the molecular stack comprises a PtIP-83 polynucleotide encoding a PtIP-83 polypeptide comprising an amino acid sequence having at least 95% sequence identity to an amino acid sequence of SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59 or SEQ ID NO: 61.

In some embodiments, the molecular stack comprises a PtIP-83 polynucleotide encoding a PtIP-83 polypeptide comprising the amino acid sequence of SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59 or SEQ ID NO: 61.

In some embodiments, the molecular stack comprises a polynucleotides encode a Cry1B polypeptide selected from Cry1Ba1 (Accession CAA29898, Cry1Ba2 (Accession CAA65003), Cry1Ba3 (Accession AAK63251), Cry1Ba4 (Accession AAK51084, Cry1Ba5 (Accession ABO20894), Cry1Ba6 (Accession ABL60921), Cry1Ba7 (Accession HQ439781), Cry1Bb1 (AAA22344), Cry1Bb2 (Accession HQ439782), Cry1Bc1 (Accession CAA86568), Cry1Bd1 (Accession AAD10292), Cry1Bd2 (Accession AAM93496), Cry1Be1 (Accession AAC32850), Cry1Be2 (Accession AAQ52387), Cry1Be3 (Accession ACV96720), Cry1Be4 (Accession HM070026), Cry1Bf1 (Accession CAC50778), Cry1Bf2 (Accession AAQ52380), Cry1Bg1 (Accession AAO39720), Cry1Bh1 (Accession HQ589331), and Cry1Bi1 (Accession KC156700).

In some embodiments, the molecular stack comprises a polynucleotide encoding a Cry1B polypeptide selected from a Cry1B of U.S. Pat. Nos. 8,772,577, 9,404,121, US Publication US 20160194364, and U.S. Ser. No. 62/607,372, which are incorporated herein by reference.

In some embodiments, the molecular stack comprises a polynucleotide encoding a Cry1B polypeptide selected from the amino acid sequence of SEQ ID NO: 63, SEQ ID NO: 109, SEQ ID NO: 111, SEQ ID NO: 221, SEQ ID NO: 223, SEQ ID NO: 224, SEQ ID NO: 225, SEQ ID NO: 226, SEQ ID NO: 227, SEQ ID NO: 228, and SEQ ID NO: 229.

In some embodiments, the molecular stack comprises a polynucleotide encoding a variant Cry1B polypeptide of US Publication US 20170226164 and WO Publication WO2017/180715, which are incorporated herein by reference.

In some embodiments, the molecular stack comprises a polynucleotide encoding a variant Cry1B polypeptide comprising the amino acid sequence of SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 84, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210 or SEQ ID NO: 211.

In some embodiments, the molecular stack comprises a polynucleotide encoding a variant Cry1B polypeptide selected from SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 84, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, and SEQ ID NO: 211.

In some embodiments, the molecular stack comprises a polynucleotide encoding a Cry1C polypeptide selected from Cry1Ca1 (Accession CAA30396), Cry1Ca2 (Accession CAA31951), Cry1Ca3 (Accession AAA22343), Cry1Ca4 (Accession CAA01886), Cry1Ca5 (Accession CAA65457), Cry1Ca6 (Accession AAF37224), Cry1Ca7 (Accession AAG50438), Cry1Ca8 (Accession AAM00264), Cry1Ca9 (Accession AAL79362), Cry1Ca10 (Accession AAN16462), Cry1Ca11 (Accession AAX53094), Cry1Ca12 (Accession HM070027), Cry1Ca13 (Accession HQ412621), Cry1Ca14 (Accession JN651493), Cry1Cb1 (Accession M97880), Cry1Cb2 (Accession AAG35409), Cry1Cb3 (Accession ACD50894), Cry1Cb-like (Accession AAX63901), Cry1Da1 (Accession CAA38099), Cry1Da2 (Accession I76415), and Cry1Da3 (Accession HQ43978).

In some embodiments, the Cry1C polypeptide comprises an amino acid sequence having at least 95% sequence identity to a Cry1Ca polypeptide.

In some embodiments, the Cry1C polypeptide comprises the amino acid sequence of a Cry1Ca polypeptide.

In some embodiments, the molecular stack comprises a polynucleotide encoding a Cry1D polypeptide selected from Cry1Da1 (Accession CAA38099), Cry1Da2 (Accession I76415), Cry1Da3 (Accession HQ439784), Cry1db1 (Accession CAA80234), Cry1db2 (Accession AAK48937), and Cry1Dc1 (Accession ABK35074).

In some embodiments, the Cry1D polypeptide comprises an amino acid sequence having at least 95% sequence identity to a Cry1Da polypeptide.

In some embodiments, the Cry1D polypeptide comprises the amino acid sequence of a Cry1Da polypeptide.

In some embodiments, the molecular stack comprises a polynucleotide encoding a Cry1J polypeptide selected from Cry1Ja1 (Accession AAA22341), Cry1Ja2 (Accession HM070030), Cry1Ja3 (Accession JQ228425), Cry1Jb1 (Accession AAA98959), Cry1Jc1 (Accession AAC31092), Cry1Jc2 (Accession AAQ52372), and Cry1Jd1 (Accession CAC50779).

In some embodiments, the molecular stack comprises a polynucleotide encoding a variant Cry1J polypeptide of US Publication Number US20170240603.

In some embodiments, the molecular stack comprises a polynucleotide encoding a Cry1J variant polypeptide comprising an amino acid sequence having at least 95% identity to SEQ ID NO: 213, SEQ ID NO: 215, SEQ ID NO: 217 or SEQ ID NO: 219.

In some embodiments, the molecular stack comprises a polynucleotide encoding a Cry1J variant polypeptide comprising the amino acid sequence of SEQ ID NO: 213, SEQ ID NO: 215, SEQ ID NO: 217 or SEQ ID NO: 219.

In some embodiments, the molecular stack comprises a polynucleotide encoding a variant Cry1J polypeptide selected from SEQ ID NO: 213, SEQ ID NO: 215, SEQ ID NO: 217 or SEQ ID NO: 219.

In some embodiments, provided are transgenic plants comprising a breeding stack comprising: a polynucleotide encoding an IPD103 polypeptide having insecticidal activity; and one or more polynucleotides selected from: a polynucleotide encoding a PtIP-83 polypeptide having insecticidal activity; a polynucleotide encoding a Cry1B polypeptide having insecticidal activity; a polynucleotide encoding a variant Cry1B polypeptide having insecticidal activity; a polynucleotide encoding a Cry1C polypeptide having insecticidal activity; a polynucleotide encoding a Cry1D polypeptide having insecticidal activity and a polynucleotide encoding a Cry1J polypeptide having insecticidal activity.

In some embodiments, the breeding stack provides insecticidal activity against *Heliothine* and/or *Spodoptera* pests species. In some embodiments, the *Heliothine* and/or *Spodoptera* pests are selected from velvetbean caterpillar (VBC) *Anticarsia gemmatalis*, soybean looper (SBL) *Pseudoplusia includens*, corn earworm (CEW) *Heliothis zea*, tobacco budworm (TBW) *Heliothis virescens*, cotton bollworm (CBW) *Helicoverpa zea*, fall armyworm (FAW) *Spodoptera frugiperda*, and southern armyworm (SAW) *Spodoptera eridania.*

In some embodiments, the breeding stack comprises a polynucleotide disclosed in PCT WO 2018/005411, which is incorporated herein by reference, encoding an IPD103 polypeptide having insecticidal activity.

In some embodiments, the breeding stack comprises a polynucleotide encoding an IPD103 polypeptide having at least 95% identity to SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36 or SEQ ID NO: 38.

In some embodiments, the breeding stack comprises a polynucleotide encoding an IPD103 polypeptide of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34, SEQ ID NO: 36 or SEQ ID NO: 38.

In some embodiments, the breeding stack comprises a PtIP-83 polynucleotide disclosed in US Publication US 21060347799 encoding a PtIP-83 polypeptide having insecticidal activity.

In some embodiments, the breeding stack comprises a PtIP-83 polynucleotide encoding a PtIP-83 polypeptide having at least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59 or SEQ ID NO: 61.

In some embodiments, the breeding stack comprises a PtIP-83 polynucleotide encoding a PtIP-83 polypeptide comprising an amino acid sequence having at least 95% sequence identity to an amino acid sequence of SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59 or SEQ ID NO: 61.

In some embodiments, the breeding stack comprises a PtIP-83 polynucleotide encoding a PtIP-83 polypeptide comprising the amino acid sequence of SEQ ID NO: 39, SEQ ID NO: 41, SEQ ID NO: 43, SEQ ID NO: 45, SEQ ID NO: 47, SEQ ID NO: 49, SEQ ID NO: 51, SEQ ID NO: 53, SEQ ID NO: 55, SEQ ID NO: 57, SEQ ID NO: 59 or SEQ ID NO: 61.

In some embodiments, the breeding stack comprises a polynucleotides encode a Cry1B polypeptide selected from Cry1Ba1 (Accession CAA29898, Cry1Ba2 (Accession CAA65003), Cry1Ba3 (Accession AAK63251), Cry1Ba4 (Accession AAK51084, Cry1Ba5 (Accession ABO20894), Cry1Ba6 (Accession ABL60921), Cry1Ba7 (Accession HQ439781), Cry1Bb1 (AAA22344), Cry1Bb2 (Accession HQ439782), Cry1Bc1 (Accession CAA86568), Cry1Bd1 (Accession AAD10292), Cry1Bd2 (Accession AAM93496), Cry1Be1 (Accession AAC32850), Cry1Be2 (Accession AAQ52387), Cry1Be3 (Accession ACV96720), Cry1Be4 (Accession HM070026), Cry1Bf1 (Accession CAC50778), Cry1Bf2 (Accession AAQ52380), Cry1Bg1 (Accession AAO39720), Cry1Bh1 (Accession HQ589331), and Cry1Bi1 (Accession KC156700).

In some embodiments, the breeding stack comprises a polynucleotide encoding a Cry1B polypeptide selected from a Cry1B of U.S. Pat. Nos. 8,772,577, 9,404,121, US Publication US 20160194364, and U.S. Ser. No. 62/607,372, which are incorporated herein by reference.

In some embodiments, the breeding stack comprises a polynucleotide encoding a Cry1B polypeptide selected from the amino acid sequence of SEQ ID NO: 63, SEQ ID NO: 109, SEQ ID NO: 111, SEQ ID NO: 221, SEQ ID NO: 223, SEQ ID NO: 224, SEQ ID NO: 225, SEQ ID NO: 226, SEQ ID NO: 227, SEQ ID NO: 228, and SEQ ID NO: 229.

In some embodiments, the breeding stack comprises a polynucleotide encoding a variant Cry1B polypeptide of US Publication US 20170226164 and WO Publication WO2017/180715, which are incorporated herein by reference.

In some embodiments, the breeding stack comprises a polynucleotide encoding a variant Cry1B polypeptide comprising the amino acid sequence of SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 84, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210 or SEQ ID NO: 211.

In some embodiments, the breeding stack comprises a polynucleotide encoding a variant Cry1B polypeptide selected from SEQ ID NO: 65, SEQ ID NO: 67, SEQ ID NO: 69, SEQ ID NO: 71, SEQ ID NO: 73, SEQ ID NO: 75, SEQ ID NO: 77, SEQ ID NO: 79, SEQ ID NO: 81, SEQ ID NO: 83, SEQ ID NO: 84, SEQ ID NO: 85, SEQ ID NO: 87, SEQ ID NO: 89, SEQ ID NO: 91, SEQ ID NO: 93, SEQ ID NO: 95, SEQ ID NO: 97, SEQ ID NO: 99, SEQ ID NO: 101, SEQ ID NO: 103, SEQ ID NO: 105, SEQ ID NO: 107, SEQ ID NO: 113, SEQ ID NO: 114, SEQ ID NO: 115, SEQ ID NO: 116, SEQ ID NO: 117, SEQ ID NO: 118, SEQ ID NO: 119, SEQ ID NO: 120, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, SEQ ID NO: 142, SEQ ID NO: 143, SEQ ID NO: 144, SEQ ID NO: 145, SEQ ID NO: 146, SEQ ID NO: 147, SEQ ID NO: 148, SEQ ID NO: 149, SEQ ID NO: 150, SEQ ID NO: 151, SEQ ID NO: 152, SEQ ID NO: 153, SEQ ID NO: 154, SEQ ID NO: 155, SEQ ID NO: 156, SEQ ID NO: 157, SEQ ID NO: 158, SEQ ID NO: 159, SEQ ID NO: 160, SEQ ID NO: 161, SEQ ID NO: 162, SEQ ID NO: 163, SEQ ID NO: 164, SEQ ID NO: 165, SEQ ID NO: 166, SEQ ID NO: 167, SEQ ID NO: 168, SEQ ID NO: 169, SEQ ID NO: 170, SEQ ID NO: 171, SEQ ID NO: 172, SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, and SEQ ID NO: 211.

In some embodiments, the breeding stack comprises a polynucleotide encoding a Cry1C polypeptide selected from Cry1Ca1 (Accession CAA30396), Cry1Ca2 (Accession CAA31951), Cry1Ca3 (Accession AAA22343), Cry1Ca4 (Accession CAA01886), Cry1Ca5 (Accession CAA65457), Cry1Ca6 (Accession AAF37224), Cry1Ca7 (Accession AAG50438), Cry1Ca8 (Accession AAM00264), Cry1Ca9 (Accession AAL79362), Cry1Ca10 (Accession AAN16462), Cry1Ca11 (Accession AAX53094), Cry1Ca12 (Accession HM070027), Cry1Ca13 (Accession HQ412621), Cry1Ca14 (Accession JN651493), Cry1Cb1 (Accession M97880), Cry1Cb2 (Accession AAG35409), Cry1Cb3 (Accession ACD50894), Cry1Cb-like (Accession AAX63901), Cry1Da1 (Accession CAA38099), Cry1Da2 (Accession I76415), and Cry1Da3 (Accession HQ43978).

In some embodiments, the Cry1C polypeptide comprises an amino acid sequence having at least 95% sequence identity to a Cry1Ca polypeptide.

In some embodiments, the Cry1C polypeptide comprises the amino acid sequence of a Cry1Ca polypeptide.

In some embodiments, the breeding stack comprises a polynucleotide encoding a Cry1D polypeptide selected from Cry1Da1 (Accession CAA38099), Cry1Da2 (Accession I76415), Cry1Da3 (Accession HQ439784), Cry1db1 (Accession CAA80234), Cry1db2 (Accession AAK48937), and Cry1Dc1 (Accession ABK35074).

In some embodiments, the Cry1D polypeptide comprises an amino acid sequence having at least 95% sequence identity to Cry1Da polypeptide.

In some embodiments, the Cry1D polypeptide comprises the amino acid sequence of a Cry1Da polypeptide.

In some embodiments, the breeding stack comprises a polynucleotide encoding a Cry1J polypeptide selected from Cry1Ja1 (Accession AAA22341), Cry1Ja2 (Accession HM070030), Cry1Ja3 (Accession JQ228425), Cry1Jb1 (Accession AAA98959), Cry1Jc1 (Accession AAC31092), Cry1Jc2 (Accession AAQ52372), and Cry1Jd1 (Accession CAC50779).

In some embodiments, the breeding stack comprises a polynucleotide encoding a variant Cry1J polypeptide of US Publication Number US20170240603.

In some embodiments, the breeding stack comprises a polynucleotide encoding a Cry1J variant polypeptide comprising an amino acid sequence having at least 95% identity to SEQ ID NO: 213, SEQ ID NO: 215, SEQ ID NO: 217 or SEQ ID NO: 219.

In some embodiments, the breeding stack comprises a polynucleotide encoding a Cry1J variant polypeptide comprising the amino acid sequence of SEQ ID NO: 213, SEQ ID NO: 215, SEQ ID NO: 217 or SEQ ID NO: 219.

In some embodiments, the breeding stack comprises a polynucleotide encoding a variant Cry1J polypeptide selected from SEQ ID NO: 213, SEQ ID NO: 215, SEQ ID NO: 217 or SEQ ID NO: 219.

In some embodiments the polynucleotides encoding the IPD103 polypeptide disclosed herein, stacked with one or more additional insect resistance traits can be stacked with one or more additional input traits (e.g., herbicide resistance, fungal resistance, virus resistance, stress tolerance, disease resistance, male sterility, stalk strength, and the like) or output traits (e.g., increased yield, modified starches, improved oil profile, balanced amino acids, high lysine or methionine, increased digestibility, improved fiber quality, drought resistance, and the like). Thus, the polynucleotide embodiments can be used to provide a complete agronomic package of improved crop quality with the ability to flexibly and cost effectively control any number of agronomic pests.

Transgenes useful for stacking include but are not limited to:

1. Transgenes that Confer Resistance to Insects or Disease and that Encode:

(A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example, Jones, et al., (1994) *Science* 266:789 (cloning of the tomato Cf-9 gene for resistance to *Cladosporium fulvum*); Martin, et al., (1993) *Science* 262:1432 (tomato Pto gene for resistance to *Pseudomonas syringae* pv. tomato encodes a protein kinase); Mindrinos, et al., (1994) *Cell* 78:1089 (*Arabidopsis* RSP2 gene for resistance to *Pseudomonas syringae*), McDowell and Woffenden, (2003) *Trends Biotechnol.* 21(4):178-83 and Toyoda, et al., (2002) *Transgenic Res.* 11(6):567-82. A plant resistant to a disease is one that is more resistant to a pathogen as compared to the wild type plant.

(B) Genes encoding a *Bacillus thuringiensis* protein, a derivative thereof or a synthetic polypeptide modeled thereon. See, for example, Geiser, et al., (1986) *Gene* 48:109, who disclose the cloning and nucleotide sequence of a Bt delta-endotoxin gene. Moreover, DNA molecules encoding delta-endotoxin genes can be purchased from American Type Culture Collection (Rockville, Md.), for example, under ATCC® Accession Numbers 40098, 67136, 31995 and 31998. Other non-limiting examples of *Bacillus thuringiensis* transgenes being genetically engineered are given in the following patents and patent applications and hereby are incorporated by reference for this purpose: U.S. Pat. Nos. 5,188,960; 5,689,052; 5,880,275; 5,986,177; 6,023,013, 6,060,594, 6,063,597, 6,077,824, 6,620,988, 6,642,030, 6,713,259, 6,893,826, 7,105,332; 7,179,965, 7,208,474; 7,227,056, 7,288,643, 7,323,556, 7,329,736, 7,449,552, 7,468,278, 7,510,878, 7,521,235, 7,544,862, 7,605,304, 7,696,412, 7,629,504, 7,705,216, 7,772,465, 7,790,846, 7,858,849 and WO 1991/14778; WO 1999/31248; WO 2001/12731; WO 1999/24581 and WO 1997/40162.

Genes encoding pesticidal proteins may also be stacked including but are not limited to: insecticidal proteins from *Pseudomonas* sp. such as PSEEN3174 (Monalysin, (2011) *PLoS Pathogens,* 7:1-13), from *Pseudomonas protegens strain CHA*0 and Pf-5 (*previously fluorescens*) (Pechy-Tarr, (2008) *Environmental Microbiology* 10:2368-2386: GenBank Accession No. EU400157); from *Pseudomonas taiwanensis* (Liu, et al., (2010) *J. Agric. Food Chem.* 58:12343-12349) and from *Pseudomonas pseudoalcaligenes* (Zhang, et al., (2009) *Annals of Microbiology* 59:45-50 and Li, et al., (2007) *Plant Cell Tiss. Organ Cult.* 89:159-168); insecticidal proteins from *Photorhabdus* sp. and *Xenorhabdus* sp. (Hinchliffe, et al., (2010) *The Open Toxinology Journal* 3:101-118 and Morgan, et al., (2001) *Applied and Envir. Micro.* 67:2062-2069), U.S. Pat. Nos. 6,048,838, and 6,379,946; a PIP-1 polypeptide of US Patent Publication US20140007292; an AfIP-1A and/or AfIP-1B polypeptide of US Patent Publication US20140033361; a PHI-4 polypeptide of US Patent Publication US20140274885 and US20160040184; a PIP-47 polypeptide of PCT Publication Number WO2015/023846, a PIP-72 polypeptide of PCT Publication Number WO2015/038734; a PtIP-50 polypeptide and a PtIP-65 polypeptide of PCT Publication Number WO2015/120270; a PtIP-83 polypeptide of PCT Publication Number WO2015/120276; a PtIP-96 polypeptide of US Publication No. 2017-0233440; an IPD079 polypeptide of US Publication No. 2018-0222947; an IPD082 polypeptide of PCT WO 2017/105987, and δ-endotoxins including, but not limited to, the Cry1, Cry2, Cry3, Cry4, Cry5, Cry6, Cry7, Cry8, Cry9, Cry10, Cry11, Cry12, Cry13, Cry14, Cry15, Cry16, Cry17, Cry18, Cry19, Cry20, Cry21, Cry22, Cry23, Cry24, Cry25, Cry26, Cry27, Cry 28, Cry 29, Cry 30, Cry31, Cry32, Cry33, Cry34, Cry35,Cry36, Cry37, Cry38, Cry39, Cry40, Cry41, Cry42, Cry43, Cry44, Cry45, Cry 46, Cry47, Cry49, Cry50, Cry51, Cry52, Cry53, Cry 54, Cry55, Cry56, Cry57, Cry58, Cry59, Cry60, Cry61, Cry62, Cry63, Cry64, Cry65, Cry66, Cry67, Cry68, Cry69, Cry70, Cry71, and Cry 72 classes of δ-endotoxin genes and the *B. thuringiensis* cytolytic Cyt1 and Cyt2 genes. Members of these classes of *B. thuringiensis* insecticidal proteins can be found in Crickmore, et al., "*Bacillus thuringiensis* toxin nomenclature" (2011), at lifesci.sussex.ac.uk/home/Neil_Crickmore/Bt/ which can be accessed on the world-wide web using the "www" prefix).

Examples of δ-endotoxins also include but are not limited to Cry1A proteins of U.S. Pat. Nos. 5,880,275 and 7,858,849; a DIG-3 or DIG-11 toxin (N-terminal deletion of α-helix 1 and/or α-helix 2 variants of Cry proteins such as Cry1A) of US Patent Numbers 8,304,604 and 8,304,605, Cry1B of U.S. patent application Ser. No. 10/525,318; Cry1C of U.S. Pat. No. 6,033,874; Cry1F of U.S. Pat. Nos. 5,188,960, 6,218,188; Cry1A/F chimeras of U.S. Pat. Nos. 7,070,982; 6,962,705 and 6,713,063); a Cry2 protein such as Cry2Ab protein of U.S. Pat. No. 7,064,249); a Cry3A protein including but not limited to an engineered hybrid insecticidal protein (eHIP) created by fusing unique combinations of variable regions and conserved blocks of at least two different Cry proteins (US Patent Application Publication Number 2010/0017914); a Cry4 protein; a Cry5 protein; a Cry6 protein; Cry8 proteins of U.S. Pat. Nos. 7,329,736, 7,449,552, 7,803,943, 7,476,781, 7,105,332, 7,378,499 and 7,462,760; a Cry9 protein such as such as members of the Cry9A, Cry9B, Cry9C, Cry9D, Cry9E, and Cry9F families; a Cry15 protein of Naimov, et al., (2008) *Applied and Environmental Microbiology* 74:7145-7151; a Cry22, a Cry34Ab1 protein of U.S. Pat. Nos. 6,127,180, 6,624,145 and 6,340,593; a CryET33 and CryET34 protein of U.S. Pat. Nos. 6,248,535, 6,326,351, 6,399,330, 6,949,626, 7,385,107 and 7,504,229; a CryET33 and CryET34 homologs of US Patent Publication Number 2006/0191034, 2012/0278954, and PCT Publication Number WO 2012/139004; a Cry35Ab1 protein of U.S. Pat. Nos. 6,083,499, 6,548,291 and 6,340,593; a Cry46 protein, a Cry 51 protein, a Cry binary toxin; a TIC901 or related toxin; TIC807 of US 2008/0295207; ET29, ET37, TIC809, TIC810, TIC812, TIC127, TIC128 of PCT US 2006/033867; AXMI-027, AXMI-036, and AXMI-038 of U.S. Pat. No. 8,236,757; AXMI-031, AXMI-039, AXMI-040, AXMI-049 of U.S. Pat. No. 7,923,602; AXMI-018, AXMI-020, and AXMI-021 of WO 2006/083891; AXMI-010 of WO 2005/038032; AXMI-003 of WO 2005/021585; AXMI-008 of US 2004/0250311; AXMI-006 of US 2004/0216186; AXMI-007 of US 2004/0210965; AXMI-009 of US 2004/0210964; AXMI-014 of US 2004/0197917; AXMI-004 of US 2004/0197916; AXMI-028 and AXMI-029 of WO 2006/119457; AXMI-007, AXMI-008, AXMI-0080rf2, AXMI-009, AXMI-014 and AXMI-004 of WO 2004/074462; AXMI-150 of U.S. Pat. No. 8,084,416; AXMI-205 of US20110023184; AXMI-011, AXMI-012, AXMI-013, AXMI-015, AXMI-019, AXMI-044, AXMI-037, AXMI-043, AXMI-033, AXMI-034, AXMI-022, AXMI-023, AXMI-041, AXMI-063, and AXMI-064 of US 2011/0263488; AXMI-R1 and related proteins of US 2010/0197592; AXMI221Z, AXMI222z, AXMI223z, AXMI224z and AXMI225z of WO 2011/103248; AXMI218, AXMI219, AXMI220, AXMI226, AXMI227, AXMI228, AXMI229, AXMI230, and AXMI231 of WO11/103247; AXMI-115, AXMI-113, AXMI-005, AXMI-163 and AXMI-184 of U.S. Pat. No. 8,334,431; AXMI-001, AXMI-002, AXMI-030, AXMI-035, and AXMI-045 of US 2010/0298211; AXMI-066 and AXMI-076 of US2009/0144852; AXMI128, AXMI130, AXMI131, AXMI133, AXMI140, AXMI141, AXMI142, AXMI143, AXMI144, AXMI146, AXMI148, AXMI149, AXMI152, AXMI153, AXMI154, AXMI155, AXMI156, AXMI157, AXMI158, AXMI162, AXMI165, AXMI166, AXMI167, AXMI168, AXMI169, AXMI170, AXMI171, AXMI172, AXMI173, AXMI174, AXMI175, AXMI176, AXMI177, AXMI178, AXMI179, AXMI180, AXMI181, AXMI182, AXMI185, AXMI186, AXMI187, AXMI188, AXMI189 of U.S. Pat. No. 8,318,900; AXMI079, AXMI080, AXMI081, AXMI082, AXMI091, AXMI092, AXMI096, AXMI097, AXMI098, AXMI099, AXMI100, AXMI101, AXMI102, AXMI103, AXMI104, AXMI107, AXMI108, AXMI109, AXMI110, AXMI111, AXMI112, AXMI114, AXMI116, AXMI117, AXMI118, AXMI119, AXMI120, AXMI121, AXMI122, AXMI123, AXMI124, AXMI1257, AXMI1268, AXMI127, AXMI129, AXMI164, AXMI151, AXMI161, AXMI183, AXMI132, AXMI138, AXMI137 of US 2010/0005543; and Cry proteins such as Cry1A and Cry3A having modified proteolytic sites of U.S. Pat. No. 8,319,019; and a Cry1Ac, Cry2Aa and Cry1Ca toxin protein from *Bacillus thuringiensis* strain VBTS 2528 of US Patent Application Publication Number 2011/0064710. Other Cry proteins can be found at Crickmore, et al., "*Bacillus thuringiensis* toxin nomenclature" (2011), at lifesci.sussex.ac.uk/home/Neil_Crickmore/Bt/ which can be accessed on the world-wide web using the "www" prefix). The insecticidal activity of Cry proteins is known to one skilled in the art (for review, see, van Frannkenhuyzen, (2009) *J. Invert. Path.* 101:1-16). The use of Cry proteins as transgenic plant traits and Cry-transgenic plants including but not limited to Cry1Ac, Cry1Ac+Cry2Ab, Cry1Ab, Cry1A.105, Cry1F, Cry1Fa2, Cry1F+Cry1Ac, Cry2Ab, Cry3A, mCry3A, Cry3Bb1, Cry34Ab1, Cry35Ab1, Vip3A, mCry3A, Cry9c and CBI-Bt have received regulatory approval (see, Sanahuja, (2011) *Plant Biotech Journal* 9:283-300 and the CERA (2010) GM Crop Database Center for Environmental Risk Assessment (CERA), ILSI Research Foundation, Washington D.C. at cera-gmc.org/index.php?action=gm_crop_database which can be accessed on the world-wide web using the "www" prefix). More than one pesticidal proteins can also be expressed in plants such as Vip3Ab & Cry1Fa (US2012/0317682), Cry1BE & Cry1F (US2012/0311746), Cry1CA & Cry1AB (US2012/0311745), Cry1F & CryCa (US2012/0317681), Cry1DA & Cry1BE (US2012/0331590), Cry1DA & Cry1Fa (US2012/0331589), Cry1AB & Cry1BE (US2012/0324606), and Cry1Fa & Cry2Aa, Cry1I or Cry1E (US2012/0324605). Pesticidal proteins also include insecticidal lipases including lipid acyl hydrolases of U.S. Pat. No. 7,491,869, and cholesterol oxidases such as from *Streptomyces* (Purcell et al. (1993) *Biochem Biophys Res Commun* 15:1406-1413). Pesticidal proteins also include VIP (vegetative insecticidal proteins) toxins of U.S. Pat. Nos. 5,877,012, 6,107,279, 6,137,033, 7,244,820, 7,615,686, and 8,237,020, and the like. Other VIP proteins can be found at lifesci.sussex.ac.uk/home/Neil_Crickmore/Bt/vip.html which can be accessed on the world-wide web using the "www" prefix). Pesticidal proteins also include toxin complex (TC) proteins, obtainable from organisms such as *Xenorhabdus, Photorhabdus* and *Paenibacillus* (see, U.S. Pat. Nos. 7,491,698 and 8,084,418). Some TC proteins have "stand alone" insecticidal activity and other TC proteins enhance the activity of the stand-alone toxins produced by the same given organism. The toxicity of a "stand-alone" TC protein (from *Photorhabdus, Xenorhabdus* or *Paenibacillus*, for example) can be enhanced by one or more TC protein "potentiators" derived from a source organism of a different genus. There are three main types of TC proteins. As referred to herein, Class A proteins ("Protein A") are stand-alone toxins. Class B proteins ("Protein B") and Class C proteins ("Protein C") enhance the toxicity of Class A proteins. Examples of Class A proteins are TcbA, TcdA, XptA1 and XptA2. Examples of Class B proteins are TcaC, TcdB, XptB1Xb and XptC1Wi. Examples of Class C proteins are TccC, XptC1Xb and XptB1Wi. Pesticidal proteins also include spider, snake and scorpion venom proteins. Examples of spider venom peptides include but are not limited to lycotoxin-1 peptides and mutants thereof (U.S. Pat. No. 8,334,366).

(C) A polynucleotide encoding an insect-specific hormone or pheromone such as an ecdysteroid and juvenile hormone, a variant thereof, a mimetic based thereon or an antagonist or agonist thereof. See, for example, the disclosure by Hammock, et al., (1990) *Nature* 344:458, of baculovirus expression of cloned juvenile hormone esterase, an inactivator of juvenile hormone.

(D) A polynucleotide encoding an insect-specific peptide which, upon expression, disrupts the physiology of the affected pest. For example, see the disclosures of, Regan, (1994) *J. Biol. Chem.* 269:9 (expression cloning yields DNA coding for insect diuretic hormone receptor); Pratt, et al., (1989) *Biochem. Biophys. Res. Comm.* 163:1243 (an allostatin is identified in *Diploptera puntata*); Chattopadhyay, et al., (2004) *Critical Reviews in Microbiology* 30(1):33-54; Zjawiony, (2004) *J Nat Prod* 67(2):300-310; Carlini and Grossi-de-Sa, (2002) *Toxicon* 40(11):1515-1539; Ussuf, et al., (2001) *Curr Sci.* 80(7):847-853 and Vasconcelos and Oliveira, (2004) *Toxicon* 44(4):385-403. See also, U.S. Pat. No. 5,266,317 to Tomalski, et al., who disclose genes encoding insect-specific toxins.

(E) A polynucleotide encoding an enzyme responsible for a hyperaccumulation of a monoterpene, a sesquiterpene, a steroid, hydroxamic acid, a phenylpropanoid derivative or another non-protein molecule with insecticidal activity.

(F) A polynucleotide encoding an enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See, PCT Application WO 1993/02197 in the name of Scott, et al., which discloses the nucleotide sequence of a callase gene. DNA molecules which contain chitinase-encoding sequences can be obtained, for example, from the ATCC® under Accession Numbers 39637 and 67152. See also, Kramer, et al., (1993) *Insect Biochem. Molec. Biol.* 23:691, who teach the nucleotide sequence of a cDNA encoding tobacco hookworm chitinase and Kawalleck, et al., (1993) *Plant Molec. Biol.* 21:673, who provide the nucleotide sequence of the parsley ubi4-2 polyubiquitin gene, and U.S. Pat. Nos. 6,563,020; 7,145,060 and 7,087,810.

(G) A polynucleotide encoding a molecule that stimulates signal transduction. For example, see the disclosure by Botella, et al., (1994) *Plant Molec. Biol.* 24:757, of nucleotide sequences for mung bean calmodulin cDNA clones, and Griess, et al., (1994) *Plant Physiol.* 104:1467, who provide the nucleotide sequence of a maize calmodulin cDNA clone.

(H) A polynucleotide encoding a hydrophobic moment peptide. See, PCT Application WO 1995/16776 and U.S. Pat. No. 5,580,852 disclosure of peptide derivatives of Tachyplesin which inhibit fungal plant pathogens) and PCT Application WO 1995/18855 and U.S. Pat. No. 5,607,914 (teaches synthetic antimicrobial peptides that confer disease resistance).

(I) A polynucleotide encoding a membrane permease, a channel former or a channel blocker. For example, see the disclosure by Jaynes, et al., (1993) *Plant Sci.* 89:43, of heterologous expression of a cecropin-beta lytic peptide analog to render transgenic tobacco plants resistant to *Pseudomonas solanacearum.*

(J) A gene encoding a viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See, Beachy, et al., (1990) *Ann. Rev. Phytopathol.* 28:451. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(K) A gene encoding an insect-specific antibody or an immunotoxin derived therefrom. Thus, an antibody targeted to a critical metabolic function in the insect gut would inactivate an affected enzyme, killing the insect. Cf. Taylor, et al., Abstract #497, SEVENTH INT'L SYMPOSIUM ON MOLECULAR PLANT-MICROBE INTERACTIONS (Edinburgh, Scotland, 1994) (enzymatic inactivation in transgenic tobacco via production of single-chain antibody fragments).

(L) A gene encoding a virus-specific antibody. See, for example, Tavladoraki, et al., (1993) *Nature* 366:469, who show that transgenic plants expressing recombinant antibody genes are protected from virus attack.

(M) A polynucleotide encoding a developmental-arrestive protein produced in nature by a pathogen or a parasite. Thus, fungal endo alpha-1,4-D-polygalacturonases facilitate fungal colonization and plant nutrient release by solubilizing plant cell wall homo-alpha-1,4-D-galacturonase. See, Lamb, et al., (1992) *Bio/Technology* 10:1436. The cloning and characterization of a gene which encodes a bean endopolygalacturonase-inhibiting protein is described by Toubart, et al., (1992) *Plant J.* 2:367.

(N) A polynucleotide encoding a developmental-arrestive protein produced in nature by a plant. For example, Logemann, et al., (1992) *Bio/Technology* 10:305, have shown that transgenic plants expressing the barley ribosome-inactivating gene have an increased resistance to fungal disease.

(O) Genes involved in the Systemic Acquired Resistance (SAR) Response and/or the pathogenesis related genes. Briggs, (1995) *Current Biology* 5(2), Pieterse and Van Loon, (2004) *Curr. Opin. Plant Bio.* 7(4):456-64 and Somssich, (2003) *Cell* 113(7):815-6.

(P) Antifungal genes (Cornelissen and Melchers, (1993) *Pl. Physiol.* 101:709-712 and Parijs, et al., (1991) *Planta* 183:258-264 and Bushnell, et al., (1998) *Can. J. of Plant Path.* 20(2):137-149. Also, see, U.S. patent application Ser. Nos. 09/950,933; 11/619,645; 11/657,710; 11/748,994; 11/774,121 and U.S. Pat. Nos. 6,891,085 and 7,306,946. LysM Receptor-like kinases for the perception of chitin fragments as a first step in plant defense response against fungal pathogens (US 2012/0110696).

(Q) Detoxification genes, such as for fumonisin, beauvericin, moniliformin and zearalenone and their structurally related derivatives. For example, see, U.S. Pat. Nos. 5,716,820; 5,792,931; 5,798,255; 5,846,812; 6,083,736; 6,538,177; 6,388,171 and 6,812,380.

(R) A polynucleotide encoding a Cystatin and cysteine proteinase inhibitors. See, U.S. Pat. No. 7,205,453.

(S) Defensin genes. See, WO 2003/000863 and U.S. Pat. Nos. 6,911,577; 6,855,865; 6,777,592 and 7,238,781.

(T) Genes conferring resistance to nematodes. See, e.g., PCT Application WO 1996/30517; PCT Application WO 1993/19181, WO 2003/033651 and Urwin, et al., (1998) *Planta* 204:472-479, Williamson, (1999) *Curr Opin Plant Bio.* 2(4):327-31; U.S. Pat. Nos. 6,284,948 and 7,301,069 and miR164 genes (WO 2012/058266).

(U) Genes that confer resistance to *Phytophthora* Root Rot, such as the Rps 1, Rps 1-a, Rps 1-b, Rps 1-c, Rps 1-d, Rps 1-e, Rps 1-k, Rps 2, Rps 3-a, Rps 3-b, Rps 3-c, Rps 4, Rps 5, Rps 6, Rps 7 and other Rps genes. See, for example, Shoemaker, et al., *Phytophthora* Root Rot Resistance Gene Mapping in Soybean, Plant Genome IV Conference, San Diego, Calif. (1995).

(V) Genes that confer resistance to Brown Stem Rot, such as described in U.S. Pat. No. 5,689,035 and incorporated by reference for this purpose.

(W) Genes that confer resistance to *Colletotrichum*, such as described in US Patent Application Publication US 2009/0035765 and incorporated by reference for this purpose. This includes the Rcg locus that may be utilized as a single locus conversion.

2. Transgenes that Confer Resistance to a Herbicide, for Example:

(A) A polynucleotide encoding resistance to a herbicide that inhibits the growing point or meristem, such as an imidazolinone or a sulfonylurea. Exemplary genes in this category code for mutant ALS and AHAS enzyme as described, for example, by Lee, et al., (1988) *EMBO J.* 7:1241 and Miki, et al., (1990) *Theor. Appl. Genet.* 80:449, respectively. See also, U.S. Pat. Nos. 5,605,011; 5,013,659; 5,141,870; 5,767,361; 5,731,180; 5,304,732; 4,761,373; 5,331,107; 5,928,937 and 5,378,824; U.S. patent application Ser. No. 11/683,737 and International Publication WO 1996/33270.

(B) A polynucleotide encoding a protein for resistance to Glyphosate (resistance imparted by mutant 5-enolpyruvl-3-phosphikimate synthase (EPSP) and aroA genes, respectively) and other phosphono compounds such as glufosinate (phosphinothricin acetyl transferase (PAT) and *Streptomyces hygroscopicus* phosphinothricin acetyl transferase (bar) genes), and pyridinoxy or phenoxy proprionic acids and cyclohexones (ACCase inhibitor-encoding genes). See, for example, U.S. Pat. No. 4,940,835 to Shah, et al., which discloses the nucleotide sequence of a form of EPSPS which can confer glyphosate resistance. U.S. Pat. No. 5,627,061 to Barry, et al., also describes genes encoding EPSPS enzymes. See also, U.S. Pat. Nos. 6,566,587; 6,338,961; 6,248,876; 6,040,497; 5,804,425; 5,633,435; 5,145,783; 4,971,908; 5,312,910; 5,188,642; 5,094,945, 4,940,835; 5,866,775; 6,225,114; 6,130,366; 5,310,667; 4,535,060; 4,769,061; 5,633,448; 5,510,471; Re. 36,449; RE 37,287 E and 5,491,288 and International Publications EP 1173580; WO 2001/66704; EP 1173581 and EP 1173582, which are incorporated herein by reference for this purpose. Glyphosate resistance is also imparted to plants that express a gene encoding a glyphosate oxido-reductase enzyme as described more fully in U.S. Pat. Nos. 5,776,760 and 5,463,175, which are incorporated herein by reference for this purpose. In addition, glyphosate resistance can be imparted to plants by the over expression of genes encoding glyphosate N-acetyltransferase. See, for example, U.S. Pat. Nos. 7,462,481; 7,405,074 and US Patent Application Publication Number US 2008/0234130. A DNA molecule encoding a mutant aroA gene can be obtained under ATCC® Accession Number 39256, and the nucleotide sequence of the mutant gene is disclosed in U.S. Pat. No. 4,769,061 to Comai. EP Application Number 0 333 033 to Kumada, et al., and U.S. Pat. No. 4,975,374 to Goodman, et al., disclose nucleotide sequences of glutamine synthetase genes which confer resistance to herbicides such as L-phosphinothricin. The nucleotide sequence of a phosphinothricin-acetyl-transferase gene is provided in EP Application Numbers 0 242 246 and 0 242 236 to Leemans, et al.; De Greef, et al., (1989) *Bio/Technology* 7:61, describe the production of transgenic plants that express chimeric bar genes coding for phosphinothricin acetyl transferase activity. See also, U.S. Pat. Nos. 5,969,213; 5,489,520; 5,550,318; 5,874,265; 5,919,675; 5,561,236; 5,648,477; 5,646,024; 6,177,616 and 5,879,903, which are incorporated herein by reference for this purpose. Exemplary genes conferring resistance to phenoxy proprionic acids and cyclohexones, such as sethoxydim and haloxyfop, are the Acc1-S1, Acc1-S2 and Acc1-S3 genes described by Marshall, et al., (1992) *Theor. Appl. Genet.* 83:435.

(C) A polynucleotide encoding a protein for resistance to herbicide that inhibits photosynthesis, such as a triazine (psbA and gs+genes) and a benzonitrile (nitrilase gene). Przibilla, et al., (1991) Plant Cell 3:169, describe the transformation of *Chlamydomonas* with plasmids encoding mutant psbA genes. Nucleotide sequences for nitrilase genes are disclosed in U.S. Pat. No. 4,810,648 to Stalker and DNA molecules containing these genes are available under ATCC® Accession Numbers 53435, 67441 and 67442. Cloning and expression of DNA coding for a glutathione S-transferase is described by Hayes, et al., (1992) *Biochem. J.* 285:173.

(D) A polynucleotide encoding a protein for resistance to Acetohydroxy acid synthase, which has been found to make plants that express this enzyme resistant to multiple types of herbicides, has been introduced into a variety of plants (see, e.g., Hattori, et al., (1995) *Mol Gen Genet.* 246:419). Other genes that confer resistance to herbicides include: a gene encoding a chimeric protein of rat cytochrome P4507A1 and yeast NADPH-cytochrome P450 oxidoreductase (Shiota, et al., (1994) *Plant Physiol* 106:17), genes for glutathione reductase and superoxide dismutase (Aono, et al., (1995) *Plant Cell Physiol* 36:1687) and genes for various phosphotransferases (Datta, et al., (1992) *Plant Mol Biol* 20:619).

(E) A polynucleotide encoding resistance to a herbicide targeting Protoporphyrinogen oxidase (protox) which is necessary for the production of chlorophyll. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306; 6,282,83 and 5,767,373 and International Publication WO 2001/12825.

(F) The aad-1 gene (originally from *Sphingobium herbicidovorans*) encodes the aryloxyalkanoate dioxygenase (AAD-1) protein. The trait confers tolerance to 2,4-dichlorophenoxyacetic acid and aryloxyphenoxypropionate (commonly referred to as “fop” herbicides such as quizalofop) herbicides. The aad-1 gene, itself, for herbicide tolerance in plants was first disclosed in WO 2005/107437 (see also, US 2009/0093366). The aad-12 gene, derived from *Delftia acidovorans*, which encodes the aryloxyalkanoate dioxygenase (AAD-12) protein that confers tolerance to 2,4-dichlorophenoxyacetic acid and pyridyloxyacetate herbicides by deactivating several herbicides with an aryloxyalkanoate moiety, including phenoxy auxin (e.g., 2,4-D, MCPA), as well as pyridyloxy auxins (e.g., fluroxypyr, triclopyr).

(G) A polynucleotide encoding a herbicide resistant dicamba monooxygenase disclosed in US Patent Application Publication 2003/0135879 for imparting dicamba tolerance;

(H) A polynucleotide molecule encoding bromoxynil nitrilase (Bxn) disclosed in U.S. Pat. No. 4,810,648 for imparting bromoxynil tolerance;

(I) A polynucleotide molecule encoding phytoene (crtl) described in Misawa, et al., (1993) *Plant J.* 4:833-840 and in Misawa, et al., (1994) *Plant J.* 6:481-489 for norflurazon tolerance.

3. Transgenes that Confer or Contribute to an Altered Grain Characteristic

Such as:

(A) Altered fatty acids, for example, by (1) Down-regulation of stearoyl-ACP to increase stearic acid content of the plant. See, Knultzon, et al., (1992) *Proc. Natl. Acad. Sci. USA* 89:2624 and WO 1999/64579 (Genes to Alter Lipid Profiles in Corn).

(2) Elevating oleic acid via FAD-2 gene modification and/or decreasing linolenic acid via FAD-3 gene modification (see, U.S. Pat. Nos. 6,063,947; 6,323,392; 6,372,965 and WO 1993/11245).

(3) Altering conjugated linolenic or linoleic acid content, such as in WO 2001/12800.

(4) Altering LEC1, AGP, Dek1, Superal1, mi1 ps, and various Ipa genes such as Ipa1, Ipa3, hpt or hggt. For example, see, WO 2002/42424, WO 1998/22604, WO 2003/011015, WO 2002/057439, WO 2003/011015, U.S. Pat. Nos. 6,423,886, 6,197,561, 6,825,397 and US Patent Application Publication Numbers US 2003/0079247, US 2003/0204870 and Rivera-Madrid, et al., (1995) *Proc. Natl. Acad. Sci.* 92:5620-5624.

(5) Genes encoding delta-8 desaturase for making long-chain polyunsaturated fatty acids (U.S. Pat. Nos. 8,058,571 and 8,338,152), delta-9 desaturase for lowering saturated fats (U.S. Pat. No. 8,063,269), *Primula* Δ6-desaturase for improving omega-3 fatty acid profiles.

(6) Isolated nucleic acids and proteins associated with lipid and sugar metabolism regulation, in particular, lipid metabolism protein (LMP) used in methods of producing transgenic plants and modulating levels of seed storage compounds including lipids, fatty acids, starches or seed storage proteins and use in methods of modulating the seed size, seed number, seed weights, root length and leaf size of plants (EP 2404499).

(7) Altering expression of a High-Level Expression of Sugar-Inducible 2 (HSI2) protein in the plant to increase or decrease expression of HSI2 in the plant. Increasing expression of HSI2 increases oil content while decreasing expression of HSI2 decreases abscisic acid sensitivity and/or increases drought resistance (US Patent Application Publication Number 2012/0066794).

(8) Expression of cytochrome b5 (Cb5) alone or with FAD2 to modulate oil content in plant seed, particularly to increase the levels of omega-3 fatty acids and improve the ratio of omega-6 to omega-3 fatty acids (US Patent Application Publication Number 2011/0191904).

(9) Nucleic acid molecules encoding wrinkled1-like polypeptides for modulating sugar metabolism (U.S. Pat. No. 8,217,223).

(B) Altered phosphorus content, for example, by the (1) Introduction of a phytase-encoding gene would enhance breakdown of phytate, adding more free phosphate to the transformed plant. For example, see, Van Hartingsveldt, et al., (1993) *Gene* 127:87, for a disclosure of the nucleotide sequence of an *Aspergillus niger* phytase gene.

(2) Modulating a gene that reduces phytate content. In maize, this, for example, could be accomplished, by cloning and then re-introducing DNA associated with one or more of the alleles, such as the LPA alleles, identified in maize mutants characterized by low levels of phytic acid, such as in WO 2005/113778 and/or by altering inositol kinase activity as in WO 2002/059324, US Patent Application Publication Number 2003/0009011, WO 2003/027243, US Patent Application Publication Number 2003/0079247, WO 1999/05298, U.S. Pat. Nos. 6,197,561, 6,291,224, 6,391,348, WO 2002/059324, US Patent Application Publication Number 2003/0079247, WO 1998/45448, WO 1999/55882, WO 2001/04147.

(C) Altered carbohydrates affected, for example, by altering a gene for an enzyme that affects the branching pattern of starch or, a gene altering thioredoxin such as NTR and/or TRX (see, U.S. Pat. No. 6,531,648. which is incorporated by reference for this purpose) and/or a gamma zein knock out or mutant such as cs27 or TUSC27 or en27 (see, U.S. Pat. No. 6,858,778 and US Patent Application Publication Number 2005/0160488, US Patent Application Publication Number 2005/0204418, which are incorporated by reference for this purpose). See, Shiroza, et al., (1988) J. Bacteriol. 170:810 (nucleotide sequence of *Streptococcus* mutant fructosyltransferase gene), Steinmetz, et al., (1985) *Mol. Gen. Genet.* 200:220 (nucleotide sequence of *Bacillus subtilis* levansucrase gene), Pen, et al., (1992) *Bio/Technology* 10:292 (production of transgenic plants that express *Bacillus licheniformis* alpha-amylase), Elliot, et al., (1993) *Plant Molec. Biol.* 21:515 (nucleotide sequences of tomato invertase genes), Søgaard, et al., (1993) *J. Biol. Chem.* 268:22480 (site-directed mutagenesis of barley alpha-amylase gene) and Fisher, et al., (1993) *Plant Physiol.* 102:1045 (maize endosperm starch branching enzyme II), WO 1999/10498 (improved digestibility and/or starch extraction through modification of UDP-D-xylose 4-epimerase, Fragile 1 and 2, Ref1, HCHL, C4H), U.S. Pat. No. 6,232,529 (method of producing high oil seed by modification of starch levels (AGP)). The fatty acid modification genes mentioned herein may also be used to affect starch content and/or composition through the interrelationship of the starch and oil pathways.

(D) Altered antioxidant content or composition, such as alteration of tocopherol or tocotrienols. For example, see, U.S. Pat. No. 6,787,683, US Patent Application Publication Number 2004/0034886 and WO 2000/68393 involving the manipulation of antioxidant levels and WO 2003/082899 through alteration of a homogentisate geranyl geranyl transferase (hggt).

(E) Altered essential seed amino acids. For example, see, U.S. Pat. No. 6,127,600 (method of increasing accumulation of essential amino acids in seeds), U.S. Pat. No. 6,080,913 (binary methods of increasing accumulation of essential amino acids in seeds), U.S. Pat. No. 5,990,389 (high lysine), WO 1999/40209 (alteration of amino acid compositions in seeds), WO 1999/29882 (methods for altering amino acid content of proteins), U.S. Pat. No. 5,850,016 (alteration of amino acid compositions in seeds), WO 1998/20133 (proteins with enhanced levels of essential amino acids), U.S. Pat. No.

5,885,802 (high methionine), U.S. Pat. No. 5,885,801 (high threonine), U.S. Pat. No. 6,664,445 (plant amino acid biosynthetic enzymes), U.S. Pat. No. 6,459,019 (increased lysine and threonine), U.S. Pat. No. 6,441,274 (plant tryptophan synthase beta subunit), U.S. Pat. No. 6,346,403 (methionine metabolic enzymes), U.S. Pat. No. 5,939,599 (high sulfur), U.S. Pat. No. 5,912,414 (increased methionine), WO 1998/56935 (plant amino acid biosynthetic enzymes), WO 1998/45458 (engineered seed protein having higher percentage of essential amino acids), WO 1998/42831 (increased lysine), U.S. Pat. No. 5,633,436 (increasing sulfur amino acid content), U.S. Pat. No. 5,559,223 (synthetic storage proteins with defined structure containing programmable levels of essential amino acids for improvement of the nutritional value of plants), WO 1996/01905 (increased threonine), WO 1995/15392 (increased lysine), US Patent Application Publication Number 2003/0163838, US Patent Application Publication Number 2003/0150014, US Patent Application Publication Number 2004/0068767, U.S. Pat. No. 6,803,498, WO 2001/79516.

4. Genes that Control Male-Sterility:

There are several methods of conferring genetic male sterility available, such as multiple mutant genes at separate locations within the genome that confer male sterility, as disclosed in U.S. Pat. Nos. 4,654,465 and 4,727,219 to Brar, et al., and chromosomal translocations as described by Patterson in U.S. Pat. Nos. 3,861,709 and 3,710,511. In addition to these methods, Albertsen, et al., U.S. Pat. No. 5,432,068, describe a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant; and thus creating a plant that is male sterile because the inducible promoter is not "on" resulting in the male fertility gene not being transcribed. Fertility is restored by inducing or turning "on", the promoter, which in turn allows the gene that, confers male fertility to be transcribed.

(A) Introduction of a deacetylase gene under the control of a tapetum-specific promoter and with the application of the chemical N-Ac-PPT (WO 2001/29237).

(B) Introduction of various stamen-specific promoters (WO 1992/13956, WO 1992/13957).

(C) Introduction of the barnase and the barstar gene (Paul, et al., (1992) *Plant Mol. Biol.* 19:611-622).

For additional examples of nuclear male and female sterility systems and genes, see also, U.S. Pat. Nos. 5,859,341; 6,297,426; 5,478,369; 5,824,524; 5,850,014 and 6,265,640, all of which are hereby incorporated by reference.

5. Genes that Create a Site for Site Specific DNA Integration.

This includes the introduction of FRT sites that may be used in the FLP/FRT system and/or Lox sites that may be used in the Cre/Loxp system. For example, see, Lyznik, et al., (2003) *Plant Cell Rep* 21:925-932 and WO 1999/25821, which are hereby incorporated by reference. Other systems that may be used include the Gin recombinase of phage Mu (Maeser, et al., (1991) Vicki Chandler, The Maize Handbook ch. 118 (Springer-Verlag 1994), the Pin recombinase of *E. coli* (Enomoto, et al., 1983) and the R/RS system of the pSRi plasmid (Araki, et al., 1992).

6. Genes that Affect Abiotic Stress Resistance

Including but not limited to flowering, ear and seed development, enhancement of nitrogen utilization efficiency, altered nitrogen responsiveness, drought resistance or tolerance, cold resistance or tolerance and salt resistance or tolerance and increased yield under stress.

(A) For example, see: WO 2000/73475 where water use efficiency is altered through alteration of malate; U.S. Pat. Nos. 5,892,009, 5,965,705, 5,929,305, 5,891,859, 6,417,428, 6,664,446, 6,706,866, 6,717,034, 6,801,104, WO 2000/060089, WO 2001/026459, WO 2001/035725, WO 2001/034726, WO 2001/035727, WO 2001/036444, WO 2001/036597, WO 2001/036598, WO 2002/015675, WO 2002/017430, WO 2002/077185, WO 2002/079403, WO 2003/013227, WO 2003/013228, WO 2003/014327, WO 2004/031349, WO 2004/076638, WO 199809521.

(B) WO 199938977 describing genes, including CBF genes and transcription factors effective in mitigating the negative effects of freezing, high salinity and drought on plants, as well as conferring other positive effects on plant phenotype.

(C) US Patent Application Publication Number 2004/0148654 and WO 2001/36596 where abscisic acid is altered in plants resulting in improved plant phenotype such as increased yield and/or increased tolerance to abiotic stress.

(D) WO 2000/006341, WO 2004/090143, U.S. Pat. Nos. 7,531,723 and 6,992,237 where cytokinin expression is modified resulting in plants with increased stress tolerance, such as drought tolerance, and/or increased yield. Also, see: WO 2002/02776, WO 2003/052063, JP 2002/281975, U.S. Pat. No. 6,084,153, WO 2001/64898, U.S. Pat. Nos. 6,177,275 and 6,107,547 (enhancement of nitrogen utilization and altered nitrogen responsiveness).

(E) For ethylene alteration, see, US Patent Application Publication Number 2004/0128719, US Patent Application Publication Number 2003/0166197 and WO 2000/32761.

(F) For plant transcription factors or transcriptional regulators of abiotic stress, see, e.g., US Patent Application Publication Number 2004/0098764 or US Patent Application Publication Number 2004/0078852.

(G) Genes that increase expression of vacuolar pyrophosphatase such as AVP1 (U.S. Pat. No. 8,058,515) for increased yield; nucleic acid encoding a HSFA4 or a HSFA5 (Heat Shock Factor of the class A4 or A5) polypeptides, an oligopeptide transporter protein (OPT4-like) polypeptide; a plastochron2-like (PLA2-like) polypeptide or a Wuschel related homeobox 1-like (WOX1-like) polypeptide (U. Patent Application Publication Number US 2011/0283420).

(H) Down regulation of polynucleotides encoding poly (ADP-ribose) polymerase (PARP) proteins to modulate programmed cell death (U.S. Pat. No. 8,058,510) for increased vigor.

(I) Polynucleotide encoding DTP21 polypeptides for conferring drought resistance (US Patent Application Publication Number US 2011/0277181).

(J) Nucleotide sequences encoding ACC Synthase 3 (ACS3) proteins for modulating development, modulating response to stress, and modulating stress tolerance (US Patent Application Publication Number US 2010/0287669).

(K) Polynucleotides that encode proteins that confer a drought tolerance phenotype (DTP) for conferring drought resistance (WO 2012/058528).

(L) Tocopherol cyclase (TC) genes for conferring drought and salt tolerance (US Patent Application Publication Number 2012/0272352).
(M) CAAX amino terminal family proteins for stress tolerance (U.S. Pat. No. 8,338,661).
(N) Mutations in the SAL1 encoding gene have increased stress tolerance, including increased drought resistant (US Patent Application Publication Number 2010/0257633).
(O) Expression of a nucleic acid sequence encoding a polypeptide selected from the group consisting of: GRF polypeptide, RAA1-like polypeptide, SYR polypeptide, ARKL polypeptide, and YTP polypeptide increasing yield-related traits (US Patent Application Publication Number 2011/0061133).
(P) Modulating expression in a plant of a nucleic acid encoding a Class III Trehalose Phosphate Phosphatase (TPP) polypeptide for enhancing yield-related traits in plants, particularly increasing seed yield (US Patent Application Publication Number 2010/0024067).

Other genes and transcription factors that affect plant growth and agronomic traits such as yield, flowering, plant growth and/or plant structure, can be introduced or introgressed into plants, see e.g., WO 1997/49811 (LHY), WO 1998/56918 (ESD4), WO 1997/10339 and U.S. Pat. No. 6,573,430 (TFL), U.S. Pat. No. 6,713,663 (FT), WO 1996/14414 (CON), WO 1996/38560, WO 2001/21822 (VRN1), WO 2000/44918 (VRN2), WO 1999/49064 (GI), WO 2000/46358 (FR1), WO 1997/29123, U.S. Pat. Nos. 6,794,560, 6,307,126 (GAI), WO 1999/09174 (D8 and Rht) and WO 2004/076638 and WO 2004/031349 (transcription factors).

7. Genes that Confer Increased Yield
(A) A transgenic crop plant transformed by a 1-Amino-Cyclopropane-1-Carboxylate Deaminase-like Polypeptide (ACCDP) coding nucleic acid, wherein expression of the nucleic acid sequence in the crop plant results in the plant's increased root growth, and/or increased yield, and/or increased tolerance to environmental stress as compared to a wild type variety of the plant (U.S. Pat. No. 8,097,769).
(B) Over-expression of maize zinc finger protein gene (Zm-ZFP1) using a seed preferred promoter has been shown to enhance plant growth, increase kernel number and total kernel weight per plant (US Patent Application Publication Number 2012/0079623).
(C) Constitutive over-expression of maize lateral organ boundaries (LOB) domain protein (Zm-LOBDP1) has been shown to increase kernel number and total kernel weight per plant (US Patent Application Publication Number 2012/0079622).
(D) Enhancing yield-related traits in plants by modulating expression in a plant of a nucleic acid encoding a VIM1 (Variant in Methylation 1-like polypeptide or a VTC2-like (GDP-L-galactose phosphorylase) polypeptide or a DUF1685 polypeptide or an ARF6-like (Auxin Responsive Factor) polypeptide (WO 2012/038893).
(E) Modulating expression in a plant of a nucleic acid encoding a Ste20-like polypeptide or a homologue thereof gives plants having increased yield relative to control plants (EP 2431472).
(F) Genes encoding nucleoside diphosphatase kinase (NDK) polypeptides and homologs thereof for modifying the plant's root architecture (US Patent Application Publication Number 2009/0064373).

8. Genes that Confer Plant Digestibility.
(A) Altering the level of xylan present in the cell wall of a plant by modulating expression of xylan synthase (U.S. Pat. No. 8,173,866).

In some embodiments, the stacked trait may be a trait or event that has received regulatory approval including but not limited to the events with regulatory approval can be found at the Center for Environmental Risk Assessment (cera-gmc.org/?action=gm_crop_database, which can be accessed using the www prefix) and at the International Service for the Acquisition of Agri-Biotech Applications (isaaa.org/gmapprovaldatabase/default.asp, which can be accessed using the www prefix).

Gene Silencing

In some embodiments, the stacked trait may be in the form of silencing of one or more polynucleotides of interest resulting in suppression of one or more target pest polypeptides. In some embodiments, the silencing is achieved using a suppression DNA construct.

In some embodiments one or more polynucleotide encoding the polypeptides of the IPD103 polypeptide or fragments or variants thereof may be stacked with one or more polynucleotides encoding one or more polypeptides having insecticidal activity or agronomic traits as set forth supra and optionally may further include one or more polynucleotides providing for gene silencing of one or more target polynucleotides as discussed infra.

"Suppression DNA construct" is a recombinant DNA construct which when transformed or stably integrated into the genome of the plant, results in "silencing" of a target gene in the plant. The target gene may be endogenous or transgenic to the plant. "Silencing," as used herein with respect to the target gene, refers generally to the suppression of levels of mRNA or protein/enzyme expressed by the target gene, and/or the level of the enzyme activity or protein functionality. The term "suppression" includes lower, reduce, decline, decrease, inhibit, eliminate and prevent. "Silencing" or "gene silencing" does not specify mechanism and is inclusive, and not limited to, anti-sense, cosuppression, viral-suppression, hairpin suppression, stem-loop suppression, RNAi-based approaches and small RNA-based approaches.

A suppression DNA construct may comprise a region derived from a target gene of interest and may comprise all or part of the nucleic acid sequence of the sense strand (or antisense strand) of the target gene of interest. Depending upon the approach to be utilized, the region may be 100% identical or less than 100% identical (e.g., at least 50% or any integer between 51% and 100% identical) to all or part of the sense strand (or antisense strand) of the gene of interest.

Suppression DNA constructs can be constructed once the target gene of interest is selected, and include, without limitation, cosuppression constructs, antisense constructs, viral-suppression constructs, hairpin suppression constructs, stem-loop suppression constructs, double-stranded RNA-producing constructs, and more generally, RNAi (RNA interference) constructs and small RNA constructs such as siRNA (short interfering RNA) constructs and miRNA (microRNA) constructs.

"Antisense inhibition" refers to the production of antisense RNA transcripts capable of suppressing the expression of the target protein.

"Antisense RNA" refers to an RNA transcript that is complementary to all or part of a target primary transcript or mRNA and that blocks the expression of a target isolated nucleic acid fragment. The complementarity of an antisense RNA may be with any part of the specific gene transcript, i.e., at the 5' non-coding sequence, 3' non-coding sequence, introns or the coding sequence.

"Cosuppression" refers to the production of sense RNA transcripts capable of suppressing the expression of the target protein. "Sense" RNA refers to RNA transcript that includes the mRNA and can be translated into protein within a cell or in vitro. Cosuppression constructs in plants have been previously designed by focusing on overexpression of a nucleic acid sequence having homology to a native mRNA, in the sense orientation, which results in the reduction of all RNA having homology to the overexpressed sequence (see, Vaucheret, et al., (1998) *Plant J.* 16:651-659 and Gura, (2000) *Nature* 404:804-808).

Another variation describes the use of plant viral sequences to direct the suppression of proximal mRNA encoding sequences (PCT Publication WO 1998/36083).

Recent work has described the use of "hairpin" structures that incorporate all or part, of an mRNA encoding sequence in a complementary orientation that results in a potential "stem-loop" structure for the expressed RNA (PCT Publication WO 1999/53050). In this case the stem is formed by polynucleotides corresponding to the gene of interest inserted in either sense or anti-sense orientation with respect to the promoter and the loop is formed by some polynucleotides of the gene of interest, which do not have a complement in the construct. This increases the frequency of cosuppression or silencing in the recovered transgenic plants. For review of hairpin suppression, see, Wesley, et al., (2003) Methods in Molecular Biology, Plant Functional Genomics: Methods and Protocols 236:273-286.

A construct where the stem is formed by at least 30 nucleotides from a gene to be suppressed and the loop is formed by a random nucleotide sequence has also effectively been used for suppression (PCT Publication WO 1999/61632).

The use of poly-T and poly-A sequences to generate the stem in the stem-loop structure has also been described (PCT Publication WO 2002/00894).

Yet another variation includes using synthetic repeats to promote formation of a stem in the stem-loop structure. Transgenic organisms prepared with such recombinant DNA fragments have been shown to have reduced levels of the protein encoded by the nucleotide fragment forming the loop as described in PCT Publication WO 2002/00904.

RNA interference refers to the process of sequence-specific post-transcriptional gene silencing in animals mediated by short interfering RNAs (siRNAs) (Fire, et al., (1998) *Nature* 391:806). The corresponding process in plants is commonly referred to as post-transcriptional gene silencing (PTGS) or RNA silencing and is also referred to as quelling in fungi. The process of post-transcriptional gene silencing is thought to be an evolutionarily-conserved cellular defense mechanism used to prevent the expression of foreign genes and is commonly shared by diverse flora and phyla (Fire, et al., (1999) *Trends Genet.* 15:358). Such protection from foreign gene expression may have evolved in response to the production of double-stranded RNAs (dsRNAs) derived from viral infection or from the random integration of transposon elements into a host genome via a cellular response that specifically destroys homologous single-stranded RNA of viral genomic RNA. The presence of dsRNA in cells triggers the RNAi response through a mechanism that has yet to be fully characterized.

The presence of long dsRNAs in cells stimulates the activity of a ribonuclease III enzyme referred to as dicer. Dicer is involved in the processing of the dsRNA into short pieces of dsRNA known as short interfering RNAs (siRNAs) (Berstein, et al., (2001) *Nature* 409:363). Short interfering RNAs derived from dicer activity are typically about 21 to about 23 nucleotides in length and comprise about 19 base pair duplexes (Elbashir, et al., (2001) *Genes Dev.* 15:188). Dicer has also been implicated in the excision of 21- and 22-nucleotide small temporal RNAs (stRNAs) from precursor RNA of conserved structure that are implicated in translational control (Hutvagner, et al., (2001) *Science* 293:834). The RNAi response also features an endonuclease complex, commonly referred to as an RNA-induced silencing complex (RISC), which mediates cleavage of single-stranded RNA having sequence complementarity to the antisense strand of the siRNA duplex. Cleavage of the target RNA takes place in the middle of the region complementary to the antisense strand of the siRNA duplex (Elbashir, et al., (2001) *Genes Dev.* 15:188). In addition, RNA interference can also involve small RNA (e.g., miRNA) mediated gene silencing, presumably through cellular mechanisms that regulate chromatin structure and thereby prevent transcription of target gene sequences (see, e.g., Allshire, (2002) *Science* 297:1818-1819; Volpe, et al., (2002) *Science* 297:1833-1837; Jenuwein, (2002) *Science* 297:2215-2218 and Hall, et al., (2002) *Science* 297:2232-2237). As such, miRNA molecules of the disclosure can be used to mediate gene silencing via interaction with RNA transcripts or alternately by interaction with particular gene sequences, wherein such interaction results in gene silencing either at the transcriptional or post-transcriptional level.

Methods and compositions are further provided which allow for an increase in RNAi produced from the silencing element. In such embodiments, the methods and compositions employ a first polynucleotide comprising a silencing element for a target pest sequence operably linked to a promoter active in the plant cell; and, a second polynucleotide comprising a suppressor enhancer element comprising the target pest sequence or an active variant or fragment thereof operably linked to a promoter active in the plant cell. The combined expression of the silencing element with suppressor enhancer element leads to an increased amplification of the inhibitory RNA produced from the silencing element over that achievable with only the expression of the silencing element alone. In addition to the increased amplification of the specific RNAi species itself, the methods and compositions further allow for the production of a diverse population of RNAi species that can enhance the effectiveness of disrupting target gene expression. As such, when the suppressor enhancer element is expressed in a plant cell in combination with the silencing element, the methods and composition can allow for the systemic production of RNAi throughout the plant; the production of greater amounts of RNAi than would be observed with just the silencing element construct alone; and, the improved loading of RNAi into the phloem of the plant, thus providing better control of phloem feeding insects by an RNAi approach. Thus, the various methods and compositions provide improved methods for the delivery of inhibitory RNA to the target organism. See, for example, US Patent Application Publication 2009/0188008.

As used herein, a "suppressor enhancer element" comprises a polynucleotide comprising the target sequence to be suppressed or an active fragment or variant thereof. It is recognized that the suppressor enhancer element need not be identical to the target sequence, but rather, the suppressor enhancer element can comprise a variant of the target sequence, so long as the suppressor enhancer element has sufficient sequence identity to the target sequence to allow for an increased level of the RNAi produced by the silencing element over that achievable with only the expression of the silencing element. Similarly, the suppressor enhancer element can comprise a fragment of the target sequence, wherein the fragment is of sufficient length to allow for an increased level of the RNAi produced by the silencing element over that achievable with only the expression of the silencing element.

It is recognized that multiple suppressor enhancer elements from the same target sequence or from different target sequences or from different regions of the same target sequence can be employed. For example, the suppressor enhancer elements employed can comprise fragments of the target sequence derived from different region of the target sequence (i.e., from the 3'UTR, coding sequence, intron, and/or 5'UTR). Further, the suppressor enhancer element can be contained in an expression cassette, as described elsewhere herein, and in specific embodiments, the suppressor enhancer element is on the same or on a different DNA vector or construct as the silencing element. The suppressor enhancer element can be operably linked to a promoter as disclosed herein. It is recognized that the suppressor enhancer element can be expressed constitutively or alternatively, it may be produced in a stage-specific manner employing the various inducible or tissue-preferred or developmentally regulated promoters that are discussed elsewhere herein.

In specific embodiments, employing both a silencing element and the suppressor enhancer element the systemic production of RNAi occurs throughout the entire plant. In further embodiments, the plant or plant parts of the disclosure have an improved loading of RNAi into the phloem of the plant than would be observed with the expression of the silencing element construct alone and, thus provide better control of phloem feeding insects by an RNAi approach. In specific embodiments, the plants, plant parts and plant cells of the disclosure can further be characterized as allowing for the production of a diversity of RNAi species that can enhance the effectiveness of disrupting target gene expression.

In specific embodiments, the combined expression of the silencing element and the suppressor enhancer element increases the concentration of the inhibitory RNA in the plant cell, plant, plant part, plant tissue or phloem over the level that is achieved when the silencing element is expressed alone.

As used herein, an "increased level of inhibitory RNA" comprises any statistically significant increase in the level of RNAi produced in a plant having the combined expression when compared to an appropriate control plant. For example, an increase in the level of RNAi in the plant, plant part or the plant cell can comprise at least about a 1%, about a 1%-5%, about a 5%-10%, about a 10%-20%, about a 20%-30%, about a 30%-40%, about a 40%-50%, about a 50%-60%, about 60-70%, about 70%-80%, about a 80%-90%, about a 90%-100% or greater increase in the level of RNAi in the plant, plant part, plant cell or phloem when compared to an appropriate control. In other embodiments, the increase in the level of RNAi in the plant, plant part, plant cell or phloem can comprise at least about a 1 fold, about a 1 fold-5 fold, about a 5 fold-10 fold, about a 10 fold-20 fold, about a 20 fold-30 fold, about a 30 fold-40 fold, about a 40 fold-50 fold, about a 50 fold-60 fold, about 60 fold-70 fold, about 70 fold-80 fold, about a 80 fold-90 fold, about a 90 fold-100 fold or greater increase in the level of RNAi in the plant, plant part, plant cell or phloem when compared to an appropriate control. Examples of combined expression of the silencing element with suppressor enhancer element for the control of Stinkbugs and *Lygus* can be found in US Patent Application Publication 2011/0301223 and US Patent Application Publication 2009/0192117.

Some embodiments relate to down-regulation of expression of target genes in insect pest species by interfering ribonucleic acid (RNA) molecules. PCT Publication WO 2007/074405 describes methods of inhibiting expression of target genes in invertebrate pests including Colorado potato beetle. PCT Publication WO 2005/110068 describes methods of inhibiting expression of target genes in invertebrate pests including in particular Western corn rootworm as a means to control insect infestation. Furthermore, PCT Publication WO 2009/091864 describes compositions and methods for the suppression of target genes from insect pest species including pests from the *Lygus* genus. Nucleic acid molecules including RNAi for targeting the vacuolar ATPase H subunit, useful for controlling a coleopteran pest population and infestation as described in US Patent Application Publication 2012/0198586. PCT Publication WO 2012/055982 describes ribonucleic acid (RNA or double stranded RNA) that inhibits or down regulates the expression of a target gene that encodes: an insect ribosomal protein such as the ribosomal protein L19, the ribosomal protein L40 or the ribosomal protein S27A; an insect proteasome subunit such as the Rpn6 protein, the Pros 25, the Rpn2 protein, the proteasome beta 1 subunit protein or the Pros beta 2 protein; an insect ζ-coatomer of the COPI vesicle, the γ-coatomer of the COPI vesicle, the β'-coatomer protein or the ζ-coatomer of the COPI vesicle; an insect Tetraspanine 2 A protein which is a putative transmembrane domain protein; an insect protein belonging to the actin family such as Actin 5C; an insect ubiquitin-5E protein; an insect Sec23 protein which is a GTPase activator involved in intracellular protein transport; an insect crinkled protein which is an unconventional myosin which is involved in motor activity; an insect crooked neck protein which is involved in the regulation of nuclear alternative mRNA splicing; an insect vacuolar H+-ATPase G-subunit protein and an insect Tbp-1 such as Tat-binding protein. PCT publication WO 2007/035650 describes ribonucleic acid (RNA or double stranded RNA) that inhibits or down regulates the expression of a target gene that encodes Snf7. US Patent Application publication 2011/0054007 describes polynucleotide silencing elements targeting RPS10. US Patent Application publication 2014/0275208 and US2015/0257389 describes polynucleotide silencing elements targeting RyanR and PAT3. US Patent Application Publications 2012/029750, US 20120297501, and 2012/0322660 describe interfering ribonucleic acids (RNA or double stranded RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene. US Patent Application Publication 2012/0164205 describe potential targets for interfering double stranded ribonucleic acids for inhibiting invertebrate pests including: a Chd3 Homologous Sequence, a Beta-Tubulin Homologous Sequence, a 40 kDa V-ATPase Homologous Sequence, a EF1α Homologous Sequence, a 26S Proteosome Subunit p28 Homologous Sequence, a Juvenile Hormone Epoxide Hydrolase Homologous Sequence, a Swelling Dependent Chloride Channel Protein Homologous Sequence, a Glucose-6-Phosphate 1-Dehydrogenase Protein Homologous Sequence, an Act42A Protein Homologous Sequence, a ADP-Ribosylation Factor 1 Homologous Sequence, a Transcription Factor IIB Protein Homologous Sequence, a Chitinase Homologous Sequences, a Ubiquitin Conjugating Enzyme Homologous Sequence, a Glyceraldehyde-3-Phosphate Dehydrogenase Homologous Sequence, an Ubiquitin B Homologous Sequence, a Juvenile Hormone Esterase Homolog, and an Alpha Tubuliln Homologous Sequence.

Use in Pesticidal Control

General methods for employing strains comprising a nucleic acid sequence of the embodiments or a variant thereof, in pesticide control or in engineering other organisms as pesticidal agents can be used.

Microorganism hosts that occupy the "phytosphere" (phylloplane, phyllosphere, rhizosphere, and/or rhizoplana) of one or more crops of interest may be selected. These microorganisms are selected so as to be capable of successfully competing in the particular environment with the wild-type microorganisms, provide for stable maintenance and expression of the gene expressing the IPD103 polypeptide and desirably provide for improved protection of the pesticide from environmental degradation and inactivation.

Pesticidal Compositions

In some embodiments, the active ingredients can be applied in the form of compositions and can be applied to the crop area or plant to be treated, simultaneously or in succession, with other compounds. These compounds can be fertilizers, weed killers, Cryoprotectants, surfactants, detergents, pesticidal soaps, dormant oils, polymers, and/or time-release or biodegradable carrier formulations that permit long-term dosing of a target area following a single application of the formulation. They can also be selective herbicides, chemical insecticides, virucides, microbicides, amoebicides, pesticides, fungicides, bacteriocides, nematocides molluscicides or mixtures of several of these preparations, if desired, together with further agriculturally acceptable carriers, surfactants or application-promoting adjuvants. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. Likewise, the formulations may be prepared into edible "baits" or fashioned into pest "traps" to permit feeding or ingestion by a target pest of the pesticidal formulation.

Methods of applying an active ingredient or an agrochemical composition that contains at least one of the IPD103 polypeptide produced by the bacterial strains include leaf application, seed coating and soil application. The number of applications and the rate of application depend on the intensity of infestation by the corresponding pest.

The composition may be formulated as a powder, dust, pellet, granule, spray, emulsion, colloid, solution or such like, and may be prepared by such conventional means as desiccation, lyophilization, homogenation, extraction, filtration, centrifugation, sedimentation or concentration of a culture of cells comprising the polypeptide. In all such compositions that contain at least one such pesticidal polypeptide, the polypeptide may be present in a concentration of from about 1% to about 99% by weight.

Lepidopteran, Dipteran, Heteropteran, nematode, Hemiptera or Coleopteran pests may be killed or reduced in numbers in a given area by the methods of the disclosure or may be prophylactically applied to an environmental area to prevent infestation by a susceptible pest. Preferably the pest ingests or is contacted with, a pesticidally-effective amount of the polypeptide. "Pesticidally-effective amount" as used herein refers to an amount of the pesticide that is able to bring about death to at least one pest or to noticeably reduce pest growth, feeding or normal physiological development. This amount will vary depending on such factors as, for example, the specific target pests to be controlled, the specific environment, location, plant, crop or agricultural site to be treated, the environmental conditions and the method, rate, concentration, stability, and quantity of application of the pesticidally-effective polypeptide composition. The formulations may also vary with respect to climatic conditions, environmental considerations, and/or frequency of application and/or severity of pest infestation.

The pesticide compositions described may be made by formulating the bacterial cell, Crystal and/or spore suspension or isolated protein component with the desired agriculturally-acceptable carrier. The compositions may be formulated prior to administration in an appropriate means such as lyophilized, freeze-dried, desiccated or in an aqueous carrier, medium or suitable diluent, such as saline or other buffer. The formulated compositions may be in the form of a dust or granular material or a suspension in oil (vegetable or mineral) or water or oil/water emulsions or as a wettable powder or in combination with any other carrier material suitable for agricultural application. Suitable agricultural carriers can be solid or liquid can be used. The term "agriculturally-acceptable carrier" covers all adjuvants, inert components, dispersants, surfactants, tackifiers, binders, etc. that are used in pesticide formulation technology in pesticide formulation. The formulations may be mixed with one or more solid or liquid adjuvants and prepared by various means, e.g., by homogeneously mixing, blending and/or grinding the pesticidal composition with suitable adjuvants using conventional formulation techniques. Suitable formulations and application methods are described in U.S. Pat. No. 6,468,523, herein incorporated by reference. The plants can also be treated with one or more chemical compositions, including one or more herbicide, insecticides or fungicides. Exemplary chemical compositions include: Fruits/Vegetables Herbicides: Atrazine, Bromacil, Diuron, Glyphosate, Linuron, Metribuzin, Simazine, Trifluralin, Fluazifop, Glufosinate, Halo sulfuron Gowan, Paraquat, Propyzamide, Sethoxydim, Butafenacil, Halosulfuron, Indaziflam; Fruits/Vegetables Insecticides: Aldicarb, *Bacillus thuriengiensis*, Carbaryl, Carbofuran, Chlorpyrifos, Cypermethrin, Deltamethrin, Diazinon, Malathion, Abamectin, Cyfluthrin/beta-cyfluthrin, Esfenvalerate, Lambda-cyhalothrin, Acequinocyl, Bifenazate, Methoxyfenozide, Novaluron, Chromafenozide, Thiacloprid, Dinotefuran, FluaCrypyrim, Tolfenpyrad, Clothianidin, Spirodiclofen, Gamma-cyhalothrin, Spiromesifen, Spinosad, Rynaxypyr, Cyazypyr, Spinoteram, Triflumuron, Spirotetramat, Imidacloprid, Flubendiamide, Thiodicarb, Metaflumizone, Sulfoxaflor, Cyflumetofen, Cyanopyrafen, Imidacloprid, Clothianidin, Thiamethoxam, Spinotoram, Thiodicarb, Flonicamid, Methiocarb, Emamectin-benzoate, Indoxacarb, Forthiazate, Fenamiphos, Cadusaphos, Pyriproxifen, Fenbutatin-oxid, Hexthiazox, Methomyl, 4-[[(6-Chlorpyridin-3-yl)methyl](2,2-difluorethyl)amino]furan-2(5H)-on; Fruits/Vegetables Fungicides: Carbendazim, Chlorothalonil, EBDCs, Sulphur, Thiophanate-methyl, Azoxystrobin, Cymoxanil, Fluazinam, Fosetyl, Iprodione, Kresoxim-methyl, Metalaxyl/mefenoxam, Trifloxystrobin, Ethaboxam, Iprovalicarb, Trifloxystrobin, Fenhexamid, Oxpoconazole fumarate, Cyazofamid, Fenamidone, Zoxamide, Picoxystrobin, Pyraclostrobin, Cyflufenamid, Boscalid; Cereals Herbicides: Isoproturon, Bromoxynil, Ioxynil, Phenoxies, Chlorsulfuron, Clodinafop, Diclofop, Diflufenican, Fenoxaprop, Florasulam, Fluoroxypyr, Metsulfuron, Triasulfuron, Flucarbazone, Iodosulfuron, Propoxycarbazone, Picolinafen, Mesosulfuron, Beflubutamid, Pinoxaden, Amidosulfuron, Thifensulfuron Methyl, Tribenuron, Flupyrsulfuron, Sulfosulfuron, Pyrasulfotole, Pyroxsulam, Flufenacet, Tralkoxydim, Pyroxasulfon; Cereals Fungicides: Carbendazim, Chlorothalonil, Azoxystrobin, Cyproconazole, Cyprodinil, Fenpropimorph, Epoxiconazole, Kresoxim-methyl, Quinoxyfen, Tebuconazole, Trifloxystrobin, Simeconazole, Picoxystrobin, Pyraclostrobin, Dimoxystrobin, Prothioconazole, Fluoxastrobin; Cereals Insecticides: Dimethoate, Lambda-cyhalthrin, Deltamethrin, alpha-Cypermethrin, β-cyfluthrin, Bifenthrin, Imidacloprid, Clothianidin, Thiamethoxam, Thiacloprid, Acetamiprid, Dinetofuran, Clorphyriphos, Metamidophos, Oxidemethon-methyl, Pirimicarb, Methiocarb; Maize Herbicides: Atrazine, Alachlor, Bromoxynil, Acetochlor, Dicamba, Clopyralid, (S—) Dimethenamid, Glufosinate, Glyphosate, Isoxaflutole, (S—) Metolachlor, Mesotrione, Nicosulfuron, Primisulfuron, Rimsulfuron, Sulcotrione, Foramsulfuron, Topramezone, Tembotrione, Saflufenacil, Thiencarbazone, Flufenacet, Pyroxasulfon; Maize Insecticides: Carbofuran, Chlorpyrifos, Bifenthrin, Fipronil, Imidacloprid, Lambda-Cyhalothrin, Tefluthrin, Terbufos, Thiamethoxam, Clothianidin, Spiromesifen, Flubendiamide, Triflumuron, Rynaxypyr, Deltamethrin, Thiodicarb, β-Cyfluthrin, Cypermethrin, Bifenthrin, Lufenuron, Triflumoron, Tefluthrin,Tebupirimphos, Ethiprole, Cyazypyr, Thiacloprid, Acetamiprid, Dinetofuran, Avermectin, Methiocarb, Spirodiclofen, Spirotetramat; Maize Fungicides: Fenitropan, Thiram, Prothioconazole, Tebuconazole, Trifloxystrobin; Rice Herbicides: Butachlor, Propanil, Azimsulfuron, Bensulfuron, Cyhalofop, Daimuron, Fentrazamide, Imazosulfuron, Mefenacet, Oxaziclomefone, Pyrazosulfuron, Pyributicarb, Quinclorac, Thiobencarb, Indanofan, Flufenacet, Fentrazamide, Halosulfuron, Oxaziclomefone, Benzobicyclon, Pyriftalid, Penoxsulam, Bispyribac, Oxadiargyl, Ethoxysulfuron, Pretilachlor, Mesotrione, Tefuryltrione, Oxadiazone, Fenoxaprop, Pyrimisulfan; Rice Insecticides: Diazinon, Fenitrothion, Fenobucarb, Monocrotophos, Benfuracarb, Buprofezin, Dinotefuran, Fipronil, Imidacloprid, Isoprocarb, Thiacloprid, Chromafenozide, Thiacloprid, Dinotefuran, Clothianidin, Ethiprole, Flubendiamide, Rynaxypyr, Deltamethrin, Acetamiprid, Thiamethoxam, Cyazypyr, Spinosad, Spinotoram, Emamectin-Benzoate, Cypermethrin, Chlorpyriphos, Cartap, Methamidophos, Etofenprox, Triazophos, 4-[[(6-Chlorpyridin-3-yl)methyl](2,2-difluorethyl)amino]furan-2(5H)-on, Carbofuran, Benfuracarb; Rice Fungicides: Thiophanate-methyl, Azoxystrobin, Carpropamid, Edifenphos, Ferimzone, Iprobenfos, Isoprothiolane, Pencycuron, Probenazole, Pyroquilon, Tricyclazole, Trifloxystrobin, Diclocymet, Fenoxanil, Simeconazole, Tiadinil; Cotton Herbicides: Diuron, Fluometuron, MSMA, Oxyfluorfen, Prometryn, Trifluralin, Carfentrazone, Clethodim, Fluazifop-butyl, Glyphosate, Norflurazon, Pendimethalin, Pyrithiobac-sodium, Trifloxysulfuron, Tepraloxydim, Glufosinate, Flumioxazin, Thidiazuron; Cotton Insecticides: Acephate, Aldicarb, Chlorpyrifos, Cypermethrin, Deltamethrin, Malathion, Monocrotophos, Abamectin, Acetamiprid, Emamectin Benzoate, Imidacloprid, Indoxacarb, Lambda-Cyhalothrin, Spinosad, Thiodicarb, Gamma-Cyhalothrin, Spiromesifen, Pyridalyl, Flonicamid, Flubendiamide, Triflumuron, Rynaxypyr, Beta-Cyfluthrin, Spirotetramat, Clothianidin, Thiamethoxam, Thiacloprid, Dinetofuran, Flubendiamide, Cyazypyr, Spinosad, Spinotoram, gamma Cyhalothrin, 4-[[(6-Chlorpyridin-3-yl)methyl](2,2-difluorethyl)amino]furan-2(5H)-on, Thiodicarb, Avermectin, Flonicamid, Pyridalyl, Spiromesifen, Sulfoxaflor, Profenophos, Thriazophos, Endosulfan; Cotton Fungicides: Etridiazole, Metalaxyl, Quintozene; Soybean Herbicides: Alachlor, Bentazone, Trifluralin, Chlorimuron-Ethyl, Cloransulam-Methyl, Fenoxaprop, Fomesafen, Fluazifop, Glyphosate, Imazamox, Imazaquin, Imazethapyr, (S-) Metolachlor, Metribuzin, Pendimethalin, Tepraloxydim, Glufosinate; Soybean Insecticides: Lambda-cyhalothrin, Methomyl, Parathion, Thiocarb, Imidacloprid, Clothianidin, Thiamethoxam, Thiacloprid, Acetamiprid, Dinetofuran, Flubendiamide, Rynaxypyr, Cyazypyr, Spinosad, Spinotoram, Emamectin-Benzoate, Fipronil, Ethiprole, Deltamethrin, β-Cyfluthrin, gamma and lambda Cyhalothrin, 4-[[(6-Chlorpyridin-3-yl)methyl](2,2-difluorethyl)amino]furan-2(5H)-on, Spirotetramat, Spinodiclofen, Triflumuron, Flonicamid, Thiodicarb, beta-Cyfluthrin; Soybean Fungicides: Azoxystrobin, Cyproconazole, Epoxiconazole, Flutriafol, Pyraclostrobin, Tebuconazole, Trifloxystrobin, Prothioconazole, Tetraconazole; Sugarbeet Herbicides: Chloridazon, Desmedipham, Ethofumesate, Phenmedipham, Triallate, Clopyralid, Fluazifop, Lenacil, Metamitron, Quinmerac, Cycloxydim, Triflusulfuron, Tepraloxydim, Quizalofop; Sugarbeet Insecticides: Imidacloprid, Clothianidin, Thiamethoxam, Thiacloprid, Acetamiprid, Dinetofuran, Deltamethrin, β-Cyfluthrin, gamma/lambda Cyhalothrin, 4-[[(6-Chlorpyridin-3-yl)methyl](2,2-difluorethyl)amino]furan-2(5H)-on, Tefluthrin, Rynaxypyr, Cyaxypyr, Fipronil, Carbofuran; Canola Herbicides: Clopyralid, Diclofop, Fluazifop, Glufosinate, Glyphosate, Metazachlor, Trifluralin Ethametsulfuron, Quinmerac, Quizalofop, Clethodim, Tepraloxydim; Canola Fungicides: Azoxystrobin, Carbendazim, Fludioxonil, Iprodione, Prochloraz, Vinclozolin; Canola Insecticides: Carbofuran organophosphates, Pyrethroids, Thiacloprid, Deltamethrin, Imidacloprid, Clothianidin, Thiamethoxam, Acetamiprid, Dinetofuran, β-Cyfluthrin, gamma and lambda Cyhalothrin, tau-Fluvaleriate, Ethiprole, Spinosad, Spinotoram, Flubendiamide, Rynaxypyr, Cyazypyr, 4-[[(6-Chlorpyridin-3-yl)methyl](2,2-difluorethyl)amino]furan-2(5H)-on.

In some embodiments, the herbicide is Atrazine, Bromacil, Diuron, Chlorsulfuron, Metsulfuron, Thifensulfuron Methyl, Tribenuron, Acetochlor, Dicamba, Isoxaflutole, Nicosulfuron, Rimsulfuron, Pyrithiobac-sodium, Flumioxazin, Chlorimuron-Ethyl, Metribuzin, Quizalofop, S-metolachlor, Hexazinne or combinations thereof.

In some embodiments, the insecticide is Esfenvalerate, Chlorantraniliprole, Methomyl, Indoxacarb, Oxamyl or combinations thereof.

Pesticidal and Insecticidal Activity

"Pest" includes but is not limited to, insects, fungi, bacteria, nematodes, mites, ticks and the like. Insect pests include insects selected from the orders Coleoptera, Diptera, Hymenoptera, Lepidoptera, Mallophaga, Homoptera, Hemiptera Orthroptera, Thysanoptera, Dermaptera, Isoptera, Anoplura, Siphonaptera, Trichoptera, etc., particularly Lepidoptera and Coleoptera.

Compounds of the embodiments display activity against insect pests, which may include economically important agronomic, forest, greenhouse, nursery ornamentals, food and fiber, public and animal health, domestic and commercial structure, household and stored product pests.

Larvae of the order Lepidoptera include, but are not limited to, armyworms, cutworms, loopers and heliothines in the family Noctuidae *Spodoptera frugiperda* JE Smith (fall armyworm); *S. exigua* Hübner (beet armyworm); *S.*

*litura* Fabricius (tobacco cutworm, cluster caterpillar); *Mamestra configurata* Walker (bertha armyworm); *M. brassicae* Linnaeus (cabbage moth); *Agrotis ipsilon* Hufnagel (black cutworm); *A. orthogonia* Morrison (western cutworm); *A. subterranea* Fabricius (granulate cutworm); *Alabama argillacea* Hübner (cotton leaf worm); *Trichoplusia ni* Hübner (cabbage looper); *Pseudoplusia includens* Walker (soybean looper); *Anticarsia gemmatalis* Hübner (velvetbean caterpillar); *Hypena scabra* Fabricius (green cloverworm); *Heliothis virescens* Fabricius (tobacco budworm); *Pseudaletia unipuncta* Haworth (armyworm); *Athetis mindara* Barnes and Mcdunnough (rough skinned cutworm); *Euxoa messoria* Harris (darksided cutworm); *Earias insulana* Boisduval (spiny bollworm); *E. vittella* Fabricius (spotted bollworm); *Helicoverpa armigera* Hübner (American bollworm); *H. zea* Boddie (corn earworm or cotton bollworm); *Melanchra picta* Harris (zebra caterpillar); *Egira* (*Xylomyges*) *curialis* Grote (citrus cutworm); borers, casebearers, webworms, coneworms, and skeletonizers from the family Pyralidae *Ostrinia nubilalis* Hübner (European corn borer); *Amyelois transitella* Walker (naval orangeworm); *Anagasta kuehniella* Zeller (Mediterranean flour moth); *Cadra cautella* Walker (almond moth); *Chilo suppressalis* Walker (rice stem borer); *C. partellus*, (sorghum borer); *Corcyra cephalonica* Stainton (rice moth); *Crambus caliginosellus* Clemens (corn root webworm); *C. teterrellus* Zincken (bluegrass webworm); *Cnaphalocrocis medinalis* Guenée (rice leaf roller); *Desmia funeralis* Hübner (grape leaffolder); *Diaphania hyalinata* Linnaeus (melon worm); *D. nitidalis* Stoll (pickleworm); *Diatraea grandiosella* Dyar (southwestern corn borer), *D. saccharalis* Fabricius (surgarcane borer); *Eoreuma loftini* Dyar (Mexican rice borer); *Ephestia elutella* Hübner (tobacco (cacao) moth); *Galleria mellonella* Linnaeus (greater wax moth); *Herpetogramma licarsisalis* Walker (sod webworm); *Homoeosoma electellum* Hulst (sunflower moth); *Elasmopalpus lignosellus* Zeller (lesser cornstalk borer); *Achroia grisella* Fabricius (lesser wax moth); *Loxostege sticticalis* Linnaeus (beet webworm); *Orthaga thyrisalis* Walker (tea tree web moth); *Maruca testulalis* Geyer (bean pod borer); *Plodia interpunctella* Hübner (Indian meal moth); *Scirpophaga incertulas* Walker (yellow stem borer); *Udea rubigalis* Guenée (celery leaftier); and leafrollers, budworms, seed worms and fruit worms in the family Tortricidae *Acleris gloverana* Walsingham (Western blackheaded budworm); *A. variana* Fernald (Eastern blackheaded budworm); *Archips argyrospila* Walker (fruit tree leaf roller); *A. rosana* Linnaeus (European leaf roller); and other *Archips* species, *Adoxophyes orana* Fischer von Rösslerstamm (summer fruit *tortrix* moth); *Cochylis hospes* Walsingham (banded sunflower moth); *Cydia latiferreana* Walsingham (filbertworm); *C. pomonella* Linnaeus (coding moth); *Platynota flavedana* Clemens (variegated leafroller); *P. stultana* Walsingham (omnivorous leafroller); *Lobesia botrana* Denis & Schiffermuller (European grape vine moth); *Spilonota ocellana* Denis & Schiffermuller (eyespotted bud moth); *Endopiza viteana* Clemens (grape berry moth); *Eupoecilia ambiguella* Hübner (vine moth); *Bonagota salubricola* Meyrick (Brazilian apple leafroller); *Grapholita molesta* Busck (oriental fruit moth); *Suleima helianthana* Riley (sunflower bud moth); *Argyrotaenia* spp.; *Choristoneura* spp.

Selected other agronomic pests in the order Lepidoptera include, but are not limited to, *Alsophila pometaria* Harris (fall cankerworm); *Anarsia lineatella* Zeller (peach twig borer); *Anisota senatoria* J. E. Smith (orange striped oakworm); *Antheraea pemyi* Guérin-Méneville (Chinese Oak Tussah Moth); *Bombyx mori* Linnaeus (Silkworm); *Bucculatrix thurberiella* Busck (cotton leaf perforator); *Colias eurytheme* Boisduval (alfalfa caterpillar); *Datana integerrima* Grote & Robinson (walnut caterpillar); *Dendrolimus sibiricus* Tschetwerikov (Siberian silk moth), *Ennomos subsignaria* Hübner (elm spanworm); *Erannis tiliaria* Harris (linden looper); *Euproctis chrysorrhoea* Linnaeus (browntail moth); *Harrisina americana* Guérin-Méneville (grapeleaf skeletonizer); *Hemileuca oliviae* Cockrell (range caterpillar); *Hyphantria cunea* Drury (fall webworm); *Keiferia lycopersicella* Walsingham (tomato pinworm); *Lambdina fiscellaria fiscellaria* Hulst (Eastern hemlock looper); *L. fiscellaria lugubrosa* Hulst (Western hemlock looper); *Leucoma salicis* Linnaeus (satin moth); *Lymantria dispar* Linnaeus (gypsy moth); *Manduca quinquemaculata* Haworth (five spotted hawk moth, tomato hornworm); *M. sexta* Haworth (tomato hornworm, tobacco hornworm); *Operophtera brumata* Linnaeus (winter moth); *Paleacrita vernata* Peck (spring cankerworm); *Papilio cresphontes* Cramer (giant swallowtail orange dog); *Phryganidia californica* Packard (California oakworm); *Phyllocnistis citrella* Stainton (citrus leafminer); *Phyllonorycter blancardella* Fabricius (spotted tentiform leafminer); *Pieris brassicae* Linnaeus (large white butterfly); *P. rapae* Linnaeus (small white butterfly); *P. napi* Linnaeus (green veined white butterfly); *Platyptilia carduidactyla* Riley (artichoke plume moth); *Plutella xylostella* Linnaeus (diamondback moth); *Pectinophora gossypiella* Saunders (pink bollworm); *Pontia protodice* Boisduval and Leconte (Southern cabbageworm); *Sabulodes aegrotata* Guenée (omnivorous looper); *Schizura concinna* J. E. Smith (red humped caterpillar); *Sitotroga cerealella* Olivier (Angoumois grain moth); *Thaumetopoea pityocampa* Schiffermuller (pine processionary caterpillar); *Tineola bisselliella* Hummel (webbing clothesmoth); *Tuta absoluta* Meyrick (tomato leafminer); *Yponomeuta padella* Linnaeus (ermine moth); *Heliothis subflexa* Guenée; *Malacosoma* spp. and *Orgyia* spp.

Of interest are larvae and adults of the order Lepidoptera, Family Noctuidae, Subfamily Heliothinae. The Heliothinae subfamily includes the following genera: *Adisura, Aedophron, Australothis, Baptarma, Chazaria, Derrima, Eutricopis, Hebdomochondra, Helicoverpa, Heliocheilus, Heliolonche, Heliothis, Heliothodes, Melaporphyria, Micriantha, Microhelia, Periphanes, Protadisura, Psectrotarsia, Pyrocleptria, Pyrrhia, Rhodoecia, Schinia*, and *Stenoecia.*

Of interest are larvae and adults of the order Coleoptera including weevils from the families Anthribidae, Bruchidae and Curculionidae (including, but not limited to: *Anthonomus grandis* Boheman (boll weevil); *Lissorhoptrus oryzophilus* Kuschel (rice water weevil); *Sitophilus granarius* Linnaeus (granary weevil); *S. oryzae* Linnaeus (rice weevil); *Hypera punctata* Fabricius (clover leaf weevil); *Cylindrocopturus adspersus* LeConte (sunflower stem weevil); *Smicronyx fulvus* LeConte (red sunflower seed weevil); *S. sordidus* LeConte (gray sunflower seed weevil); *Sphenophorus maidis* Chittenden (maize billbug)); flea beetles, cucumber beetles, rootworms, leaf beetles, potato beetles and leafminers in the family Chrysomelidae (including, but not limited to: *Leptinotarsa decemlineata* Say (Colorado potato beetle); *Diabrotica virgifera virgifera* LeConte (western corn rootworm); *D. barberi* Smith and Lawrence (northern corn rootworm); *D. undecimpunctata howardi* Barber (southern corn rootworm); *Chaetocnema pulicaria* Melsheimer (corn flea beetle); *Phyllotreta cruciferae* Goeze (Crucifer flea beetle); *Phyllotreta striolata* (stripped flea beetle); *Colaspis brunnea* Fabricius (grape *colaspis*); *Oulema melanopus* Linnaeus (cereal leaf beetle); *Zygogramma exclamationis* Fabricius (sunflower beetle)); beetles from the family Coccinellidae (including, but not limited to: *Epilachna varivestis* Mulsant (Mexican bean beetle)); chafers and other beetles from the family Scarabaeidae (including, but not limited to: *Popillia japonica* Newman (Japanese beetle); *Cyclocephala borealis* Arrow (northern masked chafer, white grub); *C. immaculata* Olivier (southern masked chafer, white grub); *Rhizotrogus majalis* Razoumowsky (European chafer); *Phyllophaga crinita* Burmeister (white grub); *Ligyrus gibbosus* De Geer (carrot beetle)); carpet beetles from the family Dermestidae; wireworms from the family Elateridae, *Eleodes* spp., *Melanotus* spp.; *Conoderus* spp.; *Limonius* spp.; *Agriotes* spp.; *Ctenicera* spp.; *Aeolus* spp.; bark beetles from the family Scolytidae and beetles from the family Tenebrionidae.

Adults and immatures of the order Diptera are of interest, including leafminers *Agromyza parvicornis* Loew (corn blotch leafminer); midges (including, but not limited to: *Contarinia sorghicola* Coquillett (sorghum midge); *Mayetiola destructor* Say (Hessian fly); *Sitodiplosis mosellana* Géhin (wheat midge); *Neolasioptera murtfeldtiana* Felt, (sunflower seed midge)); fruit flies (Tephritidae), *Oscinella frit* Linnaeus (fruit flies); maggots (including, but not limited to: *Delia platura* Meigen (seedcorn maggot); *D. coarctata* Fallen (wheat bulb fly) and other *Delia* spp., *Meromyza americana* Fitch (wheat stem maggot); *Musca domestica* Linnaeus (house flies); *Fannia canicularis* Linnaeus, *F. femoralis* Stein (lesser house flies); *Stomoxys calcitrans* Linnaeus (stable flies)); face flies, horn flies, blow flies, *Chrysomya* spp.; *Phormia* spp. and other muscoid fly pests, horse flies *Tabanus* spp.; bot flies *Gastrophilus* spp.; *Oestrus* spp.; cattle grubs *Hypoderma* spp.; deer flies *Chrysops* spp.; *Melophagus ovinus* Linnaeus (keds) and other *Brachycera*, mosquitoes *Aedes* spp.; *Anopheles* spp.; *Culex* spp.; black flies *Prosimulium* spp.; *Simulium* spp.; biting midges, sand flies, sciarids, and other *Nematocera*.

Included as insects of interest are adults and nymphs of the orders Hemiptera and Homoptera such as, but not limited to, adelgids from the family Adelgidae, plant bugs from the family Miridae, cicadas from the family Cicadidae, leafhoppers, *Empoasca* spp.; from the family Cicadellidae, planthoppers from the families Cixiidae, Flatidae, Fulgoroidea, lssidae and Delphacidae, treehoppers from the family Membracidae, psyllids from the family Psyllidae, whiteflies from the family Aleyrodidae, aphids from the family Aphididae, *phylloxera* from the family Phylloxeridae, mealybugs from the family Pseudococcidae, scales from the families Asterolecanidae, Coccidae, Dactylopiidae, Diaspididae, Eriococcidae Ortheziidae, Phoenicococcidae and Margarodidae, lace bugs from the family Tingidae, stink bugs from the family Pentatomidae, cinch bugs, *Blissus* spp.; and other seed bugs from the family Lygaeidae, spittlebugs from the family Cercopidae squash bugs from the family Coreidae and red bugs and cotton stainers from the family Pyrrhocoridae.

Agronomically important members from the order Homoptera further include, but are not limited to: *Acyrthisiphon pisum* Harris (pea aphid); *Aphis craccivora* Koch (cowpea aphid); *A. fabae* Scopoli (black bean aphid); *A. gossypii* Glover (cotton aphid, melon aphid); *A. maidiradicis* Forbes (corn root aphid); *A. pomi* De Geer (apple aphid); *A. spiraecola* Patch (spirea aphid); *Aulacorthum solani* Kaltenbach (foxglove aphid); *Chaetosiphon fragaefolii* Cockerell (strawberry aphid); *Diuraphis noxia* Kurdjumov/Mordvilko (Russian wheat aphid); *Dysaphis plantaginea* Paaserini (rosy apple aphid); *Eriosoma lanigerum* Hausmann (woolly apple aphid); *Brevicoryne brassicae* Linnaeus (cabbage aphid); *Hyalopterus pruni* Geoffroy (mealy plum aphid); *Lipaphis erysimi* Kaltenbach (turnip aphid); *Metopolophium dirrhodum* Walker (cereal aphid); *Macrosiphum euphorbiae* Thomas (potato aphid); *Myzus persicae* Sulzer (peach-potato aphid, green peach aphid); *Nasonovia ribisnigri* Mosley (lettuce aphid); *Pemphigus* spp. (root aphids and gall aphids); *Rhopalosiphum maidis* Fitch (corn leaf aphid); *R. padi* Linnaeus (bird cherry-oat aphid); *Schizaphis graminum* Rondani (greenbug); *Sipha flava* Forbes (yellow sugarcane aphid); *Sitobion avenae* Fabricius (English grain aphid); *Therioaphis maculata* Buckton (spotted alfalfa aphid); *Toxoptera aurantii* Boyer de Fonscolombe (black citrus aphid) and *T. citricida* Kirkaldy (brown citrus aphid); *Adelges* spp. (adelgids); *Phylloxera devastatrix* Pergande (pecan *phylloxera*); *Bemisia tabaci* Gennadius (tobacco whitefly, sweetpotato whitefly); *B. argentifolii* Bellows & Perring (silverleaf whitefly); *Dialeurodes citri* Ashmead (citrus whitefly); *Trialeurodes abutiloneus* (bandedwinged whitefly) and *T. vaporariorum* Westwood (greenhouse whitefly); *Empoasca fabae* Harris (potato leafhopper); *Laodelphax striatellus* Fallen (smaller brown planthopper); *Macrolestes quadrilineatus* Forbes (aster leafhopper); *Nephotettix cinticeps* Uhler (green leafhopper); *N. nigropictus* Stål (rice leafhopper); *Nilaparvata lugens* Stål (brown planthopper); *Peregrinus maidis* Ashmead (corn planthopper); *Sogatella furcifera* Horvath (white-backed planthopper); *Sogatodes orizicola* Muir (rice delphacid); *Typhlocyba pomaria* McAtee (white apple leafhopper); *Erythroneoura* spp. (grape leafhoppers); *Magicicada septendecim* Linnaeus (periodical cicada); *Icerya purchasi* Maskell (cottony cushion scale); *Quadraspidiotus perniciosus* Comstock (San Jose scale); *Planococcus citri* Risso (citrus mealybug); *Pseudococcus* spp. (other mealybug complex); *Cacopsylla pyricola* Foerster (pear *psylla*); *Trioza diospyri* Ashmead (persimmon *psylla*).

Agronomically important species of interest from the order Hemiptera include, but are not limited to: *Acrosternum hilare* Say (green stink bug); *Anasa tristis* De Geer (squash bug); *Blissus leucopterus leucopterus* Say (chinch bug); *Corythuca gossypii* Fabricius (cotton lace bug); *Cyrtopeltis modesta* Distant (tomato bug); *Dysdercus suturellus* Herrich-Schäffer (cotton stainer); *Euschistus servus* Say (brown stink bug); *E. variolarius* Palisot de Beauvois (one-spotted stink bug); Graptostethus spp. (complex of seed bugs); *Leptoglossus corculus* Say (leaf-footed pine seed bug); *Lygus lineolaris* Palisot de Beauvois (tarnished plant bug); L. *Hesperus* Knight (Western tarnished plant bug); *L. pratensis* Linnaeus (common meadow bug); *L. rugulipennis* Poppius (European tarnished plant bug); *Lygocoris pabulinus* Linnaeus (common green capsid); *Nezara viridula* Linnaeus (southern green stink bug); *Oebalus pugnax* Fabricius (rice stink bug); *Oncopeltus fasciatus* Dallas (large milkweed bug); *Pseudatomoscelis seriatus* Reuter (cotton fleahopper).

Furthermore, embodiments may be effective against Hemiptera such, *Calocoris norvegicus* Gmelin (strawberry bug); *Orthops campestris* Linnaeus; *Plesiocoris rugicollis* Fallen (apple capsid); *Cyrtopeltis modestus* Distant (tomato bug); *Cyrtopeltis notatus* Distant (suckfly); *Spanagonicus albofasciatus* Reuter (whitemarked fleahopper); *Diaphnocoris chlorionis* Say (honeylocust plant bug); *Labopidicola allii* Knight (onion plant bug); *Pseudatomoscelis seriatus* Reuter (cotton fleahopper); *Adelphocoris rapidus* Say (rapid plant bug); *Poecilocapsus lineatus* Fabricius (four-lined plant bug); *Nysius ericae* Schilling (false chinch bug); *Nysius raphanus* Howard (false chinch bug); *Nezara viridula* Linnaeus (Southern green stink bug); *Eutygaster* spp.; *Coreidae* spp.; *Pyrrhocoridae* spp.; *Tinidae* spp.; *Blostomatidae* spp.; *Reduviidae* spp. and *Cimicidae* spp.

Also included are adults and larvae of the order Acari (mites) such as *Aceria tosichella* Keifer (wheat curl mite); *Petrobia latens* Müller (brown wheat mite); spider mites and red mites in the family Tetranychidae, *Panonychus ulmi* Koch (European red mite); *Tetranychus urticae* Koch (two spotted spider mite); (*T. mcdanieli* McGregor (McDaniel mite); *T. cinnabarinus* Boisduval (carmine spider mite); *T. turkestani* Ugarov & Nikolski (strawberry spider mite); flat mites in the family Tenuipalpidae, *Brevipalpus lewisi* McGregor (citrus flat mite); rust and bud mites in the family Eriophyidae and other foliar feeding mites and mites important in human and animal health, i.e., dust mites in the family Epidermoptidae, follicle mites in the family Demodicidae, grain mites in the family Glycyphagidae, ticks in the order Ixodidae. *Ixodes scapularis* Say (deer tick); *I. holocyclus* Neumann (Australian paralysis tick); *Dermacentor variabilis* Say (American dog tick); *Amblyomma americanum* Linnaeus (lone star tick) and scab and itch mites in the families Psoroptidae, Pyemotidae and Sarcoptidae.

Insect pests of the order Thysanura are of interest, such as *Lepisma saccharina* Linnaeus (silverfish); *Thermobia domestica* Packard (firebrat).

Additional arthropod pests covered include: spiders in the order Araneae such as *Loxosceles reclusa* Gertsch and Mulaik (brown recluse spider) and the *Latrodectus mactans* Fabricius (black widow spider) and centipedes in the order Scutigeromorpha such as *Scutigera coleoptrata* Linnaeus (house centipede).

Insect pest of interest include the superfamily of stink bugs and other related insects including but not limited to species belonging to the family Pentatomidae (*Nezara viridula, Halyomorpha halys, Piezodorus guildini, Euschistus servus, Acrosternum hilare, Euschistus heros, Euschistus tristigmus, Acrosternum hilare, Dichelops furcatus, Dichelops melacanthus*, and *Bagrada hilaris* (Bagrada Bug)), the family Plataspidae (*Megacopta cribraria*—Bean plataspid) and the family Cydnidae (*Scaptocoris castanea*—Root stink bug) and Lepidoptera species including but not limited to: diamond-back moth, e.g., *Helicoverpa zea* Boddie; soybean looper, e.g., *Pseudoplusia includens* Walker and velvet bean caterpillar e.g., *Anticarsia gemmatalis* Hübner.

Methods for measuring pesticidal activity are known. See, for example, Czapla and Lang, (1990) *J. Econ. Entomol.* 83:2480-2485; Andrews, et al., (1988) *Biochem. J.* 252:199-206; Marrone, et al., (1985) *J. of Economic Entomology* 78:290-293 and U.S. Pat. No. 5,743,477, all of which are herein incorporated by reference in their entirety. Generally, the protein is mixed and used in feeding assays. See, for example Marrone, et al., (1985) *J. of Economic Entomology* 78:290-293. Such assays can include contacting plants with one or more pests and determining the plant's ability to survive and/or cause the death of the pests.

Nematodes include parasitic nematodes such as root-knot, cyst and lesion nematodes, including *Heterodera* spp., *Meloidogyne* spp. and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode) and *Globodera rostochiensis* and *Globodera pailida* (potato cyst nematodes). Lesion nematodes include *Pratylenchus* spp.

Seed Treatment

To protect and to enhance yield production and trait technologies, seed treatment options can provide additional crop plan flexibility and cost effective control against insects, weeds and diseases. Seed material can be treated, typically surface treated, with a composition comprising combinations of chemical or biological herbicides, herbicide safeners, insecticides, fungicides, germination inhibitors and enhancers, nutrients, plant growth regulators and activators, bactericides, nematocides, avicides and/or molluscicides. These compounds are typically formulated together with further carriers, surfactants or application-promoting adjuvants for formulation. The coatings may be applied by impregnating propagation material with a liquid formulation or by coating with a combined wet or dry formulation. Examples of the various types of compounds that may be used as seed treatments are provided in The Pesticide Manual: A World Compendium, C. D. S. Tomlin Ed., Published by the British Crop Production Council, which is hereby incorporated by reference.

Some seed treatments that may be used on crop seed include, but are not limited to, one or more of abscisic acid, acibenzolar-S-methyl, avermectin, amitrol, azaconazole, azospirillum, azadirachtin, azoxystrobin, *Bacillus* spp. (including one or more of *cereus, firmus, megaterium, pumilis, sphaericus, subtilis* and/or *thuringiensis* species), *bradyrhizobium* spp. (including one or more of *betae, canariense, elkanii, iriomotense, japonicum*, liaonigense, *pachyrhizi* and/or *yuanmingense*), captan, carboxin, chitosan, clothianidin, copper, cyazypyr, difenoconazole, etidiazole, fipronil, fludioxonil, fluoxastrobin, fluquinconazole, flurazole, fluxofenim, harpin protein, imazalil, imidacloprid, ipconazole, isoflavenoids, lipo-chitooligosaccharide, mancozeb, manganese, maneb, mefenoxam, metalaxyl, metconazole, myclobutanil, PCNB, penflufen, *penicillium*, penthiopyrad, permethrine, picoxystrobin, prothioconazole, pyraclostrobin, rynaxypyr, S-metolachlor, saponin, sedaxane, TCMTB, tebuconazole, thiabendazole, thiamethoxam, thiocarb, thiram, tolclofos-methyl, triadimenol, *trichoderma*, trifloxystrobin, triticonazole and/or zinc. PCNB seed coat refers to EPA Registration Number 00293500419, containing quintozen and terrazole. TCMTB refers to 2-(thiocyanomethylthio) benzothiazole.

Seed varieties and seeds with specific transgenic traits may be tested to determine which seed treatment options and application rates may complement such varieties and transgenic traits to enhance yield. For example, a variety with good yield potential but head smut susceptibility may benefit from the use of a seed treatment that provides protection against head smut, a variety with good yield potential but cyst nematode susceptibility may benefit from the use of a seed treatment that provides protection against cyst nematode, and so on. Likewise, a variety encompassing a transgenic trait conferring insect resistance may benefit from the second mode of action conferred by the seed treatment, a variety encompassing a transgenic trait conferring herbicide resistance may benefit from a seed treatment with a safener that enhances the plants resistance to that herbicide, etc. Further, the good root establishment and early emergence that results from the proper use of a seed treatment may result in more efficient nitrogen use, a better ability to withstand drought and an overall increase in yield potential of a variety or varieties containing a certain trait when combined with a seed treatment.

Methods for Killing an Insect Pest and Controlling an Insect Population

In some embodiments, methods are provided for protecting a plant from an insect pest, comprising expressing in the plant or cell thereof a polynucleotide encoding an IPD103 polypeptide and one or more polynucleotide selected from: a polynucleotide encoding a PtIP-83 polypeptide having insecticidal activity; a polynucleotide encoding a Cry1B polypeptide having insecticidal activity; a polynucleotide encoding a variant Cry1B polypeptide having insecticidal activity; a polynucleotide encoding a Cry1C polypeptide having insecticidal activity; a polynucleotide encoding a Cry1D polypeptide having insecticidal activity; and a polynucleotide encoding a Cry1J polypeptide having insecticidal activity.

In some embodiments, methods are provided for protecting a plant from Heliothinae pest species. In some embodiments, the Heliothinae pest species are selected from velvetbean caterpillar (VBC) *Anticarsia gemmatalis*, soybean looper (SBL) *Pseudoplusia includens*, corn earworm (CEW) *Heliothis zea*, tobacco budworm (TBW) *Heliothis virescens*, cotton bollworm (CBW) *Helicoverpa zea*, fall armyworm (FAW) *Spodoptera frugiperda*, and southern armyworm (SAW) *Spodoptera eridania*.

Insect Resistance Management (IRM) Strategies

Expression of *B. thuringiensis* δ-endotoxins in transgenic corn plants has proven to be an effective means of controlling agriculturally important insect pests (Perlak, et al., 1990; 1993). However, insects have evolved that are resistant to *B. thuringiensis* δ-endotoxins expressed in transgenic plants. Such resistance, should it become widespread, would clearly limit the commercial value of germplasm containing genes encoding such *B. thuringiensis* δ-endotoxins.

One way to increasing the effectiveness of the transgenic insecticides against target pests and contemporaneously reducing the development of insecticide-resistant pests is to use provide non-transgenic (i.e., non-insecticidal protein) refuges (a section of non-insecticidal crops/corn) for use with transgenic crops producing a single insecticidal protein active against target pests. The United States Environmental Protection Agency (epa.gov/oppbppdl/biopesticides/pips/bt_corn_refuge_2006. htm, which can be accessed using the www prefix) publishes the requirements for use with transgenic crops producing a single Bt protein active against target pests. In addition, the National Corn Growers Association, on their website: (ncga.com/insect-resistance-management-fact-sheet-bt-corn, which can be accessed using the www prefix) also provides similar guidance regarding refuge requirements. Due to losses to insects within the refuge area, larger refuges may reduce overall yield.

Another way of increasing the effectiveness of the transgenic insecticides against target pests and contemporaneously reducing the development of insecticide-resistant pests would be to have a repository of insecticidal genes that are effective against groups of insect pests and which manifest their effects through different modes of action.

Expression in a plant of two or more insecticidal compositions toxic to the same insect species, each insecticide being expressed at efficacious levels would be another way to achieve control of the development of resistance. This is based on the principle that evolution of resistance against two separate modes of action is far more unlikely than only one. Roush, for example, outlines two-toxin strategies, also called "pyramiding" or "stacking," for management of insecticidal transgenic crops. (The Royal Society. Phil. Trans. R. Soc. Lond. B. (1998) 353:1777-1786). Stacking or pyramiding of two different proteins each effective against the target pests and with little or no cross-resistance can allow for use of a smaller refuge. The US Environmental Protection Agency requires significantly less (generally 5%) structured refuge of non-Bt corn be planted than for single trait products (generally 20%). There are various ways of providing the IRM effects of a refuge, including various geometric planting patterns in the fields and in-bag seed mixtures, as discussed further by Roush.

In some embodiments, the transgene stacks of the disclosure are useful as an insect resistance management strategy in combination (i.e., pyramided) with other pesticidal proteins include but are not limited to Bt toxins, *Xenorhabdus* sp. or *Photorhabdus* sp. insecticidal proteins, other insecticidally active proteins, and the like.

Provided are methods of controlling Lepidoptera and/or Coleoptera insect infestation(s) in a transgenic plant that promote insect resistance management, comprising expressing in the plant at least two different insecticidal proteins having different modes of action.

In some embodiments, the methods of controlling Lepidoptera and/or Coleoptera insect infestation in a transgenic plant and promoting insect resistance management comprises the presentation of at least one of the IPD103 polypeptide insecticidal protein and one or more polypeptide selected from: a PtIP-83 polypeptide having insecticidal activity; a Cry1B polypeptide having insecticidal activity; a variant Cry1B polypeptide having insecticidal activity; a Cry1C polypeptide having insecticidal activity; a Cry1D polypeptide having insecticidal activity; and a Cry1J polypeptide having insecticidal activity.

Also provided are methods of reducing likelihood of emergence of Lepidoptera and/or Coleoptera insect resistance to transgenic plants expressing in the plants insecticidal proteins to control the insect species, comprising expression of an IPD103 polypeptide insecticidal to the insect species in combination with a second insecticidal protein to the insect species having different modes of action.

Also provided are means for effective Lepidoptera and/or Coleoptera insect resistance management of transgenic plants, comprising co-expressing at high levels in the plants two or more insecticidal proteins toxic to Lepidoptera and/or Coleoptera insects but each exhibiting a different mode of effectuating its killing activity, wherein the two or more insecticidal proteins comprise an IPD103 polypeptide and a Cry protein. Also provided are means for effective Lepidoptera and/or Coleoptera insect resistance management of transgenic plants, comprising co-expressing at high levels in the plants two or more insecticidal proteins toxic to Lepidoptera and/or Coleoptera insects but each exhibiting a different mode of effectuating its killing activity. In addition, methods are provided for obtaining regulatory approval for planting or commercialization of plants expressing proteins insecticidal to insects in the order Lepidoptera and/or Coleoptera, comprising the step of referring to, submitting or relying on insect assay binding data showing that the IPD103 polypeptide does not compete with binding sites for Cry proteins in such insects.

In some embodiments, the molecular stacks, breeding stacks and methods of the disclosure are useful for killing Heliothinae pests or controlling Heliothinae pest populations. In some embodiments, the Heliothinae pest is selected from velvetbean caterpillar (VBC) *Anticarsia gemmatalis*, soybean looper (SBL) *Pseudoplusia includens*, corn earworm (CEW) *Heliothis zea*, tobacco budworm (TBW) *Heliothis virescens*, cotton bollworm (CBW) *Helicoverpa zea*, fall armyworm (FAW) *Spodoptera frugiperda*, and southern armyworm (SAW) *Spodoptera eridania*.

Methods for Increasing Plant Yield

Methods for increasing plant yield are provided. The methods comprise providing a plant or plant cell expressing a polynucleotide encoding the pesticidal polypeptide sequence disclosed herein and growing the plant or a seed thereof in a field infested with a pest against which the polypeptide has pesticidal activity. In some embodiments, the polypeptide has pesticidal activity against a Lepidopteran, Coleopteran, Dipteran, Hemipteran or nematode pest, and the field is infested with a Lepidopteran, Hemipteran, Coleopteran, Dipteran or nematode pest.

As defined herein, the "yield" of the plant refers to the quality and/or quantity of biomass produced by the plant. "Biomass" as used herein refers to any measured plant product. An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase in yield compared to a plant not expressing the pesticidal sequence.

In specific methods, plant yield is increased as a result of improved pest resistance of a plant expressing an IPD103 polypeptide and one or more pesticidal polypeptides selected from a PtIP-83 polypeptide having insecticidal activity; a Cry1B polypeptide having insecticidal activity; a variant Cry1B polypeptide having insecticidal activity; a Cry1C polypeptide having insecticidal activity; a Cry1D polypeptide having insecticidal activity; and a Cry1J polypeptide having insecticidal activity. Expression of the pesticidal polypeptides results in a reduced ability of a pest to infest or feed on the plant, thus improving plant yield.

The following examples are offered by way of illustration and not by way of limitation.

EXPERIMENTALS

Example 1—Identification of Insecticidal Proteins Active Against Corn Earworm, European Corn Borer Fall Armyworm, Soybean Looper, and Velvet Bean Caterpillar from the Fern, *Athyrium niponicum* 'Red Beauty'

An insecticidal protein, IPD103Aa (SEQ ID NO: 2), was identified by protein purification, mass spectroscopy (MS) and PCR cloning from the commercial cultivar *Athyrium niponicum* 'Red Beauty', designated herein as NY15. Insecticidal activity against lepidopteran pests was observed from a protein extract from *Athyrium niponicum*, 'Red Beauty' with an artificial diet-based assay.

NY15 plant material was flash frozen in liquid nitrogen and stored at −80° C. The frozen sample was removed from storage and ground to a fine powder at liquid nitrogen temperatures with a GenoGrinder® 2010 (SPEX SamplePrep®, Metuchen, NJ). To extract protein, 5 mL Extraction Buffer (50 mM Tris, pH 8.0, 150 mM Potassium Chloride, 2.5 mM EDTA, 1.5% Polyvinylpolypyridone and "Complete, EDTA-free" protease inhibitor cocktail (Roche, Indianapolis, Indiana) was added per gram of fresh weight of NY15. The extracted material was clarified by centrifugation at 20,000 g for 10 min. The remaining cell pellet was re-extracted with ½ the volume of Extraction Buffer, centrifuged and the supernatants combined, filtered and desalted into 20 mM Tris, pH 8, using a Sephadex™ G25 (GE Healthcare, Piscataway, NJ) column and concentrated on 10 kDa molecular weight cutoff centrifugal concentrators (Sartorius Stedim, Goettingen, Germany).

Bioassays against Soybean Looper (SBL) (*Pseudoplusia includens*), Corn Earworm (CEW) (*Helicoverpa zea*) and European Corn Borer (ECB) (*Ostrinia nubialis*) were conducted using the desalted protein extract overlaid onto agar based Lepidoptera diet (Southland Products Inc., Lake Village, AR) in 96-well format. The sample was allowed to dry on top of the diet. A variable number of neonate insects (2-5) were placed individually into each well of the treated plate. The assay was run for four days at 27° C. and then scored for insect mortality, and various stages of stunting of insect growth. The scores were recorded numerically as dead (3), severely stunted (2) (little or no growth but alive and equivalent to a 1$^{st}$ instar larvae), stunted (1) (growth to second instar but not equivalent to controls), or normal (0). The crude NY15 extract scored 1 against CEW in each of 4 replicates of the diet-based assay.

For protein purification, extract of NY15 was generated as described above and the supernatant desalted into 20 mM Tris, pH 8, before loading onto a 15 mL Capto™ Q column (GE Healthcare) that was equilibrated in the same buffer. A linear 10 column volume gradient from 0 M to 0.3 M NaCl in 50 mM Tris, pH 8.0 was applied. Eluted 1 mL fractions were assayed against CEW in the bioassay described above. Activity against CEW was detected in fractions eluting at ~7 to 11 mS/cm conductivity. These fractions were pooled and desalted into 20 mM Tris, pH 8.7 and loaded onto a 1 ml MonoQ™ column (GE Healthcare) equilibrated in the same buffer. A linear 20 CV gradient to 40% Elution Buffer (20 mM Tris+0.35 M NaCl, pH 8.7) was applied and 1 mL fractions were collected. Activity against CEW was detected in fractions eluting at ~8.5-13.3 mS/cm$^2$ conductivity. Active fractions were pooled and desalted into 25 mM BisTris, pH 7.2 and loaded on a 4 mL Mono P™ column (GE Healthcare). An isocratic gradient of 100% Polybuffer 74 was applied and 1 mL eluate fractions assayed against CEW. The fractions were submitted directly as well as after concentrating with 10 kDa MWCO units. There were three regions of activity associated with the Mono P™ run, where Mono P™ fractions C2-3, C7-8 and D12 all showed activity against CEW. The first two regions were active at 1× and 4× concentration while fraction D12 showed activity only after 4× concentration. Denaturing electrophoresis of the Mono P™ fractions on LDS polyacrylamide gels indicated that the abundance of a protein band at approximately 20 kDa correlated directly with the three regions of eluted CEW activity.

Protein sequencing and identification were performed by MS analysis after protein digestion. Proteins for MS identification were obtained from running sample on an LDS-PAGE gel stained with Coomassie™ Brilliant Blue G-250 stain. The bands of interest were excised from the gel, de-stained, reduced with dithiothreitol and then alkylated with iodoacetamide. Following overnight digestion with trypsin, the samples were subjected to nano-liquid chromatography/electrospray tandem mass spectrometry (nano-LC/ESI-MS/MS) on a Thermo Q Exactive™ Orbitrap™ mass spectrometer (Thermo Fisher Scientific®, 81 Wyman Street, Waltham, MA 02454) interfaced with an Eksigent™ NanoLC™ Ultra 1-D Plus nano-lc system (AB Sciex™, 500 Old Connecticut Path, Framingham, MA 01701). Protein identification was done by database searches using Mascot® (Matrix Science, 10 Perrins Lane, London NW3 1QY UK). The searches were conducted against an in-house transcriptome database containing transcripts from the *Athyrium niponicum* 'Red Beauty', NY15 source plant and the public protein database Swiss-Prot using the Mascot search engine (Matrix Science). The amino acid sequences for all three gel bands aligned with the predicted protein from a NY15.

Example 2—Transcriptomic Sequencing of *Athyrium niponicum* 'Red Beauty' and Cloning of IPD103Aa A transcriptome for *Athyrium niponicum* 'Red Beauty' (NY15) was prepared as follows. Total RNA was isolated from frozen tissues with an RNeasy® kit (Qiagen®). Sequencing libraries from the resulting total RNAs were prepared using the TruSeq™ mRNA-Seq kit and protocol from Illumina®, Inc. (San Diego, CA). Briefly, mRNAs were isolated via attachment to oligo(dT) beads, fragmented to a mean size of 180 nt, reverse transcribed into cDNA by random hexamer prime, end repaired, 3' A-tailed, and ligated with Illumina® indexed TruSeq™ adapters. Ligated cDNA fragments were PCR amplified using Illumina® TruSeq™ primers and purified PCR products were checked for quality and quantity on the Agilent Bioanalyzer® DNA 7500 chip. Post quality and quantity assessment, 100 ng of the transcript library was normalized by treatment with Duplex Specific Nuclease (DSN) (Evrogen®, Moscow, Russia). Normalization was accomplished by addition of 200 mM Hepes buffer, followed by heat denaturation and five hour anneal at 68° C. Annealed library was treated with 2 μl of DSN enzyme for 25 minutes, purified by Qiagen® MinElute® columns according to manufacturer protocols, and amplified twelve cycles using Illumina® adapter specific primers. Final products were purified with Ampure® XP beads (Beckman Genomics, Danvers, MA) and checked for quality and quantity on the Agilent Bioanalyzer® DNA 7500 chip.

Normalized transcript libraries were sequenced according to manufacturer protocols on the Illumina® HiSeq® 2500. Libraries were pooled, hybridized and sequenced three per flowcell lane using onboard clustering methods followed by sequencing to a target depth of sixty million 75 bp paired end reads per normalized library.

Peptide sequences identified for IPD103Aa (SEQ ID NO: 2) by LCMS sequencing were searched against protein sequences predicted by open reading frames (ORFs) from the transcriptome assemblies for NY15. The peptides gave a perfect match to a transcript corresponding to IPD103Aa (SEQ ID NO: 2). The coding sequence was used to design primers to clone the IPD103Aa polynucleotide sequence (SEQ ID NO: 1). This clone was produced by polymerase chain reaction using the Kappa HiFi™ polymerase (Kapa Bioscience, Wilmington, MA) and the cDNA prepared from the total RNA from *Athyrium niponicum* 'Red Beauty' using the SuperScript® II kit (Thermo Fischer Scientific, Waltham, MA) as the template. PCR products were gel purified, digested with NdeI and XhoI restriction enzymes (New England Biolabs) and ligated into pET14b (Novagen®) also digested with the same enzymes. Colonies were sequenced to confirm the clone.

Example 3—Purification of IPD103Aa Expressed in *E. coli*

The polynucleotide of SEQ ID NO: 1, encoding IPD103Aa (SEQ ID NO: 2) was subcloned into the pET14b vector (Novagen®) using the NdeI/XhoI restriction sites in frame with the coding sequence for an N-terminal 6× His tag followed by a thrombin cleavage site. Chemically competent OverExpress® C41(DE3) SOLOs cells (Lucigen®) were transformed with pET plasmid DNA, containing the IPD103Aa gene for recombinant protein expression. The transformed *E. coli* cells were grown overnight at 37° C. with ampicillin selection and then inoculated to a fresh 2×YT medium (1:25) and further grown to an optical density of about 0.8. Protein expression was induced by adding 0.3 mM IPTG and cells were further grown at 16° C. for 16 hours. The *E. coli* expressed proteins were purified by immobilized metal ion chromatography using HisPur™ Cobalt resin (Clonetech, Mountain View, CA) according to the manufacturer's protocols. The purified fractions were desalted using PD-10 columns (GE Life Sciences, Pittsburgh, USA) pre-equilibrated with PBS buffer. The eluted protein was used in diet bioassays to evaluate the protein activity on larvae of a diversity of Lepidoptera.

Example 4—Identification of IPD103Aa Homologs and their Purification after Expression in *E. coli*

Gene identities may be determined by conducting BLAST™ (Basic Local Alignment Search Tool; Altschul, et al., (1993) *J. Mol. Biol.* 215:403-410; see also ncbi.nlm.nih.gov/BLAST/, which can be accessed using the www prefix) searches under default parameters for similarity to sequences. The polynucleotide sequence for IPD103Aa (SEQ ID NO: 1) was analyzed. Gene identities conducted by BLAST™ in a DUPONT PIONEER internal plant transcriptomes database identified multiple homologs of IPD103Aa protein (SEQ ID NO: 2). The IPD103Aa homologs and the organism they were identified from are shown in Table 1.

TABLE 1

| Gene Name | Source | Organism | DNA Seq | AA Seq |
|---|---|---|---|---|
| IPD103Aa | NY15 | *Athyrium niponicum* 'Red Beauty' | SEQ ID NO: 1 | SEQ ID NO: 2 |
| IPD103Ab | NY15 | *Athyrium niponicum* 'Red Beauty' | SEQ ID NO: 3 | SEQ ID NO: 4 |
| IPD103Ac | PS9092AF | *Platycerium wandae* | SEQ ID NO: 5 | SEQ ID NO: 6 |
| IPD103Ad | PS12349 | *Pteris ensiformis* 'Evergemiensis' | SEQ ID NO: 7 | SEQ ID NO: 8 |
| IPD103Ae | PS12349 | *Pteris ensiformis* 'Evergemiensis' | SEQ ID NO: 9 | SEQ ID NO: 10 |
| IPD103Ba | PS9092AF | *Platycerium wandae* | SEQ ID NO: 11 | SEQ ID NO: 12 |
| IPD103Bb | PS9092AF | *Platycerium wandae* | SEQ ID NO: 13 | SEQ ID NO: 14 |
| IPD103Bc | PS12409 | *Athyrium filix-femina* | SEQ ID NO: 15 | SEQ ID NO: 16 |
| IPD103Bd | PS7897CF | *Colysis wrightii* | SEQ ID NO: 17 | SEQ ID NO: 18 |
| IPD103Be | PS8837CF | *Nephrolepis falcata* | SEQ ID NO: 19 | SEQ ID NO: 20 |
| IPD103Bf | PS11699 | *Nephrolepis cordifolia* | SEQ ID NO: 21 | SEQ ID NO: 22 |
| IPD103Bg | PS13327 | *Polystichum tsus-simense* | SEQ ID NO: 23 | SEQ ID NO: 24 |
| IPD103Bh | PS13327 | *Polystichum tsus-simense* | SEQ ID NO: 25 | SEQ ID NO: 26 |
| IPD103Bi | PS12861 | *Thelypteris palustris* | SEQ ID NO: 27 | SEQ ID NO: 28 |
| IPD103Bj | PS12410 | *Athyrium filix-femina* | SEQ ID NO: 29 | SEQ ID NO: 30 |
| IPD103Bk | PS12337 | *Nephrolepis cordifolia* | SEQ ID NO: 31 | SEQ ID NO: 32 |
| IPD103Ca | PS9092AF | *Platycerium wandae* | SEQ ID NO: 33 | SEQ ID NO: 34 |

TABLE 1-continued

| Gene Name | Source | Organism | DNA Seq | AA Seq |
|---|---|---|---|---|
| IPD103Da | PS9539 | *Tectaria milnei* | SEQ ID NO: 35 | SEQ ID NO: 36 |
| IPD103Db | PS12356 | *Davallia tyermannii* | SEQ ID NO: 37 | SEQ ID NO: 38 |

cDNAs were generated from source organisms with identified homologs from the internal database by reverse transcription from total RNA. Homologs were PCR amplified from their respective cDNA's using primers designed to the coding sequences of each homolog. The PCR products were digested with NdeI/XhoI (New England Biolabs, Ipswich, MA) and ligated into a pET14b (Novagen) plasmid digested by the same enzymes. Cloned PCR products were confirmed by sequencing. The amino acid sequence identity of the IPD103Aa homologs as calculated using the Needleman-Wunsch algorithm, as implemented in the Needle program (EMBOSS tool suite) are shown in Table 2.

TABLE 2

| | IPD103Ab SEQ ID NO: 4 | IPD103Ac SEQ ID NO: 6 | IPD103Ad SEQ ID NO: 8 | IPD103Ae SEQ ID NO: 10 | IPD103Ba SEQ ID NO: 12 | IPD103Bb SEQ ID NO: 14 | IPD103Bc SEQ ID NO: 16 | IPD103Bd SEQ ID NO: 18 | IPD103Be SEQ ID NO: 20 |
|---|---|---|---|---|---|---|---|---|---|
| IPD103Aa SEQ ID NO: 2 | 98.8 | 98.3 | 93.6 | 93.6 | 82.0 | 86.6 | 89.5 | 93.0 | 85.5 |
| IPD103Ab SEQ ID NO: 4 | — | 98.8 | 94.7 | 94.7 | 81.4 | 86.0 | 89.0 | 94.2 | 86.0 |
| IPD103Ac SEQ ID NO: 6 | — | — | 93.6 | 93.6 | 82.5 | 87.2 | 88.4 | 93.0 | 86.0 |
| IPD103Ad SEQ ID NO: 8 | — | — | — | 99.4 | 78.6 | 83.0 | 86.0 | 92.9 | 83.0 |
| IPD103Ae SEQ ID NO: 10 | — | — | — | — | 78.6 | 83.0 | 86.5 | 92.9 | 83.6 |
| IPD103Ba SEQ ID NO: 12 | — | — | — | — | — | 92.9 | 79.7 | 83.5 | 82.5 |
| IPD103Bb SEQ ID NO: 14 | — | — | — | — | — | — | 84.2 | 87.7 | 86.6 |
| IPD103Bc SEQ ID NO: 16 | — | — | — | — | — | — | — | 86.0 | 84.3 |
| IPD103Bd SEQ ID NO: 18 | — | — | — | — | — | — | — | — | 87.7 |
| IPD103Be SEQ ID NO: 20 | — | — | — | — | — | — | — | — | — |
| IPD103Bf SEQ ID NO: 22 | — | — | — | — | — | — | — | — | — |
| IPD103Bg SEQ ID NO: 24 | — | — | — | — | — | — | — | — | — |
| IPD103Bh SEQ ID NO: 26 | — | — | — | — | — | — | — | — | — |
| IPD103Bi SEQ ID NO: 28 | — | — | — | — | — | — | — | — | — |
| IPD103Bj SEQ ID NO: 30 | — | — | — | — | — | — | — | — | — |
| IPD103Bk SEQ ID NO: 32 | — | — | — | — | — | — | — | — | — |
| IPD103Ca SEQ ID NO: 34 | — | — | — | — | — | — | — | — | — |
| IPD103Da SEQ ID NO: 36 | — | — | — | — | — | — | — | — | — |

| | IPD103Bf SEQ ID NO: 22 | IPD103Bg SEQ ID NO: 24 | IPD103Bh SEQ ID NO: 26 | IPD103Bi SEQ ID NO: 28 | IPD103Bj SEQ ID NO: 30 | IPD103Bk SEQ ID NO: 32 | IPD103Ca SEQ ID NO: 34 | IPD103Da SEQ ID NO: 36 | IPD103Db SEQ ID NO: 38 |
|---|---|---|---|---|---|---|---|---|---|
| IPD103Aa SEQ ID NO: 2 | 86.1 | 87.4 | 87.4 | 85.0 | 89.0 | 90.1 | 81.4 | 72.0 | 61.8 |
| IPD103Ab SEQ ID NO: 4 | 86.1 | 86.3 | 86.3 | 84.4 | 88.4 | 90.1 | 80.9 | 72.2 | 62.2 |
| IPD103Ac SEQ ID NO: 6 | 85.0 | 85.7 | 85.7 | 83.8 | 87.8 | 89.0 | 82.0 | 71.6 | 62.2 |
| IPD103Ad SEQ ID NO: 8 | 84.9 | 83.9 | 83.9 | 83.8 | 85.4 | 88.9 | 78.0 | 71.8 | 62.0 |
| IPD103Ae SEQ ID NO: 10 | 84.9 | 83.3 | 83.3 | 83.8 | 86.0 | 88.9 | 78.0 | 71.1 | 62.4 |
| IPD103Ba SEQ ID NO: 12 | 87.9 | 76.2 | 76.2 | 73.9 | 79.1 | 84.6 | 98.9 | 64.1 | 57.9 |
| IPD103Bb SEQ ID NO: 14 | 85.5 | 80.5 | 80.5 | 79.2 | 83.6 | 89.5 | 94.0 | 67.1 | 61.0 |
| IPD103Bc SEQ ID NO: 16 | 81.6 | 92.5 | 92.5 | 82.1 | 99.4 | 85.4 | 79.1 | 71.8 | 59.3 |

TABLE 2-continued

| | | | | | | | | | |
|---|---|---|---|---|---|---|---|---|---|
| IPD103Bd SEQ ID NO: 18 | 86.6 | 84.5 | 84.5 | 82.1 | 85.4 | 90.6 | 82.4 | 71.1 | 62.6 |
| IPD103Be SEQ ID NO: 20 | 85.6 | 81.1 | 81.1 | 77.6 | 83.7 | 89.5 | 81.4 | 69.9 | 59.9 |
| IPD103Bf SEQ ID NO: 22 | — | 79.7 | 79.7 | 77.3 | 81.0 | 95.5 | 87.4 | 67.4 | 61.7 |
| IPD103Bg SEQ ID NO: 24 | — | — | 99.4 | 80.6 | 93.1 | 83.3 | 75.7 | 71.5 | 58.1 |
| IPD103Bh SEQ ID NO: 26 | — | — | — | 80.6 | 93.1 | 83.3 | 75.7 | 71.5 | 58.1 |
| IPD103Bi SEQ ID NO: 28 | — | — | — | — | 81.5 | 84.8 | 78.6 | 71.3 | 58.7 |
| IPD103Bj SEQ ID NO: 30 | — | — | — | — | — | 84.8 | 78.6 | 71.3 | 58.7 |
| IPD103Bk SEQ ID NO: 32 | — | — | — | — | — | — | 84.1 | 70.5 | 64.5 |
| IPD103Ca SEQ ID NO: 34 | — | — | — | — | — | — | — | 63.0 | 57.4 |
| IPD103Da SEQ ID NO: 36 | — | — | — | — | — | — | — | — | 51.2 |

Example 5—Lepidoptera Assays with Purified Tagged Proteins Expressed in *E. coli*

Bioassays against the five pest species, Corn earworm (CEW) (*Helicoverpa zea*), European corn borer (ECB) (*Ostrinia nubialis*), fall armyworm (FAW) (*Spodoptera frugiperda* JE Smith), Soybean looper (SBL) (*Pseudoplusia includens*), and velvet bean caterpillar (VBC) (*Anticarsia gemmatalis* Hübner) were conducted using a dilution series of purified N-6×His-IPD103Aa (SEQ ID NO: 2) or N-6×His IPD103Ab (SEQ ID NO: 4) polypeptides incorporated into an agar-based Lepidoptera diet (Southland Products Inc., Lake Village, AR) in a 96-well plate format. Four replicates were used per sample. Two to five neonate insects were placed into each well of the treated plate. After four days of incubation at 27° C. larvae were scored for mortality or severity of stunting. The scores were recorded numerically as dead (3), severely stunted (2) (little or no growth but alive and equivalent to a $1^{st}$ instar larvae), stunted (1) (growth to second instar but not equivalent to controls), or normal (0). Results from bioassays of a dilution series of N-6×His-tagged IPD103Aa (SEQ ID NO: 2) and N-6×His IPD103Ab (SEQ ID NO: 4) against the Lepidoptera pests are shown in Table 3. Values represent the mean larval inhibition score of 4 replicate assays.

TABLE 3

| | Dose (ppm) | CEW | ECB | FAW | SBL | VBC |
|---|---|---|---|---|---|---|
| NT-6xHis | 1350 | 3 | 2 | 2 | 3 | 3 |
| IPD103Aa | 675 | 2.25 | 2 | 2 | 2 | 2 |
| (SEQ ID NO: 2) | 338 | 2 | 2 | 2 | 1.5 | 2 |
| | 169 | 2 | 2 | 2 | 2 | 2 |
| | 84 | 2 | 2 | 0.75 | 2 | 2 |
| | 42 | 2 | 1.5 | 0 | 1 | 1 |
| | 21 | 1.5 | 1.5 | 0 | 0 | 0 |
| | 11 | 0.25 | 1 | 0 | 0 | 0 |
| Buffer Control | 0 | 0 | 0 | 0 | 0 | 0 |
| NT-6xHis | 925 | 2.5 | 2 | 2 | 2 | 3 |
| IPD103Ab | 463 | 2 | 2 | 2 | 2 | 2.25 |
| (SEQ ID NO: 4) | 231 | 2 | 2 | 1.25 | 2 | 2 |
| | 116 | 2 | 2 | 1.25 | 2 | 2 |
| | 58 | 2 | 2 | 1 | 2 | 2 |
| | 29 | 1.25 | 2 | 0 | 1 | 0.5 |
| | 14 | 0.75 | 2 | 0 | 0 | 0 |
| | 7 | 0.25 | 2 | 0 | 0 | 0 |
| Buffer Control | 0 | 0 | 0 | 0 | 0 | 0 |

Example 6—Purification and Bioassay of IPD103 Homologs Expressed in *E. coli*

The genes encoding IPD103 homologs were subcloned into the pET14b vector (Novagen) using the NdeI/XhoI restriction sites in frame with an N-terminal 6× His tag followed by a thrombin cleavage site with the IPD103 homolog native stop codon. Chemically competent OverExpress® C41 (DE3) SOLOs cells (Lucigen) were transformed with pET14b plasmid DNA, containing the IPD103Aa homolog gene for recombinant protein expression. The transformed *E. coli* cells were grown overnight at 37° C. with ampicillin selection and then inoculated to a fresh 2×YT medium (1:100) and further grown to an optical density of about 0.8-1.2. Protein expression was induced by adding 1.0 mM IPTG and cells were further grown at 16° C. for 16 hours. The *E. coli* expressed proteins were purified by immobilized metal ion chromatography (IMAC) using Talon® Cobalt resin (Clonetech, Mountain View, CA) according to the manufacturer's protocols. The purified 1.5 mL fractions eluted in 250 mM imidazole were dialyzed into PBS buffer using 6K MWCO Flextubes (IBI, Peosta, IA) on a stir plate at 4 C overnight. The dialyzed protein was run in the diet assay to evaluate the insecticidal protein effects on larvae of a selection of Lepidoptera. The activity of a series of homologs of IPD103Aa is summarized in Table 4.

TABLE 4

| Homolog ID | AA Seq | CEW | ECB | FAW | SBL | VBC |
|---|---|---|---|---|---|---|
| IPD103Ab | SEQ ID NO: 4 | + | + | + | + | + |
| IPD103AC | SEQ ID NO: 6 | + | + | + | + | + |
| IPD103Ad | SEQ ID NO: 8 | + | + | + | + | + |
| IPD103Ae | SEQ ID NO: 10 | + | + | + | + | + |
| IPD103Ba | SEQ ID NO: 12 | + | + | + | + | + |
| IPD103Bb | SEQ ID NO: 14 | + | + | + | − | + |
| IPD103Bc | SEQ ID NO: 16 | + | + | + | − | + |
| IPD103Bd | SEQ ID NO: 18 | + | + | + | + | + |
| IPD103Be | SEQ ID NO: 20 | + | + | + | + | + |
| IPD103Bf | SEQ ID NO: 22 | + | + | + | + | + |
| IPD103Bg | SEQ ID NO: 24 | + | + | + | + | + |
| IPD103Bh | SEQ ID NO: 26 | + | − | + | − | + |
| IPD103Bi | SEQ ID NO: 28 | + | + | + | + | + |
| IPD103Ca | SEQ ID NO: 34 | + | + | + | + | + |
| IPD103Da | SEQ ID NO: 36 | + | + | + | + | + |

Example 7—IPD103Aa Variants with Multiple Amino Acid Substitutions

To create variants of IPD103Aa (SEQ ID NO: 2) with multiple amino acid changes, variant libraries were generated by family shuffling (Chia-Chun J. Chang et al, 1999, *Nature Biotechnology* 17, 793-797) the polynucleotide sequences of SEQ ID NO: 1, SEQ ID NO: 19, and SEQ ID NO: 37, encoding IPD103Aa (SEQ ID NO: 12), IPD103Be (SEQ ID NO: 20), and IPD103 Da (SEQ ID NO: 38). Three libraries were constructed for generating IPD103 variants. In a first library (Library11), the native polynucleotide sequence of IPD103Aa (SEQ ID NO: 1) and the native polynucleotide sequence of IPD103Be (SEQ ID NO: 19) were used as library parents. In a second library, the native polynucleotide sequence of IPD103Be (SEQ ID NO: 19) and the polynucleotide sequence of SEQ ID NO: 35 encoding the IPD103 Da polypeptide, with codons optimized to increase the similarity to SEQ ID NO: 1 were used as library parents. In a third library, native polynucleotide sequences of IPD103Aa (SEQ ID NO: 1) and IPD103Be (SEQ ID NO: 19) and the codon-optimized polynucleotide sequence of IPD103 Da (SEQ ID NO: 35) were used as library parents. The second and third libraries were picked and screened together (Library123).

After transforming the library variants into *E. coli* cells, the colonies were picked and cultured in 24-well plates for protein expression. *Cell* lysates were generated by B-PER® Protein Extraction Reagent (Thermo Scientific, Rockford, IL) and screened for CEW and/or FAW insecticidal activity. The active variants were sequenced and the amino acid substitutions were identified. From library 11, 460 variants were screened and 110 active unique variants were sequence identified. From library 123, 552 variants were screened and 78 active unique variants were sequence identified.

Table 5 summarizes the % identity of the active variants compared to IPD103Aa (SEQ ID NO: 2), the number of variants with each % identity, and the variant identification.

TABLE 5

| % Identity to IPD103Aa (SEQ ID NO: 2) | # of Unique Sequences | Variants |
|---|---|---|
| 98 | 4 | IPD103lib11reary-19, IPD103lib11reary-41, IPD103-11Reary-14, IPD103-11Reary-25 |
| 97 | 2 | IPD103lib123reary-40, IPD103lib11reary-18 |
| 96 | 10 | IPD103lib123reary-29, IPD103lib123reary-45, IPD103lib11reary-15, IPD103lib11reary-40, IPD103lib11reary-55, IPD103lib11reary-66, IPD103lib11reary-73, IPD103lib11reary-79, IPD103lib11reary-88, IPD103-11Reary-37 |
| 95 | 8 | IPD103lib11reary-07, IPD103lib11reary-44, IPD103lib11reary-50, IPD103lib11reary-65, IPD103lib11reary-69, IPD103-11Reary-16, IPD103-11Reary-29, IPD103-11Reary-34 |
| 94 | 12 | IPD103lib123reary-05, IPD103lib11reary-21, IPD103lib11reary-39, IPD103lib11reary-67, IPD103lib11reary-87, IPD103-11Reary-09, IPD103-11Reary-13, IPD103-11Reary-22, IPD103-11Reary-33, IPD103-11Reary-43, IPD103-11Reary-45, IPD103-123Reary-05 |
| 93 | 11 | IPD103lib11reary-08, IPD103lib11reary-12, IPD103lib11reary-13, IPD103lib11reary-34, IPD103lib11reary-58, IPD103lib11reary-68, IPD103lib11reary-70, IPD103lib11reary-85, IPD103-11Reary-17, IPD103-123Reary-12, IPD103-123Reary-33 |
| 92 | 21 | IPD103lib123reary-49, IPD103lib11reary-16, IPD103lib11reary-23, IPD103lib11reary-25, IPD103lib11reary-27, IPD103lib11reary-31, IPD103lib11reary-35, IPD103lib11reary-52, IPD103lib11reary-56, IPD103lib11reary-59, IPD103-11Reary-01, IPD103-11Reary-05, IPD103-11Reary-06, IPD103-11Reary-10, IPD103-11Reary-18, IPD103-11Reary-35, IPD103-11Reary-36, IPD103-11Reary-40, IPD103-11Reary-42, IPD103-123Reary-07, IPD103-123Reary-26 |
| 91 | 17 | IPD103lib123reary-48, IPD103lib11reary-17, IPD103lib11reary-29, IPD103lib11reary-32, IPD103lib11reary-42, IPD103lib11reary-45, IPD103lib11reary-51, IPD103lib11reary-53, IPD103lib11reary-63, IPD103lib11reary-64, IPD103lib11reary-80, IPD103lib11reary-82, IPD103-11Reary-11, IPD103-11Reary-21, IPD103-11Reary-24, IPD103-11Reary-44, IPD103-123Reary-31 |
| 90 | 16 | IPD103lib123reary-27, IPD103lib123reary-68, IPD103lib123reary-72, IPD103lib11reary-10, IPD103lib11reary-14, IPD103lib11reary-20, IPD103lib11reary-28, IPD103lib11reary-49, IPD103lib11reary-62, IPD103-11Reary-04, IPD103-11Reary-15, IPD103-11Reary-20, IPD103-11Reary-32, IPD103-123Reary-11, IPD103-123Reary-16, IPD103-123Reary-30 |
| 89 | 20 | IPD103lib11reary-03, IPD103lib11reary-09, IPD103lib11reary-11, IPD103lib11reary-30, IPD103lib11reary-33, IPD103lib11reary-46, IPD103lib11reary-48, IPD103lib11reary-54, IPD103lib11reary-74, IPD103lib11reary-75, IPD103lib11reary-86, IPD103-11Reary-08, IPD103-11Reary-19, IPD103-11Reary-31, IPD103-11Reary-46, IPD103-123Reary-01, IPD103-123Reary-02, IPD103-123Reary-10, IPD103-123Reary-14, IPD103-123Reary-38 |
| 88 | 11 | IPD103lib123reary-18, IPD103lib123reary-65, IPD103lib11reary-38, IPD103lib11reary-47, IPD103lib11reary-76, IPD103lib11reary-78, IPD103-11Reary-26, IPD103-11Reary-39, IPD103-123Reary-06, IPD103-123Reary-18, IPD103-123Reary-37 |
| 87 | 7 | IPD103lib123reary-15, IPD103lib123reary-59, IPD103lib11reary-01, IPD103lib11reary-22, IPD103-11Reary-38, IPD103-123Reary-13, IPD103-123Reary-35 |
| 86 | 4 | IPD103lib123reary-28, IPD103lib123reary-31, IPD103lib11reary-43, IPD103-11Reary-41 |
| 85 | 5 | IPD103lib123reary-55, IPD103lib123reary-07, IPD103lib11reary-83, IPD103-123Reary-22, IPD103-123Reary-34 |
| 84 | 3 | IPD103lib123reary-23, IPD103-123Reary-15, IPD103-123Reary-32 |
| 83 | 1 | IPD103lib123reary-30 |
| 82 | 4 | IPD103lib123reary-11, IPD103lib123reary-37, IPD103-123Reary-09, IPD103-123Reary-25 |
| 81 | 5 | IPD103lib123reary-16, IPD103lib123reary-54, IPD103lib123reary-62, IPD103-123Reary-17, IPD103-123Reary-19 |
| 80 | 1 | IPD103lib123reary-19 |
| 79 | 2 | IPD103lib123reary-38, IPD103-123Reary-28 |
| 78 | 3 | IPD103lib123reary-47, IPD103lib123reary-01, IPD103-123Reary-21 |
| 77 | 1 | IPD103-123Reary-23 |
| 76 | 8 | IPD103lib123reary-17, IPD103lib123reary-32, IPD103lib123reary-41, IPD103lib123reary-42, IPD103lib123reary-46, IPD103lib123reary-58, IPD103lib123reary-67, IPD103-123Reary-08 |

TABLE 5-continued

| % Identity to IPD103Aa (SEQ ID NO: 2) | # of Unique Sequences | Variants |
|---|---|---|
| 75 | 5 | IPD103lib123reary-14, IPD103lib123reary-39, IPD103lib123reary-69, IPD103-123Reary-24, IPD103-123Reary-40 |
| 74 | 3 | IPD103lib123reary-34, IPD103lib123reary-63, IPD103lib123reary-77 |
| 73 | 4 | IPD103lib123reary-52, IPD103lib123reary-60, IPD103lib123reary-70, IPD103lib123reary-73 |

Example 8—Vector Constructs for Expression of IPD103 Polypeptides in Plants

For testing in maize, expression vectors PHP79658, PHP70659, and PHP7600 were constructed to include a transgene cassette containing one of three different gene designs encoding IPD103Aa (SEQ ID NO: 2), the MMV ENH:MMV ENH:BYDV promoter WO 2017/095698), linked to the PINII terminator (US-2014-0130205).

Example 9—Expression and Insect Bioassay on Transient Leaf Tissues

To confirm activity of IPD103Aa (SEQ ID NO: 2) and IPD103Ab (SEQ ID NO: 4) the corresponding genes were cloned into a transient expression system under control of the viral promoter dMMV or AtUBQ10 promoter (Dey, et. al., (1999) *Plant Mol. Biol.* 40:771-782; PCT Patent Publication WO2011133387; Norris S R et al (1993) Plant Mol Biol. 21(5):895-906)). The constructs were infiltrated into leaves. The agro-infiltration method of introducing an *Agrobacterium* cell suspension to plant cells of intact tissues so that reproducible infection and subsequent plant derived transgene expression may be measured or studied (Kapila, et. al., (1997) *Plant Science* 122:101-108). Briefly, the unifoliate stage of bush bean (common bean, *Phaseolus vulgaris*) or soybean (*Glycine max*), were agro-infiltrated with normalized bacterial cell cultures of test and control strains. Leaf discs were excised from each plantlet and infested with neonates of Soy Bean Looper (SBL) (*Pseudoplusia includens*), Corn Earworm, (CEW) (*Helicoverpa zea*), [FAW], Velvet Bean Caterpillar (VBC) (*Anticarsia gemmatalis*) or European Corn Borer (ECB) (*Ostrinia nubialis*). Leaf discs from a control were generated with *Agrobacterium* containing only empty expression vector. Leaf discs from a non-infiltrated plant were used as a second control. The consumption of green leaf tissue was scored after two (CEW, VBC), three (SBL) or four (ECB) days after infestation and given scores of 0 to 9 as indicated by Table 6. The transiently expressed IPD103Aa (SEQ ID NO: 2) and homologs protected bush bean leaf discs from consumption by the infested insects while total green tissue consumption was observed for the negative control and untreated tissue. Transient protein expression of IPD103Aa (SEQ ID NO: 2) and IPD103Ab (SEQ ID NO: 4) were confirmed by a mass spectrometry-based protein identification method using extracted protein lysates from infiltrated leave tissues (Patterson, (1998) 10(22):1-24, Current Protocol in Molecular Biology published by John Wiley & Son Inc). As shown in Table 10, IPD103Aa (SEQ ID NO: 2) and all the homologs tested resulted in protection of bush bean against leaf feeding damage from a diversity of Lepidoptera. Larval feeding damage to soybean leaves transiently expressing insecticidal genes under the control of the viral promoter dMMV (Dey, et. al., (1999) *Plant Mol. Biol.* 40:771-782) was assessed using a scale described in Table 6. The effect of expression of IPD103 proteins was compared to non-agro-infiltrated controls and controls expressing DsRed2 fluorescence marker (Clontech, Mountain View, CA). Activity of selected IPD103 polypeptides, transiently expressed in bush bean, against leaf feeding damage from a selection of Lepidoptera is shown in Table 7. The average score and standard error (SE) for 6 replicate measurements are shown.

Activity of selected IPD103Aa polypeptides, transiently expressed in Soybean, against leaf feeding damage from a selection of Lepidoptera is shown in Table 8 The average leaf feeding score and standard deviation (StdDev) for 12 replicates/treatment is shown.

TABLE 6

| Leaf Feeding Score | % Consumed |
|---|---|
| 1 | 86-100 |
| 2 | 71-85 |
| 3 | 61-70 |
| 4 | 51-60 |
| 5 | 36-50 |
| 6 | 11-35 |
| 7 | 11-36 |
| 8 | 1-3 |
| 9 | 0 |

TABLE 7

| Gene | Target Insect | Avg. Leaf Damage Score | SE | Target Insect | Avg. Leaf Damage Score | SE | Target Insect | Avg. Leaf Damage Score | SE |
|---|---|---|---|---|---|---|---|---|---|
| IPD103Aa SEQ ID NO: 2 | CEW | 7.7 | 0.3 | ECB | 5.2 | 1.1 | FAW | 4.7 | 0.4 |
| IPD103Ac SEQ ID NO: 6 | | 7.5 | 0.3 | | 6.7 | 0.7 | | 4.8 | 0.7 |
| IPD103Ad SEQ ID NO: 8 | | 8.2 | 0.3 | | 3.2 | 1.2 | | 4.5 | 0.3 |
| IPD103Ae SEQ ID NO: 10 | | 7.3 | 0.3 | | 2.0 | 0.7 | | 3.8 | 0.7 |
| IPD103Ba SEQ ID NO: 12 | | 6.0 | 0.4 | | 1.8 | 0.5 | | 3.2 | 0.2 |
| IPD103Bb SEQ ID NO: 14 | | 6.3 | 0.4 | | 5.8 | 0.2 | | 3.7 | 0.2 |
| IPD103Bc SEQ ID NO: 16 | | 7.0 | 0.6 | | 3.2 | 1.4 | | 3.7 | 0.2 |
| IPD103Bd SEQ ID NO: 18 | | 7.7 | 0.3 | | 7.5 | 0.3 | | 5.7 | 0.3 |
| IPD103Be SEQ ID NO: 20 | | 7.7 | 0.3 | | 5.8 | 0.8 | | 5.5 | 0.4 |
| IPD103Bf SEQ ID NO: 22 | | 7.3 | 0.6 | | 6.2 | 0.7 | | 4.3 | 0.6 |
| IPD103Bg SEQ ID NO: 24 | | 8.0 | 0.4 | | 4.2 | 1.2 | | 4.2 | 0.6 |

TABLE 7-continued

| Gene | Target Insect | Avg. Leaf Damage Score | SE | Target Insect | Avg. Leaf Damage Score | SE | Target Insect | Avg. Leaf Damage Score | SE |
|---|---|---|---|---|---|---|---|---|---|
| IPD103Bh SEQ ID NO: 26 | | 8.0 | 0.4 | | 6.5 | 1.2 | | 6.0 | 0.8 |
| IPD103Ca SEQ ID NO: 34 | | 6.0 | 0.8 | | 3.8 | 1.5 | | 3.0 | 0.4 |
| IPD103Da SEQ ID NO: 36 | | 6.3 | 0.3 | | 3.3 | 1.1 | | 3.5 | 0.3 |
| Negative Control | | 3.7 | 1.1 | | 2.3 | 1.3 | | 2.2 | 0.2 |
| Untreated | | 3.5 | 0.4 | | 1.2 | 0.2 | | 2.8 | 0.3 |
| IPD103Aa SEQ ID NO: 2 | SBL | 6.0 | 0.4 | VBC | 8.0 | 0.0 | | | |
| IPD103Ac SEQ ID NO: 6 | | 5.2 | 0.2 | | 8.0 | 0.0 | | | |
| IPD103Ad SEQ ID NO: 8 | | 6.0 | 0.3 | | 8.2 | 0.2 | | | |
| IPD103Ae SEQ ID NO: 10 | | 6.0 | 0.4 | | 8.2 | 0.2 | | | |
| IPD103Ba SEQ ID NO: 12 | | 4.3 | 0.3 | | 5.7 | 0.7 | | | |
| IPD103Bb SEQ ID NO: 14 | | 3.8 | 0.3 | | 6.7 | 0.4 | | | |
| IPD103Bc SEQ ID NO: 16 | | 5.3 | 0.9 | | 6.5 | 0.2 | | | |
| IPD103Bd SEQ ID NO: 18 | | 6.0 | 0.4 | | 8.0 | 0.0 | | | |
| IPD103Be SEQ ID NO: 20 | | 5.3 | 0.2 | | 7.8 | 0.2 | | | |
| IPD103Bf SEQ ID NO: 22 | | 4.5 | 0.3 | | 7.7 | 0.2 | | | |
| IPD103Bg SEQ ID NO: 24 | | 5.7 | 0.6 | | 7.8 | 0.2 | | | |
| IPD103Bh SEQ ID NO: 26 | | 5.3 | 0.4 | | 8.5 | 0.2 | | | |
| IPD103Ca SEQ ID NO: 34 | | 3.8 | 0.4 | | 4.8 | 1.3 | | | |
| IPD103Da SEQ ID NO: 36 | | 4.5 | 0.5 | | 7.2 | 0.5 | | | |
| Negative Control | | 3.3 | 0.3 | | 1.0 | 0.0 | | | |
| Untreated | | 4.0 | 0.7 | | 2.7 | 1.1 | | | |

TABLE 8

| | | CEW | | SBL | | VBC | |
|---|---|---|---|---|---|---|---|
| | SEQ ID NO | Avg. Score | Std. DEV | Avg. Score | | Avg. Score | |
| IPD103Aa | SEQ ID NO: 2 | 7.8 | 0.5 | 7.8 | 0.8 | 7.2 | 0.7 |
| IPD103Bc | SEQ ID NO: 16 | 7.8 | 0.7 | 6.3 | 0.7 | 6.0 | 1.3 |
| IPD103Bd | SEQ ID NO: 18 | 8.2 | 0.4 | 7.8 | 0.6 | 6.8 | 1.8 |
| IPD103Be | SEQ ID NO: 20 | 6.8 | 0.6 | 6.7 | 0.8 | 6.4 | 1.2 |
| IPD103Bh | SEQ ID NO: 26 | 8.0 | 0.4 | 7.8 | 0.6 | 6.7 | 2.1 |
| IPD103Da | SEQ ID NO: 36 | 2.0 | 1.6 | 4.4 | 1.6 | 1.3 | 0.7 |
| DsRed control | | 1.0 | 0.0 | 1.3 | 0.5 | 1.0 | 0.0 |
| Neg. control | | 1.0 | 0.0 | 1.7 | 1.5 | 1.2 | 0.4 |

Example 10—*Agrobacterium*-Mediated Transformation of Maize and Regeneration of Transgenic Plants For *Agrobacterium*-mediated transformation of maize with nucleotide sequences of the embodiment the method of Zhao was used (U.S. Pat. No. 5,981,840 and PCT Patent Publication Number WO 1998/32326; the contents of which are hereby incorporated by reference). Briefly, immature embryos were isolated from maize and the embryos contacted with a suspension of *Agrobacterium* under conditions whereby the bacteria are capable of transferring the PHP79658, PHP70659, and PHP7600 vectors to at least one cell of at least one of the immature embryos (step 1: the infection step). In this step the immature embryos were immersed in an *Agrobacterium* suspension for the initiation of inoculation. The embryos were co-cultured for a time with the *Agrobacterium* (step 2: the co-cultivation step). The immature embryos were cultured on solid medium following the infection step. Following this co-cultivation period an optional "resting" step is contemplated. In this resting step, the embryos were incubated in the presence of at least one antibiotic to inhibit the growth of *Agrobacterium* without the addition of a selective agent for plant transformation (step 3: resting step). The immature embryos were cultured on solid medium with antibiotic, but without a selecting agent, for elimination of *Agrobacterium* and for a resting phase for the infected cells. Next, inoculated embryos were cultured on medium containing a selective agent and growing transformed callus is recovered (step 4: the selection step). The immature embryos were cultured on solid medium with a selective agent resulting in the selective growth of transformed cells. The callus was then regenerated into plants (step 5: the regeneration step), and calli grown on selective medium or cultured on solid medium to regenerate the plants.

For detection of the IPD103 proteins in leaf tissue 4 lyophilized leaf punches/sample were pulverized and resuspended in 100 μL PBS containing 0.1% Tween 20 (PBST), 1% beta-mercaoptoethanol containing 1 tablet/7 mL complete Mini proteinase inhibitor (Roche 1183615301). The suspension was sonicated for 2 min and then centrifuged at 4° C., 20,000 g for 15 min. To a supernatant aliquot ⅓ volume of 3× NuPAGE® LDS Sample Buffer (Invitrogen™ (CA, USA), 1% B-ME containing 1 tablet/7 mL complete Mini proteinase inhibitor was added. The reaction was heated at 80° C. for 10 min and then centrifuged. A supernatant sample was loaded on 4-12% Bis-Tris Midi gels with MES running buffer as per manufacturer's (Invitrogen™) instructions and transferred onto a nitrocellulose membrane using an iBlot® apparatus (Invitrogen™). The nitrocellulose membrane was incubated in PBST containing 5% skim milk powder for 2 hours before overnight incubation in affinity-purified rabbit anti-IPD103Aa polyclonal antibody in PBST overnight. The membrane was rinsed three times with PBST and then incubated in PBST for 15 min and then two times 5 min before incubating for 2 hours in PBST with goat anti-rabbit-HRP for 3 hours. The detected proteins were visualized using ECL Western Blotting Reagents (GE Healthcare cat #RPN2106) and visualized using a luminescent image analyzer (ImageQuant LAS 4000, GE Healthcare Transgenic maize plants positive for expression of the insecticidal proteins are tested for pesticidal activity using standard bioassays. Such methods include, for example, whole plant bioassays.

Example 11—Particle Bombardment Transformation and Regeneration of Transgenic Maize Plants Immature maize embryos from greenhouse donor plants are bombarded with a plasmid containing a nucleotide sequence encoding the insecticidal protein. The ears are husked and surface sterilized in 30% Clorox® bleach plus 0.5% Micro detergent for 20 minutes and rinsed two times with sterile water, The immature embryos are excised and placed embryo axis side down (scutellum side up), 25 embryos per plate, on 560Y medium for 4 hours and then aligned within the 2.5 cm target zone in preparation for bombardment. A plasmid vector DNA comprising the nucleotide sequence encoding the insecticidal protein operably linked to a promoter is precipitated onto 1.1 μm (average diameter) tungsten pellets using a $CaCl_2$) precipitation procedure as follows: 100 μl prepared tungsten particles in water: 10 μl (1 pg) DNA in Tris EDTA buffer (1 μg total DNA); 100 μl 2.5 M $CaCl_2$ and 10 μl 0.1 M spermidine.

Each reagent is added sequentially to the tungsten particle suspension, while maintained on the multitube vortexes, The final mixture is sonicated briefly and allowed to incubate under constant vortexing for 10 minutes. After the precipitation period, the tubes are centrifuged briefly, liquid removed, washed with 500 ml 100% ethanol and centrifuged for 30 seconds. Again, the liquid is removed, and 105 μl 100% ethanol is added to the final tungsten particle pellet. For particle gun bombardment, the tungsten/DNA particles are briefly sonicated and 10 μl spotted onto the center of each macrocarrier and allowed to dry about 2 minutes before bombardment. The sample plates are bombarded at level #4 in a particle gun. All samples receive a single shot at 650 PSI, with a total of ten aliquots taken from each tube of prepared particles/DNA Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored for expression of an IPD103 polypeptide by assays, for example, immunoassays and Western blotting.

Transgenic maize plants positive for expression of the insecticidal proteins are tested for pesticidal activity using standard bioassays. Such methods include, for example, root excision bioassays and whole plant bioassays. See, e.g., US Patent Application Publication Number US 2003/0120054 and International Publication Number WO 2003/018810.

Bombardment medium (560Y) comprises 4.0 g/l N6 basal salts (SIGMA C-1416), 1.0 ml/l Eriksson's Vitamin Mix (1000 times SIGMA-151 1), 0.5 mg/l thiamine HCl, 120.0 g/l sucrose, 1.0 mg/l 2,4-D and 2.88 g/l L-proline (brought to volume with D-I $H_2O$ following adjustment to pH 5.8 with KOH); 2.0 g/l Gelrite (added after bringing to volume with D-I $H_2O$) and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000 times SIGMA-151 1); 0.5 mg/l thiamine HCl, 30.0 g/l sucrose and 2.0 mg/l 2,4-D (brought to volume with D-I $H_2O$ following adjustment to pH 5.8 with KOH); 3.0 g/l Gelrite (added after bringing to volume with D-I $H_2O$) and 0.85 mg/l silver nitrate and 3.0 mg/l bialaphos (both added after sterilizing the medium and cooling to room temperature).

Plant regeneration medium (288J) comprises 4.3 g/l MS salts (GIBCO 1 1 1 17-074); 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog, (1962) Physiol. Plant. 15:473), 100 mg/l myo-inositol, 0.5 mg/l zeatin, 60 g/l sucrose and 1.0 ml/l of 0.1 mM abscisic acid (brought to volume with polished D-I $H_2O$ after adjusting to pH 5.6); 3.0 g/l Gelrite (added after bringing to volume with D-I $H_2O$) and 1.0 mg/l indoleacetic acid and 3.0 mg/l bialaphos (added after sterilizing the medium and cooling to 60° C.). Hormone-free medium (272V) comprises 4.3 g/l MS salts (GIBCO 1 1 1 17-074), 5.0 ml/l MS vitamins stock solution (0.100 g/l nicotinic acid, 0.02 g/l thiamine HCL; 0.10 g/l pyridoxine HCL and 0.40 glycine brought to volume with polished D-I $H_2O$); 0.1 g/l myoinositol and 40.0 g/l sucrose (brought to volume with polished D-I $H_2O$ after adjusting pH to 5.6) and 6 g/l bacto-agar (added after bringing to volume with polished D-I $H_2O$), sterilized and cooled to 60° C.

Example 12—Insect Control Efficacy of Stable Transformed Corn Plants Against a Spectrum of Lepidopteran Insects Leaf discs were excised from transformed maize plants and tested for insecticidal activity of IPD103Aa polypeptides against the European Corn Borer (ECB) (*Ostrinia nubilalis*), Corn Earworm, (CEW) (*Helicoverpa zea*), and Fall Armyworm (*Spodoptera frugiperda*). The constructs, PHP79658, PHP79559 and PHP79660 for the expression of three IPD103Aa gene designs were used to generate transgenic maize events to test for efficacy against feeding damage caused by lepidopteran pests provided by expression of these polypeptides. FIG. 2 demonstrates that strong protection from leaf feeding by a broad spectrum of Lepidoptera pests was conferred by expression of IPD103Aa genes.

Example 13—Greenhouse Efficacy of IPD103 Polypeptide Events

Figure 4:
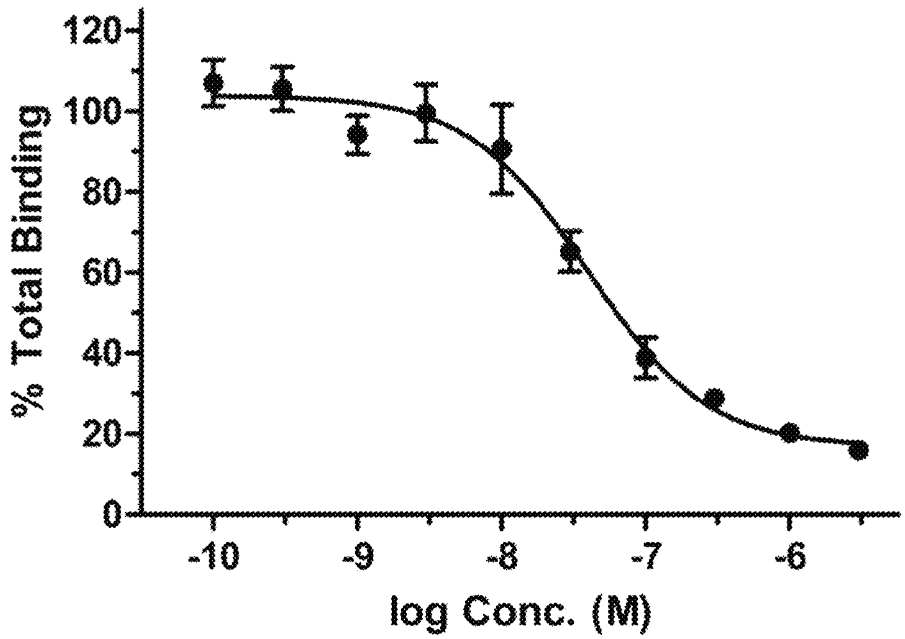
FIG. 4 shows a curve reflecting densitometry values of in-gel fluorescence, from the SDS-PAGE gel of Example 16, for homologous competition of 25 nM IPD103Aa$^{Alexa}$ binding to *Helicoverpa zea* (Corn Earworm) BBMVs normalized to the amount bound in the absence of unlabeled IPD103Aa (SEQ ID NO: 2). The solid line reflects the best fit of a square logistic equation to the data.

TO greenhouse efficacy results for events generated from PHP79658, PHP79659 and PHP79660 constructs are shown in FIG. 4. Efficacy for events derived from all 3 constructs was observed relative to negative control events (Empty) as measured by corn ear protection from corn earworm (CEW). Ear protection was measured, using a grid, as the number of square centimeters (CEWSCM) of ear feeding damage. FIG. 4 shows that a large proportion of events from PHP79658, PHP79659 and PHP79660 performed better than the negative control and have earworm injury scores of 2 $cm^2$ or less

Example 14—Transformation and Regeneration of Soybean (*Glycine max*)

Transgenic soybean lines are generated by the method of particle gun bombardment (Klein et al., *Nature* (London) 327:70-73 (1987); U.S. Pat. No. 4,945,050) using a BIO-RAD Biolistic PDS1000/He instrument and either plasmid or fragment DNA. The following stock solutions and media are used for transformation and regeneration of soybean plants:

Stock Solutions:
Sulfate 100× Stock:
37.0 g $MgSO_4 \cdot 7H_2O$, 1.69 g $MnSO_4 \cdot H_2O$, 0.86 g $ZnSO_4 \cdot 7H_2O$, 0.0025 g $CuSO_4 \cdot 5H_2O$
Halides 100× Stock:
30.0 g $CaCl_2 \cdot 2H_2O$, 0.083 g KI, 0.0025 g $CoCl_2 \cdot 6H_2O$
P, B, Mo 100× Stock:
18.5 g $KH_2PO_4$, 0.62 g $H_3BO_3$, 0.025 g $Na_2MoO_4 \cdot 2H_2O$
Fe EDTA 100× Stock:
3.724 g $Na_2EDTA$, 2.784 g $FeSO_4 \cdot 7H_2O$
2,4-D Stock:
10 mg/mL Vitamin
B5 vitamins, 1000× Stock:
100.0 g myo-inositol, 1.0 g nicotinic acid, 1.0 g pyridoxine HCl, 10 g thiamine·HCL.

Media (Per Liter):
SB199 Solid Medium:
1 package MS salts (Gibco/BRL—Cat. No. 11117-066), 1 mL B5 vitamins 1000× stock, 30 g Sucrose, 4 ml 2, 4-D (40 mg/L final concentration), pH 7.0, 2 g Gelrite
SB1 Solid Medium:
1 package MS salts (Gibco/BRL—Cat. No. 11117-066), 1 mL B5 vitamins 1000× stock, 31.5 g Glucose, 2 mL 2, 4-D (20 mg/L final concentration), pH 5.7, 8 g TC agar
SB196:
10 mL of each of the above stock solutions 1-4, 1 mL B5 Vitamin stock, 0.463 g (NH4)2 SO4, 2.83 g KNO3, 1 mL 2,4 D stock, 1 g asparagine, 10 g Sucrose, pH 5.7
SB71-4:
Gamborg's B5 salts, 20 g sucrose, 5 g TC agar, pH 5.7.
SB103:
1 pk. Murashige & Skoog salts mixture, 1 mL B5 Vitamin stock, 750 mg MgCl2 hexahydrate, 60 g maltose, 2 g gelrite, pH 5.7.
SB166:
SB103 supplemented with 5 g per liter activated charcoal.

Soybean Embryogenic Suspension Culture Initiation:

Pods with immature seeds from available soybean plants 45-55 days after planting are picked, removed from their shells and placed into a sterilized magenta box. The soybean seeds are sterilized by shaking them for 15 min in a 5% Clorox solution with 1 drop of ivory soap (i.e., 95 mL of autoclaved distilled water plus 5 mL Clorox and 1 drop of soap, mixed well). Seeds are rinsed using 2, 1-liter bottles of sterile distilled water and those less than 3 mm are placed on individual microscope slides. The small end of the seed is cut and the cotyledons pressed out of the seed coat. Cotyledons are transferred to plates containing SB199 medium (25-30 cotyledons per plate) for 2 weeks, then transferred to SB1 for 2-4 weeks. Plates are wrapped with fiber tape. After this time, secondary embryos are cut and placed into SB196 liquid medium for 7 days.

Culture Conditions:

Soybean embryogenic suspension cultures (cv. 93Y21) were maintained in 50 mL liquid medium SB196 on a rotary shaker, 100-150 rpm, 26° C. on 16:8 h day/night photoperiod at light intensity of 80-100 µE/m2/s. Cultures are subcultured every 7-14 days by inoculating up to ½ dime size quantity of tissue (clumps bulked together) into 50 mL of fresh liquid SB196.

Preparation of DNA for Bombardment:

In particle gun bombardment procedures, it is possible to use purified 1) entire plasmid DNA; or 2) DNA fragments containing only the recombinant DNA expression cassette(s) of interest. For every seventeen bombardment transformations, 85 µL of suspension is prepared containing 1 to 90 picograms (pg) of plasmid DNA per base pair of each DNA plasmid. DNA plasmids or fragments are co-precipitated onto gold particles as follows. The DNAs in suspension are added to 50 µL of a 10-60 mg/mL 0.6 µm gold particle suspension and then combined with 50 µL $CaCl_2$ (2.5 M) and 20 µL spermidine (0.1 M). The mixture is vortexed for 5 secs, spun in a microfuge for 5 secs, and the supernatant removed. The DNA-coated particles are then washed once with 150 µL of 100% ethanol, vortexed and spun in a microfuge again, then resuspended in 85 µL of anhydrous ethanol. Five µL of the DNA-coated gold particles are then loaded on each macrocarrier disk.

Tissue Preparation and Bombardment with DNA:

Approximately 100 mg of two-week-old suspension culture is placed in an empty 60 mm×15 mm petri plate and the residual liquid removed from the tissue using a pipette. The tissue is placed about 3.5 inches away from the retaining screen and each plate of tissue is bombarded once. Membrane rupture pressure is set at 650 psi and the chamber is evacuated to −28 inches of Hg. Following bombardment, the tissue from each plate is divided between two flasks, placed back into liquid media, and cultured as described above.

Selection of Transformed Embryos and Plant Regeneration:

After bombardment, tissue from each bombarded plate is divided and placed into two flasks of SB196 liquid culture maintenance medium per plate of bombarded tissue. Seven days post bombardment, the liquid medium in each flask is replaced with fresh SB196 culture maintenance medium supplemented with 100 ng/mL selective agent (selection medium). For selection of transformed soybean cells the selective agent used can be a sulfonylurea (SU) compound with the chemical name, 2-chloro-N-((4-methoxy-6 methyl-1,3,5-triazine-2-yl)aminocarbonyl) benzenesulfonamide (common names: DPX-W4189 and Chlorsulfuron). Chlorsulfuron is the active ingredient in the DuPont sulfonylurea herbicide, GLEAN®. The selection medium containing SU is replaced every two weeks for 8 weeks. After the 8 week selection period, islands of green, transformed tissue are observed growing from untransformed, necrotic embryogenic clusters. These putative transgenic events are isolated and kept in SB196 liquid medium with SU at 100 ng/mL for another 5 weeks with media changes every 1-2 weeks to generate new, clonally propagated, transformed embryogenic suspension cultures. Embryos spend a total of around 13 weeks in contact with SU. Suspension cultures are subcultured and maintained as clusters of immature embryos and also regenerated into whole plants by maturation and germination of individual somatic embryos.

Somatic embryos became suitable for germination after four weeks on maturation medium (1 week on SB166 followed by 3 weeks on SB103). They are then removed from the maturation medium and dried in empty petri dishes for up to seven days. The dried embryos are then planted in SB71-4 medium where they are allowed to germinate under the same light and temperature conditions as described above. Germinated embryos are transferred to potting medium and grown to maturity for seed production.

Example 15—Testing Cross-Resistance of Cry1Ab and Cry1F-Selected European Corn Borer To determine if Cry1Ab or Cry1F-resistant insects were cross-resistant to N-6×His-IPD103Aa (SEQ ID NO: 2), European corn borer (ECB, *Ostrinia nubilalis*) larvae susceptible or resistant to Cry1Ab (Crespo A. et al., Pest Manag Sci 65: 1071-1081, 2009) or Cry1F (Siegfried B. et al., Pest Manag Sci 70: 725-733, 2014), were treated with N-6×His-IPD103Aa (SEQ ID NO: 2). The laboratory Cry1F-selected strain (Cry1F-R) originated from a combination of five field populations collected in 2007 and was selected for resistance using increasing amounts of lyophilized leaf tissue of Cry1F-expressing maize (Alves, A, US 2012/0148497 A1, 2012).

Larval susceptibility of ECB strains resistant to Cry1Ab (Cry1Ab-res) or Cry1F (Cry1F-res) and susceptible strains (SS) to the insecticidal proteins was determined using a diet incorporated bioassay method. Briefly, 25 μL of a sample was mixed with 75 μL of artificial diet per well in a 96-well plate. Each bioassay included eight concentrations of the sample as well as the negative buffer control, four replications for each concentration, and eight individuals for each replicate. One ECB neonate larva (<24 h after hatch) was placed in each assay well. Once infested, the plates were sealed with Mylar and ventilation holes were added to each well using #1 or #2 insect pins. Plates were incubated at 27° C., 50% RH, and a photoperiod of 16:8 hours (L:D). Mortality and larval growth inhibition (defined as inhibition if larva did not enter second instar within 6 days) by each sample were scored after a 6 day exposure. Concentrations resulting in 50% mortality (LC50) or inhibition of 50% of the individuals (IC50) were calculated based on Probit analysis. The resistance ratio (RR)=(LC50 of resistant ECB)/(LC50 of susceptible ECB) was >300 fold to Cry1Ab for the Cry1A-res colony and >1000 to Cry1F for the Cry1F-res colony. Table 9 shows that the Cry1A- or Cry1F-resistant ECB were not cross-resistant to N-6×His-IPD103Aa (SEQ ID NO: 2).

TABLE 9

| ECB colony | LC/IC | ppm | Lower 95% CL | Upper 95% CL | Resistance Ratio |
|---|---|---|---|---|---|
| SS | LC50 | 128.7 | 97.1 | 187.5 | |
| | IC50 | 40.8 | 33.2 | 50 | |
| Cry1A- | LC50 | >256 (38% mortality) | | | >2 |
| res | IC50 | 194.5 | 143.3 | 314.9 | 4.8 |
| Cry1F- | LC50 | | ~256 | | ~2 |
| res | IC50 | 168.8 | 117.7 | 293.2 | 4.1 |

Example 16—Testing Cross-Resistance of Cry1A-Selected Diamondback Moth

A diet overlay assay similar to the method described by Kain et al. (J. Econ. Entomol. 97: 2073-2078, 2004) was used to determine the susceptibility of diamondback moth (DBM, *Plutella xylostella*) to N-6×His-IPD103Aa (SEQ ID NO: 2). Eight concentrations of N-6×His-IPD103Aa (SEQ ID NO: 2) plus a control and three cups (replications) for each concentration were included in each bioassay with the resistant (Cry1A-res) or susceptible DBM colony. An aliquot of 0.2 mL of IPD103Aa solution was applied to and evenly distributed over the diet surface (surface area 7 $cm^2$) of 30-mL plastic cups with 5 ml of artificial diet. Ten DBM neonates were transferred into each cup. Cups were covered with lids and held at 27° C., 50% RH, and a photoperiod of 16:8 (L:D) h and mortality or growth inhibition assessed after 5 days. Concentrations for 50% mortality (LC50) or inhibition of 50% of the individuals (IC50) were calculated based on Probit analysis. The RR was ~100 fold with Cry1A.88 for the Cry1A-res colony. Table 10 shows that the Cry1A resistant DBM were not cross-resistant to N-6×His-IPD103Aa (SEQ ID NO: 2).

TABLE 10

| DBM strain | LC/IC | μg/$cm^2$ | Lower 95% CL | Upper 95% CL | Resistance Ratio |
|---|---|---|---|---|---|
| SS | LC50 | 2.9 | 2.1 | 4.0 | |
| | IC50 | 1.7 | 1.3 | 2.2 | |
| Cry1A- | LC50 | 4.6 | 3.6 | 6.0 | 1.6 |
| res | IC50 | 1.7 | 1.2 | 2.2 | 1 |

Example 17—Site of Action of IPD103Aa

IPD103Aa (SEQ ID NO: 2) was evaluated for stability in the presence of midgut fluid extracts from *Helicoverpa zea* (Corn Earworm) and *Ostrinia nubilalis* (European Corn Borer) to determine if the full-length state represents pro-forms of the proteins and whether midgut proteolysis is required for activation to a toxic state in vivo.

The direct binding of the IPD103Aa (SEQ ID NO: 2) to *Helicoverpa zea* (Corn Earworm) brush border membrane vesicles was tested for target site identification. FIG. 4 shows the average densitometry values for bound Alexa-IPD103Aa (SEQ ID NO: 2) in the presence of different concentrations of unlabeled IPD103Aa (SEQ ID NO: 2) normalized to the amount bound in the absence of unlabeled IPD103Aa (SEQ ID NO: 2). The solid line reflects the best fit of a square logistic equation to the data. The data are best fit by a sigmoidal dose response equation having EC50 values of 38 nM.

Figure 5:
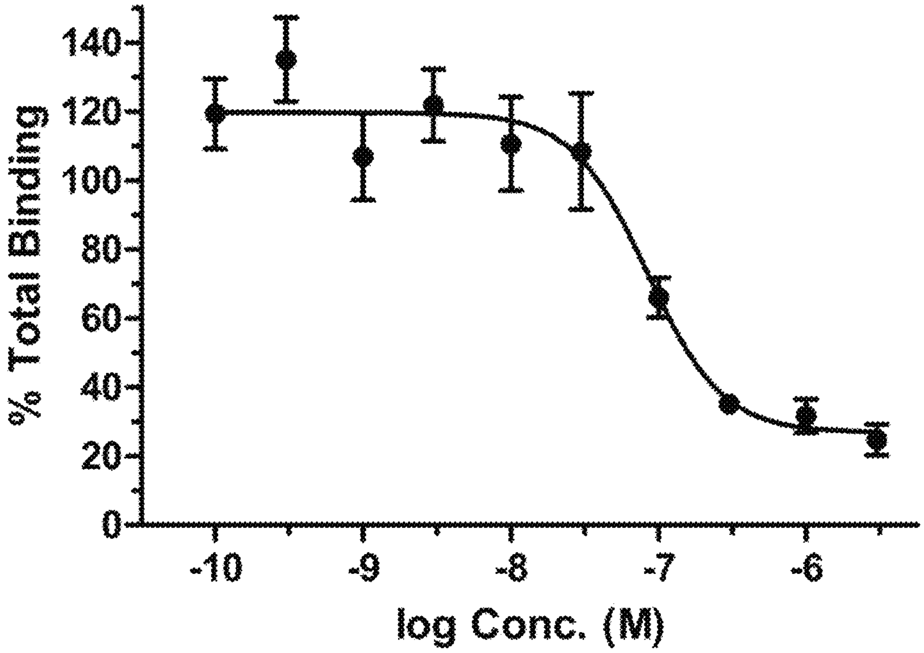
FIG. 5 shows a curve reflecting densitometry values of in-gel fluorescence, from the SDS-PAGE gel of Example 16, for homologous competition of 25 nM IPD103Aa$^{Alexa}$ binding to *Ostrinia nubilalis* (European Corn Borer) BBMVs normalized to the amount bound in the absence of unlabeled IPD103Aa (SEQ ID NO: 2). The solid line reflects the best fit of a square logistic equation to the data.

The direct binding of the IPD103Aa (SEQ ID NO: 2) to *Ostrinia nubilalis* (European Corn Borer) brush border membrane vesicles was tested for target site identification. FIG. 5 shows the average densitometry values for bound Alexa-IPD103Aa (SEQ ID NO: 2) in the presence of different concentrations of unlabeled IPD103Aa (SEQ ID NO: 2) normalized to the amount bound in the absence of unlabeled IPD103Aa (SEQ ID NO: 2). The solid line reflects the best fit of a square logistic equation to the data. The data are best fit by a sigmoidal dose response equation having EC50 values of 83 nM.

Example 18—Saturation Mutagenesis of IPD103Aa Variant

Saturation mutagenesis was performed at selected codons of the polynucleotide encoding the IPD103 variant IPD103lib11reary-54 (Example 7—Table 5). Mutants were generated by site directed mutagenesis (QuikChange® Lightning Multi Site Directed Mutagenesis Kit, Agilent Technologies). After transforming the resulting library variants into *E. coli* cells, colonies were sequence identified. Unique clones were picked and cultured in 96-well plates for protein expression. *Cell* lysates were generated by B-PER® Protein Extraction Reagent from Thermo Scientific (3747 N Meridian Rd, Rockford, IL USA 61101) and screened for CEW insecticidal activity. Table 11 summarizes the amino acid substitutions identified at each mutagenized position of IPD103lib11reary-54 and amino acid substitutions that retained insecticidal activity.

TABLE 11

| AA | Position | Identified substitutions | Active substitutions |
|---|---|---|---|
| A | 002 | G, V, L, I, P, S, T, C, N, Q, D, E, K, R | G, V, L, I, P, S, T, C, N, Q, E, K, R |
| D | 003 | G, A, V, L, I, W, F, P, S, T, C, E, R | G, A, V, L, I, W, F, P, S, T, C, E, R |
| P | 004 | G, A, L, W, S, Y, Q, D, E, K, R, H | G, A, L, W, S, Y, Q, D, E, K, R, H |
| A | 005 | G, V, L, P, S, C, Q, D, E, K, R | G, V, L, P, S, C, Q, D, E, K, R |
| T | 006 | G, A, V, L, I, P, S, N, Q, D, E, K, R | G, A, V, L, I, P, S, N, Q, D, E, K, R |
| A | 007 | G, V, L, W, F, P, T, C, D, K, R | G, V, L, W, F, P, T, C, D, K, R |
| A | 008 | G, L, W, P, S, T, Y, N, D, E, K, R | G, L, W, P, S, T, Y, N, D, E, K, R |
| R | 009 | G, A, V, L, I, W, F, P, S, T, N, D, E | G, A, V, L, I, W, F, P, S, T, N, D, E |
| E | 010 | G, A, V, L, M, W, S, K, R | G, A, V, L, M, W, S, K, R |
| A | 011 | G, V, W, P, S, T, C, Y, E, K, R, H | G, V, W, P, S, T, C, Y, E, K, R, H |
| E | 012 | G, V, L, W, P, S, T, Y, K, R, H | G, V, L, W, P, S, T, Y, K, R, H |
| E | 013 | G, V, L, I, M, W, F, S, D, K, R | G, V, L, I, M, W, F, S, D, K, R |
| E | 014 | G, A, V, L, F, S, T, C, Y, N, Q, R | G, A, V, L, F, S, T, C, Y, N, Q, R |
| V | 015 | G, A, L, I, S, Q, D, E, K, R | G, A, L, I, S, Q, D, E, K, R |
| Q | 016 | G, A, V, L, I, W, F, P, S, T, D, R, H | G, A, V, L, I, W, F, P, S, T, D, R, H |
| E | 017 | G, A, V, L, M, S, T, C, D, K, R | G, A, V, L, M, S, T, C, D, K, R |
| T | 018 | G, V, L, I, M, W, P, S, C, Q, D, E, R | G, V, L, I, M, W, P, S, C, Q, D, E, R |
| L | 019 | G, A, W, F, P, S, T, C, Y, N, Q, E, K, R | G, W, F, P, S, T, C, Y, N, Q, E, K, R |
| M | 020 | A, V, L, I, W, F, P, S, T, Q, D, E, K, R, H | S, T |
| D | 021 | G, A, V, L, W, F, S, C, N, Q, K, R, H | G, A, V, C, N, H |
| E | 022 | G, A, V, L, M, W, P, S, Y, D, R, H | G, A, M, P, S, D |
| T | 023 | G, A, V, L, I, M, W, P, S, N, Q, E, K, R, H | V, I, S |
| E | 024 | G, V, L, M, W, P, C, Y, Q, K, R | V, M, W, P, C, Q. |
| A | 025 | G, V, I, M, W, C, Y, E, R | G, V, I, M, C, E, R |
| V | 026 | G, A, L, I, M, W, S, T, Q, D, E, K, R, H | Q |
| G | 027 | A, V, L, I, M, W, P, S, C, D, K, R | |
| T | 028 | G, A, V, L, I, M, W, F, C, Q, E, K, R | A, V, I, M, C, Q, E |
| H | 029 | G, A, V, L, M, W, P, S, T, Y, N, Q, D, E, R | V, S |
| L | 030 | G, A, I, W, P, S, T, C, N, Q, D, E, K, R, H | I, P |
| D | 031 | G, A, V, L, M, F, S, T, E, R, H | S |
| F | 032 | G, A, V, L, I, M, W, P, T, N, Q, E, R, H | G, A, V, L, I, M, W, T, N, Q, E, H |
| V | 033 | G, L, M, W, F, P, S, T, C, Q, D, E, R, H | G, L, M, W, P, S, T, C, Q, E, R, H |
| A | 034 | G ,V, L, I, M, W, F, S, T, C, Y, Q, E, K, R, H | G, V, L, M, S, T, C, Y, Q, E, K, R, H |
| G | 035 | A, V, L, I, M, P, S, T, N, Q, D, K, R, H | A, M, P, S, T, N, D |
| L | 036 | G, A, M, W, P, S, T, C, Q, D, E, R | A, M |
| E | 037 | G, A, V, L, M, S, N, D, K, R | G, A, V, L, M, S, N, D, K, R |
| V | 038 | G, L, M, W, S, T, Q, E, K, R, H | L, K |
| Q | 039 | G, A, L, P, S, C, Y, N, D, E, R | A, L, C, Y, N, D, E, R |
| P | 040 | G, A, V, I, M, F, S, T, C, Q, D, E, K, R | A |
| R | 041 | G, A, V, L, I, M, W, F, P, S, T, C, N, D, E | A, V, L, I, M, F, P, S, T, N, E |
| K | 042 | G, A, V, L, M, F, P, S, T, C, Y, Q, E, R, H | G, A, V, S, T, Q, E, R |
| V | 043 | G, L, I, M, W, P, S, T, E, K, R | M, T |
| I | 044 | G, A, V, L, M, W, P, S, T, Y, E, K, R | V, M |
| T | 045 | G, A, V, L, I, W, P, S, C, Q, E, K, R | A, S, E |
| V | 046 | G, A, L, F, S, C, Y, Q, E, K, R, H | L, Q, H |
| E | 047 | G, V, L, M, W, F, S, N, K, R | |
| V | 048 | A, L, I, M, W, P, S, D, E, R, H | A, L, I, M |
| D | 049 | G, A, V, L, M, W, F, P, S, Q, R, H | |
| A | 050 | G, V, L, M, W, P, S, E, K, R | G, V, L, M, W, P, S |
| A | 051 | G, V, L, M, W, S, T, C, Q, D, E, K, R | G, V, T, C, Q |
| A | 052 | G, V, L, I, M, P, S, T, C, N, Q, D, R | G, V, L, M, P, S, T, N, Q, D |
| V | 053 | G, L, W, F, S, C, Y, Q, E, K, R, H | L |
| I | 054 | G, A, V, L, W, S, T, C, Y, E, R, H | A, V, L, W, Y |
| Q | 055 | G, V, L, I, W, P, S, C, Y, E, K, R, H | G, V, L, I, S, C, Y, E, K, H |
| Q | 056 | G, A, V, L, W, P, S, T, N, E, K, R | G, A, L, S, T, N, E, K, R |
| I | 057 | G, A, V, L, M, W, P, S, T, Y, N, D, R | V, L, T |
| R | 058 | G, A, L, M, W, P, S, T, C, Y, Q, D, K | G, A, L, M, W, P, S, T, C, Y, Q, D, K |
| E | 059 | G, A, L, M, P, S, Y, N, D, K, R | G, A, L, M, S, Y, N, D, K, R |
| I | 060 | G, A, V, L, M, W, S, T, N, Q, E, R, H | V, L, M, W, T, N, Q, E |
| F | 061 | G, A, V, L, M, W, S, Q, E, R | A, L, M, S |
| Q | 062 | G, A, V, L, M, F, P, S, T, R | G, A, V, L, M, F, S, T, R |
| T | 063 | G, A, V, L, P, S, Y, N, D, E, K, R, H | G, A, V, L, S, Y, N, D, E, K, R, H |
| M | 064 | G, A, L, I, W, P, S, T, N, Q, E, K, R | A, L, I |
| A | 065 | G, V, L, M, W, F, S, T, Q, D, E, R, H | G, V, L, M, W, F, S, T, Q, D, E, R, H |
| R | 066 | G, A, V, L, I, P, S, T, C, N, D, K, H | G, A, V, I, P, S, T, C, N, D, K, H |
| H | 067 | G, A, V, L, W, F, S, C, N, K, R | G, W, F, N, K |
| F | 068 | G, A, V, L, W, S, T, N, Q, K, R, H | A, V, L, S, T, Q, H |
| N | 069 | G, A, V, L, M, W, F, S, Y, Q, D, E, K, R | G, A, V, L, F, Y, Q, D |
| S | 070 | G, W, F, T, C, Y, N, Q, K, R | G, F, T, C, Y, N, Q, K, R |
| T | 071 | G, A, V, L, I, M, W, F, P, S, Q, E, K, R | A, L, I, S, Q, E, K, R |
| R | 072 | G, A, V, L, M, F, S, T, Y, Q, D, K, H | G, A, V, L, M, F, S, T, Y, Q, D, K, H |
| V | 073 | G, A, L, I, M, F, P, S, T, N, E, R | A, L, I, S, T |
| V | 074 | G, A, L, I, W, P, S, T, N, E, K, R, H | G, L, I, W, P, S, T, E, K, H |
| R | 075 | G, A, V, I, M, W, F, P, S, T, C, N, D, E, K | P |
| D | 076 | G, A, V, L, I, M, W, P, S, Y, N, E, R | G, A, W, P, S, Y, N |
| E | 077 | G, V, L, M, W, F, P, S, C, Y, N, Q, D, K, R, H | V, M, C, Y, N, Q, K, R, H |
| A | 078 | G, L, I, M, F, S, T, C, N, K, R, H | S, C, N |
| I | 079 | G, A, V, L, P, S, T, C, Y, N, D, E, K, R, H | G, V, P, Y, E |

TABLE 11-continued

| AA | Position | Identified substitutions | Active substitutions |
|---|---|---|---|
| K | 080 | G, A, V, L, M, W, P, S, T, C, N, D, E, R | A, V, M, S, T, C, R |
| G | 081 | A, V, L, F, S, C, Y, N, D, E, R | A, V, L, S, C, N, D, R |
| I | 082 | G, A, V, L, M, S, Y, N, D, E, K, R | L, M |
| R | 083 | A, V, I, M, W, F, P, T, C, Q, D, K, H | K |
| D | 084 | G, A, V, L, I, M, P, S, C, E, R, H | |
| H | 085 | A, V, L, I, W, F, S, C, Y, N, Q, D, K, R | |
| F | 086 | G, A, V, L, I, P, S, T, C, Y, N, D, K, R | C |
| R | 087 | G, A, V, L, W, P, S, Q, E, K, H | V, L, Q |
| A | 088 | G, V, L, I, M, P, S, T, C, Y, N, Q, D, E, R, H | V, T, C, Y |
| A | 089 | G, V, L, I, M, F, P, S, C, Y, D, K, R, H | S |
| V | 090 | G, A, L, I, M, P, S, D, R | I, M |
| P | 091 | G, V, L, M, W, F, S, T, C, E, K, R, H | |
| T | 092 | G, A, V, L, I, W, S, Y, Q, E, R, H | V, L, S |
| R | 093 | G, A, V, L, M, F, P, S, T, C, D, E, K | P, S |
| N | 094 | G, A, V, L, M, W, P, T, Y, Q, D, E, R, H | |
| V | 095 | G, A, L, I, W, P, S, T, C, N, Q, D, K, R, H | I, T, C, R |
| V | 096 | G, L, M, W, P, S, T, Y, N, Q, R, H | L |
| V | 097 | G, A, L, W, F, P, T, Y, E, R | A |
| V | 098 | G, A, L, M, W, S, Y, Q, E, K, R | A |
| H | 099 | G, A, V, L, I, M, W, F, T, Y, N, D, E, R | G, A, V, I, T, Y, N, R |
| T | 100 | G, A, V, L, M, W, P, S, C, N, Q, K, R, H | G, A, V, P, S, C, N, Q, H |
| Q | 101 | G, A, V, L, I, S, T, D, E, K, R | L, I, T, D, E, K, R |
| H | 102 | G, A, L, M, P, S, T, N, Q, D, E, R | A, S, N, Q, E, R |
| V | 103 | G, A, L, M, W, F, P, S, T, N, D, E, R | G, A, L, M, W, F, P, S, T, R |
| H | 104 | G, A, L, M, P, S, C, D, K, R | G, A, L, M, S, C, D, K, R |
| T | 105 | G, A, V, L, I, M, F, P, S, C, Y, Q, D, R | A, L, M, S, C, Y, Q |
| L | 106 | I, F, P, S, T, Y, D, R, H | I, F |
| V | 107 | L, I, M, W, P, S, T, Y, D, E, K, R, H | L, I, M, P, S, T, Y, D, E, K, R, H |
| G | 108 | V, L, M, P, S, T, C, Q, D, K | S, Q, D |
| L | 109 | I, M, W, F, P, S, T, Y, N, Q, D, E, K, R | I, M, W, F, P, S, T, Y, N, Q, D, E, K, R |
| E | 110 | G, A, V, L, I, W, F, S, T, Q, K, R | A, V, L, I, S, T, Q, K, R |
| H | 111 | G, A, V, L, W, F, P, S, T, Y, N, Q, D, R | G, A, V, L, W, F, P, S, T, Y, N, Q, D, R |
| T | 112 | G, A, V, L, M, W, P, S, Q, R | G, A, V, L, M, W, P, S, Q, R |
| H | 113 | G, A, V, L, M, W, F, P, S, N,Q, D, R | G, V, L, M, F, S, N, Q, R |
| L | 114 | G, A, V, I, M, W, P, S, N, Q, E, K, R, H | V, I, M, P, Q |
| V | 115 | G, A, L, W, P, S, R, H | G, A, L, W, P, S, R, H |
| L | 116 | G, A, V, M, S, C, Y, Q, R, H | V, M |
| Q | 117 | G, A, V, L, W, P, S, T, E, K, R, H | G, A, V, L, S, T, E, K, R, H |
| T | 118 | G, A, L, W, P, C, Y, Q, E, K, R | A, C |
| G | 119 | A, V, L, I, M, W, F, S, C, Y, N, D, E, R, H | A, V, M, S, N, D, E, H |
| I | 120 | G, A, V, L, M, W, F, S, T, Q, D, E, K, R | G, A, V, L, M, W, F, S, T, Q, E, K, R |
| F | 121 | G, V, L, M, W, P, S, Y, Q, D, E, K, R | G, V, L, M, W, S, Y, Q, E, K |
| K | 122 | G, V, P, S, T, C, Y, N, Q, R | G, P, S, T, C, N, R |
| K | 123 | G, A, V, L, M, W, P, S, T, C, Y, E, R | G, A, W, P, T, Y |
| V | 124 | G, A, W, T, C, N, Q, D, E, R | A, W, T, C, N, Q, R |
| P | 125 | G, A, V, L, W, S, T, Y, Q, E, R | G, A, V, L, W, S, T, Y, Q, E, R |
| V | 126 | G, A, I, F, P, S, T, Y, Q, E | A, I, F, S, T |
| D | 127 | G, A, V, L, M, W, P, S, C, Q, R, H | A, V, L, M, W, S, C, Q, R, H |
| I | 128 | A, V, L, M, W, P, S, Q, D, E, K, R | V, L, M |
| Y | 129 | G, A, V, L, I, M, W, F, P, S, T, D, R, H | |
| V | 130 | G, A, L, M, W, F, S, T, Y, D, E, R | A, L |
| F | 131 | G, V, L, W, S, T, E, R | |
| K | 132 | G, A, V, L, M, P, S, C, Q, E, R, H | G, A, V, L, P, S, C, Q, E, R |
| S | 133 | G, A, L, M, W, P, T, C, Y, Q, D, K, R | G, L, M, P, T, C, Q, D, K, R |
| G | 134 | A, V, L, M, W, P, C, Y, Q, E, R | |
| V | 135 | G, A, L, M, P, S, T, Q, E, K, R | G, A, L, M, P, S, T, Q, E, K, R |
| F | 136 | G, A, V, I, M, P, S, T, C, Y, N, Q, K, R | L, M, C, Y, R |
| T | 137 | G, A, V, L, W, P, S, E, R | S |
| L | 138 | G, A, V, M, W, P, S, Q, D, K, R | V, M, S, Q |
| L | 139 | G, A, V, W, F, P, S, T, C, Y, Q, E, K, R, H | A, V |
| G | 140 | A, L, M, W, P, T, C, Q, D, R | |
| D | 141 | G, V, L, M, W, S, T, N, R | G, V, M, S, T, N, R |
| G | 142 | A, V, L, P, T, C, E, K, R | A, V |
| G | 143 | A, V, L, W, S, Q, E, R | A, W, S, Q, E |
| F | 144 | G, A, V, L, W, P, S, Q, D, K, R | G, A, V, L, W, P, S, Q, K, R |
| I | 145 | G, A, V, M, W, C, Q, E, R, H | G, A, V, M, W, C, Q, E, R, H |
| N | 146 | G, L, M, W, P, S, T, E, K, R | |
| W | 147 | G, V, M, P, S, C, E, R | |
| A | 148 | G, V, L, I, M, W, P, S, Y, Q, K, R | G, S |
| W | 149 | G, A, V, L, F, S, T, N, E | |
| G | 150 | A, V, L, I, W, S, T, Y, Q, E, K, R | I, Q |
| G | 151 | V, L, M, W, S, D, E, R | S |
| F | 152 | G, A, V, L, M, W, P, S, T, C, Q, D, R, H | W |
| V | 153 | G, A, L, I, M, W, P, S, N, E, K, R | A, L, I, P |
| Q | 154 | G, V, L, W, F, P, S, T, N, D, E, K, R, H | G, V, L, W, F, P, S, T, N, D, E, K, R, H |
| E | 155 | G, V, L, M, F, P, S, N, Q, K, R | G, V, L, M, F, S, N, Q, K, R |
| V | 156 | G, A, L, M, F, P, S, Q, E, K, R | A, L, M, F, S, Q, E, K, R |
| A | 157 | G, V, L, I, M, W, P, S, T, N, Q, E, K, R, H | G, V, L, I, M, W, S, T, N, Q, E, K, R, H |

TABLE 11-continued

| AA | Position | Identified substitutions | Active substitutions |
|---|---|---|---|
| G | 158 | A, V, W, P, T, C, E, K, R | A, V, W, P, T, C, E, K, R |
| K | 159 | G, A, V, L, I, W, P, S, T, Y, Q, R, H | G, A, V, L, P, S, T, Y, Q, R,H |
| R | 160 | G, A, V, L, I, M, F, S, T, C, Y, E, K | I, M, Y, K |
| I | 161 | G, A, V, L, M, W, F, P, S, T, Y, Q, D, E, R | A, V, L |
| H | 162 | G, A, L, I, W, F, P, S, T, C, Y, Q, K, R | G, A, L, I, W, F, S, T, C, Y, Q, K, R |
| F | 163 | A, L, S, T, C, Y, D, E | |
| R | 164 | G, V, L, I, M, W, F, P, S, T, Y, N, D | V, L, I, M, S, T, N, D |
| L | 165 | G, V, I, M, W, F, P, S, N, Q, E, K, R | G, V, I, M, W, F, P, S, N, Q, E, K, R |
| P | 166 | G, A, V, L, I, M, W, S, T, C, Y, N, Q, D, E, K, R, H | A, T, C, Q |
| P | 167 | G, A, V, L, M, W, S, T, C, Y, N, D, R, H | A, N, D |
| G | 168 | A, V, L, M, W, P, S, T, Q, R, H | |
| A | 169 | G, V, L, M, W, F, S, T, C, N, Q, R, H | G, S, T, C, Q |
| L | 170 | A, V, I, M, P, S, T, Y, Q, R, H | A, V, I, M, S, T, Y, Q, R, H |
| P | 171 | G, A, V, M, W, S, T, C, E, R | G, A, V, M, W, S, T, C, E, R |

Example 19 Identification of Amino Acid Positions Affecting the Protein Stability and Function of IPD103

Additional mutagenesis was performed on selected positions within IPD103lib11reary-54. Protein was purified from the single mutants and screened for activity on CEW. Table 12 summarizes additional amino acid substitutions identified, amino acid substitutions allowing retention of insecticidal activity, and amino acid substitutions resulting in reduced protein yields from *E. coli*.

TABLE 12

| AA | Position | Identified substitutions | Active substitutions | Reduced Expression substitutions |
|---|---|---|---|---|
| A | 002 | F, H, M, W, Y | F, H, M, W, Y | |
| A | 011 | D, F, L, M, N, Q | D, F, L, M, N, Q | |
| T | 018 | A, F, H, K, N, Y | A, H, K, N | |
| M | 020 | C, G, N, Y | | |
| D | 021 | E, I, M, P, T, Y | E, P, T | M |
| G | 027 | E, F, H, N, Q, T, Y | | F |
| D | 031 | I, K, P, Q | | |
| A | 034 | D, N, P | D, N, P | |
| A | 065 | C, I, K, N, P, Y | C, I, N, Y | K, P |
| R | 066 | E, F, M, Q, S, W, Y | E, F, M, S, W, Y | |
| F | 068 | C, D, E, I, M, P, Y | C, I, M | |
| S | 070 | A, D, E, H, I, L, M, P, V | A, D, E, H, L, M, V | I, P |
| N | 094 | C, F, I, K, S | | I, K |
| H | 104 | E, Q, T, W, Y | E, Q, T, W | |
| G | 140 | E, F, H, I, K, N, S, V, Y | S | I, N, V |
| W | 147 | A, D, F, H, I, K, L, N, Q, T, Y | F | D, K |
| W | 149 | C, D, H, I, K, M, P, Q, Y | | C, D, H, K, M, Q |
| Q | 154 | A, C, I, M | A | C, I, M |
| E | 155 | A, C, D, I, T, W | A, C, D, I, T, W | |
| G | 168 | C, D, E, F , I, K, N, Y | F | |

TABLE 13

| | Primary Tier1 | | | | Prim. Tier2 | | | Sec |
|---|---|---|---|---|---|---|---|---|
| Active | SBL | VBC | CBW | SAW | CEW | FAW | GAW | TBW |
| IPD103Aa | +++ | +++ | ND | − | +++ | − | ND | +++ |
| IPD083Cb | +++ | +++ | +++ | +++ | +++ | +++ | ++ | +++ |
| Cry1B.34 | +++ | +++ | − | +++ | − | +++ | +++ | − |
| IPD103Aa | +++ | +++ | ND | − | +++ | − | ND | +++ |
| IPD083Cb | +++ | +++ | +++ | +++ | +++ | +++ | ++ | +++ |
| Cry1Ca | +++ | +++ | − | +++ | − | ++ | +++ | − |

Example 20 Transgene Insecticidal Stacks

Molecular stacks and breeding stacks can be constructed utilizing the polynucleotide sequences encoding the pesticidal proteins of the disclosure, including IPD103 (SEQ ID NO: 2), PtIP-83Cb (SEQ ID NO: 45), Cry1B variant IP1B-34 (SEQ ID NO: 91), a Cry1Ca polypeptide, and a Cry1D polypeptide. Exemplary stacks and the activity spectrums of the selected stack components against selected insect species: soybean looper (SBL); Velvetbean caterpillar (VBC); cotton bollworm (CBW); southern armyworm (SAW); corn earworm (CEW); fall armyworn (FAW); grasshopper armyworm (GAW); and tobacco budworm (TBM).

TABLE 13-continued

| | Primary Tier1 | | | | Prim. Tier2 | | | Sec |
|---|---|---|---|---|---|---|---|---|
| Active | SBL | VBC | CBW | SAW | CEW | FAW | GAW | TBW |
| IPD103Aa | +++ | +++ | ND | − | +++ | − | ND | +++ |
| Cry1D | +++ | − | +++ | +++ | +++ | +++ | − | +++ |
| IPD083Cb | +++ | +++ | +++ | +++ | +++ | +++ | ++ | +++ |
| IPD103Aa | +++ | +++ | ND | − | +++ | − | ND | +++ |
| Cry1D | +++ | − | +++ | +++ | +++ | +++ | − | +++ |
| Cry1B.34 | +++ | +++ | − | +++ | − | +++ | +++ | − |
| IPD103Aa | +++ | +++ | ND | − | +++ | − | ND | +++ |
| Cry1D | +++ | − | +++ | +++ | +++ | +++ | − | +++ |
| Cry1Ca | +++ | +++ | − | +++ | − | ++ | +++ | − |
| IPD103Aa | +++ | +++ | ND | − | +++ | − | ND | +++ |
| Cry1D | +++ | − | +++ | +++ | +++ | +++ | − | +++ |
| IPD083Cb | +++ | +++ | +++ | +++ | +++ | +++ | ++ | +++ |

TABLE 13-continued

| Active | Primary Tier1 | | | | Prim. Tier2 | | | Sec |
|---|---|---|---|---|---|---|---|---|
| | SBL | VBC | CBW | SAW | CEW | FAW | GAW | TBW |
| IPD103Aa | +++ | +++ | ND | − | +++ | − | ND | +++ |
| IPD083Cb | +++ | +++ | +++ | +++ | +++ | +++ | ++ | +++ |

"+++" = good control
"++" = fair control
"−" = no control
ND = not determined

Example 21—Identification of IPD103Aa Homologs

Additional IPD103Aa homologs were identified as described in Example 4. The IPD103Aa homologs, the organism they were identified from, the DNA sequence identifier, protein sequence identifies, and the CEW activity are shown in Table 14.

TABLE 14

| ID | Source | Organism | DNA | Protein | CEW Activity |
|---|---|---|---|---|---|
| IPD103Cd | NY-111 | *Polystichum munitum* | SEQ ID NO: 242 | SEQ ID NO: 252 | + |
| IPD103Bp | NY-167 | *Polystichum aculeatum* | SEQ ID NO: 243 | SEQ ID NO: 253 | + |
| IPD103Br | NY-167 | *Polystichum aculeatum* | SEQ ID NO: 244 | SEQ ID NO: 254 | + |
| IPD103Dc | LW14145 | *Osmunda claytoniana* | SEQ ID NO: 245 | SEQ ID NO: 255 | + |
| IPD103Dd | MB0389 | *Osmunda cinnamomea* | SEQ ID NO: 246 | SEQ ID NO: 256 | + |
| IPD103De | MB0389 | *Osmunda cinnamomea* | SEQ ID NO: 247 | SEQ ID NO: 257 | + |
| IPD103Bl | NY26 | *Asplenium ebenoides* | SEQ ID NO: 248 | SEQ ID NO: 258 | + |
| IPD103Bm | NY26 | *Asplenium ebenoides* | SEQ ID NO: 249 | SEQ ID NO: 259 | + |
| IPD103Bo | NY54 | *Gymnocarpium dryopteris* | SEQ ID NO: 250 | SEQ ID NO: 260 | + |
| IPD103Af | NY49 | *Colysis pteropus* | SEQ ID NO: 251 | SEQ ID NO: 261 | + |

The above description of various illustrated embodiments of the disclosure is not intended to be exhaustive or to limit the scope to the precise form disclosed. While specific embodiments of and examples are described herein for illustrative purposes, various equivalent modifications are possible within the scope of the disclosure, as those skilled in the relevant art will recognize. The teachings provided herein can be applied to other purposes, other than the examples described above. Numerous modifications and variations are possible in light of the above teachings and, therefore, are within the scope of the appended claims.

These and other changes may be made in light of the above detailed description. In general, in the following claims, the terms used should not be construed to limit the scope to the specific embodiments disclosed in the specification and the claims.

The entire disclosure of each document cited (including patents, patent applications, journal articles, abstracts, manuals, books or other disclosures) in the Background, Detailed Description, and Examples is herein incorporated by reference in their entireties.

Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight; temperature is in degrees centigrade; and pressure is at or near atmospheric.

That which is claimed is:

1. An insecticidal polypeptide having at least 95% sequence identity to the amino acid sequence of SEQ ID NO: 252, SEQ ID NO: 253, SEQ ID NO: 254, SEQ ID NO: 255, SEQ ID NO: 256, SEQ ID NO: 257, SEQ ID NO: 258, SEQ ID NO: 259, SEQ ID NO: 260 or SEQ ID NO: 261, wherein the insecticidal polypeptide is operably linked to a heterologous signal peptide or transit peptide.

2. The insecticidal polypeptide of claim 1, having the amino acid sequence of SEQ ID NO: 252, SEQ ID NO: 253, SEQ ID NO: 254, SEQ ID NO: 255, SEQ ID NO: 256, SEQ ID NO: 257, SEQ ID NO: 258, SEQ ID NO: 259, SEQ ID NO: 260 or SEQ ID NO: 261.

3. A polynucleotide encoding a polypeptide having at least 95% sequence identity to the amino acid sequence of SEQ ID NO: 252, SEQ ID NO: 253, SEQ ID NO: 254, SEQ ID NO: 255, SEQ ID NO: 256, SEQ ID NO: 257, SEQ ID NO: 258, SEQ ID NO: 259, SEQ ID NO: 260 or SEQ ID NO: 261, wherein the polynucleotide is operably linked to a heterologous regulatory element.

4. A DNA construct comprising the polynucleotide of claim 3.

5. A transgenic plant comprising the DNA construct of claim 4.

6. A method for controlling an insect pest population comprising contacting the insect pest population with the transgenic plant of claim 5.

7. A method for controlling an insect pest population comprising expressing, in the transgenic plant of claim 5, said polypeptide.

* * * * *

SEQUENCE LISTING

```
Sequence total quantity: 261
SEQ ID NO: 1            moltype = DNA  length = 516
FEATURE                 Location/Qualifiers
source                  1..516
                        mol_type = other DNA
                        organism = Athyrium niponicum
SEQUENCE: 1
atggcggaca aagcagcagc agcagctaga gaagctgaag aagaggtgga gacgacgatg   60
gacgagactg aggcggtggg gacgcacctg gacttcttgg gcgcggacgt gaagttgcaa  120
```

-continued

```
ccccgcaaca tcatcaccgt ggaggtggac gcggctgccg taatccaaca gatcagagag  180
atcttccaga caatggcgcg tcacttcaac tctacgaggg tggtgcggga tgaagccatc  240
aagggcattc gagaccactt cagggccgcc gtcccgactc gcaacgtggt ggtcattcac  300
actcagcacg ttcacacact ggtgggcttg gagcacaccc acctcgtctt gcagaccggc  360
atcttcaaaa aggtccccgt cgacatctat gtcttcaagt ccggcgtctt caccaacctt  420
ggagacggag gcttcatcaa ctgggcatgg ggtggcttcg tcgaccaggt cgtcggcaag  480
cgtatccact tccgcttgcc ccccggggcg ctccct                              516

SEQ ID NO: 2           moltype = AA  length = 172
FEATURE                Location/Qualifiers
source                 1..172
                       mol_type = protein
                       organism = Athyrium niponicum
SEQUENCE: 2
MADKAAAAAR EAEEEVETTM DETEAVGTHL DFLGADVKLQ PRNIITVEVD AAAVIQQIRE  60
IFQTMARHFN STRVVRDEAI KGIRDHFRAA VPTRNVVVIH TQHVHTLVGL EHTHLVLQTG  120
IFKKVPVDIY VFKSGVFTNL GDGGFINWAW GGFVDQVVGK RIHFRLPPGA LP          172

SEQ ID NO: 3           moltype = DNA  length = 513
FEATURE                Location/Qualifiers
source                 1..513
                       mol_type = other DNA
                       organism = Athyrium niponicum
SEQUENCE: 3
atggcggacc aagcagcagc agctagagaa gctgaagaag aggtggagac gacgatggac  60
gagactgagg cggtggggac gcacctggac ttcttgggcg cggacgtgaa gttgcaaccc  120
cgcaacatca tcaccgtgga ggtggacgcc gctgccgtaa tccaacagat cagagagatc  180
ttccagacaa tggcgcgtca cttcaactct acgagggtgg tgcgggatga agccatcaag  240
ggcattcgag accacttcag ggccgccgtc ccgactcgca acgtggtggt cattcacact  300
cagcacgttc acacactggt gggcttggag cacacccacc tcgtcttgca gaccggcatc  360
ttcaaaaagg tccccgtcga catctatgtc ttcaagtccg gcgtcttcac caaccttgga  420
gacggaggct tcatcaactg ggcatggggt ggcttcgtcg accaggtcgt cggcaagcgt  480
atccacttcc gcttgccccc cggggcgctc cct                                513

SEQ ID NO: 4           moltype = AA  length = 171
FEATURE                Location/Qualifiers
source                 1..171
                       mol_type = protein
                       organism = Athyrium niponicum
SEQUENCE: 4
MADQAAAARE AEEEVETTMD ETEAVGTHLD FLGADVKLQP RNIITVEVDA AAVIQQIREI  60
FQTMARHFNS TRVVRDEAIK GIRDHFRAAV PTRNVVVIHT QHVHTLVGLE HTHLVLQTGI  120
FKKVPVDIYV FKSGVFTNLG DGGFINWAWG GFVDQVVGKR IHFRLPPGAL P           171

SEQ ID NO: 5           moltype = DNA  length = 513
FEATURE                Location/Qualifiers
source                 1..513
                       mol_type = other DNA
                       organism = Platycerium wandae
SEQUENCE: 5
atggccgaac cagcagcagc agctagagaa gctgaagaag aggtggagac gacgatggac  60
gagactgagg cggtggggac gcacctggac ttcttgggcg cggacgtgaa gttgcaaccc  120
cgcaacatca tcaccgtgga ggtggacgcg gctgccgtaa tccaacagat cagagagatc  180
ttccagacaa tggcgcgtca cttcaactct acgagggtgg tgcgggatga agccatcaag  240
ggcattcgag accacttcag ggccgccgtc ccgactcgca acgtggtggt cattcacact  300
cagcacgttc acacactggt gggcttggag cacacccacc tcgtcttgca gaccggcatc  360
ttcaaaaagg tccccgtcga catctatgtc ttcaagtccg gcgtcttcac caaccttgga  420
gacggaggct tcatcaactg ggcatggggt ggcttcgtcg accaggtcgt cggcaagcgt  480
atccacttcc gcttgccccc cggggcgctc cct                                513

SEQ ID NO: 6           moltype = AA  length = 171
FEATURE                Location/Qualifiers
source                 1..171
                       mol_type = protein
                       organism = Platycerium wandae
SEQUENCE: 6
MAEPAAAARE AEEEVETTMD ETEAVGTHLD FLGADVKLQP RNIITVEVDA AAVIQQIREI  60
FQTMARHFNS TRVVRDEAIK GIRDHFRAAV PTRNVVVIHT QHVHTLVGLE HTHLVLQTGI  120
FKKVPVDIYV FKSGVFTNLG DGGFINWAWG GFVDQVVGKR IHFRLPPGAL P           171

SEQ ID NO: 7           moltype = DNA  length = 510
FEATURE                Location/Qualifiers
source                 1..510
                       mol_type = other DNA
                       organism = Pteris ensiformis
SEQUENCE: 7
atggccgacc aaggagcagc agctagagaa gctgaggaag aggtggagac gacgatggac  60
gagacggagg cggtggggac gcacctggac tttttggcgg acgtgaaggt gcagccccgc  120
aacatcatca ccgtggaggt ggacgccgct gccgtaatcc aacagatcag agagatcttc  180
```

-continued

```
caaaccatgg cacgtcactt caactctacg agggtggtgc gggatgaagc cattaagggc  240
attcgagacc acttcagggc cgccgttccg actcgcaacg tggtggtcat tcacactcag  300
cacgttcaaa cactggtggc cgtggagcac agccacatcg tcttgcagac cggcatcttc  360
aagaaggtcc ccgtcgacat ctatgttttc aagtccggcg tcttcaccaa ccttggagac  420
ggaggctaca tcaactgggc atggggtggc ttcgtagacc aggtcgtcgg caagcgtatc  480
cacttccgct tgccccccgg ggcgctccct                                   510

SEQ ID NO: 8           moltype = AA  length = 170
FEATURE                Location/Qualifiers
source                 1..170
                       mol_type = protein
                       organism = Pteris ensiformis
SEQUENCE: 8
MADQGAAARE AEEEVETTMD ETEAVGTHLD FLADVKVQPR NIITVEVDAA AVIQQIREIF  60
QTMARHFNST RVVRDEAIKG IRDHFRAAVP TRNVVVIHTQ HVQTLVAVEH SHIVLQTGIF  120
KKVPVDIYVF KSGVFTNLGD GGYINWAWGG FVDQVVGKRI HFRLPPGALP             170

SEQ ID NO: 9           moltype = DNA  length = 507
FEATURE                Location/Qualifiers
source                 1..507
                       mol_type = other DNA
                       organism = Pteris ensiformis
SEQUENCE: 9
atggccgacc aagctgcagc tagagaagct gaggaagagg tggagacgac gatggacgag  60
acggaggcgg tggggacgca cctggacttt ttggcggacg tgaaggtgca gccccgcaac  120
atcatcaccg tggaggtgga cgccgctgcc gtaatccaac agatcagaga gatcttccaa  180
accatggcac gtcacttcaa ctctacgagg gtggtgcggg atgaagccat taagggcatt  240
cgagaccact tcagggccgc cgttccgact cgcaacgtgg tggtcattca cactcagcac  300
gttcaaacac tggtggccgt ggagcacagc cacatcgtct tgcagaccgg catcttcaag  360
aaggtccccg tcgacatcta tgttttcaag tccggcgtct tcaccaacct tggagacgga  420
ggctacatca actgggcatg gggtggcttc gtagaccagg tcgtcggcaa gcgtatccac  480
ttccgcttgc cccccggggc gctccct                                      507

SEQ ID NO: 10          moltype = AA  length = 169
FEATURE                Location/Qualifiers
source                 1..169
                       mol_type = protein
                       organism = Pteris ensiformis
SEQUENCE: 10
MADQAAAREA EEEVETTMDE TEAVGTHLDF LADVKVQPRN IITVEVDAAA VIQQIREIFQ  60
TMARHFNSTR VVRDEAIKGI RDHFRAAVPT RNVVVIHTQH VQTLVAVEHS HIVLQTGIFK  120
KVPVDIYVFK SGVFTNLGDG GYINWAWGGF VDQVVGKRIH FRLPPGALP              169

SEQ ID NO: 11          moltype = DNA  length = 546
FEATURE                Location/Qualifiers
source                 1..546
                       mol_type = other DNA
                       organism = Platycerium wandae
SEQUENCE: 11
atgagagagc gagagcgaga gcgagagaga gagatggccg aaccagcagc agcagcagct  60
aaaaaagctg aagaagaggt ggagatattt atggacgaca ctgaggcggt ggggacgcat  120
ctggacttct tggcgggctt gaaggtgcag ccccgcaaga tcatcaccgt ggaggtggac  180
cccgctgccg taatccagca gatcagggag atcttccaaa ccatggcacg tcacttcaac  240
tcgacgacgg tggtgcggga tgaagccatc aagggcattc gagaccactt cagggccgcc  300
gttccgactc gcaacgtggt ggtcgttcac actcagcaca ttcacaccct ggagggcttg  360
gagcacacca accttgtctt gcagaccggc ctcttcagaa aggtccccgt cgacatctac  420
gtcttcaagt ctggcgtctt caccctcctt ggagatggag gcttcatcaa ctgggcgtgg  480
ggtggcttcg tagagcaggt cgtcggcaag cgtatccact tccgcttacc ccctggggcg  540
ctccct                                                             546

SEQ ID NO: 12          moltype = AA  length = 182
FEATURE                Location/Qualifiers
source                 1..182
                       mol_type = protein
                       organism = Platycerium wandae
SEQUENCE: 12
MRERERERER EMAEPAAAAA KKAEEEVEIF MDDTEAVGTH LDFLAGLKVQ PRKIITVEVD  60
PAAVIQQIRE IFQTMARHFN STTVVRDEAI KGIRDHFRAA VPTRNVVVVH TQHIHTLEGL  120
EHTNLVLQTG LFRKVPVDIY VFKSGVFTLL GDGGFINWAW GGFVEQVVGK RIHFRLPPGA  180
LP                                                                 182

SEQ ID NO: 13          moltype = DNA  length = 513
FEATURE                Location/Qualifiers
source                 1..513
                       mol_type = other DNA
                       organism = Platycerium wandae
SEQUENCE: 13
atggccgaac cagcagcagc agcagctaaa aaagctgaag aagaggtgga gatatttatg  60
gacgacactg aggcggtggg gacgcatctg gacttcttgg cgggcttgaa ggtgcagccc  120
```

```
cgcaagatca tcaccgtgga ggtggacccc gctgccgtaa tccagcagat aagagagatc  180
tttcaaaccc tggcacgtca cttcaactcg acgacggtgg tgcgggatga agccatcaag  240
ggcattcgag accacttcag ggccgccgtt ccgactcgca acgtggtggt cgttcacact  300
cagcacattc acaccctgga gggcttggag cacaccaacc ttgtcttgca gaccggccgc  360
ttcagaaagg tccccgtcga catctacgtc ttcaagtctg gcgtcttcac cctccttgga  420
gatggaggct tcatcaactg ggcgtggggt ggcttcgtag agcaggtcgt cggcaagcgt  480
atccacttcc gcttaccccc tggggcgctc cct                               513

SEQ ID NO: 14          moltype = AA  length = 171
FEATURE                Location/Qualifiers
source                 1..171
                       mol_type = protein
                       organism = Platycerium wandae
SEQUENCE: 14
MAEPAAAAAK KAEEEVEIFM DDTEAVGTHL DFLAGLKVQP RKIITVEVDP AAVIQQIREI  60
FQTLARHFNS TTVVRDEAIK GIRDHFRAAV PTRNVVVVHT QHIHTLEGLE HTNLVLQTGR  120
FRKVPVDIYV FKSGVFTLLG DGGFINWAWG GFVEQVVGKR IHFRLPPGAL P           171

SEQ ID NO: 15          moltype = DNA  length = 513
FEATURE                Location/Qualifiers
source                 1..513
                       mol_type = other DNA
                       organism = Athyrium filix-femina
SEQUENCE: 15
atggccgaca aagcgcctcc tcctgctaga gaagcagaag aagaggtgga ggagacgatg  60
gacgagactg aggcagtggg gacgcacctg gacttgatag cgcacctgag tgtgcaaccc  120
cgcggcatca tcaccgtgga ggtggacccc gccgctgtaa tccaacagat cagagagatc  180
ttccaaacca tggcacgtca tttcaactct acgagggtgg tacgggatga agccatcaag  240
ggcattcgag accacttcag ggccgccgtc ccgactcgca acgtggtggt cattcacact  300
caacacgttc acacactggt gggcttggag cacacccacc tcgtcttgca gaccggcatc  360
tttagaacgg tccccgtcga catctacgtc ttcaagtccg gcgtgttcac caacctcgga  420
gacggaggct tcatcaactg ggcatggggt ggcttcgtga ccgaggtcgt tgggaagcgt  480
gtccacttcc gcttgccccc cggggcactc cct                               513

SEQ ID NO: 16          moltype = AA  length = 171
FEATURE                Location/Qualifiers
source                 1..171
                       mol_type = protein
                       organism = Athyrium filix-femina
SEQUENCE: 16
MADKAPPPAR EAEEEVEETM DETEAVGTHL DLIAHLSVQP RGIITVEVDP AAVIQQIREI  60
FQTMARHFNS TRVVRDEAIK GIRDHFRAAV PTRNVVVIHT QHVHTLVGLE HTHLVLQTGI  120
FRTVPVDIYV FKSGVFTNLG DGGFINWAWG GFVTEVVGKR VHFRLPPGAL P           171

SEQ ID NO: 17          moltype = DNA  length = 510
FEATURE                Location/Qualifiers
source                 1..510
                       mol_type = other DNA
                       organism = Colysis wrightii
SEQUENCE: 17
atggccgacc aagtagcagc agcgagaggg gctgaagaag aggtggagac gacgatggac  60
gagactgagg ctgtggggac gcacctggac ttcttggcgg acgtgaaggt gcaaccccgg  120
agcatcatca ccgtggaggt ggacgccgct gctgtaatcc aacagatcag agagatcttc  180
caaaccatgg cacgtcactt caactctacg agggtggtgc gggacgaagc catcaagggg  240
attcgagacc acttccgggc cgccgtcccg actcgcaacg tggtggtcgt tcacactcag  300
cacgttcaca cactggtggg cctggagcac accaacatcg tcttgcagac cggcctcttc  360
aaaaaggtcc ccgtcgacat ctatgtcttc aagtccggcg tcttcaccct ccttggagac  420
ggaggcttca tcaactgggc atggggtggc ttcgtagacc aggtcgtcgg caagcgtatc  480
cacttccgct tgcccccggg ggcgctccct                                   510

SEQ ID NO: 18          moltype = AA  length = 170
FEATURE                Location/Qualifiers
source                 1..170
                       mol_type = protein
                       organism = Colysis wrightii
SEQUENCE: 18
MADQVAAARG AEEEVETTMD ETEAVGTHLD FLADVKVQPR SIITVEVDAA AVIQQIREIF  60
QTMARHFNST RVVRDEAIKG IRDHFRAAVP TRNVVVVHTQ HVHTLVGLEH TNIVLQTGLF  120
KKVPVDIYVF KSGVFTLLGD GGFINWAWGG FVDQVVGKRI HFRLPPGALP             170

SEQ ID NO: 19          moltype = DNA  length = 513
FEATURE                Location/Qualifiers
misc_feature           484
                       note = n is a, c, g, or t
source                 1..513
                       mol_type = other DNA
                       organism = Nephrolepis falcata
SEQUENCE: 19
atggccgacc cagcaacagc agctagagaa gctgaagaag aggtgcagga gactttgatg  60
```

-continued

```
gacgagactg aggcggtggg gacgcacctg gacttcgtgg cgggcttgga ggtgcaaccc  120
cgcaaggtca tcaccgtgga ggtggacgcc gctgccgtaa tccagcagat cagagagatc  180
ttccgaacca tggcaagtca cttcaactcg acgagggtgg tgcgggatga agccatcaag  240
ggcattcgag accacttcag ggccgccgtc ccgactcgca acgtggtggt cgttcacacc  300
cagcacattc acacactgga gggcttggag cacaccaacc tcgtcttgca gaccggcctc  360
ttcaaaaagg tccccgtcga catctacgtc ttcaagtccg gcgtcttcac cctccttgga  420
gacggaggct tcatcaactg ggcatggggt ggcttcgtac aggaggtcgc cggcaagcgt  480
atcnacttcc gcttgccccc cggggcgctc cct                                513

SEQ ID NO: 20          moltype = AA  length = 171
FEATURE                Location/Qualifiers
SITE                   162
                       note = misc_feature - Xaa can be any naturally occurring
                        amino acid
source                 1..171
                       mol_type = protein
                       organism = Nephrolepis falcata
SEQUENCE: 20
MADPATAARE AEEEVQETLM DETEAVGTHL DFVAGLEVQP RKVITVEVDA AAVIQQIREI  60
FRTMASHFNS TRVVRDEAIK GIRDHFRAAV PTRNVVVVHT QHIHTLEGLE HTNLVLQTGL  120
FKKVPVDIYV FKSGVFTLLG DGGFINWAWG GFVQEVAGKR IXFRLPPGAL P           171

SEQ ID NO: 21          moltype = DNA  length = 537
FEATURE                Location/Qualifiers
source                 1..537
                       mol_type = other DNA
                       organism = Nephrolepsis cordifolia
SEQUENCE: 21
atgcagagag agagagagag agagatggcc gaccaagctg cagcagcagc tagagaagct  60
gaagaagagg tggaggtttt tatggacgag actgaggcgg tggggacgca cctggacttc  120
ttggcgggct tgaacgttca accccgcaag gtcatcaccg tggaggtgga cgccgctgcc  180
gtaatccaac agatcagaga gatcttccaa accatggcac gtcacttcaa ctcgacgagg  240
gtggtgcggg atgaagccat caagggcatt cgcgaccact tcagggccgc cgtcccgact  300
cgcaacgtgg tggtcgttca cactcagcac attcacactc tggtggacgt ggagcacacc  360
aacctcgtct tgcagaccgg catcttcaaa aaggtccccg tcgacatcta tgtcttcaag  420
tccggcgtct tcaccctcct tggagacggc ggcttcatca actgggcatg ggtggcttc   480
gtagaccagg ttgacggcaa gcgtatccac ttccgcttgc cccccggggc gctccct     537

SEQ ID NO: 22          moltype = AA  length = 179
FEATURE                Location/Qualifiers
source                 1..179
                       mol_type = protein
                       organism = Nephrolepsis cordifolia
SEQUENCE: 22
MQRERERЕМA DQAAAAAREA EEEVEVFMDE TEAVGTHLDF LAGLNVQPRK VITVEVDAAA  60
VIQQIREIFQ TMARHFNSTR VVRDEAIKGI RDHFRAAVPT RNVVVVHTQH IHTLVDVEHT  120
NLVLQTGIFK KVPVDIYVFK SGVFTLLGDG GFINWAWGGF VDQVDGKRIH FRLPPGALP   179

SEQ ID NO: 23          moltype = DNA  length = 513
FEATURE                Location/Qualifiers
source                 1..513
                       mol_type = other DNA
                       organism = Polystichium tsus-simense
SEQUENCE: 23
atggccgaca aagtagcagc agcgcctcct cctgctagag aagcagaaga agaggtggag  60
gagacgatgg acgagactga ggcggtgggg acgcacctgg acttgatagc gaccctaccg  120
cgtggcatca tcaccgtgga ggtggactcc gccgccgtaa tccaacagat cagagagatc  180
ttccaaacca tggcacgtca tttcaactct acgagggtgg taagggatga agccatcaag  240
ggcattcgag accacttcag ggccgccatc ccgactcgca acgtggtggt cattcacact  300
caacacgttc acacactggt gggcttggag cacacccacc tcgtcttgca gaccggcatc  360
tttaaaaagg tccccgtcga cgtctacgtc ttcaagtccg gcgtgctcac caacctcgga  420
gacggaggct tcatcaactg ggcatggggt ggcttcgtga ccgaggtcgt tgggaagcgt  480
gtccacttcc gcttgccccc cggggcgctc cct                                513

SEQ ID NO: 24          moltype = AA  length = 171
FEATURE                Location/Qualifiers
source                 1..171
                       mol_type = protein
                       organism = Polystichium tsus-simense
SEQUENCE: 24
MADKVAAAPP PAREAEEEVE ETMDETEAVG THLDLIATLP RGIITVEVDS AAVIQQIREI  60
FQTMARHFNS TRVVRDEAIK GIRDHFRAAI PTRNVVVIHT QHVHTLVGLE HTHLVLQTGI  120
FKKVPVDVYV FKSGVLTNLG DGGFINWAWG GFVTEVVGKR VHFRLPPGAL P           171

SEQ ID NO: 25          moltype = DNA  length = 513
FEATURE                Location/Qualifiers
source                 1..513
                       mol_type = other DNA
                       organism = Polystichium tsus-simense
```

```
SEQUENCE: 25
atggccgaca aagtagcagc agcgcctcct cctgctagag aagcagaaga agaggtggag  60
gagacgatgg acgagactga ggcggtgggg acgcacctgg acttgatagc aaccctaccg  120
cgtggcatca tcaccgtgga ggtggacggc gccgccgtaa tccaacagat cagagagatc  180
ttccaaacca tggcacgtca tttcaactct acgagggtgg taagggatga agccatcaag  240
ggcattcgag accacttcag ggccgccatc ccgactcgca acgtggtggt cattcacact  300
caacacgttc acacactggt gggcttggag cacacccacc tcgtcttgca gaccggcatc  360
tttaaaaagg tccccgtcga cgtctacgtc ttcaagtccg gcgtgctcac caacctcgga  420
gacggaggct tcatcaactg ggcatggggt ggcttcgtga ccgaggtcgt tgggaagcgt  480
gtccacttcc gcttgccccc cggggcgctc cct                                513

SEQ ID NO: 26          moltype = AA  length = 171
FEATURE                Location/Qualifiers
source                 1..171
                       mol_type = protein
                       organism = Polystichium tsus-simense
SEQUENCE: 26
MADKVAAAPP PAREAEEEVE ETMDETEAVG THLDLIATLP RGIITVEVDG AAVIQQIREI  60
FQTMARHFNS TRVVRDEAIK GIRDHFRAAI PTRNVVVIHT QHVHTLVGLE HTHLVLQTGI  120
FKKVPVDVYV FKSGVLTNLG DGGFINWAWG GFVTEVVGKR VHFRLPPGAL P            171

SEQ ID NO: 27          moltype = DNA  length = 519
FEATURE                Location/Qualifiers
source                 1..519
                       mol_type = other DNA
                       organism = Thelypteris palustris
SEQUENCE: 27
atggccgaca aagtagcagc agcttctcgg gctcaaggag cagaagaggt ggaggatctg  60
atggacgaga cagaggcggt ggggacgcac ctggactgca tgggcggcga cgtgaaggtg  120
caagcacgcg gcatcatcac cgtggaggtg gaccccgccg ccgtaatcca acagatcaga  180
gagatcttcc aaaccctggc acgtcactac aactctacga gggtggtacg ggatgcagcc  240
atcaaggcca ttcgagacca cttcagggcc gccgtcccga ctcgcaacgt ggtggtcatc  300
cacactcaac acgttcacac actggcggac gtagagcaca gccacctcgt cttgcagacc  360
ggcatcttca agaaggtccc cgtcgacatc tacgtcttca agtccggcgt gttcaccaac  420
ctcggcgacg gaggcttcat caactgggca tggggtggct acgtgacaga ggtcgttggg  480
aagcgtatcc acttccgctt gcccccgggg gcactccct                          519

SEQ ID NO: 28          moltype = AA  length = 173
FEATURE                Location/Qualifiers
source                 1..173
                       mol_type = protein
                       organism = Thelypteris palustris
SEQUENCE: 28
MADKVAAASR AQGAEEVEDL MDETEAVGTH LDCMGGDVKV QARGIITVEV DPAAVIQQIR  60
EIFQTLARHY NSTRVVRDAA IKAIRDHFRA AVPTRNVVVI HTQHVHTLAD VEHSHLVLQT  120
GIFKKVPVDI YVFKSGVFTN LGDGGFINWA WGGYVTEVVG KRIHFRLPPG ALP          173

SEQ ID NO: 29          moltype = DNA  length = 513
FEATURE                Location/Qualifiers
source                 1..513
                       mol_type = other DNA
                       organism = Athyrium filix-femina
SEQUENCE: 29
atggccgaca aagcgcctcc tcctgctaga gaagcagaag aagaggtgga ggagacgatg  60
gacgagactg aggcagtggg gacgcacctg gacttgatag cgcacctgag tgtgcaaccc  120
cgcggcatca tcaccgtgga ggtggacccc gccgctgtaa tccaacagat cagagagatc  180
ttccaaacca tggcacgtca tttcaactct acgagggtgg tacgggatga agccatcaag  240
ggcattcgag accacttcag ggccgccgtc ccgactcgca acgtggtggt cattcacact  300
caacacgttc acacactggt gggcttggag cacacccacc tcgtcttgca gaccggcatc  360
tttagaacgg tccccgtcga catctacgtc ttcaagtccg gcgtgctcac caacctcgga  420
gacggaggct tcatcaactg ggcatggggt ggcttcgtga ccgaggtcgt tgggaagcgt  480
gtccacttcc gcttgccccc cggggcactc cct                                513

SEQ ID NO: 30          moltype = AA  length = 171
FEATURE                Location/Qualifiers
source                 1..171
                       mol_type = protein
                       organism = Athyrium filix-femina
SEQUENCE: 30
MADKAPPPAR EAEEEVEETM DETEAVGTHL DLIAHLSVQP RGIITVEVDP AAVIQQIREI  60
FQTMARHFNS TRVVRDEAIK GIRDHFRAAV PTRNVVVIHT QHVHTLVGLE HTHLVLQTGI  120
FRTVPVDIYV FKSGVLTNLG DGGFINWAWG GFVTEVVGKR VHFRLPPGAL P            171

SEQ ID NO: 31          moltype = DNA  length = 513
FEATURE                Location/Qualifiers
source                 1..513
                       mol_type = other DNA
                       organism = Nephrolepis cordifolia
SEQUENCE: 31
```

-continued

```
atggccgacc aagctgcagc agcagctaga gaagctgaag aagaggtgga ggtttttatg  60
gacgagactg aggcggtggg gacgcacctg gacttcttgg cgggcttgaa cgttcaaccc  120
cgcaaggtca tcaccgtgga ggtggacgcc gctgccgtaa tccaacagat cagagagatc  180
ttccaaacca tggcacgtca cttcaactcg acgagggtgg tgcgggatga agccatcaag  240
ggcattcgcg accacttcag ggccgccgtc ccgactcgca acgtggtggt cgttcacact  300
cagcacattc acactctggt ggacgtggag cacaccaacc tcgtcttgca gaccggcatc  360
ttcaaaaagg tccccgtcga catctatgtc ttcaagtccg gcgtcttcac cctccttgga  420
gacggcggct tcatcaactg ggcatggggt ggcttcgtag accaggttga cggcaagcgt  480
atccacttcc gcttgccccc cggggcgctc cct                                513

SEQ ID NO: 32          moltype = AA  length = 171
FEATURE                Location/Qualifiers
source                 1..171
                       mol_type = protein
                       organism = Nephrolepis cordifolia
SEQUENCE: 32
MADQAAAAAR EAEEEVEVFM DETEAVGTHL DFLAGLNVQP RKVITVEVDA AAVIQQIREI  60
FQTMARHFNS TRVVRDEAIK GIRDHFRAAV PTRNVVVVHT QHIHTLVDVE HTNLVLQTGI  120
FKKVPVDIYV FKSGVFTLLG DGGFINWAWG GFVDQVDGKR IHFRLPPGAL P           171

SEQ ID NO: 33          moltype = DNA  length = 546
FEATURE                Location/Qualifiers
source                 1..546
                       mol_type = other DNA
                       organism = Platycerium wandae
SEQUENCE: 33
atgagagagc gagagcgaga gcgagagaga gagatggccg aaccagcagc agcagcagct  60
aaaaaagctg aagaagaggt ggagatattt atggacgaca ctgaggcggt ggggacgcat  120
ctggacttct tggcgggctt gaaggtgcag ccccgcaaga tcatcaccgt ggaggtggac  180
cccgctgccg taatccagca gataagagag atctttcaaa ccctggcacg tcacttcaac  240
tcgacgacgg tggtgcggga tgaagccatc aagggcattc gagaccactt cagggccgcc  300
gttccgactc gcaacgtggt ggtcgttcac actcagcaca ttcacaccct ggagggcttg  360
gagcacacca accttgtctt gcagaccggc cgcttcagaa aggtccccgt cgacatctac  420
gtcttcaagt ctggcgtctt caccctcctt ggagatggag gcttcatcaa ctgggcgtgg  480
ggtggcttcg tggagcaggt cgtcggcaag cgtatccact tccgcttacc ccctggggcg  540
ctccct                                                              546

SEQ ID NO: 34          moltype = AA  length = 182
FEATURE                Location/Qualifiers
source                 1..182
                       mol_type = protein
                       organism = Platycerium wandae
SEQUENCE: 34
MRERERERER EMAEPAAAAA KKAEEEVEIF MDDTEAVGTH LDFLAGLKVQ PRKIITVEVD  60
PAAVIQQIRE IFQTLARHFN STTVVRDEAI KGIRDHFRAA VPTRNVVVVH TQHIHTLEGL  120
EHTNLVLQTG RFRKVPVDIY VFKSGVFTLL GDGGFINWAW GGFVEQVVGK RIHFRLPPGA  180
LP                                                                  182

SEQ ID NO: 35          moltype = DNA  length = 513
FEATURE                Location/Qualifiers
source                 1..513
                       mol_type = other DNA
                       organism = Tectaria milnei
SEQUENCE: 35
atggccgatg aggtagctgg tcatcacggt cctgcctgtg aagaagaaga agaagagatg  60
ctgatggatg agactgaggc ggtgggggtg catgcaatcg atggcctgcc ggtgcaaaac  120
cgtagcatca ttaccgtgga ggtggacgcc gcagccgtaa tccagcagat cagagagata  180
tttgcatcga tgatcaagca ctacaactcc acgcgagtgg tgcgggatga ggccatcaag  240
tccattcgag accacttcag gctcgccgtg cccactcgca acgtggtggt gattcacact  300
cagcacgttc acacactgga cgccgtggag agctcgcacc tggtcttgcg aaccggtcta  360
ttcaaaaagg tgccagtgga catcttcgtc ttcaagtctg gcgtgttcac caacctggga  420
gacgggggct tcatcaactg ggcatggggt ggctacggcg tcaaccacac tgccaagcgt  480
gttgtcttca gtcggccccc tggggcgctc cct                                513

SEQ ID NO: 36          moltype = AA  length = 171
FEATURE                Location/Qualifiers
source                 1..171
                       mol_type = protein
                       organism = Tectaria milnei
SEQUENCE: 36
MADEVAGHHG PACEEEEEEM LMDETEAVGV HAIDGLPVQN RSIITVEVDA AAVIQQIREI  60
FASMIKHYNS TRVVRDEAIK SIRDHFRLAV PTRNVVVIHT QHVHTLDAVE SSHLVLRTGL  120
FKKVPVDIFV FKSGVFTNLG DGGFINWAWG GYGVNHTAKR VVFSRPPGAL P           171

SEQ ID NO: 37          moltype = DNA  length = 375
FEATURE                Location/Qualifiers
source                 1..375
                       mol_type = other DNA
                       organism = Davallia tyermannii
```

```
SEQUENCE: 37
atggacgccg ctgccgtaat ccagcagatt agagagatct tccaatccat ggcagatgac  60
ttcagctcga cgaaggtggt gcgggatgaa gccatcaagg gcattcgaga ccacttcagg  120
gccgccgtcc cgactcgcaa cgtggtggtc gttcacaccc cgcacattca cacacagctg  180
gtggacgtgg agcacaccaa actcgtcttg aagaccggca tcttcgaaaa ggtccccgtc  240
gacatctatg tcttcaagtc cggcgtcttc accctccttg gagacggagg ctacaacaac  300
tgggcatggg gtggcttcgt agaccaggtc gtcggcaagc gtatccactt ccgcttgccc  360
cccggggcgc tccct                                                   375

SEQ ID NO: 38          moltype = AA  length = 125
FEATURE                Location/Qualifiers
source                 1..125
                       mol_type = protein
                       organism = Davallia tyermannii
SEQUENCE: 38
MDAAAVIQQI REIFQSMADD FSSTKVVRDE AIKGIRDHFR AAVPTRNVVV VHTPHIHTQL  60
VDVEHTKLVL KTGIFEKVPV DIYVFKSGVF TLLGDGGYNN WAWGGFVDQV VGKRIHFRLP  120
PGALP                                                              125

SEQ ID NO: 39          moltype = AA  length = 867
FEATURE                Location/Qualifiers
source                 1..867
                       mol_type = protein
                       organism = Adiantum pedatum
SEQUENCE: 39
MALVDYGKLF EDLNQISMGV LDRVEFSEVM VIHRMYVRLA DLNVGQLEGA EKVKRLYVFA  60
DVVELPVVEW RWPPQIPGSV TVIILCRLLQ WPTDGRQSDT ELHLTFMKLH AIQREENRWE  120
ITAADGMNWG VYIHAEEVQV GVLTMSWSSV LRVSALRSVI TSGFRAVSVF EVPGSVRSTL  180
GATLRPDHAL YSTTMQATPN ASHISAFNLR IVSPSAYRVC PLQNDTDTYL GIPADVAAVL  240
PVDVVTDPNI LLGMQTTVHI AELVKACHPS PDVVSAVGEH LNWLNKLLLP LKESTQLQGS  300
ESYKECLALL GRVHAAMKMV RIGLVVPQLQ YRMYGSLINQ MAQVAQNYDR EFKQFKLFII  360
QNQILGSYLL QQNRAFAERE LQMESFHAAV ISQRREELDN TFAKMDRLSG QMEAESSAME  420
QAKKEMDEGL RQFQNRQVAN ALFAVLSAVA QIGLAFLTAG ATAPGAVASA GQAVSIAGQA  480
AQGLRRVVEI LEQLEAVMEV VAAVKDLVDS LEQVGQIVDA PVMPELPSEA DWSIFVNEVE  540
AVAEGMPTEV SEVPVWRAKC KNVAALGREM SITAVQMSEL QYDIWVQGMM RDMARSQADR  600
LAAIQPADLT NYLEMATQMD MRTTRMLLGL LNILRIQNAA LRYEYLLMPT ELTTWPLGMD  660
TVGDLLIAQE NAALIGLMQL GPSSDFTSRH VVKDIPVNLL LDGEDWEFEI PVQAGMSSFP  720
SSWSRVRIRH LEMHFVKEAS GIGGEIIHQP TTQTGTVYIL LQGSTIFHDR RRDQVLPFQA  780
AAPLNYHYAY RLDTGDSTLT NEPSEQFANK FMQMTPFTRW RLRLSASAKE NAGLAFPTAT  840
ALDSTTQIVI TFHVTAIRQI DWRHDEE                                      867

SEQ ID NO: 40          moltype = DNA  length = 2601
FEATURE                Location/Qualifiers
source                 1..2601
                       mol_type = other DNA
                       organism = Adiantum pedatum
SEQUENCE: 40
atggctctcg tggattacgg caagcttttc gaggatctga accagataag catgggtgta  60
ctggatcggg tagagttttc agaggtgatg gtgatccaca ggatgtatgt gaggctagct  120
gatctgaatg tggggcagct cgagggagcc gagaaagtga agcggttgta tgtgtttgcg  180
gacgtggtgg agctaccagt cgtggaatgg cggtggccgc cgcaaatacc aggatcggtg  240
acggtgatca tattgtgtcg tcttcttcaa tggccaactg atgggaggca gtcggacacc  300
gagctccacc tgacattcat gaagttgcat gccatacaac gagaggaaaa tcggtgggag  360
ataaccgcag cagatggcat gaactgggga gtttacatac acgcagagga agtacaggtt  420
ggcgtgctga caatgtcatg gtcttcggta cttagagttt cggcacttcg ctctgttata  480
acctccggct ttcgcgccgt tagtgtgttt gaggtaccgg gaagtgtaag gtccacccctt  540
ggagctactt taaggcccga tcacgcctta tatagtacaa ctatgcaagc cacacccaac  600
gcatcgcata ttagtgcttt taaccttcgc atagtttccc cgtcggcata tcgtgtttgt  660
cctctccaaa atgacacaga tacctactta ggtattccag cagacgtggc ggcagttctt  720
ccagtagacg tggtgactga tcctaacatc ttgctgggca tgcagacaac ggtacacatt  780
gcggagctag tcaaggcatg tcatccgtca cccgatgttg tgagcgctgt aggggagcac  840
ctgaactggc tcaacaaact cttactccca cttaaggaat cgactcagtt gcaaggaagc  900
gagtcgtaca aggagtgcct tgcactcttg ggtcgtgttc acgctgcgat gaagatggtg  960
agaattggct tagtagtgcc ccagctgcaa tacagaatgt acggtagcct catcaaccaa  1020
atggcccaag tagcacaaaa ctacgaccga gaattcaagc aattcaaatt attcatcatc  1080
caaaatcaaa tccttggcag ctatttgctg cagcagaaca gggcatttgc tgagagggag  1140
ctgcagatgg agagctttca tgctgctgtc atttctcaaa gaagggagga gttggacaat  1200
acattcgcaa agatggaccg attgagcggg caaatggagg cagagagtag tgcaatggag  1260
caagccaaaa aggaaatgga cgaaggattg aggcagttcc agaataggca agttgcgaac  1320
gccctctttg ccgttcttag cgctgtagct cagattgggc ttgcattcct tacggctggt  1380
gcaacggctc ctggagctgt ggcgtcggcg gggcaagctg tgagcatagc aggtcaggcg  1440
gcgcaaggtc tgcgaagggt ggtggaaatt ctagagcagc tggaggctgt gatggaggtt  1500
gtggctgctg tgaaggacct cgtggattca ttggaacagg taggtcagat tgtggacgca  1560
ccggtgatgc cggaattgcc ctcagaggcg gactggtcca tttttgtgaa cgaggtggag  1620
gccgtggcag agggcatgcc aacggaagtc tcggaggttc cggtgtggag ggccaagtgc  1680
aagaatgtgg ctgcactggg tcgggagatg agcatcacgg cagtacagat gtcggagctg  1740
cagtatgaca tctgggtgca aggcatgatg cgggatatgg ctcgaagcca ggcagacagg  1800
ctggccgcaa ttcaacccgc ggaccttacc aactatttgg agatggctac ccagatggat  1860
atgcggacta cgaggatgct gctggggctc ctcaacatat tgcgcatcca gaatgcggcg  1920
```

-continued

```
ctcaggtacg agtatcttct aatgcccacg gagctcacaa catggccact gggtatggat  1980
accgtgggtg acttgctcat cgcgcaggag aatgctgcac tgataggatt aatgcagcta  2040
gggccctcat ctgatttcac gagcaggcat gtggtgaaag acatacctgt gaacttgctg  2100
ctcgatggcg aggattggga gtttgagatt cctgtgcaag ctggcatgtc cagcttccct  2160
tccagctggt ctcgcgtccg tattcggcac ctggagatgc actttgtgaa ggaggccagc  2220
ggtattggtg gtgagattat ccaccagcct accacccaga ctgggaccgt ttacatcctt  2280
ctgcagggtt ccactatctt ccatgaccgc agaagagacc aggtgttgcc ttttcaggcc  2340
gctgctccgc tcaactacca ttacgcgtac cgcctcgaca ccggcgactc cactctcaca  2400
aacgaaccct ctgaacagtt tgccaacaag ttcatgcaga tgacaccctt cacccgttgg  2460
aggcttcgtc tgtctgcgtc cgcaaaagag aatgcaggat tagcctttcc cacggctaca  2520
gcacttgact ccactaccca gattgtcatc actttccatg ttacggccat cagacaaatt  2580
gactggcggc acgacgaaga g                                            2601

SEQ ID NO: 41          moltype = AA  length = 886
FEATURE                Location/Qualifiers
source                 1..886
                       mol_type = protein
                       organism = Microsorum musifolium
SEQUENCE: 41
MEYSSLYGDV NQVSLRFQNM EFSEVMVVHR MHVRLEELDM TGVEGIEKVK RLYVLADVVE  60
LPSTATQVFQ YLRLPASISA IILCRVLYIP EVDQRPHMAQ CSLDFPFMRL HVVGSVHENV  120
GGVMQAFSSD ATPSNIGIYL HADRFIYRQA TSPASNFVLP LDVRVSFGSS TYSGPTIRPD  180
WQNLNVSNIS YGPQHLSKGP PLTSSDSDLQ RSDEIELLAQ QDVWSPLLHV AFSPTALPGN  240
IPGTQGLFRP SSACSFFHVP PPDVPANVLT DPSIILGMQM NMLIAELVLA AHNSPQVMNV  300
ITKHVLWLNK ILLQVASPND DILALLFRIQ AFMKMAKQPR FVVPRLQYHM YGSLINRMVQ  360
VAQNYDQEFK QLKLFIAQNE ILGSYLLQQN RAFAEREKEM SAFHSQVVSM RRSELQSAIQ  420
TMDNLSLQME SESEAMNEAQ ENMVEAIQEY ERKLLARALF SVIGAIASVA LAFATGGATA  480
PGAVAAAGGA VAAAGRLAAG LQKVVDILQG LQAVMEVVVA IRDIVESLKN MGQLVEAPEM  540
PEMPTDADWL IFVNEVEAVA EQVPTEVAEV PVWKAKCKNV AVLGQAMCTT AAYISELQYQ  600
ITVEKMLQEI AQRQADRLVG ISAADLSSYT EMASQIDMRT TRILLELIKM LYIQNAAIKY  660
EYLYDANEKL NSWPVSMETV WTMLLQQENA ALLGLLDLGP TNDFTVTYAV KDIPTKLLVD  720
GFDWNFEIAV EDSAIFPSGW SRVRIRYVEL KFDQQGADSS NIVIHQPSTN TGLVYMLLQG  780
SRFLHDRKHE EVMDYEASLG PVYAYAYDLN TGATTLNNIP SQQYANTFMQ MTPFNAWRLR  840
LSASAVENQG LVFPTATSPD NTTQISITFY VTAIRRIDHR QEGDVE                 886

SEQ ID NO: 42          moltype = DNA  length = 2658
FEATURE                Location/Qualifiers
source                 1..2658
                       mol_type = other DNA
                       organism = Microsorum musifolium
SEQUENCE: 42
atggaatata gcagcttgta cggtgatgtg aaccaagtga gcctgaggtt ccagaacatg  60
gagttctctg aggtcatggt ggtgcatcgg atgcatgtgc gcctcgagga gcttgacatg  120
acgggggtgg agggcatcga gaaggtgaaa cgcctgtacg tgctggcgga cgtggtggag  180
ctgccttcca cagccaccca ggtgtttcag tatctgcgcc ttcctgcctc catttcagcg  240
attatcctct gccgtgttct ctatatccct gaagttgatc agaggcccca catggctcaa  300
tgctcgctcg acttcccgtt catgcgcctc catgtcgtcg gatctgtaca cgagaatgtt  360
gggggtgtta tgcaagcctt ttcctccgac gccaccccca gcaatattgg catctacctc  420
catgctgacc gcttcatcta ccgccaggcc acatctccgg ccagcaactt tgtcttgccc  480
ctggatgtaa gggtcagctt tggcagctct acctactcgg gcccaaccat ccgtcccgac  540
tggcaaaacc ttaatgtctc caacatcagc tacgggccac agcatttgtc caagggccca  600
cccctcacat cctcagactc cgacttgcag agatctgacg agatcgagct cctggcgcag  660
caagatgttt ggagccctct tttacatgtc gcgtttagcc cgactgcact acctggcaac  720
atcccgggta cacaaggact attccgaccc tcctctgcat gcagcttctt ccatgtgccg  780
ccaccggatg tccctgcgaa cgtgctcact gatccttcca tcatcttggg catgcaaatg  840
aacatgctca ttgccgagct tgtcttggct gctcacaatt cgccgcaggt catgaacgtc  900
atcactaagc atgtgctatg gctcaacaag atcttgcttc aggttgcttc acccaatgat  960
gatattttag cactcttgtt tcgtatccaa gcattcatga agatggcaaa gcaaccgcgg  1020
tttgtggttc cacggttgca gtaccacatg tacggtagcc ttatcaatcg aatggtgcaa  1080
gtagcccaga attatgacca ggagttcaag caactcaagc ttttcatcgc acaaaatgag  1140
attttgggaa gctatttgct acaacaaaat agggcttttg cagaaaggga gaaggaaatg  1200
agtgcttttc actcgcaggt cgtgtcgatg aggagatctg agcttcagtc tgccatacaa  1260
acaatggaca atttgagttt gcaaatggaa tcagagagtg aggcgatgaa cgaagcccag  1320
gagaacatgg ttgaagcaat tcaagagtat gaaaggaaat tacttgcaag agctctattt  1380
tctgtgattg ggcaatagc aagcgttgct cttgcatttg ccactggtgg tgcaactgca  1440
ccgggggcag tggcagcagc cggaggggct gttgctgcag cagggaggtt ggcagcaggg  1500
ctccaaaagg ttgtggacat cctacaaggc ttgcaagcgg tcatggaggt tgtggtagcc  1560
ataagagaca tcgtagaatc attgaaaaac atgggtcaac tagtagaagc tcccgagatg  1620
ccagagatgc caacggatgc ggactggtta atttttgtaa atgaggtgga ggcagtggca  1680
gagcaagtgc caacagaagt ggcagaggtc ccagtgtgga aggctaagtg caagaatgtg  1740
gctgtgctag ggcaagcaat gtgcaccaca gcagcatata ttagtgagct acagtatcag  1800
atcacggtgg aaaagatgct acaagagatt gcacagcgcc aagcagacag gttggtgggg  1860
atatcagcag cagatctatc gagctacaca gagatggcat cacaaataga catgcgtaca  1920
acccgaatcc tccttgaact catcaagatg ttgtacattc aaaatgcagc aattaagtat  1980
gagtacttgt atgatgctaa tgagaagctt aattcatggc cagtgagcat ggagactgta  2040
tggaccatgc tcttgcaaca agagaatgca gctctcttgg gcttgctaga cttggggccc  2100
accaatgatt tcactgtaac ctatgctgtt aaagacatac ctaccaagtt gttagtagat  2160
gggtttgatt ggaattttga gatcgcggtg gaggattctg caatctttcc atcaggatgg  2220
tctcgtgttc gcatacgata tgttgagctt aaatttgacc aacaaggtgc tgatagtagt  2280
```

```
aacattgtca tccaccagcc tagcactaac actggcttag tctacatgct cttacaaggc  2340
tcccggttcc tccatgaccg caaacatgag gaggtgatgg actatgaggc aagcttggga  2400
cctgtatatg catatgctta tgacctcaac actggtgcaa ccactctcaa caacatcccc  2460
tcacagcaat atgccaacac atttatgcaa atgacaccct tcaacgcctg gagacttcgc  2520
ctctctgcct ctgctgtgga aaatcaggga ttggtgtttc ctacagcaac ttctcctgac  2580
aatactaccc aaatttccat cacattctat gtcactgcta ttcgacgcat agatcatcga  2640
caagagggtg atgtggag                                                2658

SEQ ID NO: 43          moltype = AA  length = 853
FEATURE                Location/Qualifiers
source                 1..853
                       mol_type = protein
                       organism = Adiantum trapeziforme
SEQUENCE: 43
MDYSTLYRDL NQISIGVDRV EFSEVMVIHR MYVRLSDLNV GELPGAGRVK RVYVFADVVE  60
LAPRATLRDQ MHMPGSVTVI VLCRLLQFPI DGSQATTLRL PFMQLHARVI EQNVKSEITA  120
TDGMNWGIYI YGEKVERSPL LPSNAILAVW ADRCTITSAR HNHVNAPGRI ISTFTLGSGV  180
TGITSMHGEP SLDPWNGVSL DSASPTAFSA LPRQSRNISF TSIPVEVVTD PSILLGMQTT  240
VLIAELVKVC RPPSPDMMSA VAEHALWLND VLLQVVQNES QLQGTAPYNE CLALLGRIEC  300
VMKIGRFVSV VPQLQYRMYG NLIKQMAQVA QNYDQEFKQF KLFIVQNQIL GSYLLQKNKA  360
LADRELQMES FHSAVISQRR QELNTAIAKM ERMSLQMEEE NRAMEQAQKE MEEGLREFQN  420
RQVARAVFAV LKAVAMIALV FVTAGATAPG AAASAGQAVS IAGQAAQALR RVVEILEGLE  480
AVMEVVAAVK DLVDSLEQVG QIVGAPEMPD MPSEADWSIF VNEIEAVAEG MPTEVSEVPA  540
WKAKCKNMAA LGREMSITAV QISELQYEIW VQGLMRDIAR SHADRLAAIQ PVDLTNHLEM  600
ATHMDMRTTS MLIGLLNMLR IQNAALMYEY LLTPTELTVW PLGMDTVANL LIAQENAALV  660
GLIQLGQSSN FTSRHVVKGI PVSLLLDGED WEFEIPVQAG MSSFPFNWTR VRIRHLEMQF  720
AQEASGGGGG EIIHQPSTRS GIVYILLQGS TIFHDRRRDE VMTFQAADPL NFQYAYRLDT  780
GEATLTNEPS EDFANTFMQM TPFTRWRLRL SASASENAEL AFPTATAPDS TTEVVITFHV  840
TAIRQVDWRQ EEE                                                     853

SEQ ID NO: 44          moltype = DNA  length = 2559
FEATURE                Location/Qualifiers
source                 1..2559
                       mol_type = other DNA
                       organism = Adiantum trapeziforme
SEQUENCE: 44
atggattaca gcacgcttta cagggacctg aaccagataa gcatcggtgt ggaccgggta  60
gagttctcag aggtgatggt gatccacagg atgtatgtaa ggttgtctga tctgaatgtg  120
ggggagctcc ccggagccgg gagagtgaag cgggtgtacg tgtttgcgga tgtggtggag  180
cttgcaccgc gtgcgacgct gcgggatcag atgcatatgc caggatcggt gacagtgatc  240
gtattgtgtc gtcttcttca atttccaatc gatgggtcgc aagctacaac tctccggctg  300
cctttcatgc agttgcatgc cagagtcata gagcaaaatg taaagtcgga gataacagca  360
acagatggca tgaattgggg aatctacata tacggggaga aagtagagag gagcccgctc  420
cttcctagca atgcaatcct tgcagtttgg gcagatcgct gtactataac ctcagcccgt  480
cacaatcatg ttaacgcacc tgggagaata atatcgactt tcacacttgg gtcgggagta  540
acgggtataa cctctatgca cggggaaccc agtttggacc cttggaatgg tgtttctctc  600
gactcagctt cccctacggc atttagtgct ttacctcgcc aaagtaggaa tatatccttc  660
acaagtattc cagtagaggt ggtgactgat cctagcatct tgctgggcat gcagaccacc  720
gtgctcattg cggagctagt caaggtatgt cgcccaccat cacccgacat gatgagtgct  780
gtagcggagc acgcgctttg gctcaatgat gtcttactcc aagttgtcca gaacgaatct  840
cagttgcaag ggactgcgcc ctacaacgag tgccttgcac ttttgggtcg cattgaatgt  900
gtgatgaaaa tcgggagatt tgtctcagta gtgcctcagc tgcaatacag aatgtatggt  960
aacctcatca aacaaatggc ccaagtagca caaaactacg accaagaatt caagcaattc  1020
aagttattca tcgtccaaaa ccaaatcctt ggcagctatt tgcttcagaa gaacaaggca  1080
ttagctgaca gggagctgca gatggagagc tttcattcag cggtcatttc tcaaagaagg  1140
caggagttga atactgccat cgcaaagatg gagcgaatga gcttgcaaat ggaggaagag  1200
aatagagcaa tggagcaagc tcaaaaggaa atggaagaag gattgaggga gttccagaat  1260
aggcaagttg caagggccgt atttgccgtt cttaaagccg tagctatgat tgcgcttgta  1320
ttcgtcacgg ctggtgcgac ggctcctgga gctgcggcgt ccgcggggca agctgtgagc  1380
atagcaggtc aggccgcaca agctctgcga agggtggtgg aaattctaga ggggctggag  1440
gctgtgatgg aggttgtggc tgctgtgaag gaccttgtgg attcattgga acaggtaggt  1500
cagattgtgg gggcaccgga gatgccggac atgccctcgg aggcggactg gtccattttt  1560
gtgaatgaga ttgaggccgt ggcagagggg atgccgacgg aagtctcgga ggttccggca  1620
tggaaggcca agtgcaagaa tatggctgca ctgggtaggg agatgagcat cacggcagta  1680
cagatttctg agctccagta tgagatctgg gtgcaaggct tgatgcggga tatagctcga  1740
agccatgcag acaggttggc tgcgattcaa cctgtggacc ttaccaacca tttggagatg  1800
gccacacaca tggatatgcg gactacaagt atgctgatag ggctcctcaa catgctgcgc  1860
atccagaatg cggcactcat gtacgagtac cttctaacac ccacggagct cacagtatgg  1920
ccactgggta tggataccgt ggccaacttg ctcattgcgc aggagaatgc tgcactggtg  1980
ggattaattc agctagggca atcgtcgaat tttacgagca gacatgtggt gaaaggcata  2040
cctgtgagct tactgctcga tggtgaggat tgggaattcg agatccctgt gcaagctggc  2100
atgtccagct tccctttcaa ctggactcgg gtcaggattc ggcacctgga gatgcaattt  2160
gcgcaggagg cgagtggtgg tggtggtggc gagattatcc accagccttc cacccggtcg  2220
gggattgttt acatcctcct gcagggctcc actatcttcc atgaccgcag aagagatgag  2280
gtgatgacct ttcaggcagc ggacccgctc aacttccaat atgcgtaccg cctcgacact  2340
ggcgaagcca ctctaacgaa tgagccctcg gaagactttg cgaacacgtt catgcagatg  2400
acacccttca ctcgctggag gcttcgtctc tctgcgtccg cctcagagaa tgcagaatta  2460
gcgtttccaa cagctacagc tcccgactcc actaccgagg ttgtcatcac gttccatgtt  2520
acggcaatta gacaagttga ctggcggcaa gaggaggag                         2559
```

```
SEQ ID NO: 45          moltype = AA  length = 852
FEATURE                Location/Qualifiers
source                 1..852
                       mol_type = protein
                       organism = Adiantum trapeziforme
SEQUENCE: 45
MDYSTLYRDL NQISMPLDRV EFSEVMVIHR MYLRLSDLNV GELPGAERVK RLYVLADVVE  60
LATFAHPQLL NTRMPGSVTV IILCRLLQFP TDGSFAAWLE LPFMELHTLI EQYRSEIKAA  120
DDAKWGTYVH AEEVQLSPLF NGWPYLVVEA QRCIITAAMH NTFNRPGWVR SITQFTTDQS  180
GRVDTTLLAR TEFGHIDLPL ETDSPTAFSV SHRQSTNLPV EYTGIPVEVV TDPNILMGMQ  240
TSVHIAELVK ACYPSPELVS AVGVHVNWLN EVLLRVVQKE SQLQGTEAYN ECLALLGRIQ  300
CVMKMGPFVS VVPQLQYRMY GSLIRQMAQV AQNYDQDFRQ LKLFIAQNQI LGSYLLQQNK  360
AFADREVQME SFHSAVISQR RQELDDAIAK MDRLSLQMEE EDRAMEQARK EMEEGLKQFQ  420
NEQVARAVFA VLKSVAMIAL AFVTAGATAP GAAASAAQAV NIAGQAAQAL RRVVEILEGL  480
EAVMEVVAAI KHLVDALDQV SQIVDAPPMP DMPSEADWSI FVNEIEAVAE GMPTEVSEVP  540
AWKAKCKNVA ALGREMCITA EQISQLQYDI WVQGLLRDIA QSHADRLAAI QPANLTNYLE  600
MAIQMDMRTT RILIGLLNIM RIQNAALMYE YLLTPTQLTA WPLRMDTVAN LLITHESAAL  660
SGLAQLGPPS DFTSRHVVKG IPVSLLLDGG DWEFEIPVQG GMSSFPSSWT RVRIRHLEMH  720
FVQEASGGGE IIHQPATQTG TIYILLQGST VFHDRRREEV MTFQAAVPLN YHYAYRLDTG  780
EATLTNEPSE QFANTFMQMT PFTHWRLRLS ASAAENKGLA FPTATAPDST TEIAITFHVT  840
AIRQIDWRQE EE                                                      852

SEQ ID NO: 46          moltype = DNA  length = 2556
FEATURE                Location/Qualifiers
source                 1..2556
                       mol_type = other DNA
                       organism = Adiantum trapeziforme
SEQUENCE: 46
atggattaca gcacgcttta cagggatctg aaccagataa gcatgcccct ggatcgggta  60
gagttctcag aggtgatggt aatccacagg atgtacttga ggttatctga tctgaatgtg  120
ggggagctcc ccggagccga gagggtgaag cggttgtatg tgttggcaga cgtggtggag  180
ctcgcaacat ttgcgcatcc acagttgctt aatacgcgga tgccaggatc ggtgacggtg  240
atcattctgt gtcgtcttct tcagtttcca actgatgggt cgttcgctgc ttggctcgag  300
ctgccgttca tggagttgca cacactcata gaacaataca ggtcagagat aaaagcagca  360
gatgacgcga aatggggaac gtatgtacac gcggaggaag tacagctcag cccgctgttt  420
aatgggtggc cttatctggt tgttgaggca cagcgctgta ttataaccgc ggccatgcac  480
aatacattta accgccctgg gtgggttcgc tccattactc aatttacaac tgatcagtcc  540
ggtcgggtag ataccacact gctcgcacga acagaattcg gccatattga tctaccactc  600
gaaacagatt ccccaacggc attcagtgtt tcacaccgcc aaagtacgaa tttgcccgta  660
gagtacaccg gtattccagt ggaggtggtg accgatccta acatcttgat gggcatgcaa  720
accagcgtgc acattgcgga gctagtgaag gcatgttacc cgtcaccaga attagtgagc  780
gctgtagggg tgcacgtgaa ttggctcaac gaagtcttgc tccgagttgt ccagaaggaa  840
tctcagttgc aagggaccga ggcctacaac gagtgccttg cgcttttagg tcgcattcaa  900
tgtgtcatga agatggggcc gtttgtctcg gtagtgccgc agctgcaata cagaatgtat  960
ggtagcctca tcagacaaat ggcccaggta gcacagaact acgaccaaga tttcaggcag  1020
ctcaagttat tcattgccca aaaccaaatc cttggcagct atttgctgca gcagaacaag  1080
gcctttgctg acagagaggt gcagatggag agctttcatt cagcggtcat ttctcaaaga  1140
aggcaggagt tggacgacgc catcgctaag atggaccgac tgagcttgca gatggaggaa  1200
gaggacagag caatggagca agcccgaaaa gaaatggaag aaggattgaa gcagttccag  1260
aatgagcaag ttgcaagggc tgtgttcgct gttcttaaat ctgtagctat gattgcgctc  1320
gcattcgtca cggctggtgc aacggctcct ggggctgcag catctgcagc gcaagctgtg  1380
aacatagccg gtcaagcggc acaagctctg cgaagggtgg tggaaattct agaggggctc  1440
gaggctgtga tggaggttgt ggctgctata aagcaccttg tggatgctct ggaccaggta  1500
agtcagattg tggatgcacc acctatgcca gacatgccct cggaggcgga ctggagtatt  1560
tttgtgaatg agattgaagc cgtggcagag gggatgccga cggaagtctc ggaggttccg  1620
gcgtggaagg ccaagtgcaa gaatgtggct gcactgggta gggagatgtg catcacggca  1680
gaacagattt cccagctcca gtatgacatc tgggtgcaag gcttgttgcg ggatatagct  1740
caaagccacg cagaccggct ggcagcgatt caacctgcta atcttaccaa ctatttggag  1800
atggcaatac agatggatat gcggactacg aggatactga tagggctcct caacataatg  1860
cgcatccaga atgcggcact tatgtatgag taccttctaa cgcccacgca gctcactgca  1920
tggccgctga gaatggatac tgtggccaac ttgctcatca cgcacgagag tgctgcactg  1980
tcaggattag ctcagttagg gcccccatcg gacttcacga gcaggcatgt agtgaaaggc  2040
atacctgtga gcttgcttct agacggtggg gattgggaat ttgagattcc tgtgcaaggt  2100
ggcatgtcca gtttcccttc cagctggact cgagtgcgga ttcggcacct ggagatgcac  2160
tttgtgcagg aggcgagcgg tggcggcgag attatccacc agcctgccac ccagacgggg  2220
accatttaca tcctcctgca gggctccact gtcttccatg atcgcagaag ggaggaggtg  2280
atgacctttc aggcagcggt tccgctcaac taccattacg cgtaccgcct cgacactgga  2340
gaagccactc ttacgaacga gccctcggaa cagtttgcca acacattcat gcagatgaca  2400
ccgttcactc actggaggct acgtctgtct gcgtccgcag cggagaataa aggattagcc  2460
tttcccacag ctacagctcc cgactccacc actgagattg ccatcacttt ccatgttacg  2520
gccattagac aaattgactg gcggcaagag gaggag                            2556

SEQ ID NO: 47          moltype = AA  length = 851
FEATURE                Location/Qualifiers
source                 1..851
                       mol_type = protein
                       organism = Adiantum trapeziforme
SEQUENCE: 47
```

```
MDYSTLYRDL NQISIGVDRV EFSEVMVIHR MYVRLSDLNV GELPGAGRVK RVYVFADVVE  60
LAPRATLRDQ MHMPGSVTVI VLCRLLQFPI DGSQATTLRL PFMQLHARVI EQNVKSEITA  120
TDGMNWGIYI YGEKVERSPL LPSNAILAVW ADRCTITSAR HNHVNAPGRI ISTFTLGSGV  180
TGITSMHGEP SLDPWNGVSL DSASPTAFSA LPRQSRNISF TSIPVEVVTD PSILLGMQTT  240
VLIAELVKVC RPPSPDMMSA VAEHALWLND VLLQVVQKES QMQGTAPYNE CLALLGRIEC  300
VMKIGRFVSV VPQLQYRMYG NLIKQMAQVA QNYDQEFKQF KLFIIQNQIF GSYLLQQNKA  360
FADRELQMES FHSAVISQRR QELNTAIAKM ERMSLQMEEE NRAMEQAQKE MEEGLREFQN  420
RQVARAVFAV LKAVAMIALA FVTAGATAPG AAASAGQAVS IAGQAAQALR RVVEILEGLE  480
AVMEVVAAVK DLVDSLEQVG HIVGAPEMPD MPSEADWSIF VNEIEAVAEG MPTEVSEVPA  540
WKAKCKNMAA LGREMSITAV QISELQYEIW VQGLMRDIAR SHADRLAAIQ PVDLTNHLEM  600
ATHMDMRTTS MLIGLLNMLR IQNAALMYEY LLTPTELTVW PLGMDTVANL LIAQENAALV  660
GLIQLGPSSN FTSRHVVKGI PVSLLLDGED WEFEIPVQAG MSSFPFNWTR VRIRHLEMQF  720
AQEASGGDEI IHQPSTRSGI VYILLQGSTI FHDRRRDEVM TFQAADPLNF QYAYRLDTGE  780
ATLTNEPSEE FANTFMQMTP FTRWRLRLSA SASENAELAF PTATAPDSTT EVVITFHVTA  840
IRQVDWRQEE E                                                      851

SEQ ID NO: 48          moltype = DNA  length = 2553
FEATURE                Location/Qualifiers
source                 1..2553
                       mol_type = other DNA
                       organism = Adiantum trapeziforme
SEQUENCE: 48
atggattaca gcacgcttta cagggacctg aaccagataa gcatcggtgt ggaccgggta  60
gagttctcag aggtgatggt gatccacagg atgtatgtaa ggttgtctga tctgaatgtg  120
ggggagctcc ccggagccgg gagagtgaag cgggtgtacg tgtttgcgga tgtggtggag  180
cttgcaccgc gtgcgacgct gcgggatcag atgcatatgc caggatcggt gacagtgatc  240
gtattgtgtc gtcttcttca atttccaatc gatgggtcgc aagctacaac tctccggctg  300
cctttcatgc agttgcatgc cagagtcata gagcaaaatg taaagtcgga gataacagca  360
acagatggca tgaattgggg aatctacata tacggggaga aagtagagag gagcccgctc  420
cttcctagca atgcaatcct tgcagtttgg gcagatcgct gtactataac ctcagcccgt  480
cacaatcatg ttaacgcacc tgggagaata atatcgactt tcacacttgg gtcgggagta  540
acgggtataa cctctatgca cggggaaccc agtttggacc cttggaatgg tgtttctctc  600
gactcagctt cccctacggc atttagtgct ttacctcgcc aaagtaggaa tatatccttc  660
acaagtattc cagtagaggt ggtgactgat cctagcatct tgctgggcat gcagaccacc  720
gtgctaattg cggagctagt caaggtatgt cgcccaccat cacccgacat gatgagtgct  780
gtagcggagc acgcgctttg gctcaatgat gtcttacttc aagttgtcca gaaagaatcg  840
cagatgcaag ggactgcgcc ctacaacgag tgccttgcac ttttgggtcg cattgaatgt  900
gtgatgaaaa tcgggagatt tgtctcagta gtgcctcagc tgcaatacag aatgtatggt  960
aacctcatca aacaaatggc ccaagtagca caaaactacg accaagaatt caagcaattc  1020
aagttattca tcatccaaaa ccaaatcttt ggcagctatt tgcttcagca gaacaaggca  1080
tttgctgaca gggagctgca gatggagagc tttcattcag cggtcatttc tcaaagaagg  1140
caggagttga atactgccat cgcaaagatg gagcgaatga gcttgcaaat ggaggaagag  1200
aatagagcaa tggagcaagc tcaaaaggaa atggaagaag gattgaggga gttccagaat  1260
aggcaagttg caagggccgt atttgccgtt cttaaagccg tagctatgat tgcgcttgca  1320
ttcgtcacgg ctggtgcgac ggctcctgga gctgcggcgt ccgcggggca agctgtgagc  1380
atagcaggtc aggccgcaca agctctgcga agggtggtgg aaattctaga ggggctggag  1440
gctgtgatgg aggttgtggc tgctgtgaag gaccttgtgg attcattgga acaggtaggt  1500
cacattgtgg gggcaccgga gatgccggac atgccctcgg aggcggactg gtccattttt  1560
gtgaatgaga ttgaggccgt ggcagagggg atgccaacgg aagtctcgga ggttccggca  1620
tggaaggcca agtgcaagaa tatggctgca ctgggtaggg agatgagcat cacggcagta  1680
cagatttctg agctccagta tgagatctgg gtgcaaggct tgatgcggga tatagctcga  1740
agccatgcag acaggttggc tgcgattcaa cctgtggacc ttaccaacca tttggagatg  1800
gccacacaca tggatatgcg gactacaagt atgctgatag ggctcctcaa tatgctgcgc  1860
atccagaatg cggcactcat gtacgagtac cttctaacac ccacggagct cacagtatgg  1920
ccactgggta tggataccgt ggccaacttg ctcattgcgc aggagaatgc tgcactggtg  1980
ggattaattc agctagggcc ctcgtcgaat tttacgagca gacatgtggt gaaaggcata  2040
cctgtgagct tgctgctcga tggtgaggat tgggagttcg agatccctgt gcaagctggc  2100
atgtccagct tccctttcaa ctggactcgg gtcaggattc ggcacctgga gatgcaattt  2160
gcgcaggagg cgagtggtgg tgacgagatt atccaccagc cttccacccg gtcggggatt  2220
gtttacatcc tcctgcaggg ctccactatc ttccatgacc gcagaagaga tgaggtgatg  2280
acctttcagg cagcggaccc gctcaacttc caatatgcgt accgcctcga cactggcgaa  2340
gccactctaa cgaatgagcc ctcggaagag tttgcgaaca cgttcatgca gatgacaccc  2400
ttcactcgct ggaggcttcg tctctctgcg tccgcctcag agaatgcaga attagcgttt  2460
ccaacagcta cagctcccga ctccactacc gaggttgtca tcacgttcca tgttacggca  2520
atcagacaag ttgactggcg gcaagaggag gag                               2553

SEQ ID NO: 49          moltype = AA  length = 851
FEATURE                Location/Qualifiers
source                 1..851
                       mol_type = protein
                       organism = Adiantum trapeziforme
SEQUENCE: 49
MDYSTLYRDL NQISIGVDRV EFSEVMVIHR MYVRLSDLNV GELPGAGRVK RVYVFADVVE  60
LAPRETLRDQ MHMPGSVTVI ILCRLLQFPI DGSQATTLRL PFMQLHARVI EQNVKSEITA  120
TDGMNWGIYI YGEKVERSPL LPSNAILAVW ADRCTITSAR HNHVNAPGRI ISTFTLGSGV  180
TGITSMHGEP SLDPWNGVSL DSASPTAFSA LPRQSRNISF TSIPVEVVTD PSILLGMQTT  240
VLIAELVKVC RPPSPDMMSA VAEHALWLND VLLQVVQKES QMQGTAPYNE CLALLGRIEC  300
VMKIGRFVSV VPQLQYRMYG NLIKQMAQVA QNYDQEFKQF KLFIIQNQIF GSYLLQQNKA  360
FADRELQMES FHSAVISQRR QELNTAIAKM ERMSLQMEEE NRAMEQAQKE MEEGLREFQN  420
```

```
RQVARAVFAV LKAVAMIALA FVTAGATAPG AAASAGQAVS IAGQAAQALR RVVEILEGLE  480
AVMEVVAAVK DLVDSLEQVG HIVGAPEMPD MPSEADWSIF VNEIEAVAEG MPTEVSEVPA  540
WKAKCKNMAA LGREMSITAV QISELQYEIW VQGLMRDIAR SHADRLAAIQ PVDLTNHLEM  600
ATHMDMRTTS MLIGLLNMLR IQNAALMYEY LLTPTELTVW PLGMDTVANL LIAQENAALV  660
GLIQLGPSSN FTSRHVVKGI PVSLLLDGED WEFEIPVQAG MSSFPFNWTR VRIRHLEMQF  720
AQEASGGDEI IHQPSTRSGI VYILLQGSTI FHDRRRDEVM TFQAADPLNF QYAYRLDTGE  780
ATLTNEPSEE FANTFMQMTP FTRWRLRLSA SASENAELAF PTATAPDSTT EVVITFHVTA  840
IRQVDWRQEE E                                                      851

SEQ ID NO: 50          moltype = DNA  length = 2553
FEATURE                Location/Qualifiers
source                 1..2553
                       mol_type = other DNA
                       organism = Adiantum trapeziforme
SEQUENCE: 50
atggattaca gcacgcttta cagggacctg aaccagataa gcatcggtgt ggaccgggta  60
gagttctcag aggtgatggt gatccacagg atgtatgtaa ggttgtctga tctgaatgtg  120
ggggagctcc ccggagccgg gagagtgaag cgggtgtacg tgtttgcgga tgtggtggag  180
cttgcaccgc gcgagacgct gcgggaccag atgcatatgc caggatcggt gacagtgatc  240
atattgtgtc ggcttcttca atttccaatc gatgggtcgc aagctacaac tctccggctg  300
cctttcatgc agttgcatgc cagagtcata gagcaaaatg taaagtcgga gataacagca  360
acagatggca tgaattgggg aatctacata tacggggaga aagtagagag gagcccgctc  420
cttcctagca atgcaatcct tgcagtttgg gcagatcgct gtactataac ctcagcccgt  480
cacaatcatg ttaacgcacc tgggagaata atatcgactt tcacacttgg gtcgggagta  540
acgggtataa cctctatgca cggggaaccc agtttggacc cttggaatgg tgtttctctc  600
gactcagctt cccctacggc atttagtgct ttacctcgcc aaagtaggaa tatatccttc  660
acaagtattc cagtagaggt ggtgactgat cctagcatct tgctgggcat gcagaccacc  720
gtgctaattg cggagctagt caaggtatgt cgcccaccat cacccgacat gatgagtgct  780
gtagcggagc acgcgctttg gctcaatgat gtcttacttc aagttgtcca gaaagaatcg  840
cagatgcaag ggactgcgcc ctacaacgag tgccttgcac ttttgggtcg cattgaatgt  900
gtgatgaaaa tcgggagatt tgtctcagta gtgcctcagc tgcaatacag aatgtatggt  960
aacctcatca aacaaatggc ccaagtagca caaaactacg accaagaatt caagcaattc  1020
aagttattca tcatccaaaa ccaaatcttt ggcagctatt tgcttcagca gaacaaggca  1080
tttgctgaca gggagctgca gatggagagc tttcattcag cggtcatttc tcaaagaagg  1140
caggagttga atactgccat cgcaaagatg gagcgaatga gcttgcaaat ggaggaagag  1200
aatagagcaa tggagcaagc tcaaaaggaa atggaagaag gattgaggga gttccagaat  1260
aggcaagttg caagggccgt atttgccgtt cttaaagccg tagctatgat tgcgcttgca  1320
ttcgtcacgg ctggtgcgac ggctcctgga gctgcggcgt ccgcggggca agctgtgagc  1380
atagcaggtc aggccgcaca agctctgcga agggtggtgg aaattctaga ggggctggag  1440
gctgtgatgg aggttgtggc tgctgtgaag gaccttgtgg attcattgga acaggtaggt  1500
cacattgtgg gggcaccgga gatgccggac atgccctcgg aggcggactg gtccattttt  1560
gtgaatgaga ttgaggccgt ggcagagggg atgccaacgg aagtctcgga ggttccggca  1620
tggaaggcca agtgcaagaa tatggctgca ctgggtaggg agatgagcat cacggcagta  1680
cagatttctg agctccagta tgagatctgg gtgcaaggct tgatgcggga tatagctcga  1740
agccatgcag acaggttggc tgcgattcaa cctgtggacc ttaccaacca tttggagatg  1800
gccacacaca tggatatgcg gactacaagt atgctgatag ggctcctcaa tatgctgcgc  1860
atccagaatg cggcactcat gtacgagtac cttctaacac ccacggagct cacagtatgg  1920
ccactgggta tggataccgt ggccaacttg ctcattgcgc aggagaatgc tgcactggtg  1980
ggattaattc agctagggcc ctcgtcgaat tttacgagca gacatgtggt gaaaggcata  2040
cctgtgagct tgctgctcga tggtgaggat tgggagttcg agatccctgt gcaagctggc  2100
atgtccagct tccctttcaa ctggactcgg gtcaggattc ggcacctgga gatgcaattt  2160
gcgcaggagg cgagtggtgg tgacgagatt atccaccagc cttccacccg gtcggggatt  2220
gtttacatcc tcctgcaggg ctccactatc ttccatgacc gcagaagaga tgaggtgatg  2280
acctttcagg cagcggaccc gctcaacttc caatatgcgt accgcctcga cactggcgaa  2340
gccactctaa cgaatgagcc ctcggaagag tttgcgaaca cgttcatgca gatgacaccc  2400
ttcactcgct ggaggcttcg tctctctgcg tccgcctcag agaatgcaga attagcgttt  2460
ccaacagcta cagctcccga ctccactacc gaggttgtca tcacgttcca tgttacggca  2520
atcagacaag ttgactggcg gcaagaggag gag                              2553

SEQ ID NO: 51          moltype = AA  length = 854
FEATURE                Location/Qualifiers
source                 1..854
                       mol_type = protein
                       organism = Adiantum peruvianum
SEQUENCE: 51
MDYSTLYRDL NQISIGVDRV EFSEVMVIHR MYVRLSDLNV GELPGAGRVK RVYVFADVVE  60
LAPRATLRDQ MHMPGSVTVI VLCRLLQFPI DGSQATTLRL PFMQLHARVI EQNVKSEITA  120
TDGMNWGIYI YGEKVERSPL LPSNAILAVW ADRCTITSAR HNHVNAPGRI ISTFTLGSGV  180
TGITSMHGEP SLDPWNGVSL DSASPTAFSA LPRQSRNISF TSIPVEVVTD PSILLGMQTT  240
VLIAELVKVC RPPSPDMMSA VAEHALWLND VLLQVVQKES QMQGTAPYNE CLALLGRIEC  300
VMKIGRFVSV VPQLQYRMYG NLIKQMAQVA QNYDQEFKQF KLFIIQNQIF GSYLLQQNKA  360
FADRELQMES FHSAVISQRR QELNTAIAKM ERMSLQMEEE NRAMEQAQKE MEEGLREFQN  420
RQVARAVFAV LKAVAMIALA FVTAGATAPG AAASAGQAVS IAGQAAQALR RVVEILEGLE  480
AVMEVVAAVK DLVDSLEQVG HIVGAPEMPD MPSEADWSIF VNEIEAVAEG MPTEVSEVPA  540
WKAKCKNMAA LGREMSITAV QISELQYEIW VQGLMRDIAR SHADRLAAIQ PVDLTNHLEM  600
ATHMDMRTTS MLIGLLNMLR IQNAALMYEY LLTPTELTVW PLGMDTVANL LIAQENAALV  660
GLIQLGPSSN FTSRHVVKGI PVSLLLDGED WEFEIPVQAG MSSFPFNWTR VRIRHLEMQF  720
AQEASGGDEI IHQPSTRSGI VYILLQGSTI FHDRRRDEVM TFQAADPLNF QYAYRLDTGE  780
ATLTNEPSEE FANTFMQMTP FTRWRLRLSA SASENAELAF PTATAPDSTT EVVITFHVTA  840
```

-continued

```
IRQVDWRQEE KEEE                                                  854

SEQ ID NO: 52          moltype = DNA  length = 2562
FEATURE                Location/Qualifiers
source                 1..2562
                       mol_type = other DNA
                       organism = Adiantum peruvianum
SEQUENCE: 52
atggattaca gcacgcttta cagggacctg aaccagataa gcatcggtgt ggaccgggta  60
gagttctcag aggtgatggt gatccacagg atgtatgtaa ggttgtctga tctgaatgtg  120
ggggagctcc ccggagccgg gagagtgaag cgggtgtacg tgtttgcgga tgtggtggag  180
cttgcaccgc gtgcgacgct gcgggatcag atgcatatgc caggatcggt gacagtgatc  240
gtattgtgtc gtcttcttca atttccaatc gatgggtcgc aagctacaac tctccggctg  300
cctttcatgc agttgcatgc cagagtcata gagcaaaatg taaagtcgga gataacagca  360
acagatggca tgaattgggg aatctacata tacggggaga aagtagagag gagcccgctc  420
cttcctagca atgcaatcct tgcagtttgg gcagatcgct gtactataac ctcagcccgt  480
cacaatcatg ttaacgcacc tgggagaata atatcgactt tcacacttgg gtcgggagta  540
acgggtataa cctctatgca cggggaaccc agtttggacc cttggaatgg tgtttctctc  600
gactcagctt cccctacggc atttagtgct ttacctcgcc aaagtaggaa tatatccttc  660
acaagtattc cagtagaggt ggtgactgat cctagcatct tgctgggcat gcagaccacc  720
gtgctaattg cggagctagt caaggtatgt cgcccaccat cacccgacat gatgagtgct  780
gtagcggagc acgcgctttg gctcaatgat gtcttacttc aagttgtcca gaaagaatcg  840
cagatgcaag ggactgcgcc ctacaacgag tgccttgcac ttttgggtcg cattgaatgt  900
gtgatgaaaa tcgggagatt tgtctcagta gtgcctcagc tgcaatacag aatgtatggt  960
aacctcatca aacaaatggc ccaagtagca caaaactacg accaagaatt caagcaattc  1020
aagttattca tcatccaaaa ccaaatcttt ggcagctatt tgcttcagca gaacaaggca  1080
tttgctgaca gggagctgca gatggagagc tttcattcag cggtcatttc tcaaagaagg  1140
caggagttga atactgccat cgcaaagatg gagcgaatga gcttgcaaat ggaggaagag  1200
aatagagcaa tggagcaagc tcaaaaggaa atggaagaag gattgaggga gttccagaat  1260
aggcaagttg caagggccgt atttgccgtt cttaaagccg tagctatgat tgcgcttgca  1320
ttcgtcacgg ctggtgcgac ggctcctgga gctgcggcgt ccgcggggca agctgtgagc  1380
atagcaggtc aggccgcaca agctctgcga agggtggtgg aaattctaga ggggctggag  1440
gctgtgatgg aggttgtggc tgctgtgaag gaccttgtgg attcattgga acaggtaggt  1500
cacattgtgg gggcaccgga gatgccggac atgccctcgg aggcggactg gtccattttt  1560
gtgaatgaga ttgaggccgt ggcagagggg atgccaacgg aagtctcgga ggttccggca  1620
tggaaggcca agtgcaagaa tatggctgca ctgggtaggg agatgagcat cacggcagta  1680
cagatttctg agctccagta tgagatctgg gtgcaaggct tgatgcggga tatagctcga  1740
agccatgcag acaggttggc tgcgattcaa cctgtggacc ttaccaacca tttggagatg  1800
gccacacaca tggatatgcg gactacaagt atgctgatag ggctcctcaa tatgctgcgc  1860
atccagaatg cggcactcat gtacgagtac cttctaacac ccacggagct cacagtatgg  1920
ccactgggta tggataccgt ggccaacttg ctcattgcgc aggagaatgc tgcactggtg  1980
ggattaattc agctagggcc ctcgtcgaat tttacgagca gacatgtggt gaaaggcata  2040
cctgtgagct tgctgctcga tggtgaggat tgggagttcg agatccctgt gcaagctggc  2100
atgtccagct tccctttcaa ctggactcgg gtcaggattc ggcacctgga gatgcaattt  2160
gcgcaggagg cgagtggtgg tgacgagatt atccaccagc cttccacccg gtcggggatt  2220
gtttacatcc tcctgcaggg ctccactatc ttccatgacc gcagaagaga tgaggtgatg  2280
acctttcagg cagcggaccc gctcaacttc caatatgcgt accgcctcga cactggcgaa  2340
gccactctaa cgaatgagcc ctcggaagag tttgcgaaca cgttcatgca gatgacaccc  2400
ttcactcgct ggaggcttcg tctctctgcg tccgcctcag agaatgcaga attagcgttt  2460
ccaacagcta cagctcccga ctccactacc gaggttgtca tcacgttcca tgttacggca  2520
atcagacaag ttgactggcg gcaggaggag aaagaggagg ag                   2562

SEQ ID NO: 53          moltype = AA  length = 852
FEATURE                Location/Qualifiers
source                 1..852
                       mol_type = protein
                       organism = Lygodium flexuosum
SEQUENCE: 53
MASVLDYSTL YRDLNQISMA VDQVEFSEVM VIHRMYVNLA DLDVAELVGA ETVKRVYVFA  60
DVVELAPGKR TQLPGSVTVI ILCRLLQFPT GGSRAATLQL PFMKVHATLI ERFRSEIAAA  120
DGMNWGTYIH GEEVQVSPLY PNNSILGVWA DRSIITSAFH NVFDEPGRVI SSTSITRAQS  180
APNNTTMSAE PGWLSGNRFL LYTVSRSAFS VLPSQSTNVS FTSIPVEVVT DPNILLGMQT  240
TVHIAELVKA GHPSPDIVSA VAEHAIWLSK VLLQVVQNES HLQGTESYNE CLALLGRVQS  300
VIKMGRFGLV VPQLQYRMYG SLIKQMAQVA QNYDQDFKRF RLFILQNQIL GSYLLEQNKA  360
FADRELQMES FHSAVISQRK GELDTAFAKM DRLSLQMEEE NGAMEQAQKE MDEGLRQFQN  420
RQVARALFAV LRAVAQIGLA FVTAGATAPG AVASAGQAVS IAGQAAQGLR RVVEILEQLE  480
AVMEVVAAVK DLVNSLEQVG QLVQAPVMPD MPSEADWSIF VNEVEAVAEG MPTEVSEVPA  540
WKAKCKNVAA LGREMSITAV QISELQYDIW VQGMMRDIAQ SQADRLAAIQ PADLTNFLEM  600
ATQMDMRTTR MLIGLLNMLR IQNAALMYEY LLTPTELTAW PLGMDTVGNL LIAQENAALL  660
GLTQLGPSSD FTSRHVVKGI PVSLLLDGED WEFEIPVQGG MSSFPSSWTR VRIRHLEMHF  720
VQESMNGGGE IIHQPATQTG TVYILLQGST IFHDRRRDEV MTFQAAAPLN YQYAYRLDTG  780
ETTLTNQPSE HFANTFMQMT PFTRWRLRLS ASAPENAGLA FPTATALDST TQIVITFHVT  840
AIRQIDWRHE EE                                                    852

SEQ ID NO: 54          moltype = DNA  length = 2556
FEATURE                Location/Qualifiers
source                 1..2556
                       mol_type = other DNA
                       organism = Lygodium flexuosum
```

SEQUENCE: 54
atggccagtg tactggatta cagcacgctt tacagggatc tgaaccagat aagcatggct 60
gtggatcagg tagagttctc agaggtgatg gtgatccaca ggatgtatgt gaatttagct 120
gacctggatg tggcggagct cgtgggagct gagacagtga agcgggtgta tgtgtttgcg 180
gatgtggtgg agcttgcacc ggggaaacgg acgcaattgc caggatcggt gacggtgatc 240
atattgtgtc gtcttcttca atttccaact ggtgggtcgc gagcagcaac tctccagctg 300
cctttcatga aggtccatgc tacactcata gagcgattta ggtcagagat agcagcagca 360
gatgggatga actggggaac gtacatacac ggggaggaag tacaggtcag cccgctgtat 420
cctaacaatt caatacttgg agtttgggca gatcgctcta ttataacctc agcctttcac 480
aatgtgttcg acgaacctgg gagagtaatt tccagtacta gtattacaag ggcacagtca 540
gcacccaaca acacgactat gtcagcagaa cccggctggc tctctggcaa tcgttttcta 600
ctttacacgg tttcccggtc ggcattcagt gttttaccta gccaaagtac gaatgtatcc 660
ttcacaagta ttccggtaga ggtggtgact gatccgaaca tcttgctggg catgcagaca 720
acagtgcaca ttgcggagct agtcaaggca ggtcacccgt cacccgacat tgtgagcgcg 780
gtagcggagc acgcgatttg gctcagcaaa gtcttgctcc aagttgtgca gaacgaatct 840
cacttgcaag ggaccgagtc ctacaacgag tgcctggcac ttttgggccg tgttcaatct 900
gtgatcaaga tggggagatt tggcttagta gtgccccagc tgcaatacag aatgtacggt 960
agcctcatca aacaaatggc ccaagtagca cagaactacg accaagattt caagcgattc 1020
cggttattca ttcttcaaaa tcaaatcctt ggcagctatt tgctggagca gaacaaggca 1080
tttgctgaca gggagctgca gatggagagc ttccattcag ccgtgatttc tcaaagaaaa 1140
ggcgagctgg acactgcctt cgcaaagatg gaccgactga gcttgcaaat ggaggaagag 1200
aatggcgcaa tggagcaagc ccaaaaggaa atggacgaag gattaaggca gttccagaat 1260
aggcaagttg caagggccct ctttgccgtt cttagagctg tagctcagat tgggcttgca 1320
ttcgtcacgg ctggtgcaac ggctcctgga gctgtggcgt ccgcggggca agccgtgagc 1380
atagcaggtc aggccgcgca aggtctgcga agggtggtgg aaatcctaga gcagctggaa 1440
gctgtgatgg aggttgtggc tgctgtgaag gaccttgtga attcattgga acaggtaggt 1500
cagttggtgc aggcaccggt gatgccggac atgccctcgg aagcggactg gtccattttt 1560
gtgaatgagg tcgaggccgt ggcagagggg atgccgacgg aagtctcgga ggttccagcg 1620
tggaaggcca agtgcaagaa tgtggctgca ctgggtcggg agatgagcat caccgcagta 1680
caaatttctg agctccagta tgacatctgg gtgcaaggca tgatgcggga tattgctcaa 1740
agccaggcag acaggctggc ggcgattcaa cccgcggacc ttaccaactt tttggagatg 1800
gcaacacaga tggatatgcg gactacaagg atgctgatag ggctcctcaa catgctccgc 1860
atccagaatg cggcactcat gtacgagtac cttcttacgc ccacggagct cacagcatgg 1920
ccgctgggta tggataccgt gggcaacttg ctcattgcgc aggagaatgc tgcactatta 1980
ggattaactc agctaggacc ctcatccgat ttcacgagca ggcatgtggt gaaaggcata 2040
cctgtgagct tgctactcga tggtgaggat tgggagttcg agatccctgt gcaaggtggc 2100
atgtccagct tcccttcaag ctggactcgc gtccggattc ggcacttgga gatgcacttt 2160
gtgcaagagt cgatgaacgg tggcggcgag attattcacc agcctgccac ccagactggg 2220
accgtttaca tcctcctgca gggctccact atcttccatg accgcagaag agacgaggtg 2280
atgacctttc aggcagcggc tccgctcaac taccagtacg cgtaccgcct cgacactggt 2340
gaaaccactc ttacgaacca gccctcggaa cactttgcca acacgttcat gcagatgaca 2400
cccttcactc gctggaggct tcgtctctct gcgtccgccc cagagaatgc aggattagcc 2460
tttcccacag ctacagctct cgactccact acccagattg tcatcacttt ccatgttacg 2520
gccattagac aaattgactg gcggcacgag gaggag 2556

SEQ ID NO: 55 moltype = AA length = 852
FEATURE Location/Qualifiers
source 1..852
mol_type = protein
organism = Adiantum peruvianum
SEQUENCE: 55
MDYSTLYRDL NQISMPLDRV EFSEVMVIHR MYLRLSDLNV GELPGAERVK RLYVFADVVE 60
LATFAYPQLL HTRMPGSVTV IILCRLLQFP TDGSFAAWLE LPFMELHTLI EQYRSEIKAA 120
DDAKWGTYVH AEEVQLSPLF NGWPYLVVEA QRCIITAAMH NTFNRPGWVR SVTQFTTDQS 180
GRVDTTLLAR TEFGHIYLPL ETDSPTAFSV SHRQSTNLPV EYTGIPVEVV TDPNILMGMQ 240
TSVHIAELVK ACYPSPELVS AVGVHVNWLN EVLLRVVQKE SQLQGTEAYN ECLALLGRIQ 300
CVMKMGPFVS VVPQLQYRMY GSLIRQMAQV AQNYDQDFRQ LKLFIAQNQI LGSYLLQQNK 360
AFADREVQME SFHSAVISQR RQELDDALAK MDRLSLQMEE EDRAMEQARK EMEEGLKQFQ 420
NEQVARAVFA VLKSVAMIAL AFVTAGATAP GAAASAAQAV NIAGQAAQAL RRVVEILEGL 480
EAVMEVVAAI KHLVDALDQV SQIVDAPPMP DMPSEADWSI FVNEIEAVAE GMPTEVSEVP 540
AWKAKCKNVA ALGREMCITA EQISQLQYDI WVQGLLRDIA QTHADRLAAI QPANLTNYLE 600
MATQMDMRTT RILIGLLNIM RIQNAALMYE YLLTPTQLTA WPLRMDTVAN LLITQESAAL 660
SGLAQLGPPS DFTSRHVVKG IPVSLLLDGG DWEFEIPVQG GMSSFPSSWT RVRIRHLEMH 720
FVQEASGGGE IIHQPATQTG TVYILLQGST VFHDRRREEV MTFQAAVPLN YHYAYRLDTG 780
EATLTNEPSE QFANTFMQMT PFTHWRLRLS ASAAENEGLA FPTATAPDST TEIAITFHVM 840
AIRQIDWRQE EE 852

SEQ ID NO: 56 moltype = DNA length = 2556
FEATURE Location/Qualifiers
source 1..2556
mol_type = other DNA
organism = Adiantum peruvianum
SEQUENCE: 56
atggattaca gcactcttta cagggatctg aaccagataa gcatgcccct ggatcgggta 60
gagttctcag aggtgatggt aatccacagg atgtacttga ggttatctga tctgaatgtg 120
ggggagctcc ccggagccga gagggtgaag cggttgtatg tgtttgcaga cgtggtggag 180
ctcgcgacat ttgcgtatcc acagttgctt catacgcgga tgccaggatc ggtgacggtg 240
atcattctgt gtcgtcttct tcagtttcca actgatgggt cgttcgctgc ttggctcgag 300
ctgccgttca tggagttgca cacactcata gaacaataca ggtcagagat aaaagcagca 360

-continued

```
gatgacgcga aatggggaac gtatgtacac gcggaggaag tacagctcag cccgctgttt  420
aatgggtggc cttatctggt tgttgaggca cagcgctgta ttataaccgc ggccatgcac  480
aatacattta accgccctgg gtgggttcgc tccgttactc aatttacaac tgatcagtcc  540
ggtcgggtag ataccacact gctcgcacga acagaattcg gccatattta tctaccactc  600
gagacagatt ccccaacggc attcagtgtt tcacaccgcc aaagtacgaa tttgcccgta  660
gagtacaccg gtattccagt agaggtggtg accgatccta acatcttgat gggcatgcaa  720
accagcgtgc acattgcgga gctagtgaag gcatgttacc cgtcaccaga attagtgagc  780
gctgtagggg tgcacgtgaa ttggctcaac gaagtcttgc tccgagttgt ccagaaggaa  840
tctcagttgc aagggaccga ggcctacaac gagtgccttg cgcttttggg tcgcattcaa  900
tgtgtcatga agatggggcc gtttgtctcg gtagtgccgc agctgcaata cagaatgtat  960
ggtagcctca tcagacaaat ggcccaggta gcacagaact acgaccaaga tttcaggcag  1020
ctcaagttat tcattgccca aaaccaaatc cttggcagct atttgctgca gcagaacaag  1080
gcatttgctg acagagaggt gcagatggag agctttcatt cagcggtcat ttctcaaaga  1140
aggcaggagt tggacgacgc cctcgctaag atggaccgac tgagcttgca gatggaggaa  1200
gaggacagag caatggagca agcccgaaaa gaaatggaag aaggattgaa gcagttccag  1260
aatgagcaag ttgcaagggc tgtgttcgct gttcttaaat ctgtagctat gattgcgctc  1320
gcattcgtca cggctggtgc aacggctcct ggggctgcag catccgcagc gcaagctgtg  1380
aacatagccg gtcaagcggc acaagctctg cgaagggtgg tggaaattct agaggggctc  1440
gaggctgtga tggaggttgt ggctgctata aagcaccttg tggatgctct ggaccaggta  1500
agtcagattg tggatgcacc acctatgcca gacatgccct cggaggcaga ctggagtatt  1560
tttgtgaatg agattgaagc cgtggcagag gggatgccga cggaagtctc ggaggttccg  1620
gcgtggaagg ccaagtgcaa gaatgtggct gcactgggta gggagatgtg catcacggca  1680
gaacagattt cccagctcca gtatgacatc tgggtgcaag gcttgttgcg ggatatagct  1740
caaacccacg cagaccggct ggcagcgatt caacctgcta atcttaccaa ctatttggag  1800
atggcaacac agatggatat gcggactacg aggatattga tagggctcct caacataatg  1860
cgcatccaga atgcggcact tatgtatgag taccttctaa cgcccacgca gctcactgca  1920
tggccgctga gaatggatac tgtggccaac ttgctcatca cgcaggagag tgctgcactg  1980
tcaggattag ctcagttagg gcccccatcg gacttcacga gcaggcatgt ggtgaaaggc  2040
atacctgtga gcttgcttct agacggtggg gattgggaat ttgagattcc tgtgcaaggt  2100
ggcatgtcca gtttcccttc cagctggact cgagtgcgga ttcggcacct ggagatgcac  2160
tttgtgcagg aggcgagcgg tggcggcgag attatccacc agcctgccac ccagacgggg  2220
accgtttaca tcctcctgca gggctccact gtcttccatg atcgcagaag ggaggaggtg  2280
atgacctttc aggcagcggt tccgctcaac taccattacg cgtaccgcct cgacactgga  2340
gaagccactc ttacgaacga gccctcggaa cagtttgcca acacattcat gcagatgaca  2400
ccgttcactc actggaggct acgtctgtct gcgtccgcag cggagaatga aggattagcc  2460
tttcccacag ctacagctcc cgactccacc actgagattg ccatcacttt ccatgttatg  2520
gccattagac aaatcgactg gcggcaagag gaggag                           2556

SEQ ID NO: 57          moltype = AA  length = 782
FEATURE                Location/Qualifiers
source                 1..782
                       mol_type = protein
                       organism = Adiantum peruvianum
SEQUENCE: 57
MDYSTLYRDL NQISIGVDRV EFSEVMVIHR MYVRLSDLNV GELPGAGRVK RVYVFADVVE  60
LAPRATLRDQ MHMPGSVTVI VLCRLLQFPI DGSQATTLRL PFMQLHARVI EQNVKSEITA  120
TDGMNWGIYI YGEKVERSPL LPSNAILAVW ADRCTITSAR HNHVNAPGRI ISTFTLGSGV  180
TGITSMHGEP SLDPWNGVSL DSASPTAFSA LPRQSRNISF TSIPVEVVTD PSILLGMQTT  240
VLIAELVKVC RPPSPDMMSA VAEHALWLND VLLQVVQKES QMQGTAPYNE CLALLGRIEC  300
VMKIGRFVSV VPQLQYRMYG NLIKQMAQVA QNYDQEFKQF KLFIIQNQIF GSYLLQQNKA  360
FADRELQMES FHSAVISQRR QELNTAIAKM ERMSLQMEEE NRAMEQAQKE MEEGLREFQN  420
RQVARAVFAV LKAVAMIALA FVTAGATAPG AAASAGQAVS IAGQAAQALR RVVEILEGLE  480
AVMEVVAAVK DLVDSLEQVG HIVGAPEMPD MPSEADWSIF VNEIEAVAEG MPTEVSEVPA  540
WKAKCKNMAA LGREMSITAV QISELQYEIW VQGLMRDIAR SHADRLAAIQ PVDLTNHLEM  600
ATHMDMRTTS MLIGLLNMLR IQNAALMYEY LLTPTELTVW PLGMDTVANL LIAQENAALV  660
GLIQLGPSSN FTSRHVVKGI PVSLLLDGED WEFEIPVQAG MSSFPFNWTR VRIRHLEMQF  720
AQEASGGDEI IHQPSTRSGI VYILLQGSTI FHDRRRDEVM TFQAADPLNF QMRTASTLAK  780
PL                                                                782

SEQ ID NO: 58          moltype = DNA  length = 2346
FEATURE                Location/Qualifiers
source                 1..2346
                       mol_type = other DNA
                       organism = Adiantum peruvianum
SEQUENCE: 58
atggattaca gcacgcttta cagggacctg aaccagataa gcatcggtgt ggaccgggta  60
gagttctcag aggtgatggt gatccacagg atgtatgtaa ggttgtctga tctgaatgtg  120
ggggagctcc ccggagccgg gagagtgaag cgggtgtacg tgtttgcgga tgtggtggag  180
cttgcaccgc gtgcgacgct gcgggatcag atgcatatgc caggatcggt gacagtgatc  240
gtattgtgtc gtcttcttca atttccaatc gatgggtcgc aagctacaac tctccggctg  300
cctttcatgc agttgcatgc cagagtcata gagcaaaatg taaagtcgga gataacagca  360
acagatggca tgaattgggg aatctacata tacggggaga aagtagagag gagcccgctc  420
cttcctagca atgcaatcct tgcagtttgg gcagatcgct gtactataac ctcagcccgt  480
cacaatcatg ttaacgcacc tgggagaata atatcgactt tcacacttgg gtcgggagta  540
acgggtataa cctctatgca cggggaaccc agtttggacc cttggaatgg tgtttctctc  600
gactcagctt cccctacggc atttagtgct ttacctcgcc aaagtaggaa tatatccttc  660
acaagtattc cagtagaggt ggtgactgat cctagcatct tgctgggcat gcagaccacc  720
gtgctaattg cggagctagt caaggtatgt cgcccaccat cacccgacat gatgagtgct  780
gtagcggagc acgcgctttg gctcaatgat gtcttacttc aagttgtcca gaaagaatcg  840
```

```
cagatgcaag ggactgcgcc ctacaacgag tgccttgcac ttttgggtcg cattgaatgt  900
gtgatgaaaa tcgggagatt tgtctcagta gtgcctcagc tgcaatacag aatgtatggt  960
aacctcatca aacaaatggc ccaagtagca caaaactacg accaagaatt caagcaattc  1020
aagttattca tcatccaaaa ccaaatcttt ggcagctatt tgcttcagca gaacaaggca  1080
tttgctgaca gggagctgca gatggagagc tttcattcag cggtcatttc tcaaagaagg  1140
caggagttga atactgccat cgcaaagatg gagcgaatga gcttgcaaat ggaggaagag  1200
aatagagcaa tggagcaagc tcaaaaggaa atggaagaag gattgaggga gttccagaat  1260
aggcaagttg caagggccgt atttgccgtt cttaaagccg tagctatgat tgcgcttgca  1320
ttcgtcacgg ctggtgcgac ggctcctgga gctgcggcgt ccgcggggca agctgtgagc  1380
atagcaggtc aggccgcaca agctctgcga agggtggtgg aaattctaga ggggctggag  1440
gctgtgatgg aggttgtggc tgctgtgaag gaccttgtgg attcattgga acaggtaggt  1500
cacattgtgg gggcaccgga gatgccggac atgccctcgg aggcggactg gtccattttt  1560
gtgaatgaga ttgaggccgt ggcagagggg atgccaacgg aagtctcgga ggttccggca  1620
tggaaggcca agtgcaagaa tatggctgca ctgggtaggg agatgagcat cacggcagta  1680
cagatttctg agctccagta tgagatctgg gtgcaaggct tgatgcggga tatagctcga  1740
agccatgcag acaggttggc tgcgattcaa cctgtggacc ttaccaacca tttggagatg  1800
gccacacaca tggatatgcg gactacaagt atgctgatag ggctcctcaa tatgctgcgc  1860
atccagaatg cggcactcat gtacgagtac cttctaacac ccacggagct cacagtatgg  1920
ccactgggta tggataccgt ggccaacttg ctcattgcgc aggagaatgc tgcactggtg  1980
ggattaattc agctagggcc ctcgtcgaat tttacgagca gacatgtggt gaaaggcata  2040
cctgtgagct tgctgctcga tggtgaggat tgggagttcg agatccctgt gcaagctggc  2100
atgtccagct tccctttcaa ctggactcgg gtcaggattc ggcacctgga gatgcaattt  2160
gcgcaggagg cgagtggtgg tgacgagatt atccaccagc cttccacccg gtcggggatt  2220
gtttacatcc tcctgcaggg ctccactatc ttccatgacc gcagaagaga tgaggtgatg  2280
acctttcagg cagcggaccc gctcaacttc caaatgcgta ccgcctcgac actggcgaag  2340
ccactc                                                             2346
```

```
SEQ ID NO: 59          moltype = AA  length = 623
FEATURE                Location/Qualifiers
source                 1..623
                       mol_type = protein
                       organism = Adiantum trapeziforme
SEQUENCE: 59
MDYSTLYRDL NQISIGVDRV EFSPDMMSAV AEHALWLNDV LLQVVQKESQ MQGTAPYNEC  60
LALLGRIECV MKIGRFVSVV PQLQYRMYGN LIKQMAQVAQ NYDQEFKQFK LFIIQNQIFG  120
SYLLQQNKAF ADRELQMESF HSAVISQRRQ ELNTAIAKME RMSLQMEEEN RAMEQAQKEM  180
EEGLREFQNR QVARAVFAVL KAVAMIALAF VTAGATAPGA AASAGQAVSI AGQAAQALRR  240
VVEILEGLEA VMEVVAAVKD LVDSLEQVGH IVGAPEMPDM PSEADWSIFV NEIEAVAEGM  300
PTEVSEVPAW KAKCKNMAAL GREMSITAVQ ISELQYEIWV QGLMRDIARS HADRLAAIQP  360
VDLTNHLEMA THMDMRTTSM LIGLLNMLRI QNAALMYEYL LTPTELTVWP LGMDTVANLL  420
IAQENAALVG LIQLGPSSNF TSRHVVKGIP VSLLLDGEDW EFEIPVQAGM SSFPFNWTRV  480
RIRHLEMQFA QEASGGDEII HQPSTRSGIV YILLQGSTIF HDRRRDEVMT FQAADPLNFQ  540
YAYRLDTGEA TLTNEPSEEF ANTFMQMTPF TRWRLRLSAS ASENAELAFP TATAPDSTTE  600
VVITFHVTAI RQVDWRQEEK EEE                                          623
```

```
SEQ ID NO: 60          moltype = DNA  length = 1869
FEATURE                Location/Qualifiers
source                 1..1869
                       mol_type = other DNA
                       organism = Adiantum trapeziforme
SEQUENCE: 60
atggattaca gcacgcttta cagggacctg aaccagataa gcatcggtgt ggaccgggta  60
gagttctcac ccgacatgat gagtgctgta gcggagcacg cgctttggct caatgatgtc  120
ttacttcaag ttgtccagaa agaatcgcag atgcaaggga ctgcgcccta caacgagtgc  180
cttgcacttt tgggtcgcat tgaatgtgtg atgaaaatcg ggagatttgt ctcagtagtg  240
cctcagctgc aatacagaat gtatggtaac ctcatcaaac aaatggccca agtagcacaa  300
aactacgacc aagaattcaa gcaattcaag ttattcatca tccaaaacca aatctttggc  360
agctatttgc ttcagcagaa caaggcattt gctgacaggg agctgcagat ggagagcttt  420
cattcagcgg tcatttctca aagaaggcag gagttgaata ctgccatcgc aaagatggag  480
cgaatgagct tgcaaatgga ggaagagaat agagcaatgg agcaagctca aaaggaaatg  540
gaagaaggat tgagggagtt ccagaatagg caagttgcaa gggccgtatt tgccgttctt  600
aaagccgtag ctatgattgc gcttgcattc gtcacggctg gtgcgacggc tcctggagct  660
gcggcgtccg cggggcaagc tgtgagcata gcaggtcagg ccgcacaagc tctgcgaagg  720
gtggtggaaa ttctagaggg gctggaggct gtgatggagg ttgtggctgc tgtgaaggac  780
cttgtggatt cattggaaca ggtaggtcac attgtggggg caccggagat gccggacatg  840
ccctcggagg cggactggtc catttttgtg aatgagattg aggccgtggc agaggggatg  900
ccaacggaag tctcggaggt tccggcatgg aaggccaagt gcaagaatat ggctgcactg  960
ggtagagaga tgagcatcac ggcagtacag atttctgagc tccagtatga gatctgggtg  1020
caaggcttga tgcgggatat agctcgaagc catgcagaca ggttggctgc gattcaacct  1080
gtggacctta ccaaccattt ggagatggcc acacacatgg atatgcggac tacaagtatg  1140
ctgatagggc tcctcaatat gctgcgcatc cagaatgcgg cactcatgta cgagtacctt  1200
ctaacaccca cggagctcac agtatggcca ctgggtatgg ataccgtggc caacttgctc  1260
attgcgcagg agaatgctgc actggtggga ttaattcagc tagggccctc gtcgaatttt  1320
acgagcagac atgtggtgaa aggcatacct gtgagcttgc tgctcgatgg tgaggattgg  1380
gagttcgaga tccctgtgca agctggcatg tccagcttcc ctttcaactg gactcgggtc  1440
aggattcggc acctggagat gcaatttgcg caggaggcga gtggtggtga cgagattatc  1500
caccagcctt ccacccggtc ggggattgtt tacatcctcc tgcagggctc cactatcttc  1560
catgaccgca gaagagatga ggtgatgacc tttcaggcag cggacccgct caacttccaa  1620
tatgcgtacc gcctcgacac tggcgaagcc actctaacga atgagccctc ggaagagttt  1680
```

-continued

```
gcgaacacgt tcatgcagat gacacccttc actcgctgga ggcttcgtct ctctgcgtcc  1740
gcctcagaga atgcagaatt agcgtttcca acagctacag ctcccgactc cactaccgag  1800
gttgtcatca cgttccatgt tacggcaatc agacaagttg actggcggca ggaggagaaa  1860
gaggaggag                                                         1869

SEQ ID NO: 61          moltype = AA  length = 691
FEATURE                Location/Qualifiers
source                 1..691
                       mol_type = protein
                       organism = Adiantum trapeziforme
SEQUENCE: 61
MDYSTLYRDL NQISIGVDRV EFSEVMVIHR MYVRLSDLNV GELPGAGRVK RVYVFADVVE  60
LAPRATLRDQ MHMPGSVTVI VLCRLLQFPI DGSQATTLRL PFMQLHARVI EQNVKSEITA  120
TDGMNWGIYI YGEKVERSPL LPSNAILAVW ADRCTITSAR HNHVNAPGRI ISTFTLGSGV  180
TGITSMHGEP SLDPWNGVSL DSASPTAFSA LPRQSRNISF TSIPVEVVTD PSILLGMQTT  240
VLIAELVKVC RPPSPDMMSA VAEHALWLND VLLQVVQKES QMQGTAPYNE CLALLGRIEC  300
VMKIGRFVSV VPQLQYRMYG NLIKQMAQVA QNYDQEFKQF KLFIIQNQIF GSYLLQQNKA  360
FADRELQMES FHSAVISQRR QELNTAIAKM ERMSLQMEEE NRAMEQAQKE MEEGLREFQN  420
RQVARAVFAV LKAVAMIALA FVTAGATAPG AAASAGQAVS IALMYEYLLT PTELTVWPLG  480
MDTVANLLIA QENAALVGLI QLGPSSNFTS RHVVKGIPVS LLLDGEDWEF EIPVQAGMSS  540
FPFNWTRVRI RHLEMQFAQE ASGGDEIIHQ PSTRSGIVYI LLQGSTIFHD RRRDEVMTFQ  600
AADPLNFQYA YRLDTGEATL TNEPSEEFAN TFMQMTPFTR WRLRLSASAS ENAELAFPTA  660
TAPDSTTEVV ITFHVTAIRQ VDWRQEEKEE E                                 691

SEQ ID NO: 62          moltype = DNA  length = 2073
FEATURE                Location/Qualifiers
source                 1..2073
                       mol_type = other DNA
                       organism = Adiantum trapeziforme
SEQUENCE: 62
atggattaca gcacgcttta cagggacctg aaccagataa gcatcggtgt ggaccgggta  60
gagttctcag aggtgatggt gatccacagg atgtatgtaa ggttgtctga tctgaatgtg  120
ggggagctcc ccggagccgg gagagtgaag cgggtgtacg tgtttgcgga tgtggtggag  180
cttgcaccgc gtgcgacgct gcgggatcag atgcatatgc caggatcggt gacagtgatc  240
gtattgtgtc gtcttcttca atttccaatc gatgggtcgc aagctacaac tctccggctg  300
cctttcatgc agttgcatgc cagagtcata gagcaaaatg taaagtcgga gataacagca  360
acagatggca tgaattgggg aatctacata tacggggaga aagtagagag gagcccgctc  420
cttcctagca atgcaatcct tgcagtttgg gcagatcgct gtactataac ctcagcccgt  480
cacaatcatg ttaacgcacc tgggagaata atatcgactt tcacacttgg gtcgggagta  540
acgggtataa cctctatgca cggggaaccc agtttggacc cttggaatgg tgtttctctc  600
gactcagctt cccctacggc atttagtgct ttacctcgcc aaagtaggaa tatatccttc  660
acaagtattc cagtagaggt ggtgactgat cctagcatct tgctgggcat gcagaccacc  720
gtgctaattg cggagctagt caaggtatgt cgcccaccat cacccgacat gatgagtgct  780
gtagcggagc acgcgctttg gctcaatgat gtcttacttc aagttgtcca gaaagaatcg  840
cagatgcaag ggactgcgcc ctacaacgag tgccttgcac ttttgggtcg cattgaatgt  900
gtgatgaaaa tcgggagatt tgtctcagta gtgcctcagc tgcaatacag aatgtatggt  960
aacctcatca aacaaatggc ccaagtagca caaaactacg accaagaatt caagcaattc  1020
aagttattca tcatccaaaa ccaaatcttt ggcagctatt tgcttcagca gaacaaggca  1080
tttgctgaca gggagctgca gatggagagc tttcattcag cggtcatttc tcaaagaagg  1140
caggagttga atactgccat cgcaaagatg gagcgaatga gcttgcaaat ggaggaagag  1200
aatagagcaa tggagcaagc tcaaaaggaa atggaagaag gattgaggga gttccagaat  1260
aggcaagttg caagggccgt atttgccgtt cttaaagccg tagctatgat tgcgcttgca  1320
ttcgtcacgg ctggtgcgac ggctcctgga gctgcggcgt ccgcggggca agctgtgagc  1380
atagcactca tgtacgagta ccttctaaca cccacggagc tcacagtatg gccactgggt  1440
atggataccg tggccaactt gctcattgcg caggagaatg ctgcactggt gggattaatt  1500
cagctagggc cctcgtcgaa ttttacgagc agacatgtgg tgaaaggcat acctgtgagc  1560
ttgctgctcg atggtgagga ttgggagttc gagatccctg tgcaagctgg catgtccagc  1620
ttccctttca actggactcg ggtcaggatt cggcacctgg agatgcaatt tgcgcaggag  1680
gcgagtggtg gtgacgagat tatccaccag ccttccaccc ggtcggggat tgtttacatc  1740
ctcctgcagg gctccactat cttccatgac cgcagaagag atgaggtgat gacctttcag  1800
gcagcggacc cgctcaactt ccaatatgcg taccgcctcg acactggcga agccactcta  1860
acgaatgagc cctcggaaga gtttgcgaac acgttcatgc agatgacacc cttcactcgc  1920
tggaggcttc gtctctctgc gtccgcctca gagaatgcag aattagcgtt tccaacagct  1980
acagctcccg actccactac cgaggttgtc atcacgttcc atgttacggc aatcagacaa  2040
gttgactggc ggcaggagga gaaagaggag gag                               2073

SEQ ID NO: 63          moltype = AA  length = 657
FEATURE                Location/Qualifiers
source                 1..657
                       mol_type = protein
                       organism = Bacillus thuringiensis
SEQUENCE: 63
MTSNRKNENE IINALSIPAV SNHSAQMDLS LDARIEDSLC IAEGNNINPL VSASTVQTGI  60
NIAGRILGVL GVPFAGQLAS FYSFLVGELW PSGRDPWEIF LEHVEQLIRQ QVTENTRNTA  120
IARLEGLGRG YRSYQQALET WLDNRNDARS RSIILERYVA LELDITTAIP LFRIRNEEVP  180
LLMVYAQAAN LHLLLLRDAS LFGSEWGMAS SDVNQYYQEQ IRYTEEYSNH CVQWYNTGLN  240
NLRGTNAESW LRYNQFRRDL TLGVLDLVAL FPSYDTRTYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTQGLTNN TSINPVTLQF TSRDVYRTES NAGTNILFTT PVNGVPWARF  420
```

-continued

```
NFINPQNIYE RGATTYSQPY QGVGIQLFDS ETELPPETTE RPNYESYSHR LSHIGLIIGN  480
TLRAPVYSWT HRSADRTNTI GPNRITQIPA VKGRFLFNGS VISGPGFTGG DVVRLNRNNG  540
NIQNRGYIEV PIQFTSTSTR YRVRVRYASV TSIELNVNLG NSSIFTNTLP ATAASLDNLQ  600
SGDFGYVEIN NAFTSATGNI VGARNFSANA EVIIDRFEFI PVTATFEAEY DLERAQK     657

SEQ ID NO: 64           moltype = DNA  length = 1971
FEATURE                 Location/Qualifiers
source                  1..1971
                        mol_type = other DNA
                        organism = Bacillus thuringiensis
SEQUENCE: 64
atgccttcaa ataggaaaaa tgagaatgaa attataaatg ccttatcgat tccagctgta  60
tcgaatcatt ccgcacaaat ggatctatcg ctagatgctc gtattgagga ttctttgtgt  120
atagccgagg ggaataatat caatccactt gttagcgcat caacagtcca aacgggtata  180
aacatagctg gtagaatatt gggcgtatta ggtgtgccgt ttgctggaca actagctagt  240
ttttatagtt ttcttgttgg ggaattatgg cctagtggca gagatccatg ggaaattttc  300
ctggaacatg tagaacaact tataagacaa caagtaacag aaaatactag gaatacggct  360
attgctcgat tagaaggtct aggaagaggc tatagatctt accagcaggc tcttgaaact  420
tggttagata accgaaatga tgcaagatca agaagcatta ttcttgagcg ctatgttgct  480
ttagaacttg acattactac tgctataccg cttttcagaa tacgaaatga agaagttcca  540
ttattaatgg tatatgctca agctgcaaat ttacacctat tattattgag agacgcatcc  600
ctttttggta gtgaatgggg gatggcatct tccgatgtta accaatatta ccaagaacaa  660
atcagatata cagaggaata ttctaaccat tgcgtacaat ggtataatac agggctaaat  720
aacttaagag ggacaaatgc tgaaagttgg ttgcggtata atcaattccg tagagaccta  780
acgttagggg tattagattt agtagcccta ttcccaagct atgatactcg cacttatcca  840
atcaatacga gtgctcagtt aacaagagaa atttatacag atccaattgg gagaacaaat  900
gcaccttcag gatttgcaag tacgaattgg tttaataata atgcaccatc gttttctgcc  960
atagaggctg ccattttcag gcctccgcat ctacttgatt ttccagaaca acttacaatt  1020
tacagtgcat caagccgttg gagtagcact caacatatga attattgggt gggacatagg  1080
cttaacttcc gcccaatagg agggacatta aatacctcaa cacaaggact tactaataat  1140
acttcaatta atcctgtaac attacagttt acgtctcgtg acgtttatag aacagaatca  1200
aatgcaggga caaatatact atttactact cctgtgaatg gagtaccttg ggctagattt  1260
aattttataa accctcagaa tatttatgaa agaggcgcca ctacctacag tcaaccgtat  1320
cagggagttg ggattcaatt atttgattca gaaactgaat taccaccaga aacaacagaa  1380
cgaccaaatt atgaatcata tagtcataga ttatctcata taggactaat cataggaaac  1440
actttgagag caccagtcta ttcttggacg catcgtagtg cagatcgtac gaatacgatt  1500
ggaccaaata gaattactca aattcctgca gtgaagggaa gatttctttt taatggttct  1560
gtaatttcag gaccaggatt tactggtgga gacgtagtta gattgaatag gaataatggt  1620
aatattcaaa atagagggta tattgaagtt ccaattcaat tcacgtcgac atctaccaga  1680
tatcgagttc gagtacgtta tgcttctgta acctcgattg agctcaatgt taatttgggc  1740
aattcatcaa tttttacgaa cacattacca gcaacagctg catcattaga taatctacaa  1800
tcaggggatt ttggttatgt tgaaatcaac aatgctttta catccgcaac aggtaatata  1860
gtaggtgcta gaaattttag tgcaaatgca gaagtaataa tagacagatt tgaatttatc  1920
ccagttactg caaccttcga ggcagaatat gatttagaaa gagcacaaaa g           1971

SEQ ID NO: 65           moltype = AA  length = 651
FEATURE                 Location/Qualifiers
REGION                  1..651
                        note = Cry1B variant
source                  1..651
                        mol_type = protein
                        organism = synthetic construct
SEQUENCE: 65
MPSNRKNENE IINAVSNHSA QMDLSLDARI EDSLCVAEVN NIDPFVSAST VQTGISIAGR  60
ILGVLGVPFA GQLASFYSFL VGELWPSGRD PWEIFMEHVE QIVRQQITDS VRDTAIARLE  120
GLGRGYRSYQ QALETWLDNR NDARSRSIIR ERYIALELDI TTAIPLFSIR NQEVPLLMVY  180
AQAANLHLLL LRDASLFGSE WGMSSSDVNQ YYQEQIRYTE EYSNHCVQWY NTGLNNLRGT  240
NAESWLRYNQ FRRDLTLGVL DLVALFPSYD TRVYPMNTSA QLTREIYTDP IGRTNAPSGF  300
ASTNWFNNNA PSFSAIEAAI FRPPHLLDFP EQLTIYSASS RWSSTQHMNY WVGHRLNFRP  360
IGGTLNTSTH GATNTSINPV TLQFTSRDVY RTESFAGTNI LFTTPVNGVP WARFNFINPQ  420
NIYERGATTY SQPYQGVGIQ LFDSETELPP ETTERPNYES YSHRLSHIGL IIGNTLRAPV  480
YSWTHRSADR TNTIGPNRIT QIPAVKGRFL FNGSVISGPG FTGGDVVRLN RNNGNIQNRG  540
YIEVPIQFTS TSTRYRVRVR YASVTSIELN VNLGNSSIFT NTLPATAASL DNLQSGDFGY  600
VEINNAFTSA TGNIVGARNF SANAEVIIDR FEFIPVTATF EAEYDLERAQ K           651

SEQ ID NO: 66           moltype = DNA  length = 1953
FEATURE                 Location/Qualifiers
misc_feature            1..1953
                        note = encodes Cry1B variant
source                  1..1953
                        mol_type = other DNA
                        organism = synthetic construct
SEQUENCE: 66
atgccttcaa ataggaaaaa tgagaatgaa attataaatg ctgtatcgaa tcattccgca  60
caaatggatc tatcgctaga tgctcgtatt gaagatagct tgtgtgtagc cgaggtgaac  120
aatattgatc catttgttag cgcatcaaca gtccaaacag gtattagtat agctggtaga  180
atattgggcg tattaggtgt gccgtttgct ggacaactag ctagttttta tagttttctt  240
gttggggaat tatggcctag cggcagagat ccatgggaaa tttttatgga acatgtcgag  300
caaattgtaa gacaacaaat aacggacagt gttagggata ccgctattgc tcgtttagaa  360
```

```
ggtctaggaa gagggtatag atcttaccag caggctcttg aaacttggtt agataaccga  420
aatgatgcaa gatcaagaag cattattcgt gagagatata ttgctttaga acttgacatt  480
actactgcta taccgctttt cagcatacga aatcaagagg ttccattatt aatggtatat  540
gctcaagctg caaatttaca cctattatta ttgagagacg catccctttt tggtagtgaa  600
tgggggatgt catcttccga tgttaaccaa tattaccaag aacaaatcag atatacagag  660
gaatattcta accattgcgt acaatggtat aatacagggc taaataactt aagagggaca  720
aatgctgaaa gttggttgcg gtataatcaa ttccgtagag atctaacgtt aggagtatta  780
gatctagtgg cactattccc aagctatgac acgcgtgttt atccaatgaa taccagtgct  840
caattaacaa gagaaattta tacagatcca attgggagaa caaatgcacc ttcaggattt  900
gcaagtacga attggtttaa taataatgca ccatcgtttt ctgccataga ggctgccatt  960
ttcaggcctc cgcatctact tgattttcca gaacaactta caatttacag tgcatcaagc  1020
cgttggagta gcactcaaca tatgaattat tgggtgggac ataggcttaa cttccgccca  1080
ataggaggga cattaaatac ctcaacgcat ggggctacca atacttctat taatcctgta  1140
acattacagt tcacatctcg agacgtttat aggactgaat catttgcagg gacaaatata  1200
ctatttacta ctcctgtgaa tggagtacct tgggctagat ttaattttat aaaccctcag  1260
aatatttatg aaagaggcgc cactacctac agtcaaccgt atcagggagt tgggattcaa  1320
ttatttgatt cagaaactga attaccacca gaaacaacag aacgaccaaa ttatgaatca  1380
tatagtcata gattatctca tataggacta atcataggaa acactttgag agcaccagtc  1440
tattcttgga cgcaccgtag tgcagatcgt acgaatacga ttggaccaaa tagaattact  1500
caaattcctg cagtgaaggg aagatttctt tttaatggtt ctgtaatttc aggaccagga  1560
tttactggtg gagacgtagt tagattgaat aggaataatg gtaatattca aaatagaggg  1620
tatattgaag ttccaattca attcacgtcg acatctacca gatatcgagt tcgagtacgt  1680
tatgcttctg taacctcgat tgagctcaat gttaatttgg gcaattcatc aatttttacg  1740
aacacattac cagcaacagc tgcatcatta gataatctac aatcagggga ttttggttat  1800
gttgaaatca acaatgcttt tacatccgca acaggtaata tagtaggtgc tagaaatttt  1860
agtgcaaatg cagaagtaat aatagacaga tttgaattta tcccagttac tgcaaccttc  1920
gaggcagaat atgatttaga aagagcacaa aag                              1953

SEQ ID NO: 67          moltype = AA  length = 655
FEATURE                Location/Qualifiers
REGION                 1..655
                       note = Cry1B variant
source                 1..655
                       mol_type = protein
                       organism = synthetic construct
SEQUENCE: 67
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ QITENARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGNTL  480
RAPVYSWTHR SADRTNTIAT NIITQIPAVK GNFLFNGSVI SGPGFTGGDL VRLNNSGNNI  540
QNRGYIEVPI QFISTSTRYR VRVRYASVTP IQLSVNWGNS NIFSSIVPAT ATSLDNLQSR  600
NFGYFESTNA FTSATGNVVG VRNFSENAGV IIDRFEFIPV TATFEAEYDL ERAQE       655

SEQ ID NO: 68          moltype = DNA  length = 1965
FEATURE                Location/Qualifiers
misc_feature           1..1965
                       note = encodes Cry1B variant
source                 1..1965
                       mol_type = other DNA
                       organism = synthetic construct
SEQUENCE: 68
atgccgagca atcgtaagaa tgaaaatgaa atcattaacg cactgtccat ccctgcagtg  60
agcaatcaca gcgcgcagat ggatttgagc ctggatgcgc gtatcgagga cagcctgtgt  120
attgccgagg gcaacaacat caatccgttg gtcagcgcga gcaccgtgca aaccggcatt  180
aacattgccg gtcgtatcct gggtgtcctg ggcgttccgt ttgcgggtca gctggcgagc  240
ttttacagct ttatcgttgg tgagttgtgg ccgtcgggtc gtgacccttg ggagattttc  300
atggagcacg tcgagcaact ggtgcgccaa cagattacgg agaatgcgcg caacaccgct  360
ctggcgcgtc tgcaaggtct gggtgcaagc ttccgcgctt accagcagtc cctggaagat  420
tggttggaaa accgtgataa tgcgcgcact cgctccgtcc tgtacacgca gtacatcgcg  480
ctggagctgg acttcttgaa cgcgatgccg ctgtttgcaa tcaacaacca gcaagtgccg  540
ctgctgatgg tctacgccca agccgcgaat ctgcacttgc tgctgctgcg cgacgcatct  600
ctgttcggta gcgaatttgg cctgaccagc caggagatcc agcgctacta tgagcgtcag  660
gccgagaaaa cgcgtgaata ctccgactac tgcgctcgtt ggtacaacac gggtctgaac  720
aatctgcgtg gcaccaacgc ggagtcctgg ctgcgttaca accagtttcg tcgcgatctg  780
accctgggtg ttttggattt ggttgcgctg tttccgagct atgacacccg catctatccg  840
atcaacacca gcgcgcaact gactcgtgaa atctatacgg acccgattgg ccgcactaat  900
gcaccgtccg gtttcgcaag caccaactgg ttcaataaca atgcaccgag cttcagcgcg  960
atcgaggccg cgatctttcg tccgccgcac ctgttggact tcccggagca gctgaccatc  1020
tactctgcat ctagccgttg gagcagcacg cagcacatga attactgggt tggccatcgt  1080
ctgaacttcc gcccgattgg tggtacgctg aacactagca cgcacggtgc cactaacacg  1140
agcatcaacc cggtgacgct gcaattcacc agccgtgatg tttaccgtac cgagtcctac  1200
gccggcatca acattctgct gaccaccccg gttaacggcg tcccttgggc tcgtttcaat  1260
tggcgtaacc cactgaatag cctgcgtggt tctttgctgt acaccattgg ttataccggc  1320
gtcggtacgc aactgtttga ctcggaaact gagctgccac cggaaactac cgagcgtccg  1380
```

```
aactacgaat cttatagcca ccgtctgtcc aatatccgtc tgatcatcgg caacaccctg  1440
cgtgcgccgg tgtacagctg gacccatcgt agcgccgatc gcacgaacac gattgccacc  1500
aacattatca cccagatccc ggcagtgaaa ggcaactttc tgtttaacgg cagcgtgatc  1560
agcggtccag gttttaccgg cggtgacctg gtgcgcctga acaacagcgg caacaatatc  1620
caaaaccgtg gttatatcga agtcccgatt caattcatca gcacgagcac ccgttaccgc  1680
gtccgtgttc gctacgcatc cgttacgccg atccaactga gcgttaactg gggcaattcc  1740
aacattttca gcagcattgt ccctgctacg gcgacctctc tggacaattt gcagagccgt  1800
aacttcggct atttcgaaag caccaacgct ttcaccagcg ctacgggcaa tgtggttggt  1860
gttcgcaatt tcagcgagaa tgcgggcgtc atcattgacc gttttgagtt tatcccggtg  1920
accgcgacct tcgaagcgga gtacgatctg gagcgtgcgc aggaa                   1965

SEQ ID NO: 69          moltype = AA  length = 655
FEATURE                Location/Qualifiers
REGION                 1..655
                       note = Cry1B variant
source                 1..655
                       mol_type = protein
                       organism = synthetic construct
SEQUENCE: 69
MPSNRKNENG IINALSIPAV SNHSAQMDLS PDARIEDSLC VAEVNNIDPF VSASTVQTGI  60
NIAGRILGVL GVPFAGQLAS FYSFIVGELW PSGRDPWEIF LEHVEQLVRQ QITENARNTA  120
LARLQGLGAS FRAYQQSLED WLENRDDART RSVLYTQYIA LELDFLNAMP LFAINNQRVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRVYP INTSAQLTRE IYTDPIGRTN  300
APSGFASTNW FNNNAPSFSA IEAAVIRPPH LLDFPEQLTI FSVLSRWSST QHMNYWVGHR  360
LESRTIRGSL STSTHGNTNT SINPVTLQFT SRDVYRTESY AGINILLTTP VNGVPWARFN  420
WRNPLNSLRG SLLYTIGYTG VGTQLFDSET ELPPETTERP NYESYSHRLS HIGLIIGNTL  480
RAPVYSWTHR SADRTNTTGP NRITQIPAVK GNFLFNGSVI SGPGFTGGDL VRLNNSGNNI  540
QNRGYLEVPI QFISTSTRYR VRVRYASVTP IQLSVNWGNS NIFSSIVPAT ATSLDNLQSR  600
DFGYFESTNA FTSATGNVVG VRNFSENAGV IIDRFEFIPV TATFEAEYDL ERAQE       655

SEQ ID NO: 70          moltype = DNA  length = 1965
FEATURE                Location/Qualifiers
misc_feature           1..1965
                       note = encodes Cry1B variant
source                 1..1965
                       mol_type = other DNA
                       organism = synthetic construct
SEQUENCE: 70
atgccgagca atcgtaagaa tgaaaatgga atcattaacg cgctgtccat ccctgcagtg  60
agcaatcaca gcgcgcagat ggatttgagc ccggatgcgc gtatcgagga cagcctgtgt  120
gtcgccgagg taaacaatat tgatccgttc gtcagcgcga gcaccgtgca aaccggcatt  180
aacattgccg gtcgtatcct gggtgtcctg ggcgttccgt ttgcgggtca gctggcgagc  240
ttttacagct ttatcgttgg tgagttgtgg ccgtcgggtc gtgacccttg ggagattttc  300
ttggagcacg tcgagcaact ggtgcgccaa cagattacgg agaatgcgcg caacaccgct  360
ctggcgcgtc tgcaaggtct gggtgcaagc ttccgcgctt accagcagtc cctggaagat  420
tggttggaaa accgtgatga tgcgcgcact cgctccgtcc tgtacacgca gtacatcgcg  480
ctggagctgg acttcttgaa cgcgatgccg ctgtttgcaa tcaacaacca gcgagtgccg  540
ctgctgatgg tctacgccca agccgcgaat ctgcacttgc tgctgctgcg cgacgcatct  600
ctgttcggta gcgaatttgg cctgaccagc caggagatcc agcgctacta tgagcgtcag  660
gccgagaaaa cgcgtgaata ctccgactac tgcgctcgtt ggtacaacac gggtctgaac  720
aatctgcgtg gcaccaacgc ggagtcctgg ctgcgttata accagtttcg tcgcgatctg  780
accctgggtg tattggattt ggttgcgctg tttccgagct atgacacccg cgtgtatccg  840
atcaacacca gcgcgcaact gactcgtgaa atctatacgg acccgattgg ccgcactaat  900
gcaccgtccg gtttcgcaag caccaactgg ttcaataaca atgcaccgag cttcagcgcg  960
atcgaggcgg ctgtcatccg tccgccgcac ctgttggact tcccggagca gctgaccatc  1020
ttttctgtgt tgtctcgttg gagcagcacg cagcacatga attactgggt tggccatcgt  1080
ctggaaagcc gcaccattcg cggtagcctg agcactagca cgcacggtaa tactaacacg  1140
agcatcaacc cggtgacgct gcaattcacc agccgtgatg tttaccgtac cgagtcctac  1200
gccggcatca acattctgct gaccaccccg gttaacggcg tcccttgggc tcgtttcaat  1260
tggcgtaacc cactgaatag cctgcgtggt tctttgctgt acaccattgg ttataccggc  1320
gtcggtacgc aactgtttga ctcggaaact gagctgccac cggaaactac cgagcgtccg  1380
aactacgaat cttatagcca ccgtctgtcc catattggtc tgatcatcgg caacaccctg  1440
cgtgcaccgg tgtacagctg gacccatcgt agcgccgatc gcacgaacac gactggtccg  1500
aaccgtatca cccagatccc ggcagtgaaa ggcaactttc tgtttaacgg cagcgtgatc  1560
agcggtccag gttttaccgg cggtgacctg gtgcgcctga acaacagcgg caacaatatc  1620
caaaaccgtg gttatctgga agtcccgatt caattcatca gcacgagcac ccgttaccgc  1680
gtccgtgttc gctacgcatc cgttacgccg atccaactga gcgttaactg gggcaattcc  1740
aacattttca gcagcattgt ccctgctacg gcgacctctc tggacaattt gcagagccgt  1800
gacttcggct atttcgaaag caccaacgct ttcaccagcg ctacgggcaa tgtggttggt  1860
gttcgcaatt tcagcgagaa tgcgggcgtc atcattgacc gttttgagtt tatcccggtg  1920
accgcgacct tcgaagcgga gtacgatctg gagcgtgcgc aggaa                   1965

SEQ ID NO: 71          moltype = AA  length = 650
FEATURE                Location/Qualifiers
REGION                 1..650
                       note = Cry1B variant
source                 1..650
                       mol_type = protein
```

```
                        organism = synthetic construct
SEQUENCE: 71
MPSNRKNENE IINAVSNHSA QMDLSPDARI EDSLCVAEVN NIDPFVSAST VQTGINIAGR  60
ILGVLGVPFA GQLASFYSFL VGELWPSGRD PWEIFMEHVE QIVRQQITEN ARNTALARLQ  120
GLGASFRAYQ QSLEDWLENR DDARTRSVLY TQYIALELDF LNAMPLFAIN NQQVPLLMVY  180
AQAANLHLLL LRDASLFGSE FGLTSQEIQR YYERQAEKTR EYSDYCARWY NTGLNNLRGT  240
NAESWLRYNQ FRRDLTLGVL DLVALFPSYD TRIYPINTSA QLTREIYTDP IGRTNAPSGF  300
ASTNWFNNNA PSFSAIEAAV IRPPHLLDFP EQLTIYSASS RWSSTQHMNY WVGHRLNFRP  360
IGGTLNTSTH GATNTSINPV TLQFTSRDVY RTESYAGINI LLTTPVNGVP WARFNWRNPL  420
NSLRGSLLYT IGYTGVGIQL FDSETELPPE TTERPNYESY SHRLSNIRLI SGNTLRAPVY  480
SWTHRSADRT NTIATNIITQ IPAVKGNFLF NGSVTSGPGF TGGDLVRLNN SGNNIQNRGY  540
LEVPIQFIST STRYRVRVRY ASVTPIQLSV NWGNSNIFSS IVPATATSLD NLQSRDFGYF  600
ESTNAFTSAT GNVVGVRNFS ENAGVIIDRF EFIPVTATFE AEYDLERAQE            650

SEQ ID NO: 72           moltype = DNA  length = 1950
FEATURE                 Location/Qualifiers
misc_feature            1..1950
                        note = encodes Cry1B variant
source                  1..1950
                        mol_type = other DNA
                        organism = synthetic construct
SEQUENCE: 72
atgccgagca atcgtaagaa tgaaaatgaa atcattaacg cagtgagcaa tcacagcgcg  60
cagatggatt tgagcccgga tgcgcgtatc gaggacagcc tgtgtgtcgc cgaggtaaac  120
aatattgatc cgttcgtcag cgcgagcacc gtgcaaaccg gcattaacat tgccggtcgt  180
atcctgggtg tcctgggcgt tccgtttgcg ggtcagctgg cgagctttta cagcttttttg 240
gttggtgagt tgtggccgtc gggtcgtgac ccttgggaga ttttcatgga gcacgtcgag  300
caaattgtgc gccaacagat tacggagaat gcgcgcaaca ccgctctggc gcgtctgcaa  360
ggtctgggtg caagcttccg cgcttaccag cagtccctgg aagattggtt ggaaaaccgt  420
gatgatgcgc gcactcgctc cgtcctgtac acgcagtaca tcgcgctgga gctggacttc  480
ttgaacgcga tgccgctgtt tgcaatcaac aaccagcaag tgccgctgct gatggtctac  540
gcccaagccg cgaatctgca cttgctgctg ctgcgcgacg catctctgtt cggtagcgaa  600
tttggcctga ccagccagga gatccagcgc tactatgagc gtcaggccga gaaaacgcgt  660
gaatactccg actactgcgc tcgttggtac aacacgggtc tgaacaatct gcgtggcacc  720
aacgcggagt cctggctgcg ttacaaccag tttcgtcgcg atctgaccct gggtgttttg  780
gatttggttg cgctgtttcc gagctatgac acccgcatct atccgatcaa caccagcgcg  840
caactgactc gtgaaatcta tacggacccg attggccgca ctaatgcacc gtccggtttc  900
gcaagcacca actggttcaa taacaatgca ccgagcttca gcgcgatcga ggcggctgtc  960
atccgtccgc cgcacctgtt ggacttcccg gagcagctga ccatctactc tgcatctagc  1020
cgttggagca gcacgcagca catgaattac tgggttggcc atcgtctgaa cttccgcccg  1080
attggtggta cgctgaacac tagcacgcac ggtgccacta acacgagcat caacccggtg  1140
acgctgcaat tcaccagccg tgatgtttac cgtaccgagt cctacgccgg gatcaacatt  1200
ctgctgacca ccccggttaa cggcgtccct tgggctcgtt tcaattggcg taacccactg  1260
aatagcctgc gtggttcttt gctgtacacc attggttata ccggcgtcgg tattcaactg  1320
tttgactcgg aaactgagct gccaccggaa actaccgagc gtccgaacta cgaatcttat  1380
agccaccgtc tgtccaatat ccgtctgatc agcggcaaca ccctgcgtgc gccggtgtac  1440
agctggaccc accgtagcgc cgatcgcacg aacacgattg ccaccaacat tatcacccag  1500
atcccggcag tgaaaggcaa ctttctgttt aacggcagcg tgaccagcgg tccaggtttt  1560
accggcggtg acctggtgcg cctgaacaac agcggcaaca atatccaaaa ccgtggttat  1620
ctggaagtcc cgattcaatt catcagcacg agcacccgtt accgcgtccg tgttcgctac  1680
gcatccgtta cgccgatcca actgagcgtt aactggggca attccaacat tttcagcagc  1740
attgtccctg ctacggcgac ctctctggac aatttgcaga gccgtgactt cggctatttc  1800
gaaagcacca acgctttcac cagcgctacg ggcaatgtgg ttggtgttcg caatttcagc  1860
gagaatgcgg gcgtcatcat tgaccgtttt gagtttatcc cggtgaccgc gaccttcgaa  1920
gcggagtacg atctggagcg tgcgcaggaa                                  1950

SEQ ID NO: 73           moltype = AA  length = 655
FEATURE                 Location/Qualifiers
REGION                  1..655
                        note = Cry1B variant
source                  1..655
                        mol_type = protein
                        organism = synthetic construct
SEQUENCE: 73
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ QITENARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGNTL  480
RAPVYSWTHR SADRTNTIAT NIITQIPAVK GNFLFNGSVI SGPGFTGGDL VRLNNSGNNI  540
QNRGYIEVPI QFISTSTRYR VRVRYASVTP IQLSVNWGNS NIFSRIVPAT AYSLDNLQSR  600
NFGYFESTNA FTSATGNVVG VRNFSENAGV IIDRFEFIPV TATFEAEYDL ERAQE       655

SEQ ID NO: 74           moltype = DNA  length = 1965
FEATURE                 Location/Qualifiers
misc_feature            1..1965
```

```
                        note = encodes Cry1B variant
source                  1..1965
                        mol_type = other DNA
                        organism = synthetic construct
SEQUENCE: 74
atgccgagca atcgtaagaa tgaaaatgaa atcattaacg cactgtccat ccctgcagtg  60
agcaatcaca gcgcgcagat ggatttgagc ctggatgcgc gtatcgagga cagcctgtgt  120
attgccgagg gcaacaacat caatccgttg gtcagcgcga gcaccgtgca aaccggcatt  180
aacattgccg gtcgtatcct gggtgtcctg ggcgttccgt ttgcgggtca gctggcgagc  240
ttttacagct ttatcgttgg tgagttgtgg ccgtcgggtc gtgacccttg ggagattttc  300
atggagcacg tcgagcaact ggtgcgccaa cagattacgg agaatgcgcg caacaccgct  360
ctggcgcgtc tgcaaggtct gggtgcaagc ttccgcgctt accagcagtc cctggaagat  420
tggttggaaa accgtgataa tgcgcgcact cgctccgtcc tgtacacgca gtacatcgcg  480
ctggagctgg acttcttgaa cgcgatgccg ctgtttgcaa tcaacaacca gcaagtgccg  540
ctgctgatgg tctacgccca agccgcgaat ctgcacttgc tgctgctgcg cgacgcatct  600
ctgttcggta gcgaatttgg cctgaccagc caggagatcc agcgctacta tgagcgtcag  660
gccgagaaaa cgcgtgaata ctccgactac tgcgctcgtt ggtacaacac gggtctgaac  720
aatctgcgtg gcaccaacgc ggagtcctgg ctgcgttaca accagtttcg tcgcgatctg  780
accctgggtg ttttggattt ggttgcgctg tttccgagct atgacacccg catctatccg  840
atcaacacca gcgcgcaact gactcgtgaa atctatacgg acccgattgg ccgcactaat  900
gcaccgtccg gtttcgcaag caccaactgg ttcaataaca atgcaccgag cttcagcgcg  960
atcgaggccg cgatctttcg tccgccgcac ctgttggact tcccggagca gctgaccatc  1020
tactctgcat ctagccgttg gagcagcacg cagcacatga attactgggt tggccatcgt  1080
ctgaacttcc gcccgattgg tggtacgctg aacactagca cgcacggtgc cactaacacg  1140
agcatcaacc cggtgacgct gcaattcacc agccgtgatg tttaccgtac cgagtcctac  1200
gccggcatca acattctgct gaccaccccg gttaacggcg tcccttgggc tcgtttcaat  1260
tggcgtaacc cactgaatag cctgcgtggt tctttgctgt acaccattgg ttataccggc  1320
gtcggtacgc aactgtttga ctcggaaact gagctgccac cggaaactac cgagcgtccg  1380
aactacgaat cttatagcca ccgtctgtcc aatatccgtc tgatcatcgg caacaccctg  1440
cgtgcgccgg tgtacagctg gacccatcgt agcgccgatc gcacgaacac gattgccacc  1500
aacattatca cccagatccc ggcagtgaaa ggcaactttc tgtttaacgg cagcgtgatc  1560
agcggtccag gttttaccgg cggtgacctg gtgcgcctga acaacagcgg caacaatatc  1620
caaaaccgtg gttatatcga agtcccgatt caattcatca gcacgagcac ccgttaccgc  1680
gtccgtgttc gctacgcatc cgttacgccg atccaactga gcgttaactg gggcaattcc  1740
aacattttca gccgcattgt ccctgctacg gcgtactctc tggacaattt gcagagccgt  1800
aacttcggct atttcgaaag caccaacgct ttcaccagcg ctacgggcaa tgtggttggt  1860
gttcgcaatt tcagcgagaa tgcgggcgtc atcattgacc gttttgagtt tatcccggtg  1920
accgcgacct tcgaagcgga gtacgatctg gagcgtgcgc aggaa                1965

SEQ ID NO: 75           moltype = AA  length = 655
FEATURE                 Location/Qualifiers
REGION                  1..655
                        note = Cry1B variant
source                  1..655
                        mol_type = protein
                        organism = synthetic construct
SEQUENCE: 75
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ QITENARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGNTL  480
RAPVYSWTHR SADRTNTIAT NIITQIPAVK GNFLFNGSVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEAEYDL ERAQE        655

SEQ ID NO: 76           moltype = DNA  length = 1965
FEATURE                 Location/Qualifiers
misc_feature            1..1965
                        note = encodes Cry1B variant
source                  1..1965
                        mol_type = other DNA
                        organism = synthetic construct
SEQUENCE: 76
atgccgagca atcgtaagaa tgaaaatgaa atcattaacg cactgtccat ccctgcagtg  60
agcaatcaca gcgcgcagat ggatttgagc ctggatgcgc gtatcgagga cagcctgtgt  120
attgccgagg gcaacaacat caatccgttg gtcagcgcga gcaccgtgca aaccggcatt  180
aacattgccg gtcgtatcct gggtgtcctg ggcgttccgt ttgcgggtca gctggcgagc  240
ttttacagct ttatcgttgg tgagttgtgg ccgtcgggtc gtgacccttg ggagattttc  300
atggagcacg tcgagcaact ggtgcgccaa cagattacgg agaatgcgcg caacaccgct  360
ctggcgcgtc tgcaaggtct gggtgcaagc ttccgcgctt accagcagtc cctggaagat  420
tggttggaaa accgtgataa tgcgcgcact cgctccgtcc tgtacacgca gtacatcgcg  480
ctggagctgg acttcttgaa cgcgatgccg ctgtttgcaa tcaacaacca gcaagtgccg  540
ctgctgatgg tctacgccca agccgcgaat ctgcacttgc tgctgctgcg cgacgcatct  600
ctgttcggta gcgaatttgg cctgaccagc caggagatcc agcgctacta tgagcgtcag  660
gccgagaaaa cgcgtgaata ctccgactac tgcgctcgtt ggtacaacac gggtctgaac  720
```

```
aatctgcgtg gcaccaacgc ggagtcctgg ctgcgttaca accagtttcg tcgcgatctg  780
accctgggtg ttttggattt ggttgcgctg tttccgagct atgacacccg catctatccg  840
atcaacacca gcgcgcaact gactcgtgaa atctatacgg acccgattgg ccgcactaat  900
gcaccgtccg gtttcgcaag caccaactgg ttcaataaca atgcaccgag cttcagcgcg  960
atcgaggccg cgatctttcg tccgccgcac ctgttggact tcccggagca gctgaccatc  1020
tactctgcat ctagccgttg gagcagcacg cagcacatga attactgggt tggccatcgt  1080
ctgaacttcc gcccgattgg tggtacgctg aacactagca cgcacggtgc cactaacacg  1140
agcatcaacc cggtgacgct gcaattcacc agccgtgatg tttaccgtac cgagtcctac  1200
gccggcatca acattctgct gaccaccccg gttaacggcg tcccttgggc tcgtttcaat  1260
tggcgtaacc cactgaatag cctgcgtggt tctttgctgt acaccattgg ttataccggc  1320
gtcggtacgc aactgtttga ctcggaaact gagctgccac cggaaactac cgagcgtccg  1380
aactacgaat cttatagcca ccgtctgtcc aatatccgtc tgatcatcgg caacaccctg  1440
cgtgcgccgg tgtacagctg gacccatcgt agcgccgatc gcacgaacac gattgccacc  1500
aacattatca cccagatccc ggcagtgaaa ggcaactttc tgtttaacgg cagcgtgatc  1560
agcggtccag gttttaccgg cggtgacctg gtgcgcctga acaacagcgg caacaatatc  1620
caaaaccgtg gttatatcga agtcccgatt caattcatca gcacgagcac ccgttaccgc  1680
gtccgtgttc gctacgcatc cgttacgccg atccgcctga gcgttaactg gggcaattcc  1740
aacattttca gcagcattgt ccctgctacg gcgacctctc tggacaattt gcagagccgt  1800
aacttcggct atttcgaaag ccgcaacgct ttcaccagcg ctacgggcaa tgtggttggt  1860
gttcgcaatt tcagcgagaa tgcgggcgtc atcattgacc gttttgagtt tatcccggtg  1920
accgcgacct tcgaagcgga gtacgatctg gagcgtgcgc aggaa                  1965

SEQ ID NO: 77          moltype = AA  length = 655
FEATURE                Location/Qualifiers
REGION                 1..655
                       note = Cry1B variant
source                 1..655
                       mol_type = protein
                       organism = synthetic construct
SEQUENCE: 77
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ QITENARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIISNTL  480
RAPVYSWTHR SADRTNTIAT NIITQIPAVK GNFLFNGSVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEAEYDL ERAQE        655

SEQ ID NO: 78          moltype = DNA  length = 1965
FEATURE                Location/Qualifiers
misc_feature           1..1965
                       note = encodes Cry1B variant
source                 1..1965
                       mol_type = other DNA
                       organism = synthetic construct
SEQUENCE: 78
atgccgagca atcgtaagaa tgaaaatgaa atcattaacg cactgtccat ccctgcagtg  60
agcaatcaca gcgcgcagat ggatttgagc ctggatgcgc gtatcgagga cagcctgtgt  120
attgccgagg gcaacaacat caatccgttg gtcagcgcga gcaccgtgca aaccggcatt  180
aacattgccg gtcgtatcct gggtgtcctg ggcgttccgt ttgcgggtca gctggcgagc  240
ttttacagct ttatcgttgg tgagttgtgg ccgtcgggtc gtgacccttg ggagattttc  300
atggagcacg tcgagcaact ggtgcgccaa cagattacgg agaatgcgcg caacaccgct  360
ctggcgcgtc tgcaaggtct gggtgcaagc ttccgcgctt accagcagtc cctggaagat  420
tggttggaaa accgtgataa tgcgcgcact cgctccgtcc tgtacacgca gtacatcgcg  480
ctggagctgg acttcttgaa cgcgatgccg ctgtttgcaa tcaacaacca gcaagtgccg  540
ctgctgatgg tctacgccca agccgcgaat ctgcacttgc tgctgctgcg cgacgcatct  600
ctgttcggta gcgaatttgg cctgaccagc caggagatcc agcgctacta tgagcgtcag  660
gccgagaaaa cgcgtgaata ctccgactac tgcgctcgtt ggtacaacac gggtctgaac  720
aatctgcgtg gcaccaacgc ggagtcctgg ctgcgttaca accagtttcg tcgcgatctg  780
accctgggtg ttttggattt ggttgcgctg tttccgagct atgacacccg catctatccg  840
atcaacacca gcgcgcaact gactcgtgaa atctatacgg acccgattgg ccgcactaat  900
gcaccgtccg gtttcgcaag caccaactgg ttcaataaca atgcaccgag cttcagcgcg  960
atcgaggccg cgatctttcg tccgccgcac ctgttggact tcccggagca gctgaccatc  1020
tactctgcat ctagccgttg gagcagcacg cagcacatga attactgggt tggccatcgt  1080
ctgaacttcc gcccgattgg tggtacgctg aacactagca cgcacggtgc cactaacacg  1140
agcatcaacc cggtgacgct gcaattcacc agccgtgatg tttaccgtac cgagtcctac  1200
gccggcatca acattctgct gaccaccccg gttaacggcg tcccttgggc tcgtttcaat  1260
tggcgtaacc cactgaatag cctgcgtggt tctttgctgt acaccattgg ttataccggc  1320
gtcggtacgc aactgtttga ctcggaaact gagctgccac cggaaactac cgagcgtccg  1380
aactacgaat cttatagcca ccgtctgtcc aatatccgtc tgatcatcag caacaccctg  1440
cgtgcgccgg tgtacagctg gacccatcgt agcgccgatc gcacgaacac gattgccacc  1500
aacattatca cccagatccc ggcagtgaaa ggcaactttc tgtttaacgg cagcgtgatc  1560
agcggtccag gttttaccgg cggtgacctg gtgcgcctga acaacagcgg caacaatatc  1620
caaaaccgtg gttatatcga agtcccgatt caattcatca gcacgagcac ccgttaccgc  1680
gtccgtgttc gctacgcatc cgttacgccg atccgcctga gcgttaactg gggcaattcc  1740
```

```
aacattttca gcagcattgt ccctgctacg gcgacctctc tggacaattt gcagagccgt  1800
aacttcggct atttcgaaag ccgcaacgct ttcaccagcg ctacgggcaa tgtggttggt  1860
gttcgcaatt tcagcgagaa tgcgggcgtc atcattgacc gttttgagtt tatcccggtg  1920
accgcgacct tcgaagcgga gtacgatctg gagcgtgcgc aggaa                  1965

SEQ ID NO: 79           moltype = AA  length = 655
FEATURE                 Location/Qualifiers
REGION                  1..655
                        note = Cry1B variant
source                  1..655
                        mol_type = protein
                        organism = synthetic construct
SEQUENCE: 79
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ AITLNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIISGTL  480
RAPVYSWTHR SADRTNTIAT NIITQIPAVK GNFLFNGSVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEAEYDL ERAQE       655

SEQ ID NO: 80           moltype = DNA  length = 1965
FEATURE                 Location/Qualifiers
misc_feature            1..1965
                        note = encodes Cry1B variant
source                  1..1965
                        mol_type = other DNA
                        organism = synthetic construct
SEQUENCE: 80
atgccgagca atcgtaagaa tgaaaatgaa atcattaacg cactgtccat ccctgcagtg  60
agcaatcaca gcgcgcagat ggatttgagc ctggatgcgc gtatcgagga cagcctgtgt  120
attgccgagg gcaacaacat caatccgttg gtcagcgcga gcaccgtgca aaccggcatt  180
aacattgccg gtcgtatcct gggtgtcctg ggcgttccgt ttgcgggtca gctggcgagc  240
ttttacagct ttatcgttgg tgagttgtgg ccgtcgggtc gtgacccttg ggagattttc  300
atggagcacg tcgagcaact ggtgcgccaa gcgattacgc tgaatgcgcg caacaccgct  360
ctggcgcgtc tgcaaggtct gggtgcaagc ttccgcgctt accagcagtc cctggaagat  420
tggttggaaa accgtgataa tgcgcgcact cgctccgtcc tgtacacgca gtacatcgcg  480
ctggagctgg acttcttgaa cgcgatgccg ctgtttgcaa tcaacaacca gcaagtgccg  540
ctgctgatgg tctacgccca agccgcgaat ctgcacttgc tgctgctgcg cgacgcatct  600
ctgttcggta gcgaatttgg cctgaccagc caggagatcc agcgctacta tgagcgtcag  660
gccgagaaaa cgcgtgaata ctccgactac tgcgctcgtt ggtacaacac gggtctgaac  720
aatctgcgtg gcaccaacgc ggagtcctgg ctgcgttaca accagtttcg tcgcgatctg  780
accctgggtg ttttggattt ggttgcgctg tttccgagct atgacacccg catctatccg  840
atcaacacca gcgcgcaact gactcgtgaa atctatacgg acccgattgg ccgcactaat  900
gcaccgtccg gtttcgcaag caccaactgg ttcaataaca atgcaccgag cttcagcgcg  960
atcgaggccg cgatctttcg tccgccgcac ctgttggact tcccggagca gctgaccatc  1020
tactctgcat ctagccgttg gagcagcacg cagcacatga attactgggt tggccatcgt  1080
ctgaacttcc gcccgattgg tggtacgctg aacactagca cgcacggtgc cactaacacg  1140
agcatcaacc cggtgacgct gcaattcacc agccgtgatg tttaccgtac cgagtcctac  1200
gccggcatca acattctgct gaccaccccg gttaacggcg tcccttgggc tcgtttcaat  1260
tggcgtaacc cactgaatag cctgcgtggt tctttgctgt acaccattgg ttataccggc  1320
gtcggtacgc aactgtttga ctcggaaact gagctgccac cggaaactac cgagcgtccg  1380
aactacgaat cttatagcca ccgtctgtcc aatatccgtc tgatcatcag cggcaccctg  1440
cgtgcgccgg tgtacagctg gacccatcgt agcgccgatc gcacgaacac gattgccacc  1500
aacattatca cccagatccc ggcagtgaaa ggcaactttc tgtttaacgg cagcgtgatc  1560
agcggtccag gttttaccgg cggtgacctg gtgcgcctga acaacagcgg caacaatatc  1620
caaaaccgtg gttatatcga agtcccgatt caattcatca gcacgagcac ccgttaccgc  1680
gtccgtgttc gctacgcatc cgttacgccg atccgcctga gcgttaactg gggcaattcc  1740
aacattttca gcagcattgt ccctgctacg gcgacctctc tggacaattt gcagagccgt  1800
aacttcggct atttcgaaag ccgcaacgct ttcaccagcg ctacgggcaa tgtggttggt  1860
gttcgcaatt tcagcgagaa tgcgggcgtc atcattgacc gttttgagtt tatcccggtg  1920
accgcgacct tcgaagcgga gtacgatctg gagcgtgcgc aggaa                  1965

SEQ ID NO: 81           moltype = AA  length = 655
FEATURE                 Location/Qualifiers
REGION                  1..655
                        note = Cry1B variant
source                  1..655
                        mol_type = protein
                        organism = synthetic construct
SEQUENCE: 81
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ AITLNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
```

```
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LYFRPINGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGNTL  480
RAPVYSWTHR SADRTNTIAT NIITQIPAVK GNFLFNGSVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEAEYDL ERAQE       655

SEQ ID NO: 82          moltype = DNA  length = 1965
FEATURE                Location/Qualifiers
misc_feature           1..1965
                       note = encodes Cry1B variant
source                 1..1965
                       mol_type = other DNA
                       organism = synthetic construct
SEQUENCE: 82
atgccgagca atcgtaagaa tgaaaatgaa atcattaacg cactgtccat ccctgcagtg  60
agcaatcaca gcgcgcagat ggatttgagc ctggatgcgc gtatcgagga cagcctgtgt  120
attgccgagg gcaacaacat caatccgttg gtcagcgcga gcaccgtgca aaccggcatt  180
aacattgccg gtcgtatcct gggtgtcctg ggcgttccgt ttgcgggtca gctggcgagc  240
ttttacagct ttatcgttgg tgagttgtgg ccgtcgggtc gtgacccttg ggagattttc  300
atggagcacg tcgagcaact ggtgcgccaa gcgattacgc tgaatgcgcg caacaccgct  360
ctggcgcgtc tgcaaggtct gggtgcaagc ttccgcgctt accagcagtc cctggaagat  420
tggttggaaa accgtgataa tgcgcgcact cgctccgtcc tgtacacgca gtacatcgcg  480
ctggagctgg acttcttgaa cgcgatgccg ctgtttgcaa tcaacaacca gcaagtgccg  540
ctgctgatgg tctacgccca agccgcgaat ctgcacttgc tgctgctgcg cgacgcatct  600
ctgttcggta gcgaatttgg cctgaccagc caggagatcc agcgctacta tgagcgtcag  660
gccgagaaaa cgcgtgaata ctccgactac tgcgctcgtt ggtacaacac gggtctgaac  720
aatctgcgtg gcaccaacgc ggagtcctgg ctgcgttaca accagtttcg tcgcgatctg  780
accctgggtg ttttggattt ggttgcgctg tttccgagct atgacacccg catctatccg  840
atcaacacca gcgcgcaact gactcgtgaa atctatacgg acccgattgg ccgcactaat  900
gcaccgtccg gtttcgcaag caccaactgg ttcaataaca atgcaccgag cttcagcgcg  960
atcgaggccg cgatctttcg tccgccgcac ctgttggact tcccggagca gctgaccatc  1020
tactctgcat ctagccgttg gagcagcacg cagcacatga attactgggt tggccatcgt  1080
ctgtatttcc gcccgattaa cggtacgctg aacactagca cgcacggtgc cactaacacg  1140
agcatcaacc cggtgacgct gcaattcacc agccgtgatg tttaccgtac cgagtcctac  1200
gccggcatca acattctgct gaccaccccg gttaacggcg tcccttgggc tcgtttcaat  1260
tggcgtaacc cactgaatag cctgcgtggt tctttgctgt acaccattgg ttataccggc  1320
gtcggtacgc aactgtttga ctcggaaact gagctgccac cggaaactac cgagcgtccg  1380
aactacgaat cttatagcca ccgtctgtcc aatatccgtc tgatcatcgg caacaccctg  1440
cgtgcgccgg tgtacagctg gacccatcgt agcgccgatc gcacgaacac gattgccacc  1500
aacattatca cccagatccc ggcagtgaaa ggcaactttc tgtttaacgg cagcgtgatc  1560
agcggtccag gttttaccgg cggtgacctg gtgcgcctga acaacagcgg caacaatatc  1620
caaaaccgtg gttatatcga agtcccgatt caattcatca gcacgagcac ccgttaccgc  1680
gtccgtgttc gctacgcatc cgttacgccg atccgcctga gcgttaactg gggcaattcc  1740
aacattttca gcagcattgt ccctgctacg gcgacctctc tggacaattt gcagagccgt  1800
aacttcggct atttcgaaag ccgcaacgct ttcaccagcg ctacgggcaa tgtggttggt  1860
gttcgcaatt tcagcgagaa tgcgggcgtc atcattgacc gttttgagtt tatcccggtg  1920
accgcgacct tcgaagcgga gtacgatctg gagcgtgcgc aggaa                  1965

SEQ ID NO: 83          moltype = AA  length = 655
FEATURE                Location/Qualifiers
REGION                 1..655
                       note = Cry1B variant
source                 1..655
                       mol_type = protein
                       organism = synthetic construct
SEQUENCE: 83
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ AITLNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LYFRPIQGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGNTL  480
RAPVYSWTHR SADRTNTIAT NIITQIPAVK GNFLFNGSVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEAEYDL ERAQE       655

SEQ ID NO: 84          moltype = DNA  length = 1965
FEATURE                Location/Qualifiers
misc_feature           1..1965
                       note = encodes Cry1B variant
source                 1..1965
                       mol_type = other DNA
                       organism = synthetic construct
SEQUENCE: 84
atgccgagca atcgtaagaa tgaaaatgaa atcattaacg cactgtccat ccctgcagtg  60
```

-continued

```
agcaatcaca gcgcgcagat ggatttgagc ctggatgcgc gtatcgagga cagcctgtgt  120
attgccgagg gcaacaacat caatccgttg gtcagcgcga gcaccgtgca aaccggcatt  180
aacattgccg gtcgtatcct gggtgtcctg ggcgttccgt ttgcgggtca gctggcgagc  240
ttttacagct ttatcgttgg tgagttgtgg ccgtcgggtc gtgacccttg ggagattttc  300
atggagcacg tcgagcaact ggtgcgccaa gcgattacgc tgaatgcgcg caacaccgct  360
ctggcgcgtc tgcaaggtct gggtgcaagc ttccgcgctt accagcagtc cctggaagat  420
tggttggaaa accgtgataa tgcgcgcact cgctccgtcc tgtacacgca gtacatcgcg  480
ctggagctgg acttcttgaa cgcgatgccg ctgtttgcaa tcaacaacca gcaagtgccg  540
ctgctgatgg tctacgccca agccgcgaat ctgcacttgc tgctgctgcg cgacgcatct  600
ctgttcggta gcgaatttgg cctgaccagc caggagatcc agcgctacta tgagcgtcag  660
gccgagaaaa cgcgtgaata ctccgactac tgcgctcgtt ggtacaacac gggtctgaac  720
aatctgcgtg gcaccaacgc ggagtcctgg ctgcgttaca accagtttcg tcgcgatctg  780
accctgggtg ttttggattt ggttgcgctg tttccgagct atgacacccg catctatccg  840
atcaacacca gcgcgcaact gactcgtgaa atctatacgg acccgattgg ccgcactaat  900
gcaccgtccg gtttcgcaag caccaactgg ttcaataaca atgcaccgag cttcagcgcg  960
atcgaggccg cgatctttcg tccgccgcac ctgttggact tcccggagca gctgaccatc  1020
tactctgcat ctagccgttg gagcagcacg cagcacatga attactgggt tggccatcgt  1080
ctgtatttcc gcccgattca gggtacgctg aacactagca cgcacggtgc cactaacacg  1140
agcatcaacc cggtgacgct gcaattcacc agccgtgatg tttaccgtac cgagtcctac  1200
gccggcatca acattctgct gaccaccccg gttaacggcg tcccttgggc tcgtttcaat  1260
tggcgtaacc cactgaatag cctgcgtggt tctttgctgt acaccattgg ttataccggc  1320
gtcggtacgc aactgtttga ctcggaaact gagctgccac cggaaactac cgagcgtccg  1380
aactacgaat cttatagcca ccgtctgtcc aatatccgtc tgatcatcgg caacaccctg  1440
cgtgcgccgg tgtacagctg gacccatcgt agcgccgatc gcacgaacac gattgccacc  1500
aacattatca cccagatccc ggcagtgaaa ggcaactttc tgtttaacgg cagcgtgatc  1560
agcggtccag gttttaccgg cggtgacctg gtgcgcctga acaacagcgg caacaatatc  1620
caaaaccgtg gttatatcga agtcccgatt caattcatca gcacgagcac ccgttaccgc  1680
gtccgtgttc gctacgcatc cgttacgccg atccgcctga gcgttaactg ggcaattcc  1740
aacattttca gcagcattgt ccctgctacg gcgacctctc tggacaattt gcagagccgt  1800
aacttcggct atttcgaaag ccgcaacgct ttcaccagcg ctacgggcaa tgtggttggt  1860
gttcgcaatt tcagcgagaa tgcgggcgtc atcattgacc gttttgagtt tatcccggtg  1920
accgcgacct tcgaagcgga gtacgatctg gagcgtgcgc aggaa                1965
```

```
SEQ ID NO: 85          moltype = AA  length = 663
FEATURE                Location/Qualifiers
REGION                 1..663
                       note = Cry1B variant
source                 1..663
                       mol_type = protein
                       organism = synthetic construct
SEQUENCE: 85
MPSNRKNENE IINAVSNHSA QMDLSLDARI EDSLCVAEVN NIDPFVSAST VQTGISIAGR  60
ILGVLGVPFA GQLASFYSFL VGELWPSGRD PWEIFMEHVE QIVRQQITDS VRDTAIARLE  120
GLGRGYRSYQ QALETWLDNR NDARSRSIIR ERYIALELDI TTAIPLFSIR NQEVPLLMVY  180
AQAANLHLLL LRDASLFGSE WGMSSSDVNQ YYQEQIRYTE EYSNHCVQWY NTGLNNLRGT  240
NAESWLRYNQ FRRDLTLGVL DLVALFPSYD TRVYPMNTSA QLTREIYTDP IGRTNAPSGF  300
ASTNWFNNNA PSFSAIEAAI FRPPHLLDFP EQLTIYSASS RWSSTQHMNY WVGHRLNFRP  360
IGGTLNTSTQ GLTNNTSINP VTLQFTSRDV YRTESNAGTN ILFTTPVNGV PWARFNFINP  420
QNIYERGATT YSQPYQGVGI QLFDSETELP PETTERPNYE SYSHRLSHIG LIIGNTLRAP  480
VYSWTHRSAT LTNTIDPERI NQIPLVKGFR VWGGTSVITG PGFTGGDILR RNTFGDFVSL  540
QVNINSPITQ RYRLRFRYAS SRDARVIVLT GAASTGVGGQ VSVNMPLQKT MEIGENLTSR  600
TFRYTDFSNP FSFRANPDII GISEQPLFGA GSISSGELYI DKIEIILADA TFEAESDLER  660
AQK                                                                663
```

```
SEQ ID NO: 86          moltype = DNA  length = 1989
FEATURE                Location/Qualifiers
misc_feature           1..1989
                       note = encodes Cry1B variant
source                 1..1989
                       mol_type = other DNA
                       organism = synthetic construct
SEQUENCE: 86
atgccttcaa ataggaaaaa tgagaatgaa attataaatg ctgtatcgaa tcattccgca  60
caaatggatc tatcgctaga tgctcgtatt gaagatagct tgtgtgtagc cgaggtgaac  120
aatattgatc catttgttag cgcatcaaca gtccaaacag gtattagtat agctggtaga  180
atattgggcg tattaggtgt gccgtttgct ggacaactag ctagttttta tagttttctt  240
gttggggaat tatggcctag cggcagagat ccatgggaaa tttttatgga acatgtcgag  300
caaattgtaa gacaacaaat aacggacagt gttagggata ccgctattgc tcgtttagaa  360
ggtctaggaa gagggtatag atcttaccag caggctcttg aaacttggtt agataaccga  420
aatgatgcaa gatcaagaag cattattcgt gagagatata ttgctttaga acttgacatt  480
actactgcta taccgctttt cagcatacga aatcaagagg ttccattatt aatggtatat  540
gctcaagctg caaatttaca cctattatta ttgagagacg catccctttt tggtagtgaa  600
tgggggatgt catcttccga tgttaaccaa tattaccaag aacaaatcag atatacagag  660
gaatattcta accattgcgt acaatggtat aatacagggc taaataactt aagagggaca  720
aatgctgaaa gttggttgcg gtataatcaa ttccgtagag atctaacgtt aggagtatta  780
gatctagtgg cactattccc aagctatgac acgcgtgttt atccaatgaa tacgagtgct  840
cagttaacaa gagaaattta tacagatcca attgggagaa caaatgcacc ttcaggattt  900
gcaagtacga attggtttaa taataatgca ccatcgtttt ctgccataga ggctgccatt  960
ttcaggcctc cgcatctact tgatttccca gaacaactta caatttacag tgcatcaagc  1020
```

```
cgttggagta gcactcaaca tatgaattat tgggtgggac ataggcttaa cttccgccca  1080
ataggaggga cattaaatac ctcaacacaa ggacttacta ataatacttc aattaatcct  1140
gtaacattac agtttacgtc tcgtgacgtt tatagaacag aatcaaatgc agggacaaat  1200
atactattta ctactcctgt gaatggagta ccttgggcta gatttaattt tataaaccct  1260
cagaatattt atgaaagagg cgccactacc tacagtcaac cgtatcaggg agttgggatt  1320
caattatttg attcagaaac tgaattacca ccagaaacaa cagaacgacc aaattatgaa  1380
tcatatagtc atagattatc tcatatagga ctaatcatag gaaacacttt gagagcacca  1440
gtctattctt ggacgcatcg tagtgcaact cttacaaata caattgatcc agagagaatt  1500
aatcaaatac ctttagtgaa aggatttaga gtttgggggg gcacctctgt cattacagga  1560
ccaggattta caggagggga tatccttcga agaaatacct ttggtgattt tgtatctcta  1620
caagtcaata ttaattcacc aattacccaa agataccgtt taagatttcg ttacgcttcc  1680
agtagggatg cacgagttat agtattaaca ggagcggcat ccacaggagt gggaggccaa  1740
gttagtgtaa atatgcctct tcagaaaact atggaaatag gggagaactt aacatctaga  1800
acatttagat ataccgattt tagtaatcct tttcatttta gagctaatcc agatataatt  1860
gggataagtg aacaacctct atttggtgca ggttctatta gtagcggtga actttatata  1920
gataaaattg aaattattct agcagatgca acatttgaag cagaatctga tttagaaaga  1980
gcacaaaag                                                          1989

SEQ ID NO: 87          moltype = AA  length = 663
FEATURE                Location/Qualifiers
REGION                 1..663
                       note = Cry1B variant
source                 1..663
                       mol_type = protein
                       organism = synthetic construct
SEQUENCE: 87
MPSNRKNENE IINAVSNHSA QMDLSLDARI EDSLCVAEVN NIDPFVSAST VQTGISIAGR  60
ILGVLGVPFA GQLASFYSFL VGELWPSGRD PWEIFMEHVE QIVRQQITDS VRDTAIARLE  120
GLGRGYRSYQ QALETWLDNR NDARSRSIIR ERYIALELDI TTAIPLFSIR NQEVPLLMVY  180
AQAANLHLLL LRDASLFGSE WGMSSSDVNQ YYQEQIRYTE EYSNHCVQWY NTGLNNLRGT  240
NAESWLRYNQ FRRDLTLGVL DLVALFPSYD TRTYPINTSA QLTREIYTDP IGRTNAPSGF  300
ASTNWFNNNA PSFSAIEAAI FRPPHLLDFP EQLTIYSASS RWSSTQHMNY WVGHRLNFRP  360
IGGTLNTSTQ GLTNNTSINP VTLQFTSRDV YRTESNAGTN ILFTTPVNGV PWARFNFINP  420
QNIYERGATT YSQPYQGVGI QLFDSETELP PETTERPNYE SYSHRLSHIG LIIGNTLRAP  480
VYSWTHRSAT LTNTIDPERI NQIPLVKGFR VWGGTSVITG PGFTGGDILR RNTFGDFVSL  540
QVNINSPITQ RYRLRFRYAS SRDARVIVLT GAASTGVGGQ VSVNMPLQKT MEIGENLTSR  600
TFRYTDFSNP FSFRANPDII GISEQPLFGA GSISSGELYI DKIEIILADA TFEAESDLEG  660
ARK                                                                663

SEQ ID NO: 88          moltype = DNA  length = 1989
FEATURE                Location/Qualifiers
misc_feature           1..1989
                       note = encodes Cry1B variant
source                 1..1989
                       mol_type = other DNA
                       organism = synthetic construct
SEQUENCE: 88
atgccttcaa ataggaaaaa tgagaatgaa attataaatg ctgtatcgaa tcattccgca  60
caaatggatc tatcgctaga tgctcgtatt gaagatagct tgtgtgtagc cgaggtgaac  120
aatattgatc catttgttag cgcatcaaca gtccaaacag gtattagtat agctggtaga  180
atattgggcg tattaggtgt gccgtttgct ggacaactag ctagttttta tagttttctt  240
gttggggaat tatggcctag cggcagagat ccatgggaaa tttttatgga acatgtcgag  300
caaattgtaa gacaacaaat aacggacagt gttagggata ccgctattgc tcgtttagaa  360
ggtctaggaa gagggtatag atcttaccag caggctcttg aaacttggtt agataaccga  420
aatgatgcaa gatcaagaag cattattcgt gagagatata ttgctttaga acttgacatt  480
actactgcta taccgctttt cagcatacga aatcaagagg ttccattatt aatggtatat  540
gctcaagctg caaatttaca cctattatta ttgagagacg catccctttt tggtagtgaa  600
tgggggatgt catcttccga tgttaaccaa tattaccaag aacaaatcag atatacagag  660
gaatattcta accattgcgt acaatggtat aatacagggc taaataactt aagagggaca  720
aatgctgaaa gttggttgcg gtataatcaa ttccgtagag atctaacgtt aggagtatta  780
gatctagtgg cactattccc aagctatgac actcgcactt atccaatcaa tacgagtgct  840
cagttaacaa gagaaattta tacagatcca attgggagaa caaatgcacc ttcaggattt  900
gcaagtacga attggtttaa taataatgca ccatcgtttt ctgccataga ggctgccatt  960
ttcaggcctc cgcatctact tgatttttcca gaacaactta caatttacag tgcatcaagc  1020
cgttggagta gcactcaaca tatgaattat tgggtgggac ataggcttaa cttccgccca  1080
ataggaggga cattaaatac ctcaacacaa ggacttacta ataatacttc aattaatcct  1140
gtaacattac agtttacgtc tcgtgacgtt tatagaacag aatcaaatgc agggacaaat  1200
atactattta ctactcctgt gaatggagta ccttgggcta gatttaattt tataaaccct  1260
cagaatattt atgaaagagg cgccactacc tacagtcaac cgtatcaggg agttgggatt  1320
caattatttg attcagaaac tgaattacca ccagaaacaa cagaacgacc aaattatgaa  1380
tcatatagtc atagattatc tcatatagga ctaatcatag gaaacacttt gagagcacca  1440
gtctattctt ggacgcatcg tagtgcaact cttacaaata caattgatcc agagagaatt  1500
aatcaaatac ctttagtgaa aggatttaga gtttgggggg gcacctctgt cattacagga  1560
ccaggattta caggagggga tatccttcga agaaatacct ttggtgattt tgtatctcta  1620
caagtcaata ttaattcacc aattacccaa agataccgtt taagatttcg ttacgcttcc  1680
agtagggatg cacgagttat agtattaaca ggagcggcat ccacaggagt gggaggccaa  1740
gttagtgtaa atatgcctct tcagaaaact atggaaatag gggagaactt aacatctaga  1800
acatttagat ataccgattt tagtaatcct tttcatttta gagctaatcc agatataatt  1860
gggataagtg aacaacctct atttggtgca ggttctatta gtagcggtga actttatata  1920
```

```
gataaaattg aaattattct agcagatgca acatttgaag cagaatctga tttagaaggg  1980
gcgcggaag                                                          1989

SEQ ID NO: 89          moltype = AA  length = 663
FEATURE                Location/Qualifiers
REGION                 1..663
                       note = Cry1B variant
source                 1..663
                       mol_type = protein
                       organism = synthetic construct
SEQUENCE: 89
MPSNRKNENE IINAVSNHSA QMDLSLDARI EDSLCVAEVN NIDPFVSAST VQTGINIAGR  60
ILGVLGVPFA GQLASFYSFL VGELWPSGRD PWEIFMEHVE QIVRQQITDS VRDTAIARLE  120
GLGRGYRSYQ QALETWLDNR NDARSRSIIL ERYIALELDI TTAIPLFSIR NQEVPLLMVY  180
AQAANLHLLL LRDASLFGSE WGMASSDVNQ YYQEQIRYTE EYSNHCVQWY NTGLNNLRGT  240
NAESWLRYNQ FRRDLTLGVL DLVALFPSYD TRTYPINTSA QLTREIYTDP IGRTNAPSGF  300
ASTNWFNNNA PSFSAIEAAI FRPPHLLDFP EQLTIYSASS RWSSTQHMNY WVGHRLNFRP  360
IGGTLNTSTQ GLTNNTSINP VTLQFTSRDV YRTESNAGTN ILFTTPVNGV PWARFNFINP  420
QNIYERGATT YSQPYQGVGI QLFDSETELP PETTERPNYE SYSHRLSHIG LIIGNTLRAP  480
VYSWTHRSAT LTNTIDPERI NQIPLVKGFR VWGGTSVITG PGFTGGDILR RNTFGDFVSL  540
QVNINSPITQ RYRLRFRYAS SRDARVIVLT GAASTGVGGQ VSVNMPLQKT MEIGENLTSR  600
TFRYTDFSNP FSFRANPDII GISEQPLFGA GSISSGELYI DKIEIILADA TFEAESDLEK  660
AQK                                                                663

SEQ ID NO: 90          moltype = DNA  length = 1989
FEATURE                Location/Qualifiers
misc_feature           1..1989
                       note = encodes Cry1B variant
source                 1..1989
                       mol_type = other DNA
                       organism = synthetic construct
SEQUENCE: 90
atgccttcaa ataggaaaaa tgagaatgaa attataaatg ctgtatcgaa tcattccgca  60
caaatggatc tatcgctaga tgctcgtatt gaagatagct tgtgtgtagc cgaggtgaac  120
aatattgatc catttgttag cgcatcaaca gtccaaacgg gtattaacat agctggtaga  180
atactaggcg tattaggggt gccgtttgct ggacaactag ctagtttttta tagttttctt  240
gttggggaat tatggcctag cggcagagat ccatgggaaa tttttatgga acatgtcgag  300
caaattgtaa gacaacaaat aacggacagt gttagggata ccgctattgc tcgtttagaa  360
ggtctaggaa gagggtatag atcttaccag caggctcttg aaacttggtt agataaccga  420
aatgatgcaa gatcaagaag cattattctt gagcgctata ttgctttaga acttgacatt  480
actactgcta taccgctttt cagcatacga aatcaagagg ttccattatt gatggtatat  540
gctcaagctg caaatttaca cctattatta ttgagagacg catccctttt tggtagtgaa  600
tgggggatgg catcttccga tgttaaccaa tattaccaag aacaaatcag atatacagag  660
gaatattcta accattgcgt acaatggtat aatacagggc taaataactt aagagggaca  720
aatgctgaaa gttggttgcg gtataatcaa ttccgtagag acctaacgtt aggggtatta  780
gatttagtag ccctattccc aagctatgat actcgcactt atccaatcaa tacgagtgct  840
cagttaacaa gagaaattta tacagatcca attgggagaa caaatgcacc ttcaggattt  900
gcaagtacga attggtttaa taataatgca ccatcgtttt ctgccataga ggctgccatt  960
ttcaggcctc cgcatctact tgattttcca gaacaactta caatttacag tgcatcaagc  1020
cgttggagta gcactcaaca tatgaattat tgggtgggac ataggcttaa cttccgccca  1080
ataggaggga cattaaatac ctcaacacaa ggacttacta ataatacttc aattaatcct  1140
gtaacattac agtttacgtc tcgtgacgtt tatagaacag aatcaaatgc agggacaaat  1200
atactattta ctactcctgt gaatggagta ccttgggcta gatttaattt tataaaccct  1260
cagaatattt atgaaagagg cgccactacc tacagtcaac cgtatcaggg agttgggatt  1320
caattatttg attcagaaac tgaattacca ccagaaacaa cagaacgacc aaattatgaa  1380
tcatatagtc atagattatc tcatatagga ctaatcatag gaaacacttt gagagcacca  1440
gtctattctt ggacgcatcg tagtgcaact cttacaaata caattgatcc agagagaatt  1500
aatcaaatac ctttagtgaa aggatttaga gtttgggggg gcacctctgt cattacagga  1560
ccaggattta caggagggga tatccttcga agaaatacct ttggtgattt tgtatctcta  1620
caagtcaata ttaattcacc aattacccaa agataccgtt taagatttcg ttacgcttcc  1680
agtagggatg cacgagttat agtattaaca ggagcggcat ccacaggagt gggaggccaa  1740
gttagtgtaa atatgcctct tcagaaaact atggaaatag gggagaactt aacatctaga  1800
acatttagat ataccgattt tagtaatcct tttcattta gagctaatcc agatataatt  1860
gggataagtg aacaacctct atttggtgca ggttctatta gtagcggtga actttatata  1920
gataaaattg aaattattct agcagatgca acatttgaag cagaatctga tttagagaaa  1980
gctcagaaa                                                          1989

SEQ ID NO: 91          moltype = AA  length = 663
FEATURE                Location/Qualifiers
REGION                 1..663
                       note = Cry1B variant
source                 1..663
                       mol_type = protein
                       organism = synthetic construct
SEQUENCE: 91
MPSNRKNENE IINAVSNHSA QMDLSLDARI EDSLCVAEVN NIDPFVSAST VQTGISIAGR  60
ILGVLGVPFA GQLASFYSFL VGELWPSGRD PWEIFLEHVE QLIRQQVTEN TRNTAIARLE  120
GLGRGYRSYQ QALETWLDNR NDARSRSIIL ERYVALELDI TTAIPLFSIR NQEVPLLMVY  180
AQAANLHLLL LRDASLFGSE WGMSSADVNQ YYQEQIRYTE EYSNHCVQWY NTGLNNLRGT  240
```

-continued

NAESWLRYNQ FRRDLTLGVL DLVALFPSYD TRTYPINTSA QLTREIYTDP IGRTNAPSGF 300
ASTNWFNNNA PSFSAIEAAI FRPPHLLDFP EQLTIYSASS RWSSTQHMNY WVGHRLNFRP 360
IGGTLNTSTQ GLTNNTSINP VTLQFTSRDV YRTESNAGTN ILFTTPVNGV PWARFNFINP 420
QNIYERGATT YSQPYQGVGI QLFDSETELP PETTERPNYE SYSHRLSHIG LIIGNTLRAP 480
VYSWTHRSAT LTNTIDPERI NQIPLVKGFR VWGGTSVITG PGFTGGDILR RNTFGDFVSL 540
QVNINSPITQ RYRLRFRYAS SRDARVIVLT GAASTGVGGQ VSVNMPLQKT MEIGENLTSR 600
TFRYTDFSNP FSFRANPDII GISEQPLFGA GSISSGELYI DKIEIILADA TFEAESDLER 660
AQK 663

SEQ ID NO: 92 moltype = DNA length = 1989
FEATURE Location/Qualifiers
misc_feature 1..1989
note = encodes Cry1B variant
source 1..1989
mol_type = other DNA
organism = synthetic construct
SEQUENCE: 92
atgccttcaa ataggaaaaa tgagaatgaa attataaatg ctgtatcgaa tcattccgca 60
caaatggatc tatcgctaga tgctcgtatt gaagatagct tgtgtgtagc cgaggtgaac 120
aatattgatc catttgttag cgcatcaaca gtccaaacag gtattagtat agctggtaga 180
atattgggcg tattaggtgt gccgtttgct ggacaactag ctagttttta tagttttctt 240
gttggggaat tatggcctag cggcagagat ccatgggaaa ttttcctgga acatgtcgaa 300
caacttataa gacaacaagt aacagaaaat actaggaata cggctattgc tcgattagaa 360
ggtctaggaa gaggctatag atcttaccag caggctcttg aaacttggtt agataaccga 420
aatgatgcaa gatcaagaag cattattctt gagcgctatg ttgctttaga acttgacatt 480
actactgcta taccgctttt cagcatacga aatcaagagg ttccattatt aatggtatat 540
gctcaagctg caaatttaca cctattatta ttgagagacg catccctttt tggtagtgaa 600
tgggggatgt catctgccga tgttaaccaa tattaccaag aacaaatcag atatacagag 660
gaatattcta accattgcgt acaatggtat aatacagggc taaataactt aagagggaca 720
aatgctgaaa gttggttgcg gtataatcaa ttccgtagag acctaacgtt aggggtatta 780
gatttagtag ccctattccc aagctatgac actcgcactt atccaatcaa tacgagtgct 840
cagttaacaa gagaaattta tacagatcca attgggagaa caaatgcacc ttcaggattt 900
gcaagtacga attggtttaa taataatgca ccatcgtttt ctgccataga ggctgccatt 960
ttcaggcctc cgcatctact tgattttcca gaacaactta caatttacag tgcatcaagc 1020
cgttggagta gcactcaaca tatgaattat tgggtgggac ataggcttaa cttccgccca 1080
ataggaggga cattaaatac ctcaacacaa ggacttacta ataatacttc aattaatcct 1140
gtaacattac agtttacgtc tcgtgacgtt tatagaacag aatcaaatgc agggacaaat 1200
atactattta ctactcctgt gaatggagta ccttgggcta gatttaattt tataaaccct 1260
cagaatattt atgaaagagg cgccactacc tacagtcaac cgtatcaggg agttgggatt 1320
caattatttg attcagaaac tgaattacca ccagaaacaa cagaacgacc aaattatgaa 1380
tcatatagtc atagattatc tcatatagga ctaatcatag gaaacacttt gagagcacca 1440
gtctattctt ggacgcatcg tagtgcaact cttacaaata caattgatcc agagagaatt 1500
aatcaaatac ctttagtgaa aggatttaga gtttgggggg gcacctctgt cattacagga 1560
ccaggattta caggagggga tatccttcga agaaatacct ttggtgattt tgtatctcta 1620
caagtcaata ttaattcacc aattacccaa agataccgtt taagatttcg ttacgcttcc 1680
agtagggatg cacgagttat agtattaaca ggagcggcat ccacaggagt gggaggccaa 1740
gttagtgtaa atatgcctct tcagaaaact atggaaatag gggagaactt aacatctaga 1800
acatttagat ataccgattt tagtaatcct tttttcattta gagctaatcc agatataatt 1860
gggataagtg aacaacctct atttggtgca ggttctatta gtagcggtga actttatata 1920
gataaaattg aaattattct agcagatgca acatttgaag cagaatctga tttagaaaga 1980
gcacaaaag 1989

SEQ ID NO: 93 moltype = AA length = 655
FEATURE Location/Qualifiers
REGION 1..655
note = Cry1B variant
source 1..655
mol_type = protein
organism = synthetic construct
SEQUENCE: 93
MPSNRKNENE IINALSIPAV SNHSAQMDLS LDARIEDSLC IAEGNNINPL VSASTVQTGI 60
NIAGRILGVL GVPFAGQLAS FYSFIVGELW PSGRDPWEIF MEHVEQLVRQ HITENARNTA 120
LARLQGLGAS FRAYQQSLED WLENRDNART RSVLYTQYIA LELDFLNAMP LFAINNQQVP 180
LLMVYAQAAN LHLLLLRDAS LFGSEFGLTS QEIQRYYERQ AEKTREYSDY CARWYNTGLN 240
NLRGTNAESW LRYNQFRRDL TLGVLDLVAL FPSYDTRIYP INTSAQLTRE IYTDPIGRTN 300
APSGFASTNW FNNNAPSFSA IEAAIFRPPH LLDFPEQLTI YSASSRWSST QHMNYWVGHR 360
LNFRPIHGTL NTSTHGATNT SINPVTLQFT SRDVYRTESY AGINILLTTP VNGVPWARFN 420
WRNPLNSLRG SLLYTIGYTG VGTQLFDSET ELPPETTERP NYESYSHRLS NIRLIISNTL 480
RAPVYSWTHR SADRTNTIAT NIITQIPAVK GNFLFNGSVI SGPGFTGGDL VRLNNSGNNI 540
YNRGYIEVPI QFISTSTRYR VRVRYASVTP IRLSVNWGNS NIFSSIVPAT ATSLDNLQSR 600
NFGYFESRNA FTSATGNVVG VRNFSENAGV IIDRFEFIPV TATFEAEYDL ERAQE 655

SEQ ID NO: 94 moltype = DNA length = 1968
FEATURE Location/Qualifiers
misc_feature 1..1968
note = encodes Cry1B variant
source 1..1968
mol_type = other DNA
organism = synthetic construct

```
SEQUENCE: 94
atgccctcca accgcaagaa cgagaacgag ataatcaacg ccctgtcgat cccagccgtc  60
tccaaccact ccgcgcagat ggacctctca ctggacgctc gcatcgagga ctcactctgc  120
atcgccgagg gcaacaacat caacccgctc gtcagcgcct cgaccgtgca gactggcatc  180
aacatcgccg gtcgcatact cggcgtcctc ggagtcccat tcgcaggtca gctggcgagc  240
ttctacagct tcatcgtcgg cgagctctgg ccatcaggtc gcgatccctg ggagatcttc  300
atggagcacg tcgagcagct ggtcaggcag cacatcacgg agaacgctcg caacacggct  360
ctcgccagac tccaaggcct cggagccagc ttcagagcct accagcagtc cctcgaggac  420
tggctcgaga accgcgacaa cgcgaggacc cggagcgtcc tctacaccca gtacatcgcg  480
ctggagctcg acttcctgaa cgcgatgcca ctcttcgcca tcaacaacca gcaggtgccg  540
ctcctcatgg tctacgccca agctgccaac ctccacctcc tgctcctcag agacgctagc  600
ctgttcggca gcgagttcgg actcacgtcg caggagatcc agcgctacta cgagcgccag  660
gcggagaaga cccgggagta cagcgactac tgcgcacgct ggtacaacac cggcctgaac  720
aacctgcgcg gcacgaacgc tgagagctgg ctccgctaca accagttccg cagggacctc  780
acactcggag tcctcgacct cgtcgcgctg ttcccgagct acgacacgcg gatctacccg  840
atcaacacga gcgcgcagct cactcgcgag atctacacgg accccatcgg tcgcacgaac  900
gctccatccg gcttcgcctc caccaactgg ttcaacaaca acgcgccgtc gttcagcgcc  960
atcgaagctg caatcttccg cccacctcac ctgctggact tcccagagca gctcaccatc  1020
tacagcgcct ccagccgctg gtccagcacg cagcacatga actactgggt cggccaccgc  1080
ctcaacttca ggcctatcca cggtaccctc aacacctcga cccacggcgc cacgaacacg  1140
tccatcaacc cggtgacgct ccagttcacg agccgggacg tctaccgcac tgagagctac  1200
gctggcatca acatcctgct cacgacgcca gtgaacggcg tcccgtgggc acgcttcaac  1260
tggaggaacc ctctcaactc cctgcgcgga tcgctcctct acaccatcgg ctacaccgga  1320
gtcggtaccc agctcttcga cagcgagacc gagctcccac ctgagaccac cgagaggccc  1380
aactacgaga gctactccca ccgcctgtcg aacatccgcc tcatcatctc caacacgctc  1440
agagctcccg tctactcctg gacgcacagg tcagctgacc ggacgaacac catcgcgacg  1500
aacatcatca cccagatccc ggccgtcaag ggcaacttcc tcttcaacgg ctccgtcatc  1560
tccggaccag gcttcaccgg aggagacctc gtccgcctca acaactccgg caacaacatc  1620
tacaaccggg gctacatcga ggtgccgatc cagttcatct ccacgagcac tcggtaccgc  1680
gtcagagtgc gctacgcgag cgtcactccg atccgcctct ccgtcaactg gggcaactcg  1740
aacatcttca gctccatcgt cccagccacc gcgactagcc tcgacaacct gcagtcccgc  1800
aacttcggct acttcgagag ccgcaacgcc ttcacgagcg cgactggcaa cgtcgtcggc  1860
gtccgcaact tctccgagaa cgccggagtg atcatcgacc gcttcgagtt catccccgtg  1920
accgcgacct tcgaggccga gtacgacctt gagagagctc aggaggcc             1968

SEQ ID NO: 95          moltype = AA  length = 655
FEATURE                Location/Qualifiers
REGION                 1..655
                       note = Cry1B variant
source                 1..655
                       mol_type = protein
                       organism = synthetic construct
SEQUENCE: 95
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITENARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIHGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGNTL  480
RAPVYSWTHR SADRTNTIAT NIITQIPAVK GNFLFNGSVI SGPGFTGGDL VRLNNSGNNI  540
YNRGYIEVPI QFISTSTRYR VRVRYASVTP IRLSVNWGNS NIFSTIVPAT ATSLDNLQSR  600
NFGYFESRNA FTSATGNVVG VRNFSENAGV IIDRFEFIPV TATFEAEYDL ERAQE       655

SEQ ID NO: 96          moltype = DNA  length = 1968
FEATURE                Location/Qualifiers
misc_feature           1..1968
                       note = encodes Cry1B variant
source                 1..1968
                       mol_type = other DNA
                       organism = synthetic construct
SEQUENCE: 96
atgccctcca accgcaagaa cgagaacgag ataatcaacg ccctgtcgat cccagccgtc  60
tccaaccact ccgcgcagat ggacctctca ctggacgctc gcatcgagga ctcactctgc  120
atcgccgagg gcaacaacat caacccgctc gtcagcgcct cgaccgtgca gactggcatc  180
aacatcgccg gtcgcatact cggcgtcctc ggagtcccat tcgcaggtca gctggcgagc  240
ttctacagct tcatcgtcgg cgagctctgg ccatcaggtc gcgatccctg ggagatcttc  300
atggagcacg tcgagcagct ggtcaggcag cacatcacgg agaacgctcg caacacggct  360
ctcgccagac tccaaggcct cggagccagc ttcagagcct accagcagtc cctcgaggac  420
tggctcgaga accgcgacaa cgcgaggacc cggagcgtcc tctacaccca gtacatcgcg  480
ctggagctcg acttcctgaa cgcgatgcca ctcttcgcca tcaacaacca gcaggtgccg  540
ctcctcatgg tctacgccca agctgccaac ctccacctcc tgctcctcag agacgctagc  600
ctgttcggca gcgagttcgg actcacgtcg caggagatcc agcgctacta cgagcgccag  660
gcggagaaga cccgggagta cagcgactac tgcgcacgct ggtacaacac cggcctgaac  720
aacctgcgcg gcacgaacgc tgagagctgg ctccgctaca accagttccg cagggacctc  780
acactcggag tcctcgacct cgtcgcgctg ttcccgagct acgacacgcg gatctacccg  840
atcaacacga gcgcgcagct cactcgcgag atctacacgg accccatcgg tcgcacgaac  900
gctccatccg gcttcgcctc caccaactgg ttcaacaaca acgcgccgtc gttcagcgcc  960
```

-continued

```
atcgaagctg caatcttccg cccacctcac ctgctggact tcccagagca gctcaccatc  1020
tacagcgcct ccagccgctg gtccagcacg cagcacatga actactgggt cggccaccgc  1080
ctcaacttca ggcctatcca cggtaccctc aacacctcga cccacggcgc cacgaacacg  1140
tccatcaacc cggtgacgct ccagttcacg agccgggacg tctaccgcac tgagagctac  1200
gctggcatca acatcctgct cacgacgcca gtgaacggcg tcccgtgggc acgcttcaac  1260
tggaggaacc ctctcaactc cctgcgcgga tcgctcctct acaccatcgg ctacaccgga  1320
gtcggtaccc agctcttcga cagcgagacc gagctcccac ctgagaccac cgagaggccc  1380
aactacgaga gctactccca ccgcctgtcg aacatccgcc tcatcatcgg caacacgctc  1440
agagctcccg tctactcctg gacgcacagg tcagctgacc ggacgaacac catcgcgacg  1500
aacatcatca cccagatccc ggccgtcaag ggcaacttcc tcttcaacgg ctccgtcatc  1560
tccggaccag gcttcaccgg aggagacctc gtccgcctca acaactccgg caacaacatc  1620
tacaaccggg gctacatcga ggtgccgatc cagttcatct ccacgagcac tcggtaccgc  1680
gtcagagtgc gctacgcgag cgtcactccg atccgcctct ccgtcaactg ggcaactcg  1740
aacatcttca gcaccatcgt cccagccacc gcgactagcc tcgacaacct gcagtcccgc  1800
aacttcggct acttcgagag ccgcaacgcc ttcacgagcg cgactggcaa cgtcgtcggc  1860
gtccgcaact tctccgagaa cgccggagtg atcatcgacc gcttcgagtt catccccgtg  1920
accgcgacct tcgaggccga gtacgacctt gagagagctc aggaggcc              1968

SEQ ID NO: 97          moltype = AA  length = 655
FEATURE                Location/Qualifiers
REGION                 1..655
                       note = Cry1B variant
source                 1..655
                       mol_type = protein
                       organism = synthetic construct
SEQUENCE: 97
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ MITLNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGSVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEAEYDL ERAQE       655

SEQ ID NO: 98          moltype = DNA  length = 1968
FEATURE                Location/Qualifiers
misc_feature           1..1968
                       note = encodes Cry1B variant
source                 1..1968
                       mol_type = other DNA
                       organism = synthetic construct
SEQUENCE: 98
atgccctcca accgcaagaa cgagaacgag ataatcaacg ccctgtcgat cccagccgtc  60
tccaaccact ccgcgcagat ggacctctca ctggacgctc gcatcgagga ctcactctgc  120
atcgccgagg gcaacaacat caacccgctc gtcagcgcct cgaccgtgca gactggcatc  180
aacatcgccg gtcgcatact cggcgtcctc ggagtcccat tcgcaggtca gctggcgagc  240
ttctacagct tcatcgtcgg cgagctctgg ccatcaggtc gcgatccctg ggagatcttc  300
atggagcacg tcgagcagct ggtcaggcag atgatcacgc tcaacgctcg caacacggct  360
ctcgccagac tccaaggcct cggagccagc ttcagagcct accagcagtc cctcgaggac  420
tggctcgaga accgcgacaa cgcgaggacc cggagcgtcc tctacaccca gtacatcgcg  480
ctggagctcg acttcctgaa cgcgatgcca ctcttcgcca tcaacaacca gcaggtgccg  540
ctcctcatgg tctacgccca agctgccaac ctccacctcc tgctcctcag agacgctagc  600
ctgttcggca gcgagttcgg actcacgtcg caggagatcc agcgctacta cgagcgccag  660
gcggagaaga cccgggagta cagcgactac tgcgcacgct ggtacaacac cggcctgaac  720
aacctgcgcg gcacgaacgc tgagagctgg ctccgctaca accagttccg cagggacctc  780
acactcggag tcctcgacct cgtcgcgctg ttcccgagct acgacacgcg gatctacccg  840
atcaacacga gcgcgcagct cactcgcgag atctacacgg accccatcgg tcgcacgaac  900
gctccatccg gcttcgcctc caccaactgg ttcaacaaca acgcgccgtc gttcagcgcc  960
atcgaagctg caatcttccg cccacctcac ctgctggact tcccagagca gctcaccatc  1020
tacagcgcct ccagccgctg gtccagcacg cagcacatga actactgggt cggccaccgc  1080
ctcaacttca ggcctatcgg cggtaccctc aacacctcga cccacggcgc cacgaacacg  1140
tccatcaacc cggtgacgct ccagttcacg agccgggacg tctaccgcac tgagagctac  1200
gctggcatca acatcctgct cacgacgcca gtgaacggcg tcccgtgggc acgcttcaac  1260
tggaggaacc ctctcaactc cctgcgcgga tcgctcctct acaccatcgg ctacaccgga  1320
gtcggtaccc agctcttcga cagcgagacc gagctcccac ctgagaccac cgagaggccc  1380
aactacgaga gctactccca ccgcctgtcg aacatccgcc tcatcatcgg cggcacgctc  1440
agagctcccg tctactcctg gacgcacagg tcagctgacc ggacgaacac catcgcgacg  1500
aacatcatca cccagatccc ggccgtcaag ggcaacttcc tcttcaacgg ctccgtcatc  1560
tccggaccag gcttcaccgg aggagacctc gtccgcctca acaactccgg caacaacatc  1620
cagaaccggg gctacatcga ggtgccgatc cagttcatct ccacgagcac tcggtaccgc  1680
gtcagagtgc gctacgcgag cgtcactccg atccgcctct ccgtcaactg ggcaactcg  1740
aacatcttca gctccatcgt cccagccacc gcgactagcc tcgacaacct gcagtcccgc  1800
aacttcggct acttcgagag ccgcaacgcc ttcacgagcg cgactggcaa cgtcgtcggc  1860
gtccgcaact tctccgagaa cgccggagtg atcatcgacc gcttcgagtt catccccgtg  1920
accgcgacct tcgaggccga gtacgacctt gagagagctc aggaggcc              1968
```

```
SEQ ID NO: 99          moltype = AA  length = 655
FEATURE                Location/Qualifiers
REGION                 1..655
                       note = Cry1B variant
source                 1..655
                       mol_type = protein
                       organism = synthetic construct
SEQUENCE: 99
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ MITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGSVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEAEYDL ERAQE       655

SEQ ID NO: 100         moltype = DNA  length = 1968
FEATURE                Location/Qualifiers
misc_feature           1..1968
                       note = encodes Cry1B variant
source                 1..1968
                       mol_type = other DNA
                       organism = synthetic construct
SEQUENCE: 100
atgccctcca accgcaagaa cgagaacgag ataatcaacg ccctgtcgat cccagccgtc  60
tccaaccact ccgcgcagat ggacctctca ctggacgctc gcatcgagga ctcactctgc  120
atcgccgagg gcaacaacat caacccgctc gtcagcgcct cgaccgtgca gactggcatc  180
aacatcgccg gtcgcatact cggcgtcctc ggagtcccat tcgcaggtca gctggcgagc  240
ttctacagct tcatcgtcgg cgagctctgg ccatcaggtc gcgatccctg ggagatcttc  300
atggagcacg tcgagcagct ggtcaggcag atgatcacga tgaacgctcg caacacggct  360
ctcgccagac tccaaggcct cggagccagc ttcagagcct accagcagtc cctcgaggac  420
tggctcgaga accgcgacaa cgcgaggacc cggagcgtcc tctacaccca gtacatcgcg  480
ctggagctcg acttcctgaa cgcgatgcca ctcttcgcca tcaacaacca gcaggtgccg  540
ctcctcatgg tctacgccca agctgccaac ctccacctcc tgctcctcag agacgctagc  600
ctgttcggca gcgagttcgg actcacgtcg caggagatcc agcgctacta cgagcgccag  660
gcggagaaga cccgggagta cagcgactac tgcgcacgct ggtacaacac cggcctgaac  720
aacctgcgcg gcacgaacgc tgagagctgg ctccgctaca accagttccg cagggacctc  780
acactcggag tcctcgacct cgtcgcgctg ttcccgagct acgacacgcg gatctacccg  840
atcaacacga gcgcgcagct cactcgcgag atctacacgg accccatcgg tcgcacgaac  900
gctccatccg gcttcgcctc caccaactgg ttcaacaaca acgcgccgtc gttcagcgcc  960
atcgaagctg caatcttccg cccacctcac ctgctggact tcccagagca gctcaccatc  1020
tacagcgcct ccagccgctg gtccagcacg cagcacatga actactgggt cggccaccgc  1080
ctcaacttca ggcctatcgg cggtaccctc aacacctcga cccacggcgc cacgaacacg  1140
tccatcaacc cggtgacgct ccagttcacg agccgggacg tctaccgcac tgagagctac  1200
gctggcatca acatcctgct cacgacgcca gtgaacggcg tcccgtgggc acgcttcaac  1260
tggaggaacc ctctcaactc cctgcgcgga tcgctcctct acaccatcgg ctacaccgga  1320
gtcggtaccc agctcttcga cagcgagacc gagctcccac ctgagaccac cgagaggccc  1380
aactacgaga gctactccca ccgcctgtcg aacatccgcc tcatcatcgg cggcacgctc  1440
agagctcccg tctactcctg gacgcacagg tcagctgacc ggacgaacac catcgcgacg  1500
aacatcatca cccagatccc ggccgtcaag ggcaacttcc tcttcaacgg ctccgtcatc  1560
tccggaccag gcttcaccgg aggagacctc gtccgcctca acaactccgg caacaacatc  1620
cagaaccggg gctacatcga ggtgccgatc cagttcatct ccacgagcac tcggtaccgc  1680
gtcagagtgc gctacgcgag cgtcactccg atccgcctct ccgtcaactg gggcaactcg  1740
aacatcttca gctccatcgt cccagccacc gcgactagcc tcgacaacct gcagtcccgc  1800
aacttcggct acttcgagag ccgcaacgcc ttcacgagcg cgactggcaa cgtcgtcggc  1860
gtccgcaact tctccgagaa cgccggagtg atcatcgacc gcttcgagtt catccccgtg  1920
accgcgacct tcgaggccga gtacgacctt gagagagctc aggaggcc               1968

SEQ ID NO: 101         moltype = AA  length = 655
FEATURE                Location/Qualifiers
REGION                 1..655
                       note = Cry1B variant
source                 1..655
                       mol_type = protein
                       organism = synthetic construct
SEQUENCE: 101
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ MITHNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
```

-continued

```
RAPVYSWTHR SADRTNTIAT NIITQIPAVK GNFLFNGSVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEAEYDL ERAQE       655

SEQ ID NO: 102         moltype = DNA  length = 1968
FEATURE                Location/Qualifiers
misc_feature           1..1968
                       note = encodes Cry1B variant
source                 1..1968
                       mol_type = other DNA
                       organism = synthetic construct
SEQUENCE: 102
atgccctcca accgcaagaa cgagaacgag ataatcaacg ccctgtcgat cccagccgtc  60
tccaaccact ccgcgcagat ggacctctca ctggacgctc gcatcgagga ctcactctgc  120
atcgccgagg gcaacaacat caacccgctc gtcagcgcct cgaccgtgca gactggcatc  180
aacatcgccg gtcgcatact cggcgtcctc ggagtcccat tcgcaggtca gctggcgagc  240
ttctacagct tcatcgtcgg cgagctctgg ccatcaggtc gcgatccctg ggagatcttc  300
atggagcacg tcgagcagct ggtcaggcag atgatcacgc acaacgctcg caacacggct  360
ctcgccagac tccaaggcct cggagccagc ttcagagcct accagcagtc cctcgaggac  420
tggctcgaga accgcgacaa cgcgaggacc cggagcgtcc tctacaccca gtacatcgcg  480
ctggagctcg acttcctgaa cgcgatgcca ctcttcgcca tcaacaacca gcaggtgccg  540
ctcctcatgg tctacgccca agctgccaac ctccacctcc tgctcctcag agacgctagc  600
ctgttcggca gcgagttcgg actcacgtcg caggagatcc agcgctacta cgagcgccag  660
gcggagaaga cccgggagta cagcgactac tgcgcacgct ggtacaacac cggcctgaac  720
aacctgcgcg gcacgaacgc tgagagctgg ctccgctaca accagttccg cagggacctc  780
acactcggag tcctcgacct cgtcgcgctg ttcccgagct acgacacgcg gatctacccg  840
atcaacacga gcgcgcagct cactcgcgag atctacacgg accccatcgg tcgcacgaac  900
gctccatccg gcttcgcctc caccaactgg ttcaacaaca acgcgccgtc gttcagcgcc  960
atcgaagctg caatcttccg cccacctcac ctgctggact tcccagagca gctcaccatc  1020
tacagcgcct ccagccgctg gtccagcacg cagcacatga actactgggt cggccaccgc  1080
ctcaacttca ggcctatcgg cggtaccctc aacacctcga cccacggcgc cacgaacacg  1140
tccatcaacc cggtgacgct ccagttcacg agccgggacg tctaccgcac tgagagctac  1200
gctggcatca acatcctgct cacgacgcca gtgaacggcg tcccgtgggc acgcttcaac  1260
tggaggaacc ctctcaactc cctgcgcgga tcgctcctct acaccatcgg ctacaccgga  1320
gtcggtaccc agctcttcga cagcgagacc gagctcccac ctgagaccac cgagaggccc  1380
aactacgaga gctactccca ccgcctgtcg aacatccgcc tcatcatcgg cggcacgctc  1440
agagctcccg tctactcctg gacgcacagg tcagctgacc ggacgaacac catcgcgacg  1500
aacatcatca cccagatccc ggccgtcaag ggcaacttcc tcttcaacgg ctccgtcatc  1560
tccggaccag gcttcaccgg aggagacctc gtccgcctca acaactccgg caacaacatc  1620
cagaaccggg gctacatcga ggtgccgatc cagttcatct ccacgagcac tcggtaccgc  1680
gtcagagtgc gctacgcgag cgtcactccg atccgcctct ccgtcaactg gggcaactcg  1740
aacatcttca gctccatcgt cccagccacc gcgactagcc tcgacaacct gcagtcccgc  1800
aacttcggct acttcgagag ccgcaacgcc ttcacgagcg cgactggcaa cgtcgtcggc  1860
gtccgcaact tctccgagaa cgccggagtg atcatcgacc gcttcgagtt catccccgtg  1920
accgcgacct tcgaggccga gtacgacctt gagagagctc aggaggcc              1968

SEQ ID NO: 103         moltype = AA  length = 655
FEATURE                Location/Qualifiers
REGION                 1..655
                       note = Cry1B variant
source                 1..655
                       mol_type = protein
                       organism = synthetic construct
SEQUENCE: 103
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGSVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEAEYDL ERAQE       655

SEQ ID NO: 104         moltype = DNA  length = 1968
FEATURE                Location/Qualifiers
misc_feature           1..1968
                       note = encodes Cry1B variant
source                 1..1968
                       mol_type = other DNA
                       organism = synthetic construct
SEQUENCE: 104
atgccctcca accgcaagaa cgagaacgag ataatcaacg ccctgtcgat cccagccgtc  60
tccaaccact ccgcgcagat ggacctctca ctggacgctc gcatcgagga ctcactctgc  120
atcgccgagg gcaacaacat caacccgctc gtcagcgcct cgaccgtgca gactggcatc  180
aacatcgccg gtcgcatact cggcgtcctc ggagtcccat tcgcaggtca gctggcgagc  240
ttctacagct tcatcgtcgg cgagctctgg ccatcaggtc gcgatccctg ggagatcttc  300
```

```
atggagcacg tcgagcagct ggtcaggcag cacatcacga tgaacgctcg caacacggct  360
ctcgccagac tccaaggcct cggagccagc ttcagagcct accagcagtc cctcgaggac  420
tggctcgaga accgcgacaa cgcgaggacc cggagcgtcc tctacaccca gtacatcgcg  480
ctggagctcg acttcctgaa cgcgatgcca ctcttcgcca tcaacaacca gcaggtgccg  540
ctcctcatgg tctacgccca agctgccaac ctccacctcc tgctcctcag agacgctagc  600
ctgttcggca gcgagttcgg actcacgtcg caggagatcc agcgctacta cgagcgccag  660
gcggagaaga cccgggagta cagcgactac tgcgcacgct ggtacaacac cggcctgaac  720
aacctgcgcg gcacgaacgc tgagagctgg ctccgctaca accagttccg cagggacctc  780
acactcggag tcctcgacct cgtcgcgctg ttcccgagct acgacacgcg gatctacccg  840
atcaacacga gcgcgcagct cactcgcgag atctacacgg accccatcgg tcgcacgaac  900
gctccatccg gcttcgcctc caccaactgg ttcaacaaca acgcgccgtc gttcagcgcc  960
atcgaagctg caatcttccg cccacctcac ctgctggact tcccagagca gctcaccatc  1020
tacagcgcct ccagccgctg gtccagcacg cagcacatga actactgggt cggccaccgc  1080
ctcaacttca ggcctatcgg cggtaccctc aacacctcga cccacggcgc cacgaacacg  1140
tccatcaacc cggtgacgct ccagttcacg agccgggacg tctaccgcac tgagagctac  1200
gctggcatca acatcctgct cacgacgcca gtgaacggcg tcccgtgggc acgcttcaac  1260
tggaggaacc ctctcaactc cctgcgcgga tcgctcctct acaccatcgg ctacaccgga  1320
gtcggtaccc agctcttcga cagcgagacc gagctcccac ctgagaccac cgagaggccc  1380
aactacgaga gctactccca ccgcctgtcg aacatccgcc tcatcatcgg cggcacgctc  1440
agagctcccg tctactcctg gacgcacagg tcagctgacc ggacgaacac catcgcgacg  1500
aacatcatca cccagatccc ggccgtcaag ggcaacttcc tcttcaacgg ctccgtcatc  1560
tccggaccag gcttcaccgg aggagacctc gtccgcctca acaactccgg caacaacatc  1620
cagaaccggg gctacatcga ggtgccgatc cagttcatct ccacgagcac tcggtaccgc  1680
gtcagagtgc gctacgcgag cgtcactccg atccgcctct ccgtcaactg gggcaactcg  1740
aacatcttca gctccatcgt cccagccacc gcgactagcc tcgacaacct gcagtcccgc  1800
aacttcggct acttcgagag ccgcaacgcc ttcacgagcg cgactggcaa cgtcgtcggc  1860
gtccgcaact tctccgagaa cgccggagtg atcatcgacc gcttcgagtt catccccgtg  1920
accgcgacct tcgaggccga gtacgacctt gagagagctc aggaggcc              1968
```

```
SEQ ID NO: 105          moltype = AA  length = 655
FEATURE                 Location/Qualifiers
REGION                  1..655
                        note = Cry1B variant
source                  1..655
                        mol_type = protein
                        organism = synthetic construct
SEQUENCE: 105
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ MITHNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPINGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGNTL  480
RAPVYSWTHR SADRTNTIAT NIITQIPAVK GNFLFNGSVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEAEYDL ERAQE        655
```

```
SEQ ID NO: 106          moltype = DNA  length = 1968
FEATURE                 Location/Qualifiers
misc_feature            1..1968
                        note = encodes Cry1B variant
source                  1..1968
                        mol_type = other DNA
                        organism = synthetic construct
SEQUENCE: 106
atgccctcca accgcaagaa cgagaacgag ataatcaacg ccctgtcgat cccagccgtc  60
tccaaccact ccgcgcagat ggacctctca ctggacgctc gcatcgagga ctcactctgc  120
atcgccgagg gcaacaacat caacccgctc gtcagcgcct cgaccgtgca gactggcatc  180
aacatcgccg gtcgcatact cggcgtcctc ggagtcccat tcgcaggtca gctggcgagc  240
ttctacagct tcatcgtcgg cgagctctgg ccatcaggtc gcgatccctg ggagatcttc  300
atggagcacg tcgagcagct ggtcaggcag atgatcacgc acaacgctcg caacacggct  360
ctcgccagac tccaaggcct cggagccagc ttcagagcct accagcagtc cctcgaggac  420
tggctcgaga accgcgacaa cgcgaggacc cggagcgtcc tctacaccca gtacatcgcg  480
ctggagctcg acttcctgaa cgcgatgcca ctcttcgcca tcaacaacca gcaggtgccg  540
ctcctcatgg tctacgccca agctgccaac ctccacctcc tgctcctcag agacgctagc  600
ctgttcggca gcgagttcgg actcacgtcg caggagatcc agcgctacta cgagcgccag  660
gcggagaaga cccgggagta cagcgactac tgcgcacgct ggtacaacac cggcctgaac  720
aacctgcgcg gcacgaacgc tgagagctgg ctccgctaca accagttccg cagggacctc  780
acactcggag tcctcgacct cgtcgcgctg ttcccgagct acgacacgcg gatctacccg  840
atcaacacga gcgcgcagct cactcgcgag atctacacgg accccatcgg tcgcacgaac  900
gctccatccg gcttcgcctc caccaactgg ttcaacaaca acgcgccgtc gttcagcgcc  960
atcgaagctg caatcttccg cccacctcac ctgctggact tcccagagca gctcaccatc  1020
tacagcgcct ccagccgctg gtccagcacg cagcacatga actactgggt cggccaccgc  1080
ctcaacttca ggcctatcaa cggtaccctc aacacctcga cccacggcgc cacgaacacg  1140
tccatcaacc cggtgacgct ccagttcacg agccgggacg tctaccgcac tgagagctac  1200
gctggcatca acatcctgct cacgacgcca gtgaacggcg tcccgtgggc acgcttcaac  1260
tggaggaacc ctctcaactc cctgcgcgga tcgctcctct acaccatcgg ctacaccgga  1320
```

-continued

```
gtcggtaccc agctcttcga cagcgagacc gagctcccac ctgagaccac cgagaggccc  1380
aactacgaga gctactccca ccgcctgtcg aacatccgcc tcatcatcgg caacacgctc  1440
agagctcccg tctactcctg gacgcacagg tcagctgacc ggacgaacac catcgcgacg  1500
aacatcatca cccagatccc ggccgtcaag ggcaacttcc tcttcaacgg ctccgtcatc  1560
tccggaccag gcttcaccgg aggagacctc gtccgcctca acaactccgg caacaacatc  1620
cagaaccggg gctacatcga ggtgccgatc cagttcatct ccacgagcac tcggtaccgc  1680
gtcagagtgc gctacgcgag cgtcactccg atccgcctct ccgtcaactg ggcaactcg  1740
aacatcttca gctccatcgt cccagccacc gcgactagcc tcgacaacct gcagtcccgc  1800
aacttcggct acttcgagag ccgcaacgcc ttcacgagcg cgactggcaa cgtcgtcggc  1860
gtccgcaact tctccgagaa cgccggagtg atcatcgacc gcttcgagtt catccccgtg  1920
accgcgacct tcgaggccga gtacgacctt gagagagctc aggaggcc             1968

SEQ ID NO: 107          moltype = AA  length = 655
FEATURE                 Location/Qualifiers
REGION                  1..655
                        note = Cry1B variant
source                  1..655
                        mol_type = protein
                        organism = synthetic construct
SEQUENCE: 107
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPINGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGNTL  480
RAPVYSWTHR SADRTNTIAT NIITQIPAVK GNFLFNGSVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEAEYDL ERAQE       655

SEQ ID NO: 108          moltype = DNA  length = 1968
FEATURE                 Location/Qualifiers
misc_feature            1..1968
                        note = encodes Cry1B variant
source                  1..1968
                        mol_type = other DNA
                        organism = synthetic construct
SEQUENCE: 108
atgccctcca accgcaagaa cgagaacgag ataatcaacg ccctgtcgat cccagccgtc  60
tccaaccact ccgcgcagat ggacctctca ctggacgctc gcatcgagga ctcactctgc  120
atcgccgagg gcaacaacat caacccgctc gtcagcgcct cgaccgtgca gactggcatc  180
aacatcgccg gtcgcatact cggcgtcctc ggagtcccat tcgcaggtca gctggcgagc  240
ttctacagct tcatcgtcgg cgagctctgg ccatcaggtc gcgatccctg ggagatcttc  300
atggagcacg tcgagcagct ggtcaggcag cacatcacga tgaacgctcg caacacggct  360
ctcgccagac tccaaggcct cggagccagc ttcagagcct accagcagtc cctcgaggac  420
tggctcgaga accgcgacaa cgcgaggacc cggagcgtcc tctacaccca gtacatcgcg  480
ctggagctcg acttcctgaa cgcgatgcca ctcttcgcca tcaacaacca gcaggtgccg  540
ctcctcatgg tctacgccca agctgccaac ctccacctcc tgctcctcag agacgctagc  600
ctgttcggca gcgagttcgg actcacgtcg caggagatcc agcgctacta cgagcgccag  660
gcggagaaga cccgggagta cagcgactac tgcgcacgct ggtacaacac cggcctgaac  720
aacctgcgcg gcacgaacgc tgagagctgg ctccgctaca accagttccg cagggacctc  780
acactcggag tcctcgacct cgtcgcgctg ttcccgagct acgacacgcg gatctacccg  840
atcaacacga gcgcgcagct cactcgcgag atctacacgg accccatcgg tcgcacgaac  900
gctccatccg gcttcgcctc caccaactgg ttcaacaaca acgcgccgtc gttcagcgcc  960
atcgaagctg caatcttccg cccacctcac ctgctggact tcccagagca gctcaccatc  1020
tacagcgcct ccagccgctg gtccagcacg cagcacatga actactgggt cggccaccgc  1080
ctcaacttca ggcctatcaa cggtacctc aacacctcga cccacggcgc cacgaacacg  1140
tccatcaacc cggtgacgct ccagttcacg agccgggacg tctaccgcac tgagagctac  1200
gctggcatca acatcctgct cacgacgcca gtgaacggcg tcccgtgggc acgcttcaac  1260
tggaggaacc ctctcaactc cctgcgcgga tcgctcctct acaccatcgg ctacaccgga  1320
gtcggtaccc agctcttcga cagcgagacc gagctcccac ctgagaccac cgagaggccc  1380
aactacgaga gctactccca ccgcctgtcg aacatccgcc tcatcatcgg caacacgctc  1440
agagctcccg tctactcctg gacgcacagg tcagctgacc ggacgaacac catcgcgacg  1500
aacatcatca cccagatccc ggccgtcaag ggcaacttcc tcttcaacgg ctccgtcatc  1560
tccggaccag gcttcaccgg aggagacctc gtccgcctca acaactccgg caacaacatc  1620
cagaaccggg gctacatcga ggtgccgatc cagttcatct ccacgagcac tcggtaccgc  1680
gtcagagtgc gctacgcgag cgtcactccg atccgcctct ccgtcaactg ggcaactcg  1740
aacatcttca gctccatcgt cccagccacc gcgactagcc tcgacaacct gcagtcccgc  1800
aacttcggct acttcgagag ccgcaacgcc ttcacgagcg cgactggcaa cgtcgtcggc  1860
gtccgcaact tctccgagaa cgccggagtg atcatcgacc gcttcgagtt catccccgtg  1920
accgcgacct tcgaggccga gtacgacctt gagagagctc aggaggcc             1968

SEQ ID NO: 109          moltype = AA  length = 655
FEATURE                 Location/Qualifiers
source                  1..655
                        mol_type = protein
                        organism = Bacillus thuringiensis
```

-continued

```
SEQUENCE: 109
MPSNRKNENE IINALSIPAV SNHSAQMDLS PDARIEDSLC IAEGNNINPL VSASTVQTGI  60
NIAGRILGVL GVPFAGQLAS FYSFIVGELW PSGRDPWEIF LEHVEQLVRQ QITENARNTA  120
LARLQGLGAS FRAYQQSLED WLENRDDART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAVIRPPH LLDFPEQLTI FSVLSRWSNT QYMNYWVGHR  360
LESRTIRGSL STSTHGNTNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLISGNTL  480
RAPVYSWTHR SADRTNTIAT NIITQIPAVK GNFLFNGSVI SGPGFTGGDL VRLNNSGNNI  540
QNRGYLEVPI QFISTSTRYR VRVRYASVTP IQLSVNWGNS NIFSSIVPAT ATSLDNLQSR  600
DFGYFESTNA FTSATGNVVG VRNFSENAGV IIDRFEFIPV TATFEAEYDL ERAQE       655

SEQ ID NO: 110         moltype = DNA  length = 1965
FEATURE                Location/Qualifiers
source                 1..1965
                       mol_type = other DNA
                       organism = Bacillus thuringiensis
SEQUENCE: 110
atgccttcaa ataggaaaaa tgagaatgaa attataaatg ctttatcgat tccagctgta  60
tcgaatcatt ccgcacaaat ggatctatca ccagatgctc gtattgagga ttctttgtgt  120
atagccgagg ggaataatat caatccactt gttagcgcat caacagtcca aacgggtatt  180
aacattgctg gtagaatact aggcgtatta ggcgtaccgt ttgctggaca actagctagt  240
ttttatagtt ttattgtcgg tgaattatgg cctagcggca gagatccgtg ggaaatcttt  300
ctagaacatg ttgaacaact tgtaagacaa caaataacag aaaatgctag gaatacggca  360
cttgctcgat tacaaggttt aggagcttcc tttagagcct atcaacaatc acttgaagac  420
tggctagaaa accgtgatga tgcaagaacg agaagtgttc tttataccca atatatagcc  480
ttagagcttg attttcttaa tgcgatgccg cttttcgcaa taaacaatca acaggttcca  540
ttattgatgg tatatgctca agctgcaaat ttacatctat tattattgag agatgcctct  600
ctttttggta gtgaatttgg gcttacatcg caggaaattc aacgttatta tgagcgccaa  660
gcggaaaaaa cgagagaata ttctgattat tgcgcaagat ggtataatac gggtttaaat  720
aatttgagag ggacaaatgc tgaaagttgg ttgcgatata atcaattccg tagagactta  780
acgctaggag tattagatct agtggcacta ttcccaagct atgacacgcg tatttatcca  840
ataaatacca gtgctcaatt aacaagagaa atttatacag atccaattgg gagaacaaat  900
gcacccttcag gatttgcaag tacgaattgg tttaataata atgcaccatc gttttctgcc  960
atagaggctg ccgttattag gcctccgcat ctacttgatt ttccagaaca gcttacaatt  1020
ttcagcgtat taagtcgatg gagtaatact caatatatga attactgggt gggacataga  1080
cttgaatcgc gaacaataag gggtcatta agtacctcga cacacggaaa taccaatact  1140
tctattaatc ctgtaacatt acagttcaca tctcgtgacg tttatagaac agaatcatat  1200
gcagggataa atatacttct aactactcct gtgaatggag taccttgggc tagatttaat  1260
tggagaaatc ccctgaattc tcttagaggt agccttctct atactatagg gtatactgga  1320
gtggggacac aactatttga ttcagaaact gaattaccac cagaaacaac agaacgacca  1380
aattatgaat cttacagtca tagattatct aatataagac taatatcagg aaacactttg  1440
agagcaccag tatattcttg gacgcaccgt agtgcagatc gtacgaatac gattgctaca  1500
aatattatta ctcaaattcc tgcagtgaag ggaaactttc tttttaatgg ttctgtaatt  1560
tcaggaccag gatttactgg tggggactta gttagattaa ataatagtgg aaataatatt  1620
caaaatagag gctaccttga ggttccgatt caattcatct ccacatctac cagatatcga  1680
gttcgtgtac gttatgcttc tgtaaccccg attcaactca gtgttaattg gggtaattca  1740
aacattttttt ccagcatagt accagctaca gctacgtcat tagataatct acaatcaagg  1800
gattttggtt attttgaaag taccaatgca tttacatctg caacaggtaa tgtagtaggt  1860
gttagaaatt ttagtgagaa tgcaggagtg ataatagaca gatttgaatt tatcccagtt  1920
actgcaacct tcgaagcaga atatgattta gaaagagcgc aagag                 1965

SEQ ID NO: 111         moltype = AA  length = 650
FEATURE                Location/Qualifiers
source                 1..650
                       mol_type = protein
                       organism = Bacillus thuringiensis
SEQUENCE: 111
MPSNRKNENE IINALSIPAV SNHSAQMDLS PDARIEDSLC VAEGNNIDPF VSASTVQTGI  60
SIAGRILGVL GVPFAGQLAS FYSFLVGELW PSGRDPWEIF MEHVEQIVRQ QITDSVRDTA  120
IARLEGLGRG YRSYQQALET WLDNRNDARS RSIIRERYIA LELDITTAIP LFSIRNQEVP  180
LLMVYAQAAN LHLLLLRDAS LFGSEWGMSS ADVNQYYQEQ IRYTEEYSNH CVQWYNTGLN  240
RLRGTTAESW VRYNQFRRDL TLGVLDLVAL FPSYDTRTYP IPTTAQLTRE VYTDPNGVVA  300
GPNNSWFRNG ASFSAIENAI IRQPHLYDFL TNLTIYTRRS QVGTTIMNLW AGHRITFNRI  360
QGGSTSEMVY GAITNPVSVS DIPFVNRDVY RTVSLAGGLG SLSGIRYGLT RVDFDMIFRN  420
HPDIVTGLFY HPGHAGIATQ VKDSETELPP ETTEQPNYRA FSHLLSHISM GPTTQDVPPV  480
YSWTHQSADR TNTINSDRIT QIPLVKAHTL QSGTTVVKGP GFTGGDILRR TSGGPFAFSN  540
VNLDFNLSQR YRARIRYAST TNLRIYVTVA GERIFAGQFD KTMDAGAPLT FQSFSYATIN  600
TAFTFPERSS SLTVGADTFS SGNEVYVDRF ELIPVTATFE AESDLERARK            650

SEQ ID NO: 112         moltype = DNA  length = 1950
FEATURE                Location/Qualifiers
source                 1..1950
                       mol_type = other DNA
                       organism = Bacillus thuringiensis
SEQUENCE: 112
atgccttcaa ataggaaaaa tgagaatgaa attataaatg ctttatcgat tccagctgta  60
tcgaatcatt ccgcacaaat ggatctatca ccagatgctc gcattgagga tagcttgtgt  120
```

-continued

```
gtagccgagg ggaacaatat tgatccattt gttagcgcat caacagtcca aacaggtatt  180
agtatagctg gtagaatatt aggcgtatta ggggtgccgt ttgccggaca actagctagt  240
ttttatagtt ttcttgttgg ggaattatgg cctagcggca gagatccatg ggaaattttt  300
atggaacatg tcgaacaaat tgtaagacaa caaataacgg acagtgttag ggataccgct  360
attgctcgtt tagaaggtct aggaagaggg tatagatctt accagcaggc tcttgaaact  420
tggttagata accgaaatga tgcaagatca agaagcatta ttcgtgagag atatattgct  480
ttagaacttg acattactac tgctataccg cttttcagca tacgaaatca agaggttcca  540
ttattaatgg tatatgctca agctgcaaat ttacacctat tattattgag agacgcatcc  600
ctttttggta gtgaatgggg gatgtcatct gccgatgtta accaatatta ccaagaacaa  660
atcagatata cagaggaata ttctaaccat tgcgtacaat ggtataatac agggctaaat  720
agattaagag ggacaactgc cgaaagttgg gtacggtata atcaattccg tagagaccta  780
acattaggtg tattagattt agtggcacta ttcccaagct atgacactcg gacttatccc  840
attccaacta ccgcccaact tacaagagaa gtgtatacag atccaaacgg tgttgtagca  900
ggacccaata atagttggtt tagaaatgga gcttcgtttt ccgctataga aaacgcaatt  960
attcgacaac ctcacctata tgattttcta acgaacctta caatttacac gagaagaagt  1020
caagtaggca ctacaattat gaatttgtgg gcagggcata gaatcacgtt taatagaata  1080
caaggtggtt ctactagtga aatggtgtat ggggctatta ctaacccagt tagtgttagt  1140
gacataccat ttgtcaatcg ggatgtttac cgaactgtat cattagctgg tgggcttggc  1200
tctctgagtg gaatacgtta tggtttaact agagttgatt ttgatatgat atttcgtaac  1260
catcctgata tagtaactgg attattttat catccgggac acgcgggcat tgcaacccaa  1320
gtaaaagatt cagaaacaga attaccacct gaaacgacag aacagccaaa ttatagagca  1380
tttagtcatc tactaagtca tatttcaatg ggtccaacga ctcaagacgt acctccagta  1440
tattcttgga cacaccagag tgcagatcgt acgaatacaa tcaattcgga taggataaca  1500
caaataccat tggtaaaggc gcataccctc caatcgggta ccactgtagt aaaagggcca  1560
gggtttacag gaggggatat cctccgtcga acaagtggag gaccatttgc ttttagtaat  1620
gttaatctag attttaactt gtcacaaagg tatcgtgcta gaattcgtta tgcctctact  1680
actaacctaa gaatttacgt aacggttgca ggtgaacgaa tttttgctgg tcaatttgac  1740
aaaactatgg atgctggtgc cccattaaca ttccaatctt ttagttacgc aactattaat  1800
acagctttta cattcccaga aagatcgagc agcttgactg taggtgccga tacgtttagt  1860
tcaggtaatg aagtttatgt agatagattt gaattaatcc cagttactgc aaccttcgag  1920
gcagaatctg atttagaaag agcgcggaag                                   1950
```

```
SEQ ID NO: 113         moltype = AA  length = 655
FEATURE                Location/Qualifiers
REGION                 1..655
                       note = Cry1B variant
source                 1..655
                       mol_type = protein
                       organism = synthetic construct
SEQUENCE: 113
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LYFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEAEYDL ERAQE       655
```

```
SEQ ID NO: 114         moltype = AA  length = 655
FEATURE                Location/Qualifiers
REGION                 1..655
                       note = Cry1B variant
source                 1..655
                       mol_type = protein
                       organism = synthetic construct
SEQUENCE: 114
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFRSTSTRYR VRVRYASVTP IRLSVNWGNS NIFSSIVPAT ATSLDNLQSR  600
NFGYFESRNA FTSATGNVVG VRNFSENAGV IIDRFEFIPV TATFEAEYDL ERAQE       655
```

```
SEQ ID NO: 115         moltype = AA  length = 655
FEATURE                Location/Qualifiers
REGION                 1..655
                       note = Cry1B variant
source                 1..655
                       mol_type = protein
                       organism = synthetic construct
```

```
SEQUENCE: 115
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFLAEYDL ERAQE       655

SEQ ID NO: 116         moltype = AA  length = 655
FEATURE                Location/Qualifiers
REGION                 1..655
                       note = Cry1B variant
source                 1..655
                       mol_type = protein
                       organism = synthetic construct
SEQUENCE: 116
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFTAEYDL ERAQE       655

SEQ ID NO: 117         moltype = AA  length = 655
FEATURE                Location/Qualifiers
REGION                 1..655
                       note = Cry1B variant
source                 1..655
                       mol_type = protein
                       organism = synthetic construct
SEQUENCE: 117
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEHEYDL ERAQE       655

SEQ ID NO: 118         moltype = AA  length = 655
FEATURE                Location/Qualifiers
REGION                 1..655
                       note = Cry1B variant
source                 1..655
                       mol_type = protein
                       organism = synthetic construct
SEQUENCE: 118
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LYFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLSNLQSR  600
NFGYFHSRNA FTSATGNVVG VRNFSENAGV IIDRFEFIPV TATFEAEYDL ERAQE       655

SEQ ID NO: 119         moltype = AA  length = 655
FEATURE                Location/Qualifiers
REGION                 1..655
                       note = Cry1B variant
source                 1..655
                       mol_type = protein
```

```
                         organism = synthetic construct
SEQUENCE: 119
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LYFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLSNLQSR  600
NFGYFQSRNA FTSATGNVVG VRNFSENAGV IIDRFEFIPV TATFEAEYDL ERAQE       655

SEQ ID NO: 120           moltype = AA  length = 655
FEATURE                  Location/Qualifiers
REGION                   1..655
                         note = Cry1B variant
source                   1..655
                         mol_type = protein
                         organism = synthetic construct
SEQUENCE: 120
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LYFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLSTLQSR  600
NFGYFHSRNA FTSATGNVVG VRNFSENAGV IIDRFEFIPV TATFEAEYDL ERAQE       655

SEQ ID NO: 121           moltype = AA  length = 655
FEATURE                  Location/Qualifiers
REGION                   1..655
                         note = Cry1B variant
source                   1..655
                         mol_type = protein
                         organism = synthetic construct
SEQUENCE: 121
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LYFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLSVLQSR  600
NFGYFESRNA FTSATGNVVG VRNFSENAGV IIDRFEFIPV TATFEAEYDL ERAQE       655

SEQ ID NO: 122           moltype = AA  length = 655
FEATURE                  Location/Qualifiers
REGION                   1..655
                         note = Cry1B variant
source                   1..655
                         mol_type = protein
                         organism = synthetic construct
SEQUENCE: 122
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LYFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLSVLQSR  600
NFGYFQSRNA FTSATGNVVG VRNFSENAGV IIDRFEFIPV TATFEAEYDL ERAQE       655

SEQ ID NO: 123           moltype = AA  length = 655
FEATURE                  Location/Qualifiers
REGION                   1..655
                         note = Cry1B variant
source                   1..655
```

```
                         mol_type = protein
                         organism = synthetic construct
SEQUENCE: 123
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LYFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDTLQSR  600
NFGYFQSRNA FTSATGNVVG VRNFSENAGV IIDRFEFIPV TATFEAEYDL ERAQE       655

SEQ ID NO: 124           moltype = AA  length = 655
FEATURE                  Location/Qualifiers
REGION                   1..655
                         note = Cry1B variant
source                   1..655
                         mol_type = protein
                         organism = synthetic construct
SEQUENCE: 124
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LYFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDVLQSR  600
NFGYFHSRNA FTSATGNVVG VRNFSENAGV IIDRFEFIPV TATFEAEYDL ERAQE       655

SEQ ID NO: 125           moltype = AA  length = 655
FEATURE                  Location/Qualifiers
REGION                   1..655
                         note = Cry1B variant
source                   1..655
                         mol_type = protein
                         organism = synthetic construct
SEQUENCE: 125
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFRSTSTRYR VRVRYASVTP IRLSVNWGNS NIFSSIVPAT ATSLDTLQSR  600
NFGYFHSRNA FTSATGNVVG VRNFSENAGV IIDRFEFIPV TATFEAEYDL ERAQE       655

SEQ ID NO: 126           moltype = AA  length = 655
FEATURE                  Location/Qualifiers
REGION                   1..655
                         note = Cry1B variant
source                   1..655
                         mol_type = protein
                         organism = synthetic construct
SEQUENCE: 126
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFRSTSTRYR VRVRYASVTP IRLSVNWGNS NIFSSIVPAT ATSLDVLQSR  600
NFGYFHSRNA FTSATGNVVG VRNFSENAGV IIDRFEFIPV TATFEAEYDL ERAQE       655

SEQ ID NO: 127           moltype = AA  length = 655
FEATURE                  Location/Qualifiers
REGION                   1..655
                         note = Cry1B variant
```

-continued

```
source                  1..655
                        mol_type = protein
                        organism = synthetic construct
SEQUENCE: 127
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HLTYNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEHEYDL ERAQE       655

SEQ ID NO: 128          moltype = AA  length = 655
FEATURE                 Location/Qualifiers
REGION                  1..655
                        note = Cry1B variant
source                  1..655
                        mol_type = protein
                        organism = synthetic construct
SEQUENCE: 128
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITYNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTR QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEHEYDL ERAQE       655

SEQ ID NO: 129          moltype = AA  length = 655
FEATURE                 Location/Qualifiers
REGION                  1..655
                        note = Cry1B variant
source                  1..655
                        mol_type = protein
                        organism = synthetic construct
SEQUENCE: 129
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITYNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGHNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEHEYDL ERAQE       655

SEQ ID NO: 130          moltype = AA  length = 655
FEATURE                 Location/Qualifiers
REGION                  1..655
                        note = Cry1B variant
source                  1..655
                        mol_type = protein
                        organism = synthetic construct
SEQUENCE: 130
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEAEYDL ERAQE       655

SEQ ID NO: 131          moltype = AA  length = 655
FEATURE                 Location/Qualifiers
REGION                  1..655
```

```
                        note = Cry1B variant
source                  1..655
                        mol_type = protein
                        organism = synthetic construct
SEQUENCE: 131
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI GGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEAEYDL ERAQE       655

SEQ ID NO: 132          moltype = AA  length = 655
FEATURE                 Location/Qualifiers
REGION                  1..655
                        note = Cry1B variant
source                  1..655
                        mol_type = protein
                        organism = synthetic construct
SEQUENCE: 132
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNESGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEAEYDL ERAQE       655

SEQ ID NO: 133          moltype = AA  length = 655
FEATURE                 Location/Qualifiers
REGION                  1..655
                        note = Cry1B variant
source                  1..655
                        mol_type = protein
                        organism = synthetic construct
SEQUENCE: 133
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFPSTSTRYR VRVRYASVTP IRLSVNWGNS NIFSSIVPAT ATSLDNLQSR  600
NFGYFESRNA FTSATGNVVG VRNFSENAGV IIDRFEFIPV TATFEAEYDL ERAQE       655

SEQ ID NO: 134          moltype = AA  length = 655
FEATURE                 Location/Qualifiers
REGION                  1..655
                        note = Cry1B variant
source                  1..655
                        mol_type = protein
                        organism = synthetic construct
SEQUENCE: 134
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFQSTSTRYR VRVRYASVTP IRLSVNWGNS NIFSSIVPAT ATSLDNLQSR  600
NFGYFESRNA FTSATGNVVG VRNFSENAGV IIDRFEFIPV TATFEAEYDL ERAQE       655

SEQ ID NO: 135          moltype = AA  length = 655
FEATURE                 Location/Qualifiers
```

-continued

```
REGION                  1..655
                        note = Cry1B variant
source                  1..655
                        mol_type = protein
                        organism = synthetic construct
SEQUENCE: 135
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASATP IRLSVNWGNS NIFSSIVPAT ATSLDNLQSR  600
NFGYFESRNA FTSATGNVVG VRNFSENAGV IIDRFEFIPV TATFEAEYDL ERAQE       655

SEQ ID NO: 136          moltype = AA  length = 655
FEATURE                 Location/Qualifiers
REGION                  1..655
                        note = Cry1B variant
source                  1..655
                        mol_type = protein
                        organism = synthetic construct
SEQUENCE: 136
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASGTP IRLSVNWGNS NIFSSIVPAT ATSLDNLQSR  600
NFGYFESRNA FTSATGNVVG VRNFSENAGV IIDRFEFIPV TATFEAEYDL ERAQE       655

SEQ ID NO: 137          moltype = AA  length = 655
FEATURE                 Location/Qualifiers
REGION                  1..655
                        note = Cry1B variant
source                  1..655
                        mol_type = protein
                        organism = synthetic construct
SEQUENCE: 137
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TALFEAEYDL ERAQE       655

SEQ ID NO: 138          moltype = AA  length = 655
FEATURE                 Location/Qualifiers
REGION                  1..655
                        note = Cry1B variant
source                  1..655
                        mol_type = protein
                        organism = synthetic construct
SEQUENCE: 138
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLSTLQSR  600
NFGYFESRNA FTSATGNVVG VRNFSENAGV IIDRFEFIPV TATFEAEYDL ERAQE       655

SEQ ID NO: 139          moltype = AA  length = 655
```

```
FEATURE                Location/Qualifiers
REGION                 1..655
                       note = Cry1B variant
source                 1..655
                       mol_type = protein
                       organism = synthetic construct
SEQUENCE: 139
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LYFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLSTLQSR  600
NFGYFQSRNA FTSATGNVVG VRNFSENAGV IIDRFEFIPV TATFEAEYDL ERAQE       655

SEQ ID NO: 140         moltype = AA  length = 655
FEATURE                Location/Qualifiers
REGION                 1..655
                       note = Cry1B variant
source                 1..655
                       mol_type = protein
                       organism = synthetic construct
SEQUENCE: 140
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LYFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLSVLQSR  600
NFGYFHSRNA FTSATGNVVG VRNFSENAGV IIDRFEFIPV TATFEAEYDL ERAQE       655

SEQ ID NO: 141         moltype = AA  length = 655
FEATURE                Location/Qualifiers
REGION                 1..655
                       note = Cry1B variant
source                 1..655
                       mol_type = protein
                       organism = synthetic construct
SEQUENCE: 141
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LYFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDTLQSR  600
NFGYFHSRNA FTSATGNVVG VRNFSENAGV IIDRFEFIPV TATFEAEYDL ERAQE       655

SEQ ID NO: 142         moltype = AA  length = 655
FEATURE                Location/Qualifiers
REGION                 1..655
                       note = Cry1B variant
source                 1..655
                       mol_type = protein
                       organism = synthetic construct
SEQUENCE: 142
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LYFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDVLQSR  600
NFGYFQSRNA FTSATGNVVG VRNFSENAGV IIDRFEFIPV TATFEAEYDL ERAQE       655
```

-continued

```
SEQ ID NO: 143         moltype = AA  length = 655
FEATURE                Location/Qualifiers
REGION                 1..655
                       note = Cry1B variant
source                 1..655
                       mol_type = protein
                       organism = synthetic construct
SEQUENCE: 143
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFRSTSTRYR VRVRYASVTP IRLSVNWGNS NIFSSIVPAT ATSLSNLQSR  600
NFGYFHSRNA FTSATGNVVG VRNFSENAGV IIDRFEFIPV TATFEAEYDL ERAQE       655

SEQ ID NO: 144         moltype = AA  length = 655
FEATURE                Location/Qualifiers
REGION                 1..655
                       note = Cry1B variant
source                 1..655
                       mol_type = protein
                       organism = synthetic construct
SEQUENCE: 144
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFRSTSTRYR VRVRYASVTP IRLSVNWGNS NIFSSIVPAT ATSLDVLQSR  600
NFGYFQSRNA FTSATGNVVG VRNFSENAGV IIDRFEFIPV TATFEAEYDL ERAQE       655

SEQ ID NO: 145         moltype = AA  length = 655
FEATURE                Location/Qualifiers
REGION                 1..655
                       note = Cry1B variant
source                 1..655
                       mol_type = protein
                       organism = synthetic construct
SEQUENCE: 145
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFRSTSTRYR VRVRYASVTP IRLSVNWGNS NIFSSIVPAT ATSLSNLQSR  600
NFGYFQSRNA FTSATGNVVG VRNFSENAGV IIDRFEFIPV TATFEAEYDL ERAQE       655

SEQ ID NO: 146         moltype = AA  length = 655
FEATURE                Location/Qualifiers
REGION                 1..655
                       note = Cry1B variant
source                 1..655
                       mol_type = protein
                       organism = synthetic construct
SEQUENCE: 146
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFRSTSTRYR VRVRYASVTP IRLSVNWGNS NIFSSIVPAT ATSLSTLQSR  600
NFGYFESRNA FTSATGNVVG VRNFSENAGV IIDRFEFIPV TATFEAEYDL ERAQE       655
```

```
SEQ ID NO: 147          moltype = AA  length = 655
FEATURE                 Location/Qualifiers
REGION                  1..655
                        note = Cry1B variant
source                  1..655
                        mol_type = protein
                        organism = synthetic construct
SEQUENCE: 147
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFRSTSTRYR VRVRYASVTP IRLSVNWGNS NIFSSIVPAT ATSLSTLQSR  600
NFGYFHSRNA FTSATGNVVG VRNFSENAGV IIDRFEFIPV TATFEAEYDL ERAQE       655

SEQ ID NO: 148          moltype = AA  length = 655
FEATURE                 Location/Qualifiers
REGION                  1..655
                        note = Cry1B variant
source                  1..655
                        mol_type = protein
                        organism = synthetic construct
SEQUENCE: 148
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFRSTSTRYR VRVRYASVTP IRLSVNWGNS NIFSSIVPAT ATSLSVLQSR  600
NFGYFESRNA FTSATGNVVG VRNFSENAGV IIDRFEFIPV TATFEAEYDL ERAQE       655

SEQ ID NO: 149          moltype = AA  length = 655
FEATURE                 Location/Qualifiers
REGION                  1..655
                        note = Cry1B variant
source                  1..655
                        mol_type = protein
                        organism = synthetic construct
SEQUENCE: 149
MPSNRKNENE IINALSIPAV SNHSAQMDLS LDARIEDSLC IAEGNNINPL VSASTVQTGI  60
NIAGRILGVL GVPEAGQLAS FYSFIVGELW PSGRDPWEIF MEHVEQLVRQ SITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEAEYDL ERAQE       655

SEQ ID NO: 150          moltype = AA  length = 655
FEATURE                 Location/Qualifiers
REGION                  1..655
                        note = Cry1B variant
source                  1..655
                        mol_type = protein
                        organism = synthetic construct
SEQUENCE: 150
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ SLTMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDNLQSR  600
```

-continued

```
NFGYFESRNA FTSATGNVVG VRNFSENAGV IIDRFEFIPV TATFEAEYDL ERAQE       655

SEQ ID NO: 151         moltype = AA  length = 655
FEATURE                Location/Qualifiers
REGION                 1..655
                       note = Cry1B variant
source                 1..655
                       mol_type = protein
                       organism = synthetic construct
SEQUENCE: 151
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ SITYNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEAEYDL ERAQE       655

SEQ ID NO: 152         moltype = AA  length = 655
FEATURE                Location/Qualifiers
REGION                 1..655
                       note = Cry1B variant
source                 1..655
                       mol_type = protein
                       organism = synthetic construct
SEQUENCE: 152
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ SITMNARNTA  120
LARLQGLGAS FRAYQQSLED WLENRDNAAT RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEAEYDL ERAQE       655

SEQ ID NO: 153         moltype = AA  length = 655
FEATURE                Location/Qualifiers
REGION                 1..655
                       note = Cry1B variant
source                 1..655
                       mol_type = protein
                       organism = synthetic construct
SEQUENCE: 153
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ SITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTR QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEAEYDL ERAQE       655

SEQ ID NO: 154         moltype = AA  length = 655
FEATURE                Location/Qualifiers
REGION                 1..655
                       note = Cry1B variant
source                 1..655
                       mol_type = protein
                       organism = synthetic construct
SEQUENCE: 154
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ SITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTR QEIQRYYERQ AEKTREYSDY CARWYNTGLN  240
NLMGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
```

```
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEAEYDL ERAQE       655

SEQ ID NO: 155          moltype = AA  length = 655
FEATURE                 Location/Qualifiers
REGION                  1..655
                        note = Cry1B variant
source                  1..655
                        mol_type = protein
                        organism = synthetic construct
SEQUENCE: 155
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ SITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLVGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEAEYDL ERAQE       655

SEQ ID NO: 156          moltype = AA  length = 655
FEATURE                 Location/Qualifiers
REGION                  1..655
                        note = Cry1B variant
source                  1..655
                        mol_type = protein
                        organism = synthetic construct
SEQUENCE: 156
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ SITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGQNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEAEYDL ERAQE       655

SEQ ID NO: 157          moltype = AA  length = 655
FEATURE                 Location/Qualifiers
REGION                  1..655
                        note = Cry1B variant
source                  1..655
                        mol_type = protein
                        organism = synthetic construct
SEQUENCE: 157
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ SITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGHNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEAEYDL ERAQE       655

SEQ ID NO: 158          moltype = AA  length = 655
FEATURE                 Location/Qualifiers
REGION                  1..655
                        note = Cry1B variant
source                  1..655
                        mol_type = protein
                        organism = synthetic construct
SEQUENCE: 158
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ SITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGKNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
```

-continued

```
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEAEYDL ERAQE       655

SEQ ID NO: 159          moltype = AA  length = 655
FEATURE                 Location/Qualifiers
REGION                  1..655
                        note = Cry1B variant
source                  1..655
                        mol_type = protein
                        organism = synthetic construct
SEQUENCE: 159
MPSNRKNENE IINALSIPAV SNHSAQMDLS LDARIEDSLC IAEGNNINPL VSASTVQTGI  60
NIAGRILGVL GVPEAGQLAS FYSFIVGELW PSGRDPWEIF MEHVEQLVRQ HITYNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEAEYDL ERAQE       655

SEQ ID NO: 160          moltype = AA  length = 655
FEATURE                 Location/Qualifiers
REGION                  1..655
                        note = Cry1B variant
source                  1..655
                        mol_type = protein
                        organism = synthetic construct
SEQUENCE: 160
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HLTYNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEAEYDL ERAQE       655

SEQ ID NO: 161          moltype = AA  length = 655
FEATURE                 Location/Qualifiers
REGION                  1..655
                        note = Cry1B variant
source                  1..655
                        mol_type = protein
                        organism = synthetic construct
SEQUENCE: 161
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITYNARNTA  120
LARLQGLGAS FRAYQQSLED WLENRDNAAT RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEAEYDL ERAQE       655

SEQ ID NO: 162          moltype = AA  length = 655
FEATURE                 Location/Qualifiers
REGION                  1..655
                        note = Cry1B variant
source                  1..655
                        mol_type = protein
                        organism = synthetic construct
SEQUENCE: 162
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITYNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTR QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
```

-continued

```
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEAEYDL ERAQE       655

SEQ ID NO: 163          moltype = AA  length = 655
FEATURE                 Location/Qualifiers
REGION                  1..655
                        note = Cry1B variant
source                  1..655
                        mol_type = protein
                        organism = synthetic construct
SEQUENCE: 163
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITYNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLMGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEAEYDL ERAQE       655

SEQ ID NO: 164          moltype = AA  length = 655
FEATURE                 Location/Qualifiers
REGION                  1..655
                        note = Cry1B variant
source                  1..655
                        mol_type = protein
                        organism = synthetic construct
SEQUENCE: 164
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITYNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLVGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEAEYDL ERAQE       655

SEQ ID NO: 165          moltype = AA  length = 655
FEATURE                 Location/Qualifiers
REGION                  1..655
                        note = Cry1B variant
source                  1..655
                        mol_type = protein
                        organism = synthetic construct
SEQUENCE: 165
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITYNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGQNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEAEYDL ERAQE       655

SEQ ID NO: 166          moltype = AA  length = 655
FEATURE                 Location/Qualifiers
REGION                  1..655
                        note = Cry1B variant
source                  1..655
                        mol_type = protein
                        organism = synthetic construct
SEQUENCE: 166
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITYNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGHNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
```

```
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEAEYDL ERAQE       655

SEQ ID NO: 167         moltype = AA  length = 655
FEATURE                Location/Qualifiers
REGION                 1..655
                       note = Cry1B variant
source                 1..655
                       mol_type = protein
                       organism = synthetic construct
SEQUENCE: 167
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITYNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGKNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEAEYDL ERAQE       655

SEQ ID NO: 168         moltype = AA  length = 655
FEATURE                Location/Qualifiers
REGION                 1..655
                       note = Cry1B variant
source                 1..655
                       mol_type = protein
                       organism = synthetic construct
SEQUENCE: 168
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITYNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LYFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDVLQSR  600
NFGYFHSRNA FTSATGNVVG VRNFSENAGV IIDRFEFIPV TATFEAEYDL ERAQE       655

SEQ ID NO: 169         moltype = AA  length = 655
FEATURE                Location/Qualifiers
REGION                 1..655
                       note = Cry1B variant
source                 1..655
                       mol_type = protein
                       organism = synthetic construct
SEQUENCE: 169
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HLTYNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LYFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDVLQSR  600
NFGYFHSRNA FTSATGNVVG VRNFSENAGV IIDRFEFIPV TATFEAEYDL ERAQE       655

SEQ ID NO: 170         moltype = AA  length = 655
FEATURE                Location/Qualifiers
REGION                 1..655
                       note = Cry1B variant
source                 1..655
                       mol_type = protein
                       organism = synthetic construct
SEQUENCE: 170
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITYNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTR QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
```

-continued

```
APSGFASTNW FNNNAPSFSA IEAAIFRPPH LLDFPEQLTI YSASSRWSST QHMNYWVGHR  360
LYFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDVLQSR  600
NFGYFHSRNA FTSATGNVVG VRNFSENAGV IIDRFEFIPV TATFEAEYDL ERAQE       655

SEQ ID NO: 171         moltype = AA  length = 655
FEATURE                Location/Qualifiers
REGION                 1..655
                       note = Cry1B variant
source                 1..655
                       mol_type = protein
                       organism = synthetic construct
SEQUENCE: 171
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITYNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGHNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LYFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDVLQSR  600
NFGYFHSRNA FTSATGNVVG VRNFSENAGV IIDRFEFIPV TATFEAEYDL ERAQE       655

SEQ ID NO: 172         moltype = AA  length = 655
FEATURE                Location/Qualifiers
REGION                 1..655
                       note = Cry1B variant
source                 1..655
                       mol_type = protein
                       organism = synthetic construct
SEQUENCE: 172
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITYNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGKNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LYFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDVLQSR  600
NFGYFHSRNA FTSATGNVVG VRNFSENAGV IIDRFEFIPV TATFEAEYDL ERAQE       655

SEQ ID NO: 173         moltype = AA  length = 655
FEATURE                Location/Qualifiers
REGION                 1..655
                       note = Cry1B variant
source                 1..655
                       mol_type = protein
                       organism = synthetic construct
SEQUENCE: 173
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGKNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LYFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDVLQSR  600
NFGYFHSRNA FTSATGNVVG VRNFSENAGV IIDRFEFIPV TATFEAEYDL ERAQE       655

SEQ ID NO: 174         moltype = AA  length = 655
FEATURE                Location/Qualifiers
REGION                 1..655
                       note = Cry1B variant
source                 1..655
                       mol_type = protein
                       organism = synthetic construct
SEQUENCE: 174
MPSNRKNENE IINALSIPAV SNHSAQMDLS LDARIEDSLC IAEGNNINPL VSASTVNTGI  60
NIAGRILGVL GVPFAGQLAS FYSFIVGELW PSGRDPWEIF MEHVEQLVRQ HITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
```

-continued

```
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEHEYDL ERAQE       655

SEQ ID NO: 175          moltype = AA  length = 655
FEATURE                 Location/Qualifiers
REGION                  1..655
                        note = Cry1B variant
source                  1..655
                        mol_type = protein
                        organism = synthetic construct
SEQUENCE: 175
MPSNRKNENE IINALSIPAV SNHSAQMDLS LDARIEDSLC IAEGNNINPL VSASTVQTGI  60
NIAGRIMGVL GVPFAGQLAS FYSFIVGELW PSGRDPWEIF MEHVEQLVRQ HITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEHEYDL ERAQE       655

SEQ ID NO: 176          moltype = AA  length = 655
FEATURE                 Location/Qualifiers
REGION                  1..655
                        note = Cry1B variant
source                  1..655
                        mol_type = protein
                        organism = synthetic construct
SEQUENCE: 176
MPSNRKNENE IINALSIPAV SNHSAQMDLS LDARIEDSLC IAEGNNINPL VSASTVQTGI  60
NIAGRILGVL GVPFAGNLAS FYSFIVGELW PSGRDPWEIF MEHVEQLVRQ HITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEHEYDL ERAQE       655

SEQ ID NO: 177          moltype = AA  length = 655
FEATURE                 Location/Qualifiers
REGION                  1..655
                        note = Cry1B variant
source                  1..655
                        mol_type = protein
                        organism = synthetic construct
SEQUENCE: 177
MPSNRKNENE IINALSIPAV SNHSAQMDLS LDARIEDSLC IAEGNNINPL VSASTVQTGI  60
NIAGRILGVL GVPFAGQLIS FYSFIVGELW PSGRDPWEIF MEHVEQLVRQ HITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEHEYDL ERAQE       655

SEQ ID NO: 178          moltype = AA  length = 655
FEATURE                 Location/Qualifiers
REGION                  1..655
                        note = Cry1B variant
source                  1..655
                        mol_type = protein
                        organism = synthetic construct
SEQUENCE: 178
MPSNRKNENE IINALSIPAV SNHSAQMDLS LDARIEDSLC IAEGNNINPL VSASTVQTGI  60
NIAGRILGVL GVPFAGQLAQ FYSFIVGELW PSGRDPWEIF MEHVEQLVRQ HITMNARNTA  120
LARLQGLGAS FRAYQQSLED WLENRDNART RSVLYTQYIA LELDFLNAMP LFAINNQQVP  180
```

-continued

```
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEHEYDL ERAQE       655

SEQ ID NO: 179          moltype = AA  length = 655
FEATURE                 Location/Qualifiers
REGION                  1..655
                        note = Cry1B variant
source                  1..655
                        mol_type = protein
                        organism = synthetic construct
SEQUENCE: 179
MPSNRKNENE IINALSIPAV SNHSAQMDLS LDARIEDSLC IAEGNNINPL VSASTVQTGI  60
NIAGRILGVL GVPFAGQLAS FYAFIVGELW PSGRDPWEIF MEHVEQLVRQ HITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEHEYDL ERAQE       655

SEQ ID NO: 180          moltype = AA  length = 655
FEATURE                 Location/Qualifiers
REGION                  1..655
                        note = Cry1B variant
source                  1..655
                        mol_type = protein
                        organism = synthetic construct
SEQUENCE: 180
MPSNRKNENE IINALSIPAV SNHSAQMDLS LDARIEDSLC IAEGNNINPL VSASTVQTGI  60
NIAGRILGVL GVPFAGQLAS FYRFIVGELW PSGRDPWEIF MEHVEQLVRQ HITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEHEYDL ERAQE       655

SEQ ID NO: 181          moltype = AA  length = 655
FEATURE                 Location/Qualifiers
REGION                  1..655
                        note = Cry1B variant
source                  1..655
                        mol_type = protein
                        organism = synthetic construct
SEQUENCE: 181
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEHLVRQ HITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEHEYDL ERAQE       655

SEQ ID NO: 182          moltype = AA  length = 655
FEATURE                 Location/Qualifiers
REGION                  1..655
                        note = Cry1B variant
source                  1..655
                        mol_type = protein
                        organism = synthetic construct
SEQUENCE: 182
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITMNARNTA  120
```

-continued

```
LARLQGLGAS FRAYQQSLED WLENRTNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEHEYDL ERAQE       655

SEQ ID NO: 183          moltype = AA  length = 655
FEATURE                 Location/Qualifiers
REGION                  1..655
                        note = Cry1B variant
source                  1..655
                        mol_type = protein
                        organism = synthetic construct
SEQUENCE: 183
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS REIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEHEYDL ERAQE       655

SEQ ID NO: 184          moltype = AA  length = 655
FEATURE                 Location/Qualifiers
REGION                  1..655
                        note = Cry1B variant
source                  1..655
                        mol_type = protein
                        organism = synthetic construct
SEQUENCE: 184
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ VEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEHEYDL ERAQE       655

SEQ ID NO: 185          moltype = AA  length = 655
FEATURE                 Location/Qualifiers
REGION                  1..655
                        note = Cry1B variant
source                  1..655
                        mol_type = protein
                        organism = synthetic construct
SEQUENCE: 185
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTVEYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEHEYDL ERAQE       655

SEQ ID NO: 186          moltype = AA  length = 655
FEATURE                 Location/Qualifiers
REGION                  1..655
                        note = Cry1B variant
source                  1..655
                        mol_type = protein
                        organism = synthetic construct
SEQUENCE: 186
MPSNRKNENE IINALSIPAV SNHSAQMDLS LDARIEDSLC IAEGNNINPL VSASTVQTGI  60
```

-continued

```
NIAGRILGVL GVPFAGQLAS FYSFIVGELW PSGRDPWEIF MEHVEQLVRQ HITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTRDYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEHEYDL ERAQE       655

SEQ ID NO: 187          moltype = AA  length = 655
FEATURE                 Location/Qualifiers
REGION                  1..655
                        note = Cry1B variant
source                  1..655
                        mol_type = protein
                        organism = synthetic construct
SEQUENCE: 187
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CAKWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEHEYDL ERAQE       655

SEQ ID NO: 188          moltype = AA  length = 655
FEATURE                 Location/Qualifiers
REGION                  1..655
                        note = Cry1B variant
source                  1..655
                        mol_type = protein
                        organism = synthetic construct
SEQUENCE: 188
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARRYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEHEYDL ERAQE       655

SEQ ID NO: 189          moltype = AA  length = 655
FEATURE                 Location/Qualifiers
REGION                  1..655
                        note = Cry1B variant
source                  1..655
                        mol_type = protein
                        organism = synthetic construct
SEQUENCE: 189
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNASSW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEHEYDL ERAQE       655

SEQ ID NO: 190          moltype = AA  length = 655
FEATURE                 Location/Qualifiers
REGION                  1..655
                        note = Cry1B variant
source                  1..655
                        mol_type = protein
                        organism = synthetic construct
SEQUENCE: 190
```

-continued

```
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITYNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEHEYDL ERAQE       655

SEQ ID NO: 191         moltype = AA  length = 655
FEATURE                Location/Qualifiers
REGION                 1..655
                       note = Cry1B variant
source                 1..655
                       mol_type = protein
                       organism = synthetic construct
SEQUENCE: 191
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITYNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGQNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEHEYDL ERAQE       655

SEQ ID NO: 192         moltype = AA  length = 655
FEATURE                Location/Qualifiers
REGION                 1..655
                       note = Cry1B variant
source                 1..655
                       mol_type = protein
                       organism = synthetic construct
SEQUENCE: 192
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITYNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGKNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEHEYDL ERAQE       655

SEQ ID NO: 193         moltype = AA  length = 655
FEATURE                Location/Qualifiers
REGION                 1..655
                       note = Cry1B variant
source                 1..655
                       mol_type = protein
                       organism = synthetic construct
SEQUENCE: 193
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HITMNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGKNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEHEYDL ERAQE       655

SEQ ID NO: 194         moltype = AA  length = 655
FEATURE                Location/Qualifiers
REGION                 1..655
                       note = Cry1B variant
source                 1..655
                       mol_type = protein
                       organism = synthetic construct
```

```
SEQUENCE: 194
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HLTYNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGHNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEHEYDL ERAQE       655

SEQ ID NO: 195          moltype = AA  length = 655
FEATURE                 Location/Qualifiers
REGION                  1..655
                        note = Cry1B variant
source                  1..655
                        mol_type = protein
                        organism = synthetic construct
SEQUENCE: 195
MPSNRKNENE IINALSIPAV SNHSAQMDLS LDARIEDSLC IAEGNNINPL VSASTVQTGI  60
NIAGRILGVL GVPFAGQLAS FYSFIVGELW PSGRDPWEIF MEHVEQLVRQ HLTYNARNTA  120
LARLQGLGAS FRAYQQSLED WLENRDNART RSVLYTQYIA LELDFLNAMP LFAINNQQVP  180
LLMVYAQAAN LHLLLLRDAS LFGSEFGLTR QEIQRYYERQ AEKTREYSDY CARWYNTGLN  240
NLRGHNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTHGATNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLIIGGTL  480
RAPVYSWTHR SADRTNTIAT NIITQIPAVK GNFLFNGLVI SGPGFTGGDL VRLNNSGNNI  540
QNRGYIEVPI QFISTSTRYR VRVRYASVTP IRLSVNWGNS NIFSSIVPAT ATSLDNLQSR  600
NFGYFESRNA FTSATGNVVG VRNFSENAGV IIDRFEFIPV TATFEHEYDL ERAQE       655

SEQ ID NO: 196          moltype = AA  length = 655
FEATURE                 Location/Qualifiers
REGION                  1..655
                        note = Cry1B variant
source                  1..655
                        mol_type = protein
                        organism = synthetic construct
SEQUENCE: 196
MPSNRKNENE IINALSIPAV SNHSAQMDLS LDARIEDSLC IAEGNNINPL VSASTVQTGI  60
NIAGRILGVL GVPFAGQLAS FYSFLVGELW PSGRDPWEIF LEHVEQLIRQ QVTENTRNTA  120
IARLEGLGRG YRSYQQALET WLDNRNDARS RSIILERYVA LELDITTAIP LFRIRNEEVP  180
LLMVYAQAAN LHLLLLRDAS LFGSEWGMAS SDVNQYYQEQ IRYTEEYSNH CVQWYNTGLN  240
NLRGTNAESW LRYNQFRRDL TLGVLDLVAL FPSYDTRTYP INTSAQLTRE IYTDPIGRTN  300
APSGFASTNW FNNNAPSFSA IEAAVIRPPH LLDFPEQLTI FSVLSRWSNT QYMNYWVGHR  360
LESRTIRGSL STSTHGNTNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLISGNTL  480
RAPVYSWTHR SADRTNTIAT NIITQIPAVK GNFLFNGSVI SGPGFTGGDL VRLNNSGNNI  540
QNRGYLEVPI QFISTSTRYR VRVRYASVTP IQLSVNWGNS NIFSSIVPAT ATSLDNLQSR  600
DFGYFESTNA FTSATGNVVG VRNFSENAGV IIDRFEFIPV TATFEAEYDL ERAQE       655

SEQ ID NO: 197          moltype = AA  length = 657
FEATURE                 Location/Qualifiers
REGION                  1..657
                        note = Cry1B variant
source                  1..657
                        mol_type = protein
                        organism = synthetic construct
SEQUENCE: 197
MTSNRKNENE IINALSIPAV SNHSAQMDLS PDARIEDSLC IAEGNNINPL VSASTVQTGI  60
NIAGRILGVL GVPFAGQLAS FYSFIVGELW PSGRDPWEIF LEHVEQLVRQ QITENARNTA  120
LARLQGLGAS FRAYQQSLED WLENRDDART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTQGLTNN TSINPVTLQF TSRDVYRTES NAGTNILFTT PVNGVPWARF  420
NFINPQNIYE RGATTYSQPY QGVGIQLFDS ETELPPETTE RPNYESYSHR LSHIGLIIGN  480
TLRAPVYSWT HRSADRTNTI ATNIITQIPA VKGNFLFNGS VISGPGFTGG DLVRLNNSGN  540
NIQNRGYLEV PIQFISTSTR YRVRVRYASV TPIQLSVNWG NSNIFSSIVP ATATSLDNLQ  600
SRDFGYFEST NAFTSATGNV VGVRNFSENA GVIIDRFEFI PVTATFEAEY DLERAQE     657

SEQ ID NO: 198          moltype = AA  length = 655
FEATURE                 Location/Qualifiers
REGION                  1..655
                        note = Cry1B variant
source                  1..655
                        mol_type = protein
```

```
                         organism = synthetic construct
SEQUENCE: 198
MTSNRKNENE IINALSIPAV SNHSAQMDLS PDARIEDSLC IAEGNNINPL VSASTVQTGI  60
NIAGRILGVL GVPFAGQLAS FYSFIVGELW PSGRDPWEIF LEHVEQLIRQ QVTENTRNTA  120
IARLEGLGRG YRSYQQALET WLDNRNDARS RSIILERYVA LELDITTAIP LFRIRNEEVP  180
LLMVYAQAAN LHLLLLRDAS LFGSEWGMAS SDVNQYYQEQ IRYTEEYSNH CVQWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAVIRPPH LLDFPEQLTI FSVLSRWSNT QYMNYWVGHR  360
LESRTIRGSL STSTHGNTNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLISGNTL  480
RAPVYSWTHR SADRTNTIAT NIITQIPAVK GNFLFNGSVI SGPGFTGGDL VRLNNSGNNI  540
QNRGYLEVPI QFISTSTRYR VRVRYASVTP IQLSVNWGNS NIFSSIVPAT ATSLDNLQSR  600
DFGYFESTNA FTSATGNVVG VRNFSENAGV IIDRFEFIPV TATFEAEYDL ERAQE       655

SEQ ID NO: 199           moltype = AA  length = 657
FEATURE                  Location/Qualifiers
REGION                   1..657
                         note = Cry1B variant
source                   1..657
                         mol_type = protein
                         organism = synthetic construct
SEQUENCE: 199
MPSNRKNENE IINALSIPAV SNHSAQMDLS LDARIEDSLC IAEGNNINPL VSASTVQTGI  60
NIAGRILGVL GVPFAGQLAS FYSFLVGELW PSGRDPWEIF LEHVEQLVRQ QITENARNTA  120
LARLQGLGAS FRAYQQSLED WLENRDDART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRTYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTQGLTNN TSINPVTLQF TSRDVYRTES NAGTNILFTT PVNGVPWARF  420
NFINPQNIYE RGATTYSQPY QGVGIQLFDS ETELPPETTE RPNYESYSHR LSHIGLIIGN  480
TLRAPVYSWT HRSADRTNTI GPNRITQIPA VKGRFLFNGS VISGPGFTGG DVVRLNRNNG  540
NIQNRGYIEV PIQFTSTSTR YRVRVRYASV TSIELNVNLG NSSIFTNTLP ATAASLDNLQ  600
SGDFGYVEIN NAFTSATGNI VGARNFSANA EVIIDRFEFI PVTATFEAEY DLERAQK     657

SEQ ID NO: 200           moltype = AA  length = 654
FEATURE                  Location/Qualifiers
REGION                   1..654
                         note = Cry1B variant
source                   1..654
                         mol_type = protein
                         organism = synthetic construct
SEQUENCE: 200
TSNRKNENEI INALSIPAVS NHSAQMDLSP DARIEDSLCI AEGNNINPLV SASTVQTGIN  60
IAGRILGVLG VPFAGQLASF YSFIVGELWP SGRDPWEIFL EHVEQLVRQQ VTENTRNTAI  120
ARLEGLGRGY RSYQQALETW LDNRDDARTR SVLYTQYIAL ELDFLNAMPL FAINNQQVPL  180
LMVYAQAANL HLLLLRDASL FGSEFGLTSQ EIQRYYERQA EKTREYSDYC ARWYNTGLNN  240
LRGTNAESWL RYNQFRRDLT LGVLDLVALF PSYDTRIYPI NTSAQLTREI YTDPIGRTNA  300
PSGFASTNWF NNNAPSFSAI EAAVIRPPHL LDFPEQLTIF SVLSRWSNTQ YMNYWVGHRL  360
ESRTIRGSLS TSTHGNTNTS INPVTLQFTS RDVYRTESYA GINILLTTPV NGVPWARFNW  420
RNPLNSLRGS LLYTIGYTGV GTQLFDSETE LPPETTERPN YESYSHRLSN IRLISGNTLR  480
APVYSWTHRS ADRTNTIATN IITQIPAVKG NFLFNGSVIS GPGFTGGDLV RLNNSGNNIQ  540
NRGYLEVPIQ FISTSTRYRV RVRYASVTPI QLSVNWGNSN IFSSIVPATA TSLDNLQSRD  600
FGYFESTNAF TSATGNVVGV RNFSENAGVI IDRFEFIPVT ATFEAEYDLE RAQE        654

SEQ ID NO: 201           moltype = AA  length = 655
FEATURE                  Location/Qualifiers
REGION                   1..655
                         note = Cry1B variant
source                   1..655
                         mol_type = protein
                         organism = synthetic construct
SEQUENCE: 201
MTSNRKNENE IINALSIPAV SNHSAQMDLS PDARIEDSLC IAEGNNINPL VSASTVQTGI  60
NIAGRILGVL GVPFAGQLAS FYSFIVGELW PSGRDPWEIF LEHVEQLVRQ QITENARNTA  120
LARLQGLGAS FRAYQQSLED WLENRNDARS RSIILERYVA LELDITTAIP LFRIRNEEVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAVIRPPH LLDFPEQLTI FSVLSRWSNT QYMNYWVGHR  360
LESRTIRGSL STSTHGNTNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLISGNTL  480
RAPVYSWTHR SADRTNTIAT NIITQIPAVK GNFLFNGSVI SGPGFTGGDL VRLNNSGNNI  540
QNRGYLEVPI QFISTSTRYR VRVRYASVTP IQLSVNWGNS NIFSSIVPAT ATSLDNLQSR  600
DFGYFESTNA FTSATGNVVG VRNFSENAGV IIDRFEFIPV TATFEAEYDL ERAQE       655

SEQ ID NO: 202           moltype = AA  length = 655
FEATURE                  Location/Qualifiers
REGION                   1..655
                         note = Cry1B variant
source                   1..655
```

```
                         mol_type = protein
                         organism = synthetic construct
SEQUENCE: 202
MTSNRKNENE IINALSIPAV SNHSAQMDLS PDARIEDSLC IAEGNNINPL VSASTVQTGI  60
NIAGRILGVL GVPFAGQLAS FYSFIVGELW PSGRDPWEIF LEHVEQLVRQ QITENARNTA  120
LARLQGLGAS FRAYQQSLED WLENRDDART RSVLYTQYIA LELDFLNAMP LFAINNQQVP  180
LLMVYAQAAN LHLLLLRDAS LFGSEWGMAS SDVNQYYQEQ IRYTEEYSNH CVQWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAVIRPPH LLDFPEQLTI FSVLSRWSNT QYMNYWVGHR  360
LESRTIRGSL STSTHGNTNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLISGNTL  480
RAPVYSWTHR SADRTNTIAT NIITQIPAVK GNFLFNGSVI SGPGFTGGDL VRLNNSGNNI  540
QNRGYLEVPI QFISTSTRYR VRVRYASVTP IQLSVNWGNS NIFSSIVPAT ATSLDNLQSR  600
DFGYFESTNA FTSATGNVVG VRNFSENAGV IIDRFEFIPV TATFEAEYDL ERAQE       655

SEQ ID NO: 203           moltype = AA  length = 655
FEATURE                  Location/Qualifiers
REGION                   1..655
                         note = Cry1B variant
source                   1..655
                         mol_type = protein
                         organism = synthetic construct
SEQUENCE: 203
MTSNRKNENE IINALSIPAV SNHSAQMDLS PDARIEDSLC IAEGNNINPL VSASTVQTGI  60
NIAGRILGVL GVPFAGQLAS FYSFIVGELW PSGRDPWEIF LEHVEQLVRQ QVTENTRNTA  120
IARLEGLGRG YRSYQQALET WLDNRNDARS RSIILERYVA LELDITTAIP LFRIRNEEVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAVIRPPH LLDFPEQLTI FSVLSRWSNT QYMNYWVGHR  360
LESRTIRGSL STSTHGNTNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLISGNTL  480
RAPVYSWTHR SADRTNTIAT NIITQIPAVK GNFLFNGSVI SGPGFTGGDL VRLNNSGNNI  540
QNRGYLEVPI QFISTSTRYR VRVRYASVTP IQLSVNWGNS NIFSSIVPAT ATSLDNLQSR  600
DFGYFESTNA FTSATGNVVG VRNFSENAGV IIDRFEFIPV TATFEAEYDL ERAQE       655

SEQ ID NO: 204           moltype = AA  length = 655
FEATURE                  Location/Qualifiers
REGION                   1..655
                         note = Cry1B variant
source                   1..655
                         mol_type = protein
                         organism = synthetic construct
SEQUENCE: 204
MTSNRKNENE IINALSIPAV SNHSAQMDLS PDARIEDSLC IAEGNNINPL VSASTVQTGI  60
NIAGRILGVL GVPFAGQLAS FYSFIVGELW PSGRDPWEIF LEHVEQLVRQ QITENARNTA  120
LARLQGLGAS FRAYQQSLED WLENRNDARS RSIILERYVA LELDITTAIP LFRIRNEEVP  180
LLMVYAQAAN LHLLLLRDAS LFGSEWGMAS SDVNQYYQEQ IRYTEEYSNH CVQWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAVIRPPH LLDFPEQLTI FSVLSRWSNT QYMNYWVGHR  360
LESRTIRGSL STSTHGNTNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLISGNTL  480
RAPVYSWTHR SADRTNTIAT NIITQIPAVK GNFLFNGSVI SGPGFTGGDL VRLNNSGNNI  540
QNRGYLEVPI QFISTSTRYR VRVRYASVTP IQLSVNWGNS NIFSSIVPAT ATSLDNLQSR  600
DFGYFESTNA FTSATGNVVG VRNFSENAGV IIDRFEFIPV TATFEAEYDL ERAQE       655

SEQ ID NO: 205           moltype = AA  length = 655
FEATURE                  Location/Qualifiers
REGION                   1..655
                         note = Cry1B variant
source                   1..655
                         mol_type = protein
                         organism = synthetic construct
SEQUENCE: 205
MTSNRKNENE IINALSIPAV SNHSAQMDLS PDARIEDSLC IAEGNNINPL VSASTVQTGI  60
NIAGRILGVL GVPFAGQLAS FYSFIVGELW PSGRDPWEIF LEHVEQLVRQ QVTENTRNTA  120
IARLEGLGRG YRSYQQALET WLDNRDDART RSVLYTQYIA LELDFLNAMP LFAINNQQVP  180
LLMVYAQAAN LHLLLLRDAS LFGSEWGMAS SDVNQYYQEQ IRYTEEYSNH CVQWYNTGLN  240
NLRGTNAESW LRYNQFRRDL TLGVLDLVAL FPSYDTRIYP INTSAQLTRE IYTDPIGRTN  300
APSGFASTNW FNNNAPSFSA IEAAVIRPPH LLDFPEQLTI FSVLSRWSNT QYMNYWVGHR  360
LESRTIRGSL STSTHGNTNT SINPVTLQFT SRDVYRTESY AGINILLTTP VNGVPWARFN  420
WRNPLNSLRG SLLYTIGYTG VGTQLFDSET ELPPETTERP NYESYSHRLS NIRLISGNTL  480
RAPVYSWTHR SADRTNTIAT NIITQIPAVK GNFLFNGSVI SGPGFTGGDL VRLNNSGNNI  540
QNRGYLEVPI QFISTSTRYR VRVRYASVTP IQLSVNWGNS NIFSSIVPAT ATSLDNLQSR  600
DFGYFESTNA FTSATGNVVG VRNFSENAGV IIDRFEFIPV TATFEAEYDL ERAQE       655

SEQ ID NO: 206           moltype = AA  length = 657
FEATURE                  Location/Qualifiers
REGION                   1..657
                         note = Cry1B variant
```

```
source                  1..657
                        mol_type = protein
                        organism = synthetic construct
SEQUENCE: 206
MPSNRKNENE IINALSIPAV SNHSAQMDLS LDARIEDSLC IAEGNNINPL VSASTVQTGI  60
NIAGRILGVL GVPFAGQLAS FYSFLVGELW PSGRDPWEIF LEHVEQLVRQ QITENARNTA  120
LARLQGLGAS FRAYQQSLED WLENRDDARS RSIILERYVA LELDITTAIP LFRIRNEEVP  180
LLMVYAQAAN LHLLLLRDAS LFGSEWGMAS SDVNQYYQEQ IRYTEEYSNH CVQWYNTGLN  240
NLRGTNAESW LRYNQFRRDL TLGVLDLVAL FPSYDTRTYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTQGLTNN TSINPVTLQF TSRDVYRTES NAGTNILFTT PVNGVPWARF  420
NFINPQNIYE RGATTYSQPY QGVGIQLFDS ETELPPETTE RPNYESYSHR LSHIGLIIGN  480
TLRAPVYSWT HRSADRTNTI GPNRITQIPA VKGRFLFNGS VISGPGFTGG DVVRLNRNNG  540
NIQNRGYIEV PIQFTSTSTR YRVRVRYASV TSIELNVNLG NSSIFTNTLP ATAASLDNLQ  600
SGDFGYVEIN NAFTSATGNI VGARNFSANA EVIIDRFEFI PVTATFEAEY DLERAQK     657

SEQ ID NO: 207          moltype = AA  length = 657
FEATURE                 Location/Qualifiers
REGION                  1..657
                        note = Cry1B variant
source                  1..657
                        mol_type = protein
                        organism = synthetic construct
SEQUENCE: 207
MPSNRKNENE IINALSIPAV SNHSAQMDLS LDARIEDSLC IAEGNNINPL VSASTVQTGI  60
NIAGRILGVL GVPFAGQLAS FYSFLVGELW PSGRDPWEIF LEHVEQLIRQ QVTENTRNTA  120
IARLEGLGRG YRSYQQALET WLDNRNDART RSVLYTQYIA LELDFLNAMP LFAINNQQVP  180
LLMVYAQAAN LHLLLLRDAS LFGSEWGMAS SDVNQYYQEQ IRYTEEYSNH CVQWYNTGLN  240
NLRGTNAESW LRYNQFRRDL TLGVLDLVAL FPSYDTRTYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTQGLTNN TSINPVTLQF TSRDVYRTES NAGTNILFTT PVNGVPWARF  420
NFINPQNIYE RGATTYSQPY QGVGIQLFDS ETELPPETTE RPNYESYSHR LSHIGLIIGN  480
TLRAPVYSWT HRSADRTNTI GPNRITQIPA VKGRFLFNGS VISGPGFTGG DVVRLNRNNG  540
NIQNRGYIEV PIQFTSTSTR YRVRVRYASV TSIELNVNLG NSSIFTNTLP ATAASLDNLQ  600
SGDFGYVEIN NAFTSATGNI VGARNFSANA EVIIDRFEFI PVTATFEAEY DLERAQK     657

SEQ ID NO: 208          moltype = AA  length = 657
FEATURE                 Location/Qualifiers
REGION                  1..657
                        note = Cry1B variant
source                  1..657
                        mol_type = protein
                        organism = synthetic construct
SEQUENCE: 208
MPSNRKNENE IINALSIPAV SNHSAQMDLS LDARIEDSLC IAEGNNINPL VSASTVQTGI  60
NIAGRILGVL GVPFAGQLAS FYSFLVGELW PSGRDPWEIF LEHVEQLIRQ QVTENTRNTA  120
IARLEGLGRG YRSYQQALET WLDNRNDARS RSIILERYVA LELDITTAIP LFRIRNEEVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRTYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTQGLTNN TSINPVTLQF TSRDVYRTES NAGTNILFTT PVNGVPWARF  420
NFINPQNIYE RGATTYSQPY QGVGIQLFDS ETELPPETTE RPNYESYSHR LSHIGLIIGN  480
TLRAPVYSWT HRSADRTNTI GPNRITQIPA VKGRFLFNGS VISGPGFTGG DVVRLNRNNG  540
NIQNRGYIEV PIQFTSTSTR YRVRVRYASV TSIELNVNLG NSSIFTNTLP ATAASLDNLQ  600
SGDFGYVEIN NAFTSATGNI VGARNFSANA EVIIDRFEFI PVTATFEAEY DLERAQK     657

SEQ ID NO: 209          moltype = AA  length = 657
FEATURE                 Location/Qualifiers
REGION                  1..657
                        note = Cry1B variant
source                  1..657
                        mol_type = protein
                        organism = synthetic construct
SEQUENCE: 209
MPSNRKNENE IINALSIPAV SNHSAQMDLS LDARIEDSLC IAEGNNINPL VSASTVQTGI  60
NIAGRILGVL GVPFAGQLAS FYSFLVGELW PSGRDPWEIF LEHVEQLVRQ QITENARNTA  120
LARLQGLGAS FRAYQQSLED WLENRDDART RSVLYTQYIA LELDFLNAMP LFAINNQQVP  180
LLMVYAQAAN LHLLLLRDAS LFGSEWGMAS SDVNQYYQEQ IRYTEEYSNH CVQWYNTGLN  240
NLRGTNAESW LRYNQFRRDL TLGVLDLVAL FPSYDTRTYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTQGLTNN TSINPVTLQF TSRDVYRTES NAGTNILFTT PVNGVPWARF  420
NFINPQNIYE RGATTYSQPY QGVGIQLFDS ETELPPETTE RPNYESYSHR LSHIGLIIGN  480
TLRAPVYSWT HRSADRTNTI GPNRITQIPA VKGRFLFNGS VISGPGFTGG DVVRLNRNNG  540
NIQNRGYIEV PIQFTSTSTR YRVRVRYASV TSIELNVNLG NSSIFTNTLP ATAASLDNLQ  600
SGDFGYVEIN NAFTSATGNI VGARNFSANA EVIIDRFEFI PVTATFEAEY DLERAQK     657

SEQ ID NO: 210          moltype = AA  length = 657
FEATURE                 Location/Qualifiers
REGION                  1..657
```

```
                        note = Cry1B variant
source                  1..657
                        mol_type = protein
                        organism = synthetic construct
SEQUENCE: 210
MPSNRKNENE IINALSIPAV SNHSAQMDLS LDARIEDSLC IAEGNNINPL VSASTVQTGI  60
NIAGRILGVL GVPFAGQLAS FYSFLVGELW PSGRDPWEIF LEHVEQLIRQ QVTENTRNTA  120
IARLEGLGRG YRSYQQALET WLDNRNDART RSVLYTQYIA LELDFLNAMP LFAINNQQVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRTYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTQGLTNN TSINPVTLQF TSRDVYRTES NAGTNILFTT PVNGVPWARF  420
NFINPQNIYE RGATTYSQPY QGVGIQLFDS ETELPPETTE RPNYESYSHR LSHIGLIIGN  480
TLRAPVYSWT HRSADRTNTI GPNRITQIPA VKGRFLFNGS VISGPGFTGG DVVRLNRNNG  540
NIQNRGYIEV PIQFTSTSTR YRVRVRYASV TSIELNVNLG NSSIFTNTLP ATAASLDNLQ  600
SGDFGYVEIN NAFTSATGNI VGARNFSANA EVIIDRFEFI PVTATFEAEY DLERAQK     657

SEQ ID NO: 211          moltype = AA  length = 657
FEATURE                 Location/Qualifiers
REGION                  1..657
                        note = Cry1B variant
source                  1..657
                        mol_type = protein
                        organism = synthetic construct
SEQUENCE: 211
MPSNRKNENE IINALSIPAV SNHSAQMDLS LDARIEDSLC IAEGNNINPL VSASTVQTGI  60
NIAGRILGVL GVPFAGQLAS FYSFLVGELW PSGRDPWEIF LEHVEQLVRQ QITENARNTA  120
LARLQGLGAS FRAYQQSLED WLENRDDARS RSIILERYVA LELDITTAIP LFRIRNEEVP  180
LLMVYAQAAN LHLLLLRDAS LFGSEFGLTS QEIQRYYERQ AEKTREYSDY CARWYNTGLN  240
NLRGTNAESW LRYNQFRRDL TLGVLDLVAL FPSYDTRTYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTQGLTNN TSINPVTLQF TSRDVYRTES NAGTNILFTT PVNGVPWARF  420
NFINPQNIYE RGATTYSQPY QGVGIQLFDS ETELPPETTE RPNYESYSHR LSHIGLIIGN  480
TLRAPVYSWT HRSADRTNTI GPNRITQIPA VKGRFLFNGS VISGPGFTGG DVVRLNRNNG  540
NIQNRGYIEV PIQFTSTSTR YRVRVRYASV TSIELNVNLG NSSIFTNTLP ATAASLDNLQ  600
SGDFGYVEIN NAFTSATGNI VGARNFSANA EVIIDRFEFI PVTATFEAEY DLERAQK     657

SEQ ID NO: 212          moltype = DNA  length = 3501
FEATURE                 Location/Qualifiers
source                  1..3501
                        mol_type = other DNA
                        organism = Bacillus thuringiensis
SEQUENCE: 212
atggagatca acaatcagaa gcagtgcatc ccatacaact gtctgtctaa ccccgaagag  60
gtcctccttg atggtgagcg tatccttccc gacattgatc cactggaggt tagtctctca  120
ctcctccagt tcttgctcaa caacttcgtg ccaggaggtg gcttcatctc cggattggtt  180
gacaagatct ggggcgcatt gagaccctca gagtgggacc tgttcctcgc tcagatcgag  240
cgcttgatcg accagaggat tgaggctacc gtcagagcca aggctatcac tgagctggag  300
ggactgggta ggaactacca gatctatgcc gaggctttca aggagtggga ctctgaccct  360
gacaacgagg ctgcaaagtc tcgcgtgatc gacaggttcc gtatcctcga tgggcttatc  420
gaggccaaca tcccttcctt ccgtatcatc gagttcgagg tcccactgct gtccgtctat  480
gtccaagcag ccaacttgca cctcgcattg ctcagggact ctgtgatctt tggcgaaagg  540
tggggattga ctaccaagaa cgtgaacgac atctacaacc gccagatccg cgagatccac  600
gagtactcca accactgcgt cgacacctac aacaccgagc tggagagact cggctttcgc  660
tcaatcgctc agtggcgcat ctacaaccag ttccgtaggg agctgactct caccgtcttg  720
gacatcgtcg cactgtttcc caactacgac tctaggctgt accctatcca gaccttctcc  780
cagcttacta gggagatcgt gaccagtcca gtctcagagt tctactacgg tgtcatcaac  840
tccgggaaca tcatcggtac cctcactgag cagcagatcc gcagacctca cttgatggac  900
ttcttcaact ccatgatcat gtacacctcc gacaaccgta aggagcacta ctggagtgga  960
ctggagatga ctgcctactt taccggattc gcaggtgcac aagtgtcctt cccactggtc  1020
ggtacacgtg gagaatccgc acctccactt actgtcaggt ctgtcaacga cggcatctac  1080
cgtatcctct cagctccctt ctactcagca cccttccttg gaaccatcgt ccttggatca  1140
cgcggtgaga agttcgactt cgcactgaac aacatctccc ctccaccttc caccatctac  1200
agacaccctg gaactgtgga ctcacttgtc tctatcccac ctcaggacaa ctccgttcca  1260
cctcacagag gatcttccca ccgtctgagt cacgtgacta tgagagcctc cagtcccatc  1320
tttcactgga cccacagatc tgctaccacc accaacacca tcaaccccaa cgccatcatc  1380
cagataccct tggtcaaggc cttcaacctg cactctggag ctacagttgt tcgcggacca  1440
ggcttcactg gtggagacat cttgaggcgt accaacaccg ggacattcgc agacatgcgt  1500
gtgaacatca ccggaccact gtctcagagg tatagggtga ggattcgcta tgccagtacc  1560
actgacctcc agttcttcac caggatcaac ggtaccaccg tcaacatcgg caacttcacc  1620
aggaccatga actctggaga caacctggaa tccgggaact tccgtactgc agggttctcc  1680
actcccttca gcttctccaa cgcacagtca accttcactc tgggtacaca gcctttctcc  1740
aaccaggagg tgtacatcga taggatcgag tttgtgccag ctgaggtgac cttcgaagcc  1800
gagtctgacc ttgagcgtgc tcagaaagcc gtgaacgcac tgttcacttc caccaaccag  1860
ctcggtctga agaccgatgt gactgactac cagatcgacc aggtctcaaa cctggttgag  1920
tgccttagtg acgagttctg cttggacgag aagcgtgagc tgtctgagaa ggtcaagcac  1980
gctaaacgcc tgtccgacaa gcgcaatctc ctgcaagacc ccaacttcac ctccatcaac  2040
cgtcaactcg atcgtggttg gcgtggatca actgacatca ccatccaagg tgggaacgac  2100
gtcttcaagg agaactacgt taccttgcca ggtaccttcg acgagtgcta ccctacctac  2160
```

```
ctgtaccaga tcatcgacga gtctaagctg aaggcctaca ctcgctatga actgagaggg  2220
tacatcgagg actcccagga cctcgaagtc tacctgatcc gctacaacgc caagcacgag  2280
accgtcaatg ttcctgggac aggatctctg tggcctctgt ccgttgagag tcctataggc  2340
agatgtggtg agcctaaccg atgcgttcct cacattgagt ggaaccctga cctggactgt  2400
tcatgtcgtg acggagagaa gtgtgctcac cactcacacc acttctcctt ggacattgac  2460
gtcggatgca ctgacctcaa tgaggacttg ggagtctggg tgatcttcaa gatcaagacc  2520
caggacggtc acgctaggtt gggtaacctc gaattcctgg aggagaagcc attgctcggt  2580
gaagcattgg ctcgcgtcaa acgcgctgag aagaagtggc gtgacaaacg tgagcagctc  2640
cagttcgaga ccaacatcgt ctacaaggag gctaaggagt cagtggatgc cctcttcgtg  2700
gactcccact acaatcgtct gcaagccgac accaacatca ccatgatcca cgctgcagac  2760
aaacgtgtcc acaggatcag ggaagcttac ttgccagagt tgtccgtgat accaggtgtg  2820
aatgctgaca tcttcgagga gctggaagga ctgatcttca cagccttcag tctctacgac  2880
gctcgcaaca tcatcaagaa cggcgacttc aacaacggtc tctcctgctg gaacgtcaag  2940
ggtcacgtgg acattcagca gaacgaccac agatctgttc tggtcgtgcc tgaatgggag  3000
tccgaggtct cacaggaagt gcgtgtttgc ccaggtagag ggtacattct cagggtgact  3060
gcttacaagg agggctatgg cgaaggatgc gtgaccatac acgagatcga ggacaacacc  3120
gacgagctga agttctccaa ctgcatcgag gaggaggttt accctactga cactggcaac  3180
gactacactg ctcaccaggg tactactgga tgtgcagacg cttgcaactc ccgtaacgtc  3240
ggctacgagg acggttacga gatcaacacc actgccagtg tcaactacaa gcctacctac  3300
gaggaggaga tgtacaccga tgtgaggagg gacaaccact gcgagtacga cagagggtat  3360
ggtaaccaca caccactgcc tgctgggtat gtgaccaagg agctggagta cttccctgaa  3420
accgacactg tgtggataga gatcggtgag actgaaggca ccttcatcgt ggattccgtc  3480
gagctgctcc ttatggagga g                                           3501

SEQ ID NO: 213          moltype = AA  length = 1167
FEATURE                 Location/Qualifiers
source                  1..1167
                        mol_type = protein
                        organism = Bacillus thuringiensis
SEQUENCE: 213
MEINNQKQCI PYNCLSNPEE VLLDGERILP DIDPLEVSLS LLQFLLNNFV PGGGFISGLV  60
DKIWGALRPS EWDLFLAQIE RLIDQRIEAT VRAKAITELE GLGRNYQIYA EAFKEWESDP  120
DNEAAKSRVI DRFRILDGLI EANIPSFRII EFEVPLLSVY VQAANLHLAL LRDSVIFGER  180
WGLTTKNVND IYNRQIREIH EYSNHCVDTY NTELERLGFR SIAQWRIYNQ FRRELTLTVL  240
DIVALFPNYD SRLYPIQTFS QLTREIVTSP VSEFYYGVIN SGNIIGTLTE QQIRRPHLMD  300
FFNSMIMYTS DNRREHYWSG LEMTAYFTGF AGAQVSFPLV GTRGESAPPL TVRSVNDGIY  360
RILSAPFYSA PFLGTIVLGS RGEKFDFALN NISPPPSTIY RHPGTVDSLV SIPPQDNSVP  420
PHRGSSHRLS HVTMRASSPI FHWTHRSATT TNTINPNAII QIPLVKAFNL HSGATVVRGP  480
GFTGGDILRR TNTGTFADMR VNITGPLSQR YRVRIRYAST TDLQFFTRIN GTTVNIGNFT  540
RTMNSGDNLE SGNFRTAGFS TPFSFSNAQS TFTLGTQPFS NQEVYIDRIE FVPAEVTFEA  600
ESDLERAQKA VNALFTSTNQ LGLKTDVTDY QIDQVSNLVE CLSDEFCLDE KRELSEKVKH  660
AKRLSDKRNL LQDPNFTSIN RQLDRGWRGS TDITIQGGND VFKENYVTLP GTFDECYPTY  720
LYQKIDESKL KAYTRYELRG YIEDSQDLEV YLIRYNAKHE TVNVPGTGSL WPLSVESPIG  780
RCGEPNRCVP HIEWNPDLDC SCRDGEKCAH HSHHFSLDID VGCTDLNEDL GVWVIFKIKT  840
QDGHARLGNL EFLEEKPLLG EALARVKRAE KKWRDKREQL QFETNIVYKE AKESVDALFV  900
DSHYNRLQAD TNITMIHAAD KRVHRIREAY LPELSVIPGV NADIFEELEG LIFTAFSLYD  960
ARNIIKNGDF NNGLSCWNVK GHVDIQQNDH RSVLVVPEWE SEVSQEVRVC PGRGYILRVT  1020
AYKEGYGEGC VTIHEIEDNT DELKFSNCIE EEVYPTDTGN DYTAHQGTTG CADACNSRNV  1080
GYEDGYEINT TASVNYKPTY EEEMYTDVRR DNHCEYDRGY GNHTPLPAGY VTKELEYFPE  1140
TDTVWIEIGE TEGTFIVDSV ELLLMEE                                     1167

SEQ ID NO: 214          moltype = DNA  length = 3501
FEATURE                 Location/Qualifiers
misc_feature            1..3501
                        note = Cry1J variant coding sequence
source                  1..3501
                        mol_type = other DNA
                        organism = synthetic construct
SEQUENCE: 214
atggagatca acaatcagaa gcagtgcatc ccatacaact gtctgtctaa ccccgaagag  60
gtcctccttg atggtgagcg tatccttccc gacattgatc cactggaggt tagtctctca  120
ctcctccagt tcttgctcaa caacttcgtg ccaggaggtg gcttcatctc cggattggtt  180
gacaagatct ggggcgcatt gagaccctca gagtgggacc tgttcctcgc tcagatcgag  240
cgcttgatcg accagaggat tgaggctacc gtcagagcca aggctatcac tgagctggag  300
ggactgggta ggaactacca gatctatgcc gaggctttca aggagtggga ctctgaccct  360
gacaacgagg ctgcaaagtc tcgcgtgatc gacaggttcc gtatcctcga tgggcttatc  420
gaggccaaca tcccttcctt ccgtatcatc gagttcgagg tcccactgct gtccgtctat  480
gtccaagcag ccaacttgca cctcgcattg ctcagggact ctgtgatctt tggcgaaagg  540
tggggattga ctaccaagaa cgtgaacgac atctacaacc gccagatccg cgagatccac  600
gagtactcca accactgcgt cgacacctac aacaccgagc tggagagact cggctttcgc  660
tcaatcgctc agtggcgcat ctacaaccag ttccgtaggg agctgactct caccgtcttg  720
gacatcgtcg cactgtttcc caactacgac tctaggctgt accctatcca gaccttctcc  780
cagcttacta gggagatcgt gaccagtcca gtctcagagt tctactacgg tgtcatcaac  840
tccgggaaca tcatcggtac cctcactgag cagcagatcc gcagacctca cttgatggac  900
ttcttcaact ccatgatcat gtacacctcc gacaaccgta aggagcacta ctggagtgga  960
ctggagatga ctgcctactt taccggattc gcaggtgcac aagtgtcctt cccactggtc  1020
ggtacacgtg gagaatccgc acctccactt actgtcaggt ctgtcaacga cggcatctac  1080
cgtatcctct cagctcccttt ctactcagca cccttccttg gaaccatcgt ccttggatca  1140
cgcggtgaga agttcgactt cgcactgaac aacatctccc ctccaccttc caccatctac  1200
```

```
agacaccctg gaactgtgga ctcacttgtc tctatcccac ctcaggacaa ctccgttcca  1260
cctcacagag gatcttccca ccgtctgagt cacgtgacta tgagagcctc cagtcccatc  1320
tttcactgga cccacagatc tgctaccacc accaacacca tcaaccccaa cgccatcatc  1380
cagataccct tggtcaaggc cttcaacctg cactctggag ctacagttgt tcgcggacca  1440
ggcttcactg gtggagacat cttgaggcgt accaacaccg ggacattcgc agacatgcgt  1500
gtgaacatca ccggaccact gtctcagagg tatagggtga ggattcgcta tgccagtacc  1560
actgacctcc agttcttcac caggatcaac ggtaccaccg tcaacatcgg caacttcacc  1620
aggaccatga actctggaga caacctggaa tccgggaact tccgtactgc agggttctcc  1680
actcccttca gcttctccaa cgcacagtca accttcactc tgggtacaca ggctttctcc  1740
aaccaggagg tgtacatcga taggatcgag tttgtgccag ctgaggtgac cttcgaagcc  1800
gagtctgacc ttgagcgtgc tcagaaagcc gtgaacgcac tgttcacttc caccaaccag  1860
ctcggtctga agaccgatgt gactgactac cagatcgacc aggtctcaaa cctggttgag  1920
tgccttagtg acgagttctg cttggacgag aagcgtgagc tgtctgagaa ggtcaagcac  1980
gctaaacgcc tgtccgacaa gcgcaatctc ctgcaagacc ccaacttcac ctccatcaac  2040
cgtcaactcg atcgtggttg gcgtggatca actgacatca ccatccaagg tgggaacgac  2100
gtcttcaagg agaactacgt taccttgcca ggtaccttcg acgagtgcta ccctacctac  2160
ctgtaccaga tcatcgacga gtctaagctg aaggcctaca ctcgctatga actgagaggg  2220
tacatcgagg actcccagga cctcgaagtc tacctgatcc gctacaacgc caagcacgag  2280
accgtcaatg ttcctgggac aggatctctg tggcctctgt ccgttgagag tcctataggc  2340
agatgtggtg agcctaaccg atgcgttcct cacattgagt ggaaccctga cctggactgt  2400
tcatgtcgtg acggagagaa gtgtgctcac cactcacacc acttctcctt ggacattgac  2460
gtcggatgca ctgacctcaa tgaggacttg ggagtctggg tgatcttcaa gatcaagacc  2520
caggacggtc acgctaggtt gggtaacctc gaattcctgg aggagaagcc attgctcggt  2580
gaagcattgg ctcgcgtcaa acgcgctgag aagaagtggc gtgacaaacg tgagcagctc  2640
cagttcgaga ccaacatcgt ctacaaggag gctaaggagt cagtggatgc cctcttcgtg  2700
gactcccact acaatcgtct gcaagccgac accaacatca ccatgatcca cgctgcagac  2760
aaacgtgtcc acaggatcag ggaagcttac ttgccagagt tgtccgtgat accaggtgtg  2820
aatgctgaca tcttcgagga gctggaagga ctgatcttca cagccttcag tctctacgac  2880
gctcgcaaca tcatcaagaa cggcgacttc aacaacggtc tctcctgctg gaacgtcaag  2940
ggtcacgtgg acattcagca gaacgaccac agatctgttc tggtcgtgcc tgaatgggag  3000
tccgaggtct cacaggaagt gcgtgtttgc ccaggtagag ggtacattct cagggtgact  3060
gcttacaagg agggctatgg cgaaggatgc gtgaccatac acgagatcga ggacaacacc  3120
gacgagctga agttctccaa ctgcatcgag gaggaggttt accctactga cactggcaac  3180
gactacactg ctcaccaggg tactactgga tgtgcagacg cttgcaactc ccgtaacgtc  3240
ggctacgagg acggttacga gatcaacacc actgccagtg tcaactacaa gcctacctac  3300
gaggaggaga tgtacaccga tgtgaggagg gacaaccact gcgagtacga cagagggtat  3360
ggtaaccaca caccactgcc tgctgggtat gtgaccaagg agctggagta cttccctgaa  3420
accgacactg tgtggataga gatcggtgag actgaaggca ccttcatcgt ggattccgtc  3480
gagctgctcc ttatggagga g                                             3501

SEQ ID NO: 215          moltype = AA  length = 1167
FEATURE                 Location/Qualifiers
REGION                  1..1167
                        note = Cry1J variant
source                  1..1167
                        mol_type = protein
                        organism = synthetic construct
SEQUENCE: 215
MEINNQKQCI PYNCLSNPEE VLLDGERILP DIDPLEVSLS LLQFLLNNFV PGGGFISGLV  60
DKIWGALRPS EWDLFLAQIE RLIDQRIEAT VRAKAITELE GLGRNYQIYA EAFKEWESDP  120
DNEAAKSRVI DRFRILDGLI EANIPSFRII EFEVPLLSVY VQAANLHLAL LRDSVIFGER  180
WGLTTKNVND IYNRQIREIH EYSNHCVDTY NTELERLGFR SIAQWRIYNQ FRRELTLTVL  240
DIVALFPNYD SRLYPIQTFS QLTREIVTSP VSEFYYGVIN SGNIIGTLTE QQIRRPHLMD  300
FFNSMIMYTS DNRREHYWSG LEMTAYFTGF AGAQVSFPLV GTRGESAPPL TVRSVNDGIY  360
RILSAPFYSA PFLGTIVLGS RGEKFDFALN NISPPPSTIY RHPGTVDSLV SIPPQDNSVP  420
PHRGSSHRLS HVTMRASSPI FHWTHRSATT TNTINPNAII QIPLVKAFNL HSGATVVRGP  480
GFTGGDILRR TNTGTFADMR VNITGPLSQR YRVRIRYAST TDLQFFTRIN GTTVNIGNFT  540
RTMNSGDNLE SGNFRTAGFS TPFSFSNAQS TFTLGTQVFS NQEVYIDRIE FVPAEVTFEA  600
ESDLERAQKA VNALFTSTNQ LGLKTDVTDY QIDQVSNLVE CLSDEFCLDE KRELSEKVKH  660
AKRLSDKRNL LQDPNFTSIN RQLDRGWRGS TDITIQGGND VFKENYVTLP GTFDECYPTY  720
LYQKIDESKL KAYTRYELRG YIEDSQDLEV YLIRYNAKHE TVNVPGTGSL WPLSVESPIG  780
RCGEPNRCVP HIEWNPDLDC SCRDGEKCAH HSHHFSLDID VGCTDLNEDL GVWVIFKIKT  840
QDGHARLGNL EFLEEKPLLG EALARVKRAE KKWRDKREQL QFETNIVYKE AKESVDALFV  900
DSHYNRLQAD TNITMIHAAD KRVHRIREAY LPELSVIPGV NADIFEELEG LIFTAFSLYD  960
ARNIIKNGDF NNGLSCWNVK GHVDIQQNDH RSVLVVPEWE SEVSQEVRVC PGRGYILRVT  1020
AYKEGYGEGC VTIHEIEDNT DELKFSNCIE EEVYPTDTGN DYTAHQGTTG CADACNSRNV  1080
GYEDGYEINT TASVNYKPTY EEEMYTDVRR DNHCEYDRGY GNHTPLPAGY VTKELEYFPE  1140
TDTVWIEIGE TEGTFIVDSV ELLLMEE                                       1167

SEQ ID NO: 216          moltype = DNA  length = 3501
FEATURE                 Location/Qualifiers
misc_feature            1..3501
                        note = soybean optimized coding sequence
source                  1..3501
                        mol_type = other DNA
                        organism = synthetic construct
SEQUENCE: 216
atggagatca acaatcagaa gcaatgcatc ccatacaact gcctgtctaa cccagaggag  60
gtccttctcg acggagaacg tatactccca gacattgacc cactggaagt ctccttgtca  120
```

```
ctgctccagt tcctgctcaa caacttcgtg ccaggtggag gtttcatctc cggactcgtt  180
gacaagatct ggggagctct gagacccagt gagtgggacc tctttcttgc tcagatcgag  240
aggctcatcg atcagaggat tgaggctaca gtcagagcca aggccatcac agagttggaa  300
ggccttggca ggaactacca gatctatgca gaagccttca aggactggga atctgatcct  360
gacaacgagg ctgcaaagtc tcgtgtcatc gacaggttta ggatactgga tggcttgatc  420
gaggctaaca tcccatcctt ccgtatcatt gagttcgagg tgcccttgct ctcagtctat  480
gtgcaagctg ccaaccttca cttggcattg ctcagagact ccgtgatctt tggcgaacgt  540
tggggcctta ccaccaagaa cgtcaacgac atctacaacc gtcagattcg cgagattcac  600
gagtattcca accactgcgt ggacacctac aacaccgagt tggaacgcct gggattcagg  660
agtatcgcac agtggaggat ctacaaccag ttccgtcgcg aacttactct cactgtcctc  720
gatatcgtcg cactctttcc caactacgac tcacgtctgt accctatcca gaccttctcc  780
caactgactc gagagatcgt cacttcacca gtctccgagt tctactatgg agtgatcaac  840
tcaggcaaca tcatcggcac tctcacagag cagcagatcc gtagacctca cctgatggac  900
ttcttcaact ccatgatcat gtacacctct gacaaccgtc gtgagcacta ctggagtgga  960
ctggagatga cagcctactt cactggattc gcaggtgcac aggtcagttt cccactggtc  1020
ggaaccagag gtgaatctgc accacctctg actgtcaggt cagtcaacga cggtatctat  1080
cgcattctca gtgctccctt ctactcagca ccattcctcg gtaccatagt cctgggtagt  1140
agaggtgaga agttcgactt cgccctcaac aacatctcac ctcctccctc aaccatctac  1200
cgacaccctg gaactgttga ttccttggtc agtatcccac ctcaggacaa ttccgttcca  1260
ccacatcgtg gctcatcaca caggctctct cacgttacca tgagggcatc tagtccaatc  1320
ttccactgga ctcacaggtc agctactacc accaacacca tcaaccctaa cgctatcatt  1380
cagatccctt tggtgaaagc cttcaatctg cactctggtg ccacagttgt tagaggacct  1440
ggcttcacag gtggagacat actccgtagg accaacactg gaaccttcgc tgacatgcgt  1500
gtcaacatca ctggtccctt gagtcagagg tacagagtcc gcatacgtta cgcctctacc  1560
actgatctgc agttcttcac acgcatcaac ggtaccaccg tgaacattgg gaactttacc  1620
cgtaccatga actcaggcga caaccttgag tctggtaact ttaggaccgc aggtttcagt  1680
acacccttct ccttctccaa tgcccagtca acattcacct tgggtacaca acccttctcc  1740
aaccaggaag tctacattga ccgtatcgag tttgtgccag tcgaggtcac attcgaggct  1800
gaaagtgacc ttgagagagc tcagaaggca gtcaacgctc tgttcactag taccaaccag  1860
cttggactga agactgatgt gacagactat cagatcgacc aagtgtccaa cctcgttgag  1920
tgcttgtcag acgagttctg cctggacgag aaacgcgagt tgtccgagaa ggtcaagcac  1980
gctaaacgcc tctctgacaa gcgcaatctg ctccaagacc ctaacttcac atccatcaac  2040
cgtcaactcg atcgtggatg gagaggttcc accgacatca ccattcaagg aggcaacgac  2100
gtcttcaagg agaactacgt cacacttccc gggactttcg acgagtgcta tccaacctac  2160
ctctaccaga tcatcgacga gtccaagctc aaagcctaca ctcgctacga actccgtggg  2220
tacatcgagg atagtcagga cctggaggtg tatctgatcc gttacaacgc taagcacgag  2280
actgtcaatg tcccaggaac tggtagtctc tggcccttgt ccgttgagtc tcctattgga  2340
cgttgtggag aacccaatcg ctgtgtccct cacatcgagt ggaacccaga cttggattgc  2400
tcatgccgtg atggagagaa gtgcgcacac cattcacacc acttctcact ggacattgat  2460
gtcgggtgca ctgatctcaa cgaggatctt ggagtctggg tgatcttcaa gatcaagacc  2520
caggatggac acgcaaggtt gggtaacctt gagttcctgg aggagaagcc tttgctggga  2580
gaagctttgg caagggtcaa gcgtgccgag aagaagtggc gtgacaagcg tgaacagctc  2640
cagttcgaga ccaacatcgt ctacaaggag gctaaggagt cagtggacgc actgttcgtg  2700
gactctcact acaacaggtt gcaagccgac accaacatca ccatgattca cgcagctgac  2760
aagagggttc accgcattag agaggcatac ttgccagagc tctcagtcat ccctggtgtc  2820
aacgctgaca tcttcgaaga gctggaggga ctgatcttta cagccttctc cctgtacgat  2880
gctcgcaaca tcatcaagaa cggcgacttc aacaacggct tgtcctgctg gaacgtgaaa  2940
ggccacgttg atatccagca gaacgaccac agatccgtcc tggttgtccc tgaatgggaa  3000
tccgaggtta gtcaggaagt tcgcgtgtgt cctggacgtg gatacattct cagagtgacc  3060
gcttacaagg agggatacgg tgaaggatgc gtgactatcc acgagatcga ggacaacacc  3120
gacgagctca agttctccaa ctgcattgag gaggaagtgt accctactga cactgggaac  3180
gactacactg ctcaccaagg cactactgga tgtgctgatg catgcaactc tcgcaacgtt  3240
gggtacgagg atggatacga gatcaacacc acagcctccg tcaactacaa gcctacctac  3300
gaagaggaga tgtacaccga cgttaggcgt gacaaccact gtgagtacga tcgtggatac  3360
ggcaaccaca ctccattgcc agctggttat gtcaccaagg agctcgagta cttcccagag  3420
accgatactg tctggatcga gataggagag actgagggta ccttcatcgt tgacagtgtc  3480
gaactcttgc tgatggagga g                                           3501
```

```
SEQ ID NO: 217         moltype = AA  length = 1167
FEATURE                Location/Qualifiers
REGION                 1..1167
                       note = Cry1J variant
source                 1..1167
                       mol_type = protein
                       organism = synthetic construct
SEQUENCE: 217
MEINNQKQCI PYNCLSNPEE VLLDGERILP DIDPLEVSLS LLQFLLNNFV PGGGFISGLV  60
DKIWGALRPS EWDLFLAQIE RLIDQRIEAT VRAKAITELE GLGRNYQIYA EAFKDWESDP  120
DNEAAKSRVI DRFRILDGLI EANIPSFRII EFEVPLLSVY VQAANLHLAL LRDSVIFGER  180
WGLTTKNVND IYNRQIREIH EYSNHCVDTY NTELERLGFR SIAQWRIYNQ FRRELTLTVL  240
DIVALFPNYD SRLYPIQTFS QLTREIVTSP VSEFYYGVIN SGNIIGTLTE QQIRRPHLMD  300
FFNSMIMYTS DNRREHYWSG LEMTAYFTGF AGAQVSFPLV GTRGESAPPL TVRSVNDGIY  360
RILSAPFYSA PFLGTIVLGS RGEKFDFALN NISPPPSTIY RHPGTVDSLV SIPPQDNSVP  420
PHRGSSHRLS HVTMRASSPI FHWTHRSATT TNTINPNAII QIPLVKAFNL HSGATVVRGP  480
GFTGGDILRR TNTGTFADMR VNITGPLSQR YRVRIRYAST TDLQFFTRIN GTTVNIGNFT  540
RTMNSGDNLE SGNFRTAGFS TPFSFSNAQS TFTLGTQPFS NQEVYIDRIE FVPVEVTFEA  600
ESDLERAQKA VNALFTSTNQ LGLKTDVTDY QIDQVSNLVE CLSDEFCLDE KRELSEKVKH  660
AKRLSDKRNL LQDPNFTSIN RQLDRGWRGS TDITIQGGND VFKENYVTLP GTFDECYPTY  720
LYQIIDESKL KAYTRYELRG YIEDSQDLEV YLIRYNAKHE TVNVPGTGSL WPLSVESPIG  780
```

-continued

```
RCGEPNRCVP HIEWNPDLDC SCRDGEKCAH HSHHFSLDID VGCTDLNEDL GVWVIFKIKT  840
QDGHARLGNL EFLEEKPLLG EALARVKRAE KKWRDKREQL QFETNIVYKE AKESVDALFV  900
DSHYNRLQAD TNITMIHAAD KRVHRIREAY LPELSVIPGV NADIFEELEG LIFTAFSLYD  960
ARNIIKNGDF NNGLSCWNVK GHVDIQQNDH RSVLVVPEWE SEVSQEVRVC PGRGYILRVT  1020
AYKEGYGEGC VTIHEIEDNT DELKFSNCIE EEVYPTDTGN DYTAHQGTTG CADACNSRNV  1080
GYEDGYEINT TASVNYKPTY EEEMYTDVRR DNHCEYDRGY GNHTPLPAGY VTKELEYFPE  1140
TDTVWIEIGE TEGTFIVDSV ELLLMEE                                    1167

SEQ ID NO: 218         moltype = DNA  length = 3501
FEATURE                Location/Qualifiers
misc_feature           1..3501
                       note = soybean optimized coding sequence
source                 1..3501
                       mol_type = other DNA
                       organism = synthetic construct
SEQUENCE: 218
atggagatca acaatcagaa gcaatgcatc ccatacaact gcctgtctaa cccagaggag  60
gtccttctcg acggagaacg tatactccca gacattgacc cactggaagt ctccttgtca  120
ctgctccagt tcctgctcaa caacttcgtg ccaggtggag gtttcatctc cggactcgtt  180
gacaagatct ggggagctct gagacccagt gagtgggacc tctttcttgc tcagatcgag  240
aggctcatcg atcagaggat tgaggctaca gtcagagcca aggccatcac agagttggaa  300
ggccttggca ggaactacca gatctatgca gaagccttca aggactggga atctgatcct  360
gacaacgagg ctgcaaagtc tcgtgtcatc gacaggttta ggatactgga tggcttgatc  420
gaggctaaca tcccatcctt ccgtatcatt gagttcgagg tgcccttgct ctcagtctat  480
gtgcaagctg ccaaccttca cttggcattg ctcagagact ccgtgatctt tggcgaacgt  540
tggggcctta ccaccaagaa cgtcaacgac atctacaacc gtcagattcg cgagattcac  600
gagtattcca accactgcgt ggacacctac aacaccgagt tggaacgcct gggattcagg  660
agtatcgcac agtggaggat ctacaaccag ttccgtcgcg aacttactct cactgtcctc  720
gatatcgtcg cactctttcc caactacgac tcacgtctgt accctatcca gaccttctcc  780
caactgactc gagagatcgt cacttcacca gtctccgagt tctactatgg agtgatcaac  840
tcaggcaaca tcatcggcac tctcacagag cagcagatcc gtagacctca cctgatggac  900
ttcttcaact ccatgatcat gtacacctct gacaaccgtc gtgagcacta ctggagtgga  960
ctggagatga cagcctactt cactggattc gcaggtgcac aggtcagttt cccactggtc  1020
ggaaccagag gtgaatctgc accacctctg actgtcaggt cagtcaacga cggtatctat  1080
cgcattctca gtgctccctt ctactcagca ccattcctcg gtaccatagt cctgggtagt  1140
agaggtgaga agttcgactt cgccctcaac aacatctcac ctcctccctc aaccatctac  1200
cgacaccctg gaactgttga ttccttggtc agtatcccac ctcaggacaa ttccgttcca  1260
ccacatcgtg gctcatcaca caggctctct cacgttacca tgagggcatc tagtccaatc  1320
ttccactgga ctcacaggtc agctactacc accaacacca tcaaccctaa cgctatcatt  1380
cagatccctt tggtgaaagc cttcaatctg cactctggtg ccacagttgt tagaggacct  1440
ggcttcacag gtggagacat actccgtagg accaacactg gaaccttcgc tgacatgcgt  1500
gtcaacatca ctggtccctt gagtcagagg tacagagtcc gcatacgtta cgcctctacc  1560
actgatctgc agttcttcac acgcatcaac ggtaccaccg tgaacattgg gaactttacc  1620
cgtaccatga actcaggcga caaccttgag tctggtaact ttaggaccgc aggtttcagt  1680
acacccttct ccttctccaa tgcccagtca acattcacct tgggtacaca agtcttctcc  1740
aaccaggaag tctacattga ccgtatcgag tttgtgccag tcgaggtcac attcgaggct  1800
gaaagtgacc ttgagagagc tcagaaggca gtcaacgctc tgttcactag taccaaccag  1860
cttggactga agactgatgt gacagactat cagatcgacc aagtgtccaa cctcgttgag  1920
tgcttgtcag acgagttctg cctggacgag aaacgcgagt tgtccgagaa ggtcaagcac  1980
gctaaacgcc tctctgacaa gcgcaatctg ctccaagacc ctaacttcac atccatcaac  2040
cgtcaactcg atcgtggatg gagaggttcc accgacatca ccattcaagg aggcaacgac  2100
gtcttcaagg agaactacgt cacacttccc gggactttcg acgagtgcta tccaacctac  2160
ctctaccaga tcatcgacga gtccaagctc aaagcctaca ctcgctacga actccgtggg  2220
tacatcgagg atagtcagga cctggaggtg tatctgatcc gttacaacgc taagcacgag  2280
actgtcaatg tcccaggaac tggtagtctc tggcccttgt ccgttgagtc tcctattgga  2340
cgttgtggag aacccaatcg ctgtgtccct cacatcgagt ggaacccaga cttggattgc  2400
tcatgccgtg atggagagaa gtgcgcacac cattcacacc acttctcact ggacattgat  2460
gtcgggtgca ctgatctcaa cgaggatctt ggagtctggg tgatcttcaa gatcaagacc  2520
caggatggac acgcaaggtt gggtaacctt gagttcctgg aggagaagcc tttgctggga  2580
gaagctttgg caagggtcaa gcgtgccgag aagaagtggc gtgacaagcg tgaacagctc  2640
cagttcgaga ccaacatcgt ctacaaggag gctaaggagt cagtggacgc actgttcgtg  2700
gactctcact acaacaggtt gcaagccgac accaacatca ccatgattca cgcagctgac  2760
aagagggttc accgcattag agaggcatac ttgccagagc tctcagtcat ccctggtgtc  2820
aacgctgaca tcttcgaaga gctggaggga ctgatcttta cagccttctc cctgtacgat  2880
gctcgcaaca tcatcaagaa cggcgacttc aacaacggct tgtcctgctg gaacgtgaaa  2940
ggccacgttg atatccagca gaacgaccac agatccgtcc tggttgtccc tgaatgggaa  3000
tccgaggtta gtcaggaagt tcgcgtgtgt cctggacgtg gatacattct cagagtgacc  3060
gcttacaagg agggatacgg tgaaggatgc gtgactatcc acgagatcga ggacaacacc  3120
gacgagctca agttctccaa ctgcattgag gaggaagtgt accctactga cactgggaac  3180
gactacactg ctcaccaagg cactactgga tgtgctgatg catgcaactc tcgcaacgtt  3240
gggtacgagg atggatacga gatcaacacc acagcctccg tcaactacaa gcctacctac  3300
gaagaggaga tgtacaccga cgttaggcgt gacaaccact gtgagtacga tcgtggatac  3360
ggcaaccaca ctccattgcc agctggttat gtcaccaagg agctcgagta cttcccagag  3420
accgatactg tctggatcga gataggagag actgagggta ccttcatcgt tgacagtgtc  3480
gaactcttgc tgatggagga g                                          3501

SEQ ID NO: 219         moltype = AA  length = 1167
FEATURE                Location/Qualifiers
REGION                 1..1167
```

```
                        note = Cry1J variant
source                  1..1167
                        mol_type = protein
                        organism = synthetic construct
SEQUENCE: 219
MEINNQKQCI PYNCLSNPEE VLLDGERILP DIDPLEVSLS LLQFLLNNFV PGGGFISGLV  60
DKIWGALRPS EWDLFLAQIE RLIDQRIEAT VRAKAITELE GLGRNYQIYA EAFKDWESDP  120
DNEAAKSRVI DRFRILDGLI EANIPSFRII EFEVPLLSVY VQAANLHLAL LRDSVIFGER  180
WGLTTKNVND IYNRQIREIH EYSNHCVDTY NTELERLGFR SIAQWRIYNQ FRRELTLTVL  240
DIVALFPNYD SRLYPIQTFS QLTREIVTSP VSEFYYGVIN SGNIIGTLTE QQIRRPHLMD  300
FFNSMIMYTS DNRREHYWSG LEMTAYFTGF AGAQVSFPLV GTRGESAPPL TVRSVNDGIY  360
RILSAPFYSA PFLGTIVLGS RGEKFDFALN NISPPPSTIY RHPGTVDSLV SIPPQDNSVP  420
PHRGSSHRLS HVTMRASSPI FHWTHRSATT TNTINPNAII QIPLVKAFNL HSGATVVRGP  480
GFTGGDILRR TNTGTFADMR VNITGPLSQR YRVRIRYAST TDLQFFTRIN GTTVNIGNFT  540
RTMNSGDNLE SGNFRTAGFS TPFSFSNAQS TFTLGTQVFS NQEVYIDRIE FVPVEVTFEA  600
ESDLERAQKA VNALFTSTNQ LGLKTDVTDY QIDQVSNLVE CLSDEFCLDE KRELSEKVKH  660
AKRLSDKRNL LQDPNFTSIN RQLDRGWRGS TDITIQGGND VFKENYVTLP GTFDECYPTY  720
LYQIIDESKL KAYTRYELRG YIEDSQDLEV YLIRYNAKHE TVNVPGTGSL WPLSVESPIG  780
RCGEPNRCVP HIEWNPDLDC SCRDGEKCAH HSHHFSLDID VGCTDLNEDL GVWVIFKIKT  840
QDGHARLGNL EFLEEKPLLG EALARVKRAE KKWRDKREQL QFETNIVYKE AKESVDALFV  900
DSHYNRLQAD TNITMIHAAD KRVHRIREAY LPELSVIPGV NADIFEELEG LIFTAFSLYD  960
ARNIIKNGDF NNGLSCWNVK GHVDIQQNDH RSVLVVPEWE SEVSQEVRVC PGRGYILRVT  1020
AYKEGYGEGC VTIHEIEDNT DELKFSNCIE EEVYPTDTGN DYTAHQGTTG CADACNSRNV  1080
GYEDGYEINT TASVNYKPTY EEEMYTDVRR DNHCEYDRGY GNHTPLPAGY VTKELEYFPE  1140
TDTVWIEIGE TEGTFIVDSV ELLLMEE                                    1167

SEQ ID NO: 220          moltype = DNA  length = 3771
FEATURE                 Location/Qualifiers
source                  1..3771
                        mol_type = other DNA
                        organism = Bacillus thuringiensis
SEQUENCE: 220
ttgacttcaa ataggaaaaa tgagaatgaa attataaatg ctttatcgat tccaacggta  60
tcgaatcctt ccacgcaaat gaatctatca ccagatgctc gtattgaaga tagcttgtgt  120
gtagccgagg tgaacaatat tgatccattt gttagcgcat caacagtcca aacgggtata  180
aacatagctg gtagaatatt gggcgtatta ggtgtgccgt ttgctggaca actagctagt  240
ttttatagtt ttcttgttgg tgaattatgg cctagtggca gagatccatg ggaaattttc  300
ctggaacatg tagaacaact tataagacaa caagtaacag aaaatactag gaatacggct  360
attgctcgat tagaaggtct aggaagaggc tatagatctt accagcaggc tcttgaaact  420
tggttagata accgaaatga tgcaagatca agaagcatta ttcttgagcg ctatgttgct  480
ttagaacttg acattactac tgctataccg cttttcagaa tacgaaatca agaggttcca  540
ttattaatgg tatatgctca agctgcaaat ttacacctat tattattgag ggacgcatcc  600
ctttttggta gtgaatgggg gacggcatct tccgatgtta accaatatta ccaagaacaa  660
atcagatata cagaggaata ttctaaccat tgcgtacaat ggtataatac ggggctaaat  720
aacttaagag ggacaaatgc tgaaagttgg gtacggtata atcaattccg cagagaccta  780
acattagggg tattagatct agtggcccta ttcccaagtt atgacactcg cacttatcca  840
atcaatacga gtgctcagtt aacaagagaa gtttatacag acgcaattgg gaccgtacat  900
ccgagtcaag cttttgcaag tacgacttgg tttaataata atgcaccatc gttttctgcc  960
atagaagctg ccgttatcag gcctccgcat ctacttgatt ttccagaaca acttacaatt  1020
tacagcacat taagtcgatg gagtaacact cagtttatga atatatgggc aggtcataga  1080
cttgaatccc gcccaatagc agggtcatta aatacctcta cacaaggatc taccaatact  1140
tctattaatc ctgtaacatt acagtttacg tctcgagaca tttataggac tgaatcattg  1200
gcagggctaa atatatttat aactcaacct gttaatgggg ttccttgggt tagatttaat  1260
tggagaaatc ccctgaattc tcttagaggt agccttctct atacgatagg gtatactgga  1320
gttgggacgc aattacaaga ttcagaaact gaattacccc cagaaacaac agaacgacca  1380
aattatgaat catatagtca tagattatct catataggac tcatttcatc atctcatgtg  1440
agagcattgg tatattcttg gacgcaccgt agtgcagatc gtacgaatac gattggacca  1500
aatagaatta ctcaaattcc tgcagtgaag ggaagatttc tttttaatgg ctctgtaatt  1560
tcaggaccag gatttactgg tggagacgta gttagattga ataggaataa tggtaatatt  1620
caaaatagag ggtatattga agttccaatt caattcacgt cgacatctac cagatatcga  1680
gttcgagtac gttatgcttc tgtaacctcg attgagctca atgttaattg gggcaattca  1740
tcaattttta cgaacacatt accagcaaca gctgcatcat tagataatct acaatcaggg  1800
gattttggtt atgttgaaat caacaatgct tttacatccg caacaggtaa tatagtaggt  1860
gttagaaatt ttagtgcaaa tgcagaggta ataatagaca gatttgaatt tatcccagtt  1920
actgcaacct tcgaggcaaa atatgattta gaaagagcac aaaaggcggt gaatgctctg  1980
tttacttcta caaatccaag aagattgaag acagatgtga cagattatca tattgaccaa  2040
gtgtccaatc tggtggtatg tttatcagat gaattttgct tggatgagaa gcgagaatta  2100
tttgagaaag tgaaatatgc gaagcgactc agtgatgaaa gaaacttact ccaagatcca  2160
aacttcacat tcatcaatgg gcaaccaagt tttgcatcca tcgatggaca atcaaacttc  2220
acctctatta atgagctatc taatcatgga tggtggggca gtgcgaatgt taccattcag  2280
gaagggaatg acgtatttaa agagaattac gtcacactac cgggtacttt taatgagtgt  2340
tatccaaatt atttatatca aaaaatagga gagtcagaat taaaggctta tacgcgctat  2400
caattaagag ggtatattga agatagtcaa gatctagaga tttatttaat tcgttacaat  2460
gcaaagcatg aaacattaaa tgttccaggt accgagtccc tatggccgct ttcagttgaa  2520
agcccaatcg gaaggtgcgg agaaccaaat cgatgcgcac cacattttgg atggaatcct  2580
gatctagatt gttcctgcag agatagagaa aaatgtgcgc atcattccca tcatttcact  2640
ttggatattg atgttggatg cacagacttg caagaggatc taggcgtgtg ggttgtattc  2700
aagattaaga cgcaggaagg ttatgcaaga ttaggaaatc tggaatttat cgaagagaaa  2760
ccattaattg gagaagcact gtctcgtgtg aagagagcgg aaaaaaaatg gagagacaaa  2820
```

```
agggaaaaac tacaagtgga aacaaaacga gtatatatag acgcaaaaga agctgtggat  2880
gctttattcg tagattctca atatgataga ttacaagcag atacaaacat cggtatgatt  2940
catgcggcag atagacttgt tcatcggatc cacgaggctt atcttccaga actacctttc  3000
attccaggaa taaatgtggt gatttttgaa gaattagaaa accgtatttc tactgcattt  3060
tccttatatg atgcgagaaa tgtcattaaa aatggcgatt tcaataatgg attgacatgc  3120
tggaacgtga aagggcatgt agaggtacag cagctgaaca atcatcgttc ggtccttgtc  3180
atcccggaat gggaagcaga agtttcacaa aaggtgcgcg tctgtccagg tcgtggctat  3240
attcttcgtg tcacagcgta caaagaggga tatggggaag gctgcgtaac tattcatgaa  3300
gtcgataata atacagacca attgaagttt agcaactgtg agaaaggaca agtatatcca  3360
ggtaatacga tagcatgtaa tgattataat aagaatcatg gtgcgaatgc atgtagttct  3420
cgtaatcgtg gatatgacga attctatgga aacaccccag ctgattattc tgcaaatcaa  3480
aaagaatacg ggggtgcgta cacttcccac aatcatgcat atggcgaatc ttatgaaagt  3540
aattcgtcca taccagctga ttatgcgccg gtttatgaag aagaagcgta tacacatgga  3600
cgaagaggta attcttgtga atataacaga gggtatacac cattaccagc tggttatgtg  3660
acagcagagt tagaatactt cccagaaacg gatacagtat gggttgagat tggagaaacg  3720
gaaggaacat ttatcgtgga caatgtggaa ttactcctta tggaggaata g           3771
```

```
SEQ ID NO: 221          moltype = AA  length = 1256
FEATURE                 Location/Qualifiers
source                  1..1256
                        mol_type = protein
                        organism = Bacillus thuringiensis
SEQUENCE: 221
MTSNRKNENE IINALSIPTV SNPSTQMNLS PDARIEDSLC VAEVNNIDPF VSASTVQTGI  60
NIAGRILGVL GVPFAGQLAS FYSFLVGELW PSGRDPWEIF LEHVEQLIRQ QVTENTRNTA  120
IARLEGLGRG YRSYQQALET WLDNRNDARS RSIILERYVA LELDITTAIP LFRIRNQEVP  180
LLMVYAQAAN LHLLLLRDAS LFGSEWGTAS SDVNQYYQEQ IRYTEEYSNH CVQWYNTGLN  240
NLRGTNAESW VRYNQFRRDL TLGVLDLVAL FPSYDTRTYP INTSAQLTRE VYTDAIGTVH  300
PSQAFASTTW FNNNAPSFSA IEAAVIRPPH LLDFPEQLTI YSTLSRWSNT QFMNIWAGHR  360
LESRPIAGSL NTSTQGSTNT SINPVTLQFT SRDIYRTESL AGLNIFITQP VNGVPWVRFN  420
WRNPLNSLRG SLLYTIGYTG VGTQLQDSET ELPPETTERP NYESYSHRLS HIGLISSSHV  480
RALVYSWTHR SADRTNTIGP NRITQIPAVK GRFLFNGSVI SGPGFTGGDV VRLNRNNGNI  540
QNRGYIEVPI QFTSTSTRYR VRVRYASVTS IELNVNWGNS SIFTNTLPAT AASLDNLQSG  600
DFGYVEINNA FTSATGNIVG VRNFSANAEV IIDRFEFIPV TATFEAKYDL ERAQKAVNAL  660
FTSTNPRRLK TDVTDYHIDQ VSNLVVCLSD EFCLDEKREL FEKVKYAKRL SDERNLLQDP  720
NFTFINGQPS FASIDGQSNF TSINELSNHG WWGSANVTIQ EGNDVFKENY VTLPGTFNEC  780
YPNYLYQKIG ESELKAYTRY QLRGYIEDSQ DLEIYLIRYN AKHETLNVPG TESLWPLSVE  840
SPIGRCGEPN RCAPHFGWNP DLDCSCRDRE KCAHHSHHFT LDIDVGCTDL QEDLGVWVVF  900
KIKTQEGYAR LGNLEFIEEK PLIGEALSRV KRAEKKWRDK REKLQVETKR VYIDAKEAVD  960
ALFVDSQYDR LQADTNIGMI HAADRLVHRI HEAYLPELPF IPGINVVIFE ELENRISTAF  1020
SLYDARNVIK NGDFNNGLTC WNVKGHVEVQ QLNNHRSVLV IPEWEAEVSQ KVRVCPGRGY  1080
ILRVTAYKEG YGEGCVTIHE VDNNTDQLKF SNCEKGQVYP GNTIACNDYN KNHGANACSS  1140
RNRGYDEFYG NTPADYSANQ KEYGGAYTSH NHAYGESYES NSSIPADYAP VYEEEAYTHG  1200
RRGNSCEYNR GYTPLPAGYV TAELEYFPET DTVWVEIGET EGTFIVDNVE LLLMEE      1256
```

```
SEQ ID NO: 222          moltype = DNA  length = 3714
FEATURE                 Location/Qualifiers
source                  1..3714
                        mol_type = other DNA
                        organism = Bacillus thuringiensis
SEQUENCE: 222
ttgaattcaa ataggaaaaa tgagaacgaa attatagatg cttcatttat tcccgcagta  60
tccaatgagt ctgttacaat ctctaaagaa tatgcacaaa caaatcaatt acaaaacaat  120
agcattgagg atggtttgtg tatagccgaa ggggaatata ttgatccatt tgttagcgca  180
tcaacagtcc aaacggggat tagtatcgct ggtagaatat tgggtgtatt aggtgtgccg  240
tttgccggac aattagctag tttttatagt tttattgttg gtgaattatg gcctaaaggc  300
agagaccaat gggaaatttt tatggaacat gtagaacaac ttgtaagaca acaaataaca  360
gcaaatgcta ggaatacggc ccttgctcga ttacaaggtt taggagattc ctttagagcc  420
tatcaacagt cacttgaaga ttggctagag aaccgtaatg atgcaagaac gagaagtgtt  480
ctttatactc aatatatagc cttagagctt gattttctaa atgcgatgcc gcttttcgca  540
ataagagagc aagaggttcc cttattaatg gtatacgctc aagctgcaaa cttgcaccta  600
ttattattga gagacgcctc cctttatggt cgtgaatttg ggcttacctc ccaagaaatt  660
caacgttatt atgaacgcca agtagaaaga acgagggact attctgacca ttgcgtgcaa  720
tggtataata cgggtctaaa taacttaaga gggacaaatg ctgaaagttg ggtgcggtat  780
aatcaattcc gtagagacct aacattaggg gtattagatc tagtggcact attcccaagc  840
tatgacactc gcacttatcc aataaatacg agtgctcagt taacaaggga agtttataca  900
gacgcaattg gagcaacagg ggtaaatatg gcaagtatga attggtataa taataatgca  960
ccttcgtttt ccgctataga gactgcggtt atccgaagcc cgcatctact tgattttcta  1020
gaacaactta aaatttttag cgcttcatca cgatggagta atactaggca tatgacttat  1080
tggcgggggc acacgattca atctcggcca ataagagggg cattaattac ctcgacacac  1140
ggaaatacca atacttctat taaccctgta acattccagt tcccgtcccg agacgtttat  1200
aggactgaat catatgcagg agtgcttcta tggggaattt accttgaacc tattcatggt  1260
gttcctactg ttagatttaa ttttaggaac cctcagaata cttttgaaag aggtactgct  1320
aactatagtc aaccctatga gtcacctggg cttcaattaa aagattcaga aactgaatta  1380
ccaccagaaa caacagaacg accaaattat gaatcatata gtcatagatt atctcacata  1440
gggatcattt tacaaactag gttgaatgta ccggtatatt cttggacgca tcgtagtgca  1500
gatcgtacaa atacaattgg accaaataga attactcaaa ttcctgcagt gaagggaaac  1560
cttcttttta atggttctgt aatttcagga ccaggattta ctggtgggga cttagttaga  1620
ttaaataata gtggaaataa tattcaaaat agaggctatc ttgaggttcc aattcaattc  1680
```

-continued

```
acatcgacat ctaccagata tcgagttcgt gtacgttatg cttctgtaac cccgattcac  1740
ctcagtgtta attggggtaa ttcaaacatt ttttccagca cagttccagc tacagctgcg  1800
tcattagata atctacaatc aagggatttt ggttattttg aaagtaccaa tgcatttaca  1860
tctgtaacag gtaatgtagt aggtgtaaga aattttagtg aaaatgccag agtgataata  1920
gacagatttg aatttattcc agttactgca accttcgaag cagaatacga tttagaaagg  1980
gcgcaagagg cggtgaatgc tctgtttact aatacgaatc caagaagatt gaaaacagat  2040
gtgacagatt atcatattga tcaagtatcc aatttagtgg cgtgtttatc ggatgaattc  2100
tgcttagatg aaaagagaga attacttgag aaagtgaaat atgcgaaacg actcagtgat  2160
gaaagaaact tactccaaga tccaaacttc acatccatca ataagcaacc agacttcata  2220
tctactaatg agcaatcgaa tttcacatct atccatgaac aatctgaaca tggatggtgg  2280
ggaagtgaga acattacaat ccaggaagga aatgacgtat ttaaagagaa ttacgtcaca  2340
ctaccaggta cttataatga gtgttatccg acgtatttat atcaaaaaat aggagagtcg  2400
gaattaaaag cttatactcg ctaccaatta agaggttata ttgaagatag tcaagattta  2460
gagatatatt tgattcgtta taatgcgaaa catgaaacat tggatgttcc aggtaccgag  2520
tccgtatggc cgctttcagt tgaaagccca atcagaaggt gcggagaacc gaatcgatgc  2580
gcaccacatt ttgaatggaa tcctgatcta gattgttcct gcagagatgg agaaaaatgt  2640
gcgcatcatt cccatcattt ctctttggat attgatgttg gatgcataga cttgcatgag  2700
aacctaggcg tgtgggtggt attcaagatt aagacgcagg aaggtcatgc aagactaggg  2760
aacctggaat ttattgaaga gaaaccatta ttaggagaag cactgtctcg tgtgaagaga  2820
gcagagaaaa aatggagaga caaacgtgaa aaactacaat tggaaacaaa acgagtatat  2880
acagaggcaa aagaagctgt ggatgcttta tttgtagatt ctcaatatga tagattacaa  2940
gcggatacaa acattggcat gattcatgcg gcagataaac ttgttcatcg aattcgagag  3000
gcgtatcttt cagaattatc tgttatccca ggtgtaaatg cggaaatttt tgaagaatta  3060
gaaggtcgca ttatcactgc aatctcccta tacgatgcga gaaatgtcgt taaaaatggt  3120
gattttaata atggattagc atgctggaat gtaaaagggc atgtagatgt acaacagagc  3180
catcaccgtt ctgtccttgt tatcccagaa tgggaagcag aagtgtcaca agcagttcgc  3240
gtctgtccgg ggcgtggcta tatcctccgt gtcacagcgt acaaagaggg atatggagag  3300
ggttgtgtaa cgatccatga aatcgagaac aatacagacg aactaaaatt taaaaactgt  3360
gaagaagagg aagtgtatcc aacggataca ggaacgtgta atgattatac tgcacaccaa  3420
ggtacagcag catgtaattc ccgtaatgct ggatatgagg atgcatatga agttgatact  3480
acagcatctg ttaattacaa accgacttat gaagaagaaa cgtatacaga tgtacgaaga  3540
gataatcatt gtgaatatga cagagggtat gtgaattatc caccagtacc agctggttat  3600
atgacaaaag aattagaata cttcccagaa accgataagg tatggattga gattggagaa  3660
acggaaggga agtttattgt agacagcgtg gaattactcc ttatggagga atag        3714
```

```
SEQ ID NO: 223          moltype = AA  length = 1237
FEATURE                 Location/Qualifiers
source                  1..1237
                        mol_type = protein
                        organism = Bacillus thuringiensis
SEQUENCE: 223
MNSNRKNENE IIDASFIPAV SNESVTISKE YAQTNQLQNN SIEDGLCIAE GEYIDPFVSA  60
STVQTGISIA GRILGVLGVP FAGQLASFYS FIVGELWPKG RDQWEIFMEH VEQLVRQQIT  120
ANARNTALAR LQGLGDSFRA YQQSLEDWLE NRNDARTRSV LYTQYIALEL DFLNAMPLFA  180
IREQEVPLLM VYAQAANLHL LLLRDASLYG REFGLTSQEI QRYYERQVER TRDYSDHCVQ  240
WYNTGLNNLR GTNAESWVRY NQFRRDLTLG VLDLVALFPS YDTRTYPINT SAQLTREVYT  300
DAIGATGVNM ASMNWYNNNA PSFSAIETAV IRSPHLLDFL EQLKIFSASS RWSNTRHMTY  360
WRGHTIQSRP IRGALITSTH GNTNTSINPV TFQFPSRDVY RTESYAGVLL WGIYLEPIHG  420
VPTVRFNFRN PQNTFERGTA NYSQPYESPG LQLKDSETEL PPETTERPNY ESYSHRLSHI  480
GIILQTRLNV PVYSWTHRSA DRTNTIGPNR ITQIPAVKGN LLFNGSVISG PGFTGGDLVR  540
LNNSGNNIQN RGYLEVPIQF TSTSTRYRVR VRYASVTPIH LSVNWGNSNI FSSTVPATAA  600
SLDNLQSRDF GYFESTNAFT SVTGNVVGVR NFSENARVII DRFEFIPVTA TFEAEYDLER  660
AQEAVNALFT NTNPRRLKTD VTDYHIDQVS NLVACLSDEF CLDEKRELLE KVKYAKRLSD  720
ERNLLQDPNF TSINKQPDFI STNEQSNFTS IHEQSEHGWW GSENITIQEG NDVFKENYVT  780
LPGTYNECYP TYLYQKIGES ELKAYTRYQL RGYIEDSQDL EIYLIRYNAK HETLDVPGTE  840
SVWPLSVESP IRRCGEPNRC APHFEWNPDL DCSCRDGEKC AHHSHHFSLD IDVGCIDLHE  900
NLGVWVVFKI KTQEGHARLG NLEFIEEKPL LGEALSRVKR AEKKWRDKRE KLQLETKRVY  960
TEAKEAVDAL FVDSQYDRLQ ADTNIGMIHA ADKLVHRIRE AYLSELSVIP GVNAEIFEEL  1020
EGRIITAISL YDARNVVKNG DFNNGLACWN VKGHVDVQQS HHRSVLVIPE WEAEVSQAVR  1080
VCPGRGYILR VTAYKEGYGE GCVTIHEIEN NTDELKFKNC EEEEVYPTDT GTCNDYTAHQ  1140
GTAACNSRNA GYEDAYEVDT TASVNYKPTY EEETYTDVRR DNHCEYDRGY VNYPPVPAGY  1200
MTKELEYFPE TDKVWIEIGE TEGKFIVDSV ELLLMEE                           1237
```

```
SEQ ID NO: 224          moltype = AA  length = 650
FEATURE                 Location/Qualifiers
source                  1..650
                        mol_type = protein
                        organism = Bacillus thuringiensis
SEQUENCE: 224
MTSNRKNENE IINAVSNHSA QMDLLPDARI EDSLCIAEGN NIDPFVSAST VQTGINIAGR  60
ILGVLGVPFA GQLASFYSFL VGELWPRGRD QWEIFLEHVE QLINQQITEN ARNTALARLQ  120
GLGDSFRAYQ QSLEDWLENR DDARTRSVLY TQYIALELDF LNAMPLFAIR NQEVPLLMVY  180
AQAANLHLLL LRDASLFGSE FGLTSQEIQR YYERQVERTR DYSDYCVEWY NTGLNSLRGT  240
NAASWVRYNQ FRRDLTLGVL DLVALFPSYD TRTYPINTSA QLTREVYTDA IGATGVNMAS  300
MNWYNNNAPS FSAIEAAAIR SPHLLDFLEQ LTIFSASSRW SNTRHMTYWR GHTIQSRPIG  360
GGLNTSTHGA TNTSINPVTL RFASRDVYRT ESYAGVLLWG IYLEPIHGVP TVRFNFTNPQ  420
NISDRGTANY SQPYESPGLQ LKDSETELPP ETTERPNYES YSHRLSHIGI ILQSRVNVPV  480
YSWTHRSADR TNTIGPNRIT QIPMVKASEL PQGTTVVRGP GFTGGDILRR TNTGGFGPIR  540
VTVNGPLTQR YRIGFRYAST VDFDFFVSRG GTTVNNFRFL RTMNSGDELK YGNFVRRAFT  600
```

-continued

```
TPFTFTQIQD IIRTSIQGLS GNGEVYIDKI EIIPVTATFE AEYDLERAQE           650

SEQ ID NO: 225         moltype = AA  length = 655
FEATURE                Location/Qualifiers
source                 1..655
                       mol_type = protein
                       organism = Bacillus thuringiensis
SEQUENCE: 225
MTSNRKNENE IINALSIPTV SNPSTQMNLS PDARIEDSLC VAEVNNIDPF VSASTVQTGI  60
NIAGRILGVL GVPFAGQLAS FYSFLVGELW PSGRDPWEIF LEHVEQLIRQ QVTENTRNTA  120
IARLEGLGRG YRSYQQALET WLDNRNDARS RSIILERYVA LELDITTAIP LFRIRNEEVP  180
LLMVYAQAAN LHLLLLRDAS LFGSEWGMAS SDVNQYYQEQ IRYTEEYSNH CVQWYNTGLN  240
NLRGTNAESW LRYNQFRRDL TLGVLDLVAL FPSYDTRTYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTQGLTNN TSINPVTLQF TSRDVYRTES NAGTNILFTT PVNGVPWARF  420
NFINPQNIYE RGATTYSQPY QGVGIQLFDS ETELPPETTE RPNYESYSHR LSHIGLIIGN  480
TLRAPVYSWT HRSADRTNTI GPNRITQIPL VKALNLHSGV TVVGGPGFTG GDILRRTNTG  540
TFGDIRLNIN VPLSQRYRVR IRYASTTDLQ FFTRINGTTV NIGNFSRTMN RGDNLEYRSF  600
RTAGFSTPFN FLNAQSTFTL GAQSFSNQEV YIDRVEFVPA EVTFEAEYDL ERAQK       655

SEQ ID NO: 226         moltype = AA  length = 655
FEATURE                Location/Qualifiers
source                 1..655
                       mol_type = protein
                       organism = Bacillus thuringiensis
SEQUENCE: 226
MTSNRKNENE IINALSIPTV SNPSTQMNLS PDARIEDSLC VAEVNNIDPF VSASTVQTGI  60
NIAGRILGVL GVPFAGQLAS FYSFLVGELW PSGRDPWEIF LEHVEQLIRQ QVTENTRNTA  120
IARLEGLGRG YRSYQQALET WLDNRNDARS RSIILERYVA LELDITTAIP LFRIRNEEVP  180
LLMVYAQAAN LHLLLLRDAS LFGSEWGMAS SDVNQYYQEQ IRYTEEYSNH CVQWYNTGLN  240
NLRGTNAESW LRYNQFRRDL TLGVLDLVAL FPSYDTRTYP INTSAQLTRE IYTDPIGRTN  300
APSGFASTNW FNNNAPSFSA IEAAIFRPPH LLDFPEQLTI YSASSRWSST QHMNYWVGHR  360
LNFRPIGGTL NTSTQGLTNN TSINPVTLQF TSRDVYRTES NAGTNILFTT PVNGVPWARF  420
NFINPQNIYE RGATTYSQPY QGVGIQLFDS ETELPPETTE RPNYESYSHR LSHIGLIIGN  480
TLRAPVYSWT HRSADRTNTI GPNRITQIPL VKALNLHSGV TVVGGPGFTG GDILRRTNTG  540
TFGDIRLNIN VPLSQRYRVR IRYASTTDLQ FFTRINGTTV NIGNFSRTMN RGDNLEYRSF  600
RTAGFSTPFN FLNAQSTFTL GAQSFSNQEV YIDRVEFVPA EVTFEAEYDL ERAQK       655

SEQ ID NO: 227         moltype = AA  length = 653
FEATURE                Location/Qualifiers
source                 1..653
                       mol_type = protein
                       organism = Bacillus thuringiensis
SEQUENCE: 227
MTSNRKNENE IINALSIPAV SNHSAQMNLS TDARIEDSLC IAEGNNIDPF VSASTVQTGI  60
NIAGRILGVL GVPFAGQIAS FYSFLVGELW PRGRDPWEIF LEHVEQLIRQ QVTENTRDTA  120
LARLQGLGNS FRAYQQSLED WLENRDDART RSVLYTQYIA LELDFLNAMP LFAIRNQEVP  180
LLMVYAQAAN LHLLLLRDAS LFGSEFGLTS QEIQRYYERQ VEKTREYSDY CARWYNTGLN  240
NLRGTNAESW LRYNQFRRDL TLGVLDLVAL FPSYDTRVYP MNTSAQLTRE IYTDPIGRTN  300
APSGFASTNW FNNNAPSFSA IEAAVIRPPH LLDFPEQLTI FSVLSRWSNT QYMNYWVGHR  360
LESRTIRGSL STSTHGNTNT SINPVTLQFT SRDVYRTESF AGINILLTTP VNGVPWARFN  420
WRNPLNSLRG SLLYTIGYTG VGTQLFDSET ELPPETTERP NYESYSHRLS NIRLISGNTL  480
RAPVYSWTHR SADRTNTISS DSITQIPLVK SFNLNSGTSV VSGPGFTGGD IIRTNVNGSV  540
LSMGLNFNNT SLQRYRVRVR YAASQTMVLR VTVGGSTTFD QGFPSTMSAN ESLTSQSFRF  600
AEFPVGISAS GSQTAGISIS NNAGRQTFHF DKIEFIPITA TFEAEYDLER AQE         653

SEQ ID NO: 228         moltype = AA  length = 654
FEATURE                Location/Qualifiers
source                 1..654
                       mol_type = protein
                       organism = Bacillus thuringiensis
SEQUENCE: 228
MTSNRKNENE IINALSIPAV SNHSTQMDLS PDARIEDSLC IAEGNNINPL VSASTVQTGI  60
NIAGRILGVL GVPFAGQIAS FYSFLVGELW PRGRDQWEIF LEHVEQLINQ QITENARNTA  120
LARLQGLGDS FRAYQQSLED WLENRDDART RSVLYTQYIA LELDFLNAMP LFAIRNQEVP  180
LLMVYAQAAN LHLLLLRDAS LFGSEFGLTS QEIQRYYERQ VEQTRDYSDY CVEWYNTGLN  240
SLRGTNAASW VRYNQFRRDL TLGVLDLVAL FPSYDTRTYP INTSAQLTRE VYTDAIGATG  300
VNMASMNWYN NNAPSFSAIE TAVIRSPHLL DFLEQLTIFS TSSRWSATRH MTYWRGHTIQ  360
SRPIGGGLNT STHGSTNTSI NPVRLSFFSR DVYWTESYAG VLLWGIYLEP IHGVPTVRFN  420
FRNPQNTFER GTANYSQPYE SPGLQLKDSE TELPPETTER PNYESYSHRL SHIGLISQSR  480
VHVPVYSWTH RSADRTNTIS SDSITQIPLV KSFNLNSGTS VVSGPGFTGG DIIRTNVNGS  540
VLSMGLNFNN TSLQRYRVRV RYAASQTMVL RVTVGGSTTF DQGFPSTMSA NESLTSQSFR  600
FAEFPVGISA SGSQTAGISI SNNAGRQTFH FDKIEFIPIT ATFEAEYDLE RAQE        654

SEQ ID NO: 229         moltype = AA  length = 661
FEATURE                Location/Qualifiers
source                 1..661
                       mol_type = protein
                       organism = Bacillus thuringiensis
```

```
SEQUENCE: 229
MNSNRKNENE IIDASFIPAV SNESVTISKE YAQTNQLQNN SIEDGLCIAE GEYIDPFVSA  60
STVQTGISIA GRILGVLGVP FAGQLASFYS FIVGELWPKG RDQWEIFMEH VEQLVRQQIT  120
ANARNTALAR LQGLGDSFRA YQQSLEDWLE NRNDARTRSV LYTQYIALEL DFLNAMPLFA  180
IREQEVPLLM VYAQAANLHL LLLRDASLYG REFGLTSQEI QRYYERQVER TRDYSDHCVQ  240
WYNTGLNNLR GTNAESWVRY NQFRRDLTLG VLDLVALFPS YDTRTYPINT SAQLTREVYT  300
DAIGATGVNM ASMNWYNNNA PSFSAIETAV IRSPHLLDFL EQLKIFSASS RWSNTRHMTY  360
WRGHTIQSRP IRGALITSTH GNTNTSINPV TFQFPSRDVY RTESYAGVLL WGIYLEPIHG  420
VPTVRFNFRN PQNTFERGTA NYSQPYESPG LQLKDSETEL PPETTERPNY ESYSHRLSHI  480
GIILQTRLNV PVYSWTHRSA DRTNTISSDS ITQIPLVKSF NLNSGTSVVS GPGFTGGDII  540
RTNVNGSVLS MGLNFNNTSL QRYRVRVRYA ASQTMVLRVT VGGSTTFDQG FPSTMSANES  600
LTSQSFRFAE FPVGISASGS QTAGISISNN AGRQTFHFDK IEFIPITATF EAEYDLERAQ  660
E                                                                 661

SEQ ID NO: 230          moltype = AA  length = 1164
FEATURE                 Location/Qualifiers
source                  1..1164
                        mol_type = protein
                        organism = Bacillus thuringiensis
SEQUENCE: 230
MDNNPNINEC IPYNCLSNPE EVLLDGERIS TGNSSIDISL SLVQFLVSNF VPGGGFLVGL  60
IDFVWGIVGP SQWDAFLVQI EQLINERIAE FARNAAIANL EGLGNNFNIY VEAFKEWEED  120
PKNPATRTRV IDRFRILDGL LERDIPSFRI SGFEVPLLSV YAQAANLHLA ILRDSVIFGE  180
RWGLTTINVN ENYNRLIRHI DEYADHCANT YNRGLNNLPK STYQDWITYN RLRRDLTLTV  240
LDIAAFFPNY DNRRYPIQPV GQLTREVYTD PLINFNPQLQ SVAQLPTFNV MENSAIRNPH  300
LFDILNNLTI FTDWFSVGRN FYWGGHRVIS SLIGGGNITS PIYGREANQE PPRSFTFNGP  360
VFRTLSNPTL RLLQQPWPAP PFNLRGVEGV EFSTPTNSFT YRGRGTVDSL TELPPEDNSV  420
PPREGYSHRL CHATFVQRSG TPFLTTGVVF SWTHRSATLT NTIDPERINQ IPLVKGFRVW  480
GGTSVITGPG FTGGDILRRN TFGDFVSLQV NINSPITQRY RLRFRYASSR DARVIVLTGA  540
ASTGVGGQVS VNMPLQKTME IGENLTSRTF RYTDFSNPFS FRANPDIIGI SEQPLFGAGS  600
ISSGELYIDK IEIILADATL EAESDLERAQ KAVNALFTSS NQIGLKTDVT DYHIDRVSNL  660
VECLSDEFCL DEKKELSEKV KHAKRLSDER NLLQDPNFRG INRQLDRGWR GSTDITIQGG  720
DDVFKENYVT LLGTFDECYP TYLYQKIDES KLKAYTRYQL RGYIEDSQDL EIYLIRYNAK  780
HETVNVPGTG SLWPLSAPSP IGKCAHHSHH FSLDIDVGCT DLNEDLGVWV IFKIKTQDGH  840
ARLGNLEFLE EKPLVGEALA RVKRAEKKWR DKREKLEWET NIVYKEAKES VDALFVNSQY  900
DRLQADTNIA MIHAADKRVH SIREAYLPEL SVIPGVNAAI FEELEGRIFT AFSLYDARNV  960
IKNGDFNNGL SCWNVKGHVD VEEQNNHRSV LVVPEWEAEV SQEVRVCPGR GYILRVTAYK  1020
EGYGEGCVTI HEIENNTDEL KFSNCVEEEV YPNNTVTCND YTATQEEYEG TYTSRNRGYD  1080
GAYESNSSVP ADYASAYEEK AYTDGRRDNP CESNRGYGDY TPLPAGYVTK ELEYFPETDK  1140
VWIEIGETEG TFIVDSVELL LMEE                                        1164

SEQ ID NO: 231          moltype = AA  length = 605
FEATURE                 Location/Qualifiers
source                  1..605
                        mol_type = protein
                        organism = Bacillus thuringiensis
SEQUENCE: 231
MAEGNNLNQC IPYNCLSNPK DIILGDERLE TGNTVADITL GIVNLLFSEF VPGGGFILGL  60
LDLIWGSIGR SQWDLFLEQI EQLIKQRIEE FARNQAISRL EGLSDLYKTY ARAFSDWEAD  120
PTNPALREEM RIQFNDMNSA IITALPLFRV QNYEVALLSV YVQAANLHLS ILRDVSVFGE  180
RWGYDTATIN NRYSDLTSLI HVYTNHCVDT YNQGLRRLEG RFLTDWIVYN RFRRQLTISV  240
LDIVAFFPNY DIRTYPIQTA TQLTREVYLD LPFINENLSP AASYPTFSAA ESAIIRSPHL  300
VDFLNSFTIY TDSLARYAYW GGHLVNSFRT GTTTNLIRSP LYGREGNTER PVTITASPSV  360
PIFRTLSYIT GLDNSNPVAG IEGVEFQNTI SRSIYRKSGP IDSFSELPPQ DASVSPAIGY  420
SHRLCHATFL ERISGPRIAG TVFSWTHRSA SPTNEVSPSR ITQIPWVKAH TLASGASVIK  480
GPGFTGGDIL TRNSMGELGT LRVTFTGRLP QSYYIRFRYA SVANRSGTFR YSQPPSYGIS  540
FPKTMDAGEP LTSRSFAHTT LFTPITFSRA QEEFDLYIQS GVYIDRIEFI PVTATFEAEY  600
DLERA                                                             605

SEQ ID NO: 232          moltype = DNA  length = 2256
FEATURE                 Location/Qualifiers
misc_feature            1..2256
                        note = variant of MP589FL
source                  1..2256
                        mol_type = other DNA
                        organism = synthetic construct
SEQUENCE: 232
atggagggaa ataatctaaa tcaatgcata ccttacaatt gtttaagtaa tcctaaggac  60
ataatattag gtgatgaaag gctagaaact ggtaatactg tagcagacat taccttaggg  120
attgtcaatc tattgttttc tgagtttgtt cctggtggag gctttatact aggattactg  180
gatttaatat gggggtctat aggtcgttcc caatgggatc tatttctgga acagattgaa  240
caattgatta agcaaagaat agaagaattt gctaggaatc aggcaatttc aagattggag  300
gggctaagcg atctttataa gacctatgct agagcgttta gcgattggga ggcagatccg  360
actaatccag cattaaggga agaaatgcgt atacaattta atgacatgaa tagtgctatc  420
ataacggctc tcccactttt tagagttcaa aattatgaag ttgctctttt atctgtttat  480
gttcaagctg caaacttaca tttatctatt ttaagagatg tttcagtctt tggagaaaga  540
tggggatatg atacagcaac tatcaataat cgctatagtg acttaactag ccttattcat  600
gtttatacta atcattgtgt ggatacgtat aatcagggat taaggcgttt ggaaggtcgt  660
tttcttaccg attggattgt atataatcgt ttccgaagac aattaacaat ttcagtatta  720
```

```
gatattgttg catttttcc aaattatgat attcgaacat atccaattca aacagctact 780
cagctaacga gggaaatcta tctggattta cctttatta atgaaaatct ttctcctgca 840
gcaagctatc cctcattctc agatgctgaa agtgctataa tcaggagtcc tcatttagtg 900
gactttttaa atagcttcac tatttataca gatagtcttg ctcgatattt atattgggga 960
gggcatcggg tgaattttac ccgttcagga gttactactt ttatacaatc accactatat 1020
ggaagggaag gaaatgcaga gcgttctgta attatttcgg catcatctag cgtaccaata 1080
tttagaacac tttcatatgt tactggcctt gacaatgcaa atcctgtagc tggaattgaa 1140
ggagtggaat tccaaaatac tataagtaga agtatctatc gtaaaagtgg tccaattgat 1200
tcttttaatg aattaccacc tcaagatgcc agtgtatctc cttcaattgg gtatagtcac 1260
cgtttatgtc atgccacatt tttagaacgg attagtggac caagaattgc aggtgtcgtt 1320
ttttcctgga cacatcgtag tgctagccct actaatgaag taagttcatc tagaattaca 1380
caaattccat gggtaaaggc gcatactctt gcgtctggtg cctccgttat taaagggcct 1440
ggatttacag gtggagatat actaactagg aataccttag gcgaactggg gactttaaga 1500
gtaacttttg caggaagatt atcacaaagt tattatatac gtttccgtta tgcttccgta 1560
gctaatagga gtggtatatt tagctattca cagccaactt catatggaat ttcctttcca 1620
aaaactatgg atgcagatga atcattaaca tctcgttcat ttgcacttgc tacacttgct 1680
acaccgctaa cctttagaag gcaagaagaa ttaaatctac aaataccatc aggtacttat 1740
atagatcgaa ttgagtttgt tccagtcgat gaaaccttta caacagaatc tgatctggat 1800
agagcacaac aggcggtgaa tgcgctgttt acttcttcca atcaaatcgg cttaaaaaca 1860
gatgtgacgg attatcatat tgatcaagta tccaatttag tggattgttt atcggatgaa 1920
ttttgtctgg atgaaaagcg agaattgtcc gagaaagtca aacatgcgaa gcgactcagt 1980
gatgagcgga atttacttca agatccaaac tttagaggaa tcaatagaca accagaccgt 2040
ggttggagag gaagtacaga tattaccatc caaggaggag atgacgtatt caaagagaat 2100
tacgttacac taccaggtac ctttgatgag tgctatccaa cgtatttata tcaaaaaata 2160
gatgagtcga aattaaaagc ctatacccgt taccaattaa gagggtatat cgaagatagt 2220
caagacttag aaatctattt aattcgctac aattga 2256
```

```
SEQ ID NO: 233          moltype = AA  length = 751
FEATURE                 Location/Qualifiers
REGION                  1..751
                        note = variant of MP589FL aa
source                  1..751
                        mol_type = protein
                        organism = synthetic construct
SEQUENCE: 233
MEGNNLNQCI PYNCLSNPKD IILGDERLET GNTVADITLG IVNLLFSEFV PGGGFILGLL 60
DLIWGSIGRS QWDLFLEQIE QLIKQRIEEF ARNQAISRLE GLSDLYKTYA RAFSDWEADP 120
TNPALREEMR IQFNDMNSAI ITALPLFRVQ NYEVALLSVY VQAANLHLSI LRDVSVFGER 180
WGYDTATINN RYSDLTSLIH VYTNHCVDTY NQGLRRLEGR FLTDWIVYNR FRRQLTISVL 240
DIVAFFPNYD IRTYPIQTAT QLTREIYLDL PFINENLSPA ASYPSFSDAE SAIIRSPHLV 300
DFLNSFTIYT DSLARYLYWG GHRVNFTRSG VTTFIQSPLY GREGNAERSV IISASSSVPI 360
FRTLSYVTGL DNANPVAGIE GVEFQNTISR SIYRKSGPID SFNELPPQDA SVSPSIGYSH 420
RLCHATFLER ISGPRIAGVV FSWTHRSASP TNEVSSSRIT QIPWVKAHTL ASGASVIKGP 480
GFTGGDILTR NTLGELGTLR VTFAGRLSQS YYIRFRYASV ANRSGIFSYS QPTSYGISFP 540
KTMDADESLT SRSFALATLA TPLTFRRQEE LNLQIPSGTY IDRIEFVPVD ETFTTESDLD 600
RAQQAVNALF TSSNQIGLKT DVTDYHIDQV SNLVDCLSDE FCLDEKRELS EKVKHAKRLS 660
DERNLLQDPN FRGINRQPDR GWRGSTDITI QGGDDVFKEN YVTLPGTFDE CYPTYLYQKI 720
DESKLKAYTR YQLRGYIEDS QDLEIYLIRY N 751
```

```
SEQ ID NO: 234          moltype = DNA  length = 3492
FEATURE                 Location/Qualifiers
source                  1..3492
                        mol_type = other DNA
                        organism = Bacillus thuringiensis
SEQUENCE: 234
atggagggaa ataatctaaa tcaatgcata ccttacaatt gtttaagtaa tcctaaggac 60
ataatattag gtgatgaaag gctagaaact ggtaatactg tagcagacat taccttaggg 120
attgtcaatc tattgtttc tgagtttgtt cctggtggag gctttatact aggattactg 180
gatttaatat gggggtctat aggtcgttcc caatgggatc tatttctgga acagattgaa 240
caattgatta agcaaagaat agaagaattt gctaggaatc aggcaatttc aagattggag 300
gggctaagcg atctttataa gacctatgct agagcgttta gcgattggga ggcagatccg 360
actaatccag cattaaggga agaaatgcgt atacaattta atgacatgaa tagtgctatc 420
ataacggctc tcccactttt tagagttcaa aattatgaag ttgctctttt atctgtttat 480
gttcaagctg caaacttaca tttatctatt ttaagagatg tttcagtctt tggagaaaga 540
tggggatatg atacagcaac tatcaataat cgctatagtg acttaactag ccttattcat 600
gtttatacta atcattgtgt ggatacgtat aatcagggat taaggcgttt ggaaggtcgt 660
tttcttaccg attggattgt atataatcgt ttccgaagac aattaacaat ttcagtatta 720
gatattgttg catttttcc aaattatgat attcgaacat atccaattca aacagctact 780
cagctaacga gggaaatcta tctggattta cctttatta atgaaaatct ttctcctgca 840
gcaagctatc cctcattctc agatgctgaa agtgctataa tcaggagtcc tcatttagtg 900
gactttttaa atagcttcac tatttataca gatagtcttg ctcgatattt atattgggga 960
gggcatcggg tgaattttac ccgttcagga gttactactt ttatacaatc accactatat 1020
ggaagggaag gaaatgcaga gcgttctgta attatttcgg catcatctag cgtaccaata 1080
tttagaacac tttcatatgt tactggcctt gacaatgcaa atcctgtagc tggaattgaa 1140
ggagtggaat tccaaaatac tataagtaga agtatctatc gtaaaagtgg tccaattgat 1200
tcttttaatg aattaccacc tcaagatgcc agtgtatctc cttcaattgg gtatagtcac 1260
cgtttatgtc atgccacatt tttagaacgg attagtggac caagaattgc aggtgtcgtt 1320
ttttcctgga cacatcgtag tgctagccct actaatgaag taagttcatc tagaattaca 1380
caaattccat gggtaaaggc gcatactctt gcgtctggtg cctccgttat taaagggcct 1440
```

```
ggatttacag gtggagatat actaactagg aataccttag gcgaactggg gactttaaga  1500
gtaacttttg caggaagatt atcacaaagt tattatatac gtttccgtta tgcttccgta  1560
gctaatagga gtggtatatt tagctattca cagccaactt catatggaat ttcctttcca  1620
aaaactatgg atgcagatga atcattaaca tctcgttcat ttgcacttgc tacacttgct  1680
acaccgctaa cctttagaag gcaagaagaa ttaaatctac aaataccatc aggtacttat  1740
atagatcgaa ttgagtttgt tccagtcgat gaaaccttta caacagaatc tgatctggat  1800
agagcacaac aggcggtgaa tgcgctgttt acttcttcca atcaaatcgg cttaaaaaca  1860
gatgtgacgg attatcatat tgatcaagta tccaatttag tggattgttt atcggatgaa  1920
ttttgtctgg atgaaaagcg agaattgtcc gagaaagtca aacatgcgaa gcgactcagt  1980
gatgagcgga atttacttca agatccaaac tttagaggaa tcaatagaca accagaccgt  2040
ggttggagag gaagtacaga tattaccatc caaggaggag atgacgtatt caaagagaat  2100
tacgttacac taccaggtac ctttgatgag tgctatccaa cgtatttata tcaaaaaata  2160
gatgagtcga aattaaaagc ctatacccgt tatcaattaa gagggtatat cggggatagt  2220
caagacttag aaatctattt aattcgttac aatgcaaaac acgaaatagt aaatgtacca  2280
ggtacaggga gtttatggac tctttctgta gaaaattcaa ttggaccttg tggagaaccg  2340
aatcgatgcg cgccacacct tgaatggaat cctaatctag agtgttcttg cagagaaggg  2400
gaaaaatgtg cccatcattc ccatcatttc tccttggaca ttgatgttgg atgtacagac  2460
ttaaatgagg acttaggtgt atgggcgata ttcaagatta agacgcaaga tggccatgca  2520
agactaggaa atctagagtt tctcgaagag aaaccactat taggggaagc actagctcgt  2580
gtgaaaagag cggagaagaa atggagagac aaacgcgaaa aattggaatg ggaaacaaat  2640
attgtttata aagaggcaaa agaatctgta gatgctttat ttgtgaactc tcaatatgat  2700
agattacaag cggatacgaa tatcgcgatg attcatgcgg cagataaacg cgttcataga  2760
attagagaag cataccttcc agaattatct gtaattccgg gtgtaaatgc gggcattttc  2820
gaagaattag agggacgcat tttcacagcc tactctctat atgatgcgag aaatgtcatt  2880
aaaaatggcg atttcaataa tggtttattg tgctggaact tgaaagggca tgtagatgta  2940
gaagaacaaa acaaccatcg ttcagtcctt gttgtcccgg aatgggaagc agaggtgtcc  3000
caagaagttc gtgtctgtcc aggtcgtggc tatatccttc gtgttacagc gtacaaagag  3060
ggatatggag agggctgcgt aaccatccat gagatcgaag acaatacaga cgaactgaaa  3120
ttcagcaact gtgtagaaga ggaagtatat ccaaacaaca cggtaacgtg taatgattat  3180
actgcgactc aagaagaata tgagggtacg tacacttctc gtaatcgagg atatgacgga  3240
gcctatgaaa gcaattcttc tgtaccagct gattatgcat cagcctatga agaaaaagcg  3300
tatacagatg gaagaagaga gaatccttgt gaatctaata gaggatatgg ggattacgcg  3360
ccactaccag ctggttatgt gacaaaggaa ttagagtact tcccagaaac cgataaggta  3420
tggattgaga tcggagaaac ggaaggaaca ttcattgtgg atagtgtgga attactcctt  3480
atggaggaat aa                                                      3492
```

```
SEQ ID NO: 235          moltype = AA  length = 1163
FEATURE                 Location/Qualifiers
source                  1..1163
                        mol_type = protein
                        organism = Bacillus thuringiensis
SEQUENCE: 235
MEGNNLNQCI PYNCLSNPKD IILGDERLET GNTVADITLG IVNLLFSEFV PGGGFILGLL  60
DLIWGSIGRS QWDLFLEQIE QLIKQRIEEF ARNQAISRLE GLSDLYKTYA RAFSDWEADP  120
TNPALREEMR IQFNDMNSAI ITALPLFRVQ NYEVALLSVY VQAANLHLSI LRDVSVFGER  180
WGYDTATINN RYSDLTSLIH VYTNHCVDTY NQGLRRLEGR FLTDWIVYNR FRRQLTISVL  240
DIVAFFPNYD IRTYPIQTAT QLTREIYLDL PFINENLSPA ASYPSFSDAE SAIIRSPHLV  300
DFLNSFTIYT DSLARYLYWG GHRVNFTRSG VTTFIQSPLY GREGNAERSV IISASSSVPI  360
FRTLSYVTGL DNANPVAGIE GVEFQNTISR SIYRKSGPID SFNELPPQDA SVSPSIGYSH  420
RLCHATFLER ISGPRIAGVV FSWTHRSASP TNEVSSSRIT QIPWVKAHTL ASGASVIKGP  480
GFTGGDILTR NTLGELGTLR VTFAGRLSQS YYIRFRYASV ANRSGIFSYS QPTSYGISFP  540
KTMDADESLT SRSFALATLA TPLTFRRQEE LNLQIPSGTY IDRIEFVPVD ETFTTESDLD  600
RAQQAVNALF TSSNQIGLKT DVTDYHIDQV SNLVDCLSDE FCLDEKRELS EKVKHAKRLS  660
DERNLLQDPN FRGINRQPDR GWRGSTDITI QGGDDVFKEN YVTLPGTFDE CYPTYLYQKI  720
DESKLKAYTR YQLRGYIGDS QDLEIYLIRY NAKHEIVNVP GTGSLWTLSV ENSIGPCGEP  780
NRCAPHLEWN PNLECSCREG EKCAHHSHHF SLDIDVGCTD LNEDLGVWAI FKIKTQDGHA  840
RLGNLEFLEE KPLLGEALAR VKRAEKKWRD KREKLEWETN IVYKEAKESV DALFVNSQYD  900
RLQADTNIAM IHAADKRVHR IREAYLPELS VIPGVNAGIF EELEGRIFTA YSLYDARNVI  960
KNGDFNNGLL CWNLKGHVDV EEQNNHRSVL VVPEWEAEVS QEVRVCPGRG YILRVTAYKE  1020
GYGEGCVTIH EIEDNTDELK FSNCVEEEVY PNNTVTCNDY TATQEEYEGT YTSRNRGYDG  1080
AYESNSSVPA DYASAYEEKA YTDGRRENPC ESNRGYGDYA PLPAGYVTKE LEYFPETDKV  1140
WIEIGETEGT FIVDSVELLL MEE                                          1163
```

```
SEQ ID NO: 236          moltype = DNA  length = 2259
FEATURE                 Location/Qualifiers
misc_feature            1..2259
                        note = variant of MP589FL
source                  1..2259
                        mol_type = other DNA
                        organism = synthetic construct
SEQUENCE: 236
atggaaggca acaacctgaa ccagtgcatt ccgtataact gcctgagcaa cccgaaagat  60
attattctgg gcgatgaacg tctggaaacc ggcaacaccg tggcggatat taccctgggc  120
attgtgaacc tgctgtttag cgaatttgtg ccgggcggcg gctttattct gggcctgctg  180
gatctgattt ggggcagcat tggccgtagc cagtgggatc tgtttctgga acagattgaa  240
cagctgatta aacagcgtat tgaagaattt gcgcgtaacc aggcgattag ccgtctggaa  300
ggcctgagcg atctgtataa aacctatgcg cgtgcgttta gcgattggga agcggatccg  360
accaacccgg cgctgcgtga agaaatgcgt attcagttta acgatatgaa cagcgcgatt  420
attaccgcgc tgccgctgtt tcgtgtgcag aactatgaag tggcgctgct gagcgtgtat  480
```

```
gtgcaggcgg cgaacctgca tctgagcatt ctgcgtgatg tgagcgtgtt tggcgaacgt  540
tggggctatg ataccgcgac cattaacaac cgttatagcg atctgaccag cctgattcat  600
gtgtatacca accattgcgt ggatacctat aaccagggcc tgcgtcgtct ggaaggccgt  660
tttctgaccg attggattgt gtataaccgt tttcgtcgtc agctgaccat tagcgtgctg  720
gatattgtgg cgtttttttcc gaactatgat attcgtacct atccgattca gaccgcgacc  780
cagctgaccc gtgaagtgta tctggatctg ccgtttatta acgaaaacct gagcccggcg  840
gcgagctatc cgacctttag cgcggcggaa agcgcgatta ttcgtagccc gcatctggtg  900
gattttctga acagctttac catttatacc gatagcctgg cgcgttatgc gtattggggc  960
ggccatctgg tgaacagctt tcgtaccggc accaccacca acctgattcg tagcccgctg  1020
tatggccgtg aaggcaacac cgaacgtccg gtgaccatta ccgcgagccc gagcgtgccg  1080
atttttcgta ccctgagcta tattaccggc ctggataaca gcaacccggt ggcgggcatt  1140
gaaggcgtgg aatttcagaa caccattagc cgtagcattt atcgtaaaag cggcccgatt  1200
gatagcttta gcgaactgcc gccgcaggat gcgagcgtga gcccggcgat tggctatagc  1260
catcgtctgt gccatgcgac ctttctggaa cgtattagcg gcccgcgtat tgcgggcacc  1320
gtgtttagct ggacccatcg tagcgcgagc ccgaccaacg aagtgagccc gagccgtatt  1380
acccagattc cgtgggtgaa agcgcatacc ctggcgagcg gcgcgagcgt gattaaaggc  1440
ccgggcttta ccggcggcga tattctgacc cgtaacagca tgggcgaact gggcaccctg  1500
cgtgtgacct ttaccggccg tctgccgcag agctattata ttcgttttcg ttatgcgagc  1560
gtggcgaacc gtagcggcac ctttcgttat agccagccgc cgagctatgg cattagcttt  1620
ccgaaaacca tggatgcggg cgaaccgctg accagccgta gctttgcgca taccaccctg  1680
tttaccccga ttacctttag ccgtgcgcag gaagaatttg atctgtatat tcagagcggc  1740
gtgtatattg atcgtattga atttattccg gtgaccgcga cctttgaagc ggaatatgat  1800
ctggaacgtg cgcagaaagt ggtgaacgcg ctgtttacca gcaccaacca gctgggcctg  1860
aaaaccgatg tgaccgatta tcatattgat caggtgagca acctggtggc gtgcctgagc  1920
gatgaatttt gcctggatga aaaacgtgaa ctgagcgaaa aagtgaaaca tgcgaaacgt  1980
ctgagcgatg aacgtaacct gctgcaggat ccgaactttc gtggcattaa ccgtcagccg  2040
gatcgtggct ggcgtggcag caccgatatt accattcagg gcggcgatga tgtgtttaaa  2100
gaaaactatg tgaccctgcc gggcaccttt gatgaatgct atccgaccta tctgtatcag  2160
aaaattgatg aaagcaaact gaaagcgtat acccgttatc agctgcgtgg ctatattgaa  2220
gatagccagg atctggaaat ttatctgatt cgttataac                        2259

SEQ ID NO: 237          moltype = AA  length = 753
FEATURE                 Location/Qualifiers
REGION                  1..753
                        note = variant of MP589FL
source                  1..753
                        mol_type = protein
                        organism = synthetic construct
SEQUENCE: 237
MEGNNLNQCI PYNCLSNPKD IILGDERLET GNTVADITLG IVNLLFSEFV PGGGFILGLL  60
DLIWGSIGRS QWDLFLEQIE QLIKQRIEEF ARNQAISRLE GLSDLYKTYA RAFSDWEADP  120
TNPALREEMR IQFNDMNSAI ITALPLFRVQ NYEVALLSVY VQAANLHLSI LRDVSVFGER  180
WGYDTATINN RYSDLTSLIH VYTNHCVDTY NQGLRRLEGR FLTDWIVYNR FRRQLTISVL  240
DIVAFFPNYD IRTYPIQTAT QLTREVYLDL PFINENLSPA ASYPTFSAAE SAIIRSPHLV  300
DFLNSFTIYT DSLARYAYWG GHLVNSFRTG TTTNLIRSPL YGREGNTERP VTITASPSVP  360
IFRTLSYITG LDNSNPVAGI EGVEFQNTIS RSIYRKSGPI DSFSELPPQD ASVSPAIGYS  420
HRLCHATFLE RISGPRIAGT VFSWTHRSAS PTNEVSPSRI TQIPWVKAHT LASGASVIKG  480
PGFTGGDILT RNSMGELGTL RVTFTGRLPQ SYYIRFRYAS VANRSGTFRY SQPPSYGISF  540
PKTMDAGEPL TSRSFAHTTL FTPITFSRAQ EEFDLYIQSG VYIDRIEFIP VTATFEAEYD  600
LERAQKVVNA LFTSTNQLGL KTDVTDYHID QVSNLVACLS DEFCLDEKRE LSEKVKHAKR  660
LSDERNLLQD PNFRGINRQP DRGWRGSTDI TIQGGDDVFK ENYVTLPGTF DECYPTYLYQ  720
KIDESKLKAY TRYQLRGYIE DSQDLEIYLI RYN                              753

SEQ ID NO: 238          moltype = DNA  length = 2259
FEATURE                 Location/Qualifiers
misc_feature            1..2259
                        note = variant of MP589FL
source                  1..2259
                        mol_type = other DNA
                        organism = synthetic construct
SEQUENCE: 238
atggaaggca acaacctgaa ccagtgcatt ccgtataact gcctgaccaa cccgaaagat  60
attattctgg gcgatgaacg tctggaaacc ggcaacaccg tggcggatat taccctgggc  120
attgtgaacc tgctgtttac cgaatttgtg ccgggcggcg gctttattct gggcctgctg  180
gatgtgattt ggggcagcat tggccgtagc cagtgggaac tgtttctgga acagattgaa  240
cagctgatta aacagcgtat tgaagaattt gcgcgtaacc aggcgattag ccgtctggaa  300
ggcctgagcg atctgtataa aacctatgcg cgtgcgttta gcgattggga agcggatccg  360
accaacccgg cgctgcgtga agaaatgcgt attcagttta acgatatgaa cagcgcgatt  420
attaccgcgc tgccgctgtt tcgtgtgcag aactatgaag tggcgctgct gagcgtgtat  480
gtgcaggcgg cgaacctgca tctgagcatt ctgcgtgatg tgagcgtgtt tggcgaacgt  540
tggggctatg ataccgcgac cattaacaac cgttatagcg atctgaccag cctgattcat  600
gtgtatacca accattgcgt ggatacctat aaccagggcc tgcgtcgtct ggaaggccgt  660
tttctgaccg attggattgt gtataaccgt tttcgtcgtc agctgaccat tagcgtgctg  720
gatattgtgg cgtttttttcc gaactatgat attcgtacct atccgattca gaccgcgacc  780
cagctgaccc gtgaagtgta tctggatctg ccgtttatta acgaaaacct gagcccggcg  840
gcgagctatc cgacctttag cgcggcggaa agcgcgatta ttcgtagccc gcatctggtg  900
gattttctga acagctttac catttatacc gatagcctgg cgcgttatgc gtattggggc  960
ggccatctgg tgaacagctt tcgtaccggc accaccacca acctgattcg tagcccgctg  1020
tatggccgtg aaggcaacac cgaacgtccg gtgaccatta ccgcgagccc gagcgtgccg  1080
```

```
atttttcgta ccctgagcta tattaccggc ctggataaca gcaacccggt ggcgggcatt  1140
gaaggcgtgg aatttcagaa caccattagc cgtagcattt atcgtaaaag cggccccgatt  1200
gatagcttta gcgaactgcc gccgcaggat gcgagcgtga gcccggcgat tggctatagc  1260
catcgtctgt gccatgcgac ctttctggaa cgtattagcg gcccgcgtat tgcgggcacc  1320
gtgtttagct ggacccatcg tagcgcgagc ccgaccaacg aagtgagccc gagccgtatt  1380
acccagattc cgtgggtgaa agcgcatacc ctggcgagcg gcgcgagcgt gattaaaggc  1440
ccgggcttta ccggcggcga tattctgacc cgtaacagca tgggcgaact gggcaccctg  1500
cgtgtgagct ttaccggccg tctgccgcag agctattata ttcgttttcg ttatgcgagc  1560
gtggcgaacc gtaccggcac ctttcgttat agccagccgc cgagctatgg cctgagcttt  1620
ccgaaaacca tggatgcggg cgaaccgctg accagccgta gctttgcgca taccaccctg  1680
tttaccccga ttacctttag ccgtgcgcag gaagaatttg atctgtatat tcagagcggc  1740
gtgtatattg atcgtattga atttattccg gtgaccgcga cctttgaagc ggaatatgat  1800
ctggaacgtg cgcagaaagt ggtgaacgcg ctgtttacca gcaccaacca gctgggcctg  1860
aaaaccgatg tgaccgatta tcatattgat caggtgagca acctggtggc gtgcctgagc  1920
gatgaatttt gcctggatga aaaacgtgaa ctgagcgaaa aagtgaaaca tgcgaaacgt  1980
ctgagcgatg aacgtaacct gctgcaggat ccgaactttc gtggcattaa ccgtcagccg  2040
gatcgtggct ggcgtggcag caccgatatt accattcagg gcggcgatga tgtgtttaaa  2100
gaaaactatg tgaccctgcc gggcaccttt gatgaatgct atccgaccta tctgtatcag  2160
aaaattgatg aaagcaaact gaaagcgtat acccgttatc agctgcgtgg ctatattgaa  2220
gatagccagg atctggaaat ttatctgatt cgttataac                        2259
```

```
SEQ ID NO: 239          moltype = AA  length = 753
FEATURE                 Location/Qualifiers
REGION                  1..753
                        note = variant of MP589FL
source                  1..753
                        mol_type = protein
                        organism = synthetic construct
SEQUENCE: 239
MEGNNLNQCI PYNCLTNPKD IILGDERLET GNTVADITLG IVNLLFTEFV PGGGFILGLL  60
DVIWGSIGRS QWELFLEQIE QLIKQRIEEF ARNQAISRLE GLSDLYKTYA RAFSDWEADP  120
TNPALREEMR IQFNDMNSAI ITALPLFRVQ NYEVALLSVY VQAANLHLSI LRDVSVFGER  180
WGYDTATINN RYSDLTSLIH VYTNHCVDTY NQGLRRLEGR FLTDWIVYNR FRRQLTISVL  240
DIVAFFPNYD IRTYPIQTAT QLTREVYLDL PFINENLSPA ASYPTFSAAE SAIIRSPHLV  300
DFLNSFTIYT DSLARYAYWG GHLVNSFRTG TTTNLIRSPL YGREGNTERP VTITASPSVP  360
IFRTLSYITG LDNSNPVAGI EGVEFQNTIS RSIYRKSGPI DSFSELPPQD ASVSPAIGYS  420
HRLCHATFLE RISGPRIAGT VFSWTHRSAS PTNEVSPSRI TQIPWVKAHT LASGASVIKG  480
PGFTGGDILT RNSMGELGTL RVSFTGRLPQ SYYIRFRYAS VANRTGTFRY SQPPSYGLSF  540
PKTMDAGEPL TSRSFAHTTL FTPITFSRAQ EEFDLYIQSG VYIDRIEFIP VTATFEAEYD  600
LERAQKVVNA LFTSTNQLGL KTDVTDYHID QVSNLVACLS DEFCLDEKRE LSEKVKHAKR  660
LSDERNLLQD PNFRGINRQP DRGWRGSTDI TIQGGDDVFK ENYVTLPGTF DECYPTYLYQ  720
KIDESKLKAY TRYQLRGYIE DSQDLEIYLI RYN                              753
```

```
SEQ ID NO: 240          moltype = DNA  length = 2259
FEATURE                 Location/Qualifiers
misc_feature            1..2259
                        note = variant of MP589FL
source                  1..2259
                        mol_type = other DNA
                        organism = synthetic construct
SEQUENCE: 240
atggaaggca acaacctgaa ccagtgcatt ccgtataact gcctgaccaa cccgaaagat  60
attattctgg gcgatgaacg tctggaaacc ggcaacaccg tggcggatat taccctgggc  120
attgtgaacc tgctgtttac cgaatttgtg ccgggcggcg gctttattct gggcctgctg  180
gatgtgattt ggggcagcat tggccgtagc cagtgggaac tgtttctgga acagattgaa  240
cagctgatta aacagcgtat tgatgatttt gcgcgtaacc aggcgattag ccgtctggaa  300
ggcctgagcg atctgtataa aacctatgcg cgtgcgttta gcgattggga agcggatccg  360
accaacccgg cgctgcgtga agaaatgcgt attcagttta acgatatgaa cagcgcgatt  420
attaccgcgc tgccgctgtt tcgtgtgcag aactatgaag tggcgctgct gagcgtgtat  480
gtgcaggcgg cgaacctgca tctgagcatt ctgcgtgatg tgagcgtgtt tggcgaacgt  540
tggggctatg ataccgcgac cattaacaac cgttatagcg atctgaccag cctgattcat  600
gtgtatacca accattgcgt ggatacctat aaccagggcc tgcgtcgtct ggaaggccgt  660
tttctgaccg attggattgt gtataaccgt tttcgtcgtc agctgaccat tagcgtgctg  720
gatattgtgg cgtttttccc gaactatgat attcgtacct atccgattca gaccgcgacc  780
cagctgaccc gtgaagtgta tctggatctg ccgtttatta acgaaaacct gagcccggcg  840
gcgagctatc cgacctttag cgcggcggaa agcgcgatta ttcgtagccc gcatctggtg  900
gattttatta acagctttac catttatacc gatagcctgg cgcgttatgc gtattggggc  960
ggccatctgg tgaacagctt tcgtaccggc accaccacca acctgattcg tagcccgctg  1020
tatggccgtg aaggcaacac cgaacgtccg gtgaccatta ccgcgagccc gagcgtgccg  1080
atttttcgta ccctgagcta tattaccggc ctggataaca gcaacccggt ggcgggcatt  1140
gaaggcgtgg aatttcagaa caccattagc cgtagcattt atcgtaaaag cggccccgatt  1200
gatagcttta gcgaactgcc gccgcaggat gcgagcgtga gcccggcgat tggctatagc  1260
catcgtctgt gccatgcgac ctttctggaa cgtattagcg gcccgcgtat tgcgggcacc  1320
gtgtttagct ggacccatcg tagcgcgagc ccgaccaacg aagtgagccc gagccgtatt  1380
acccagattc cgtgggtgaa agcgcatacc ctggcgagcg gcgcgagcgt gattaaaggc  1440
ccgggcttta ccggcggcga tattctgacc cgtaacagca tgggcgaact gggcaccctg  1500
cgtgtgagct ttaccggccg tctgccgcag agctattata ttcgttttcg ttatgcgagc  1560
gtggcgaacc gtaccggcac ctttcgttat agccagccgc cgagctatgg cctgagcttt  1620
ccgaaaacca tggatgcggg cgaaccgctg accagccgta gctttgcgca taccaccctg  1680
```

```
tttaccccga ttacctttag ccgtgcgcag gaagaatttg atctgtatat tcagagcggc  1740
gtgtatattg atcgtattga atttattccg gtgaccgcga cctttgaagc ggaatatgat  1800
ctggaacgtg cgcagaaagt ggtgaacgcg ctgtttacca gcaccaacca gctgggcctg  1860
aaaaccgatg tgaccgatta tcatattgat caggtgagca acctggtggc gtgcctgagc  1920
gatgaatttt gcctggatga aaaacgtgaa ctgagcgaaa aagtgaaaca tgcgaaacgt  1980
ctgagcgatg aacgtaacct gctgcaggat ccgaactttc gtggcattaa ccgtcagccg  2040
gatcgtggct ggcgtggcag caccgatatt accattcagg gcggcgatga tgtgtttaaa  2100
gaaaactatg tgaccctgcc gggcaccttt gatgaatgct atccgaccta tctgtatcag  2160
aaaattgatg aaagcaaact gaaagcgtat acccgttatc agctgcgtgg ctatattgaa  2220
gatagccagg atctggaaat ttatctgatt cgttataac                        2259

SEQ ID NO: 241         moltype = AA  length = 753
FEATURE                Location/Qualifiers
REGION                 1..753
                       note = variant of MP589FL
source                 1..753
                       mol_type = protein
                       organism = synthetic construct
SEQUENCE: 241
MEGNNLNQCI PYNCLTNPKD IILGDERLET GNTVADITLG IVNLLFTEFV PGGGFILGLL  60
DVIWGSIGRS QWELFLEQIE QLIKQRIDDF ARNQAISRLE GLSDLYKTYA RAFSDWEADP  120
TNPALREEMR IQFNDMNSAI ITALPLFRVQ NYEVALLSVY VQAANLHLSI LRDVSVFGER  180
WGYDTATINN RYSDLTSLIH VYTNHCVDTY NQGLRRLEGR FLTDWIVYNR FRRQLTISVL  240
DIVAFFPNYD IRTYPIQTAT QLTREVYLDL PFINENLSPA ASYPTFSAAE SAIIRSPHLV  300
DFINSFTIYT DSLARYAYWG GHLVNSFRTG TTTNLIRSPL YGREGNTERP VTITASPSVP  360
IFRTLSYITG LDNSNPVAGI EGVEFQNTIS RSIYRKSGPI DSFSELPPQD ASVSPAIGYS  420
HRLCHATFLE RISGPRIAGT VFSWTHRSAS PTNEVSPSRI TQIPWVKAHT LASGASVIKG  480
PGFTGGDILT RNSMGELGTL RVSFTGRLPQ SYYIRFRYAS VANRTGTFRY SQPPSYGLSF  540
PKTMDAGEPL TSRSFAHTTL FTPITFSRAQ EEFDLYIQSG VYIDRIEFIP VTATFEAEYD  600
LERAQKVVNA LFTSTNQLGL KTDVTDYHID QVSNLVACLS DEFCLDEKRE LSEKVKHAKR  660
LSDERNLLQD PNFRGINRQP DRGWRGSTDI TIQGGDDVFK ENYVTLPGTF DECYPTYLYQ  720
KIDESKLKAY TRYQLRGYIE DSQDLEIYLI RYN                               753

SEQ ID NO: 242         moltype = DNA  length = 498
FEATURE                Location/Qualifiers
source                 1..498
                       mol_type = other DNA
                       organism = Polystichum munitum
SEQUENCE: 242
atggccgaca acgcaaaaga agaggtggag gatatgatgg accagactga ggcggtgggg  60
acgcacctgg acgtttttgc cgggctgaag gtgcaaccgc gcagtatcat caccgtagag  120
gtggatggcg ccgccgtaat ccaacagatc agagagatct tcacaagcct ggcagctcac  180
ttcaactcta cgagggtggt acgggatgaa gccatcaagg gcattcgaga ccacttcagg  240
gccgccatcc cgactcgcaa cgtggtggtc attcacactc aacacgttcg cacactggtg  300
gacgtggagc acagccacct cgtcctgcag accggcctct ttaaaaaggt ccccgtcgac  360
atctacgtct tcaagtccgg cgtcttcact aacctcggag acggaggctt tatcaactgg  420
gcatggggtg gcttcgtgag cgaggtcaat gggaagcgta tccacttcgt cttgcccccc  480
ggggcgctcc cgcctaat                                                498

SEQ ID NO: 243         moltype = DNA  length = 498
FEATURE                Location/Qualifiers
source                 1..498
                       mol_type = other DNA
                       organism = Polystichum aculeatum
SEQUENCE: 243
atggccgaca aagcaaaaga agaggtggag gatacgatgg acgagactga ggcggtgggg  60
acgcacctgg acttctttag cgggttgaag gtgcaacccc gcaaggtcat caccgtagag  120
gtggatgccg ccgccgtaat ccaacagatc agagagatct tcacaagcat ggcagctcac  180
ttcaactcta cgagggtggt acgggatgaa gccatcaagg gcattcgaga ccacttcagg  240
gccgccatcc cgactcgcaa cgtggtggtc attcacactc aacacgttca cacactggtg  300
gacttggagc acagccacct cgtcttgcag accggcatct ttaaaaaggt ccccgtcgac  360
atctacgtct tcaagtccgg cgtgttcact aacctcggag acggaggctt tatcaactgg  420
gcatggggtg gcttcgtgag cgaggtcaat gggaagcgta tccacttcgt cttgcccccc  480
ggggcgctcc cgcctaat                                                498

SEQ ID NO: 244         moltype = DNA  length = 498
FEATURE                Location/Qualifiers
source                 1..498
                       mol_type = other DNA
                       organism = Polystichum aculeatum
SEQUENCE: 244
atggccgaca aagcaaaaga agaggtggag gatacgatgg acgagactga ggcggtgggg  60
acgcacctgg acttctttag cgggttgaag gtgcaacccc gcaaggtcat caccgtagag  120
gcggatgccg ccgccgtaat ccaacagatc agagagatct tcacaagcat ggcagctcac  180
ttcaactcta cgagggtggt acgggatgaa gccatcaagg gcattcgaga ccacttcagg  240
gccgccatcc cgactcgcaa cgtggtggtc attcacactc aacacgttca cacactggtg  300
gacttggagc acagccacct cgtcttgcag accggcatct ttaaaaaggt ccccgtcgac  360
atctacgtct tcaagtccgg cgtgttcact aacctcggag acggaggctt tatcaactgg  420
gcatggggtg gcttcgtgag cgaggtcaat gggaagcgta tccacttcgt cttgcccccc  480
```

```
ggggcgctcc cgcctaat                                                498

SEQ ID NO: 245         moltype = DNA  length = 510
FEATURE                Location/Qualifiers
source                 1..510
                       mol_type = other DNA
                       organism = Osmunda claytoniana
SEQUENCE: 245
atggccgagc atcatgatgt cagccaggcc gaactgcagc gcgaggagga ggaagctctc  60
aagccgtcgc tcgacgaaac tgaggaagtg ggcgtgcagc tctcgggtat caacccacgc  120
aatatcatca ccatcgaggt cgacgctgcc gctgtcatcc agcagataag ggagaccttc  180
agatatcttg cgagtattta caactccact agggtgcaac gggatgcagc gatcaaggcc  240
atccgagacc acttcctggt ggccatcccc actcgcaatg tggtcgtaat ccacacccag  300
catgtgcaga ctctggtcga cgcggagcac acatctatga agttgaagac gggaatcttc  360
acctcaacca cagtcgaagt ctatgtcttc aagtctggcg tcttgaccaa tctgggagac  420
ggcggcttca tcaactgggc ctggggggc tacaccagct ccgtcgttgg caaacgagtt  480
gtcttcgtga acccgccggg ggcgcttccc                                   510

SEQ ID NO: 246         moltype = DNA  length = 513
FEATURE                Location/Qualifiers
source                 1..513
                       mol_type = other DNA
                       organism = Osmunda cinnamomea
SEQUENCE: 246
atggcggaac atcatggtgt cagccaggcc gaactggagc gcgaggagga ggaagctgct  60
ctcaagccga cgctcaatga aactgaggaa gtgggagtgc agctctcgaa tatcgaccca  120
cgcaggatca tcaccgtcga ggtcgaccct gccgctgtca tccagcagat aagggaaacc  180
ttcagtgatc ttgcgagaat ttacaactcc actagggtgc aacgggatgc agcgatcaag  240
gccatccgag accacttcct ggtggccatc cccactcgca atgttgtggt gatccacacc  300
cagcacgtgc gtactctggt agccgaggag cacacatctt tgaggttgaa gacgggaatc  360
tttaccacaa ccacagtgca aatctatgtc ttcaagtctg gcgtcttcac taatctggga  420
gacggcggct acatcaactg ggcctggggg ggctacatta actccgtcaa tggcaaacaa  480
atcaatttca ggaacccgcc gggggcgctt ccc                               513

SEQ ID NO: 247         moltype = DNA  length = 513
FEATURE                Location/Qualifiers
source                 1..513
                       mol_type = other DNA
                       organism = Osmunda cinnamomea
SEQUENCE: 247
atggcggaac atcatgatgt cagccaggcc gaactggagc gcgaggagga ggaagctgct  60
ctcaagccga cgctcaatga aactgaggaa gtgggagtgc agctctcgaa tatcgaccca  120
cgcaggatca tcaccgtcga ggtcgaccct gccgctgtca tccagcagat aagggaaacc  180
ttcagtgatc ttgcgagaat ttacaactcc actagggtgc aacgggatgc agcgatcaag  240
gccatccgag accacttcct ggtggccatc cccactcgca atgttgtggt gatccacacc  300
cagcacgtgc gtactctggt agccgaggag cacacatctt tgaggttgaa gacgggaatc  360
tttaccacaa ccacagtgca aatctatgtc ttcaagtctg gcgtcttcac caatctggga  420
gacggcggct acatcaactg ggcctggggg ggctacatta actccgtcaa tggcaaacaa  480
atcaatttca ggaacccgcc gggggcgctt ccc                               513

SEQ ID NO: 248         moltype = DNA  length = 522
FEATURE                Location/Qualifiers
source                 1..522
                       mol_type = other DNA
                       organism = Asplenium ebenoides
SEQUENCE: 248
atggccgaca aagcagcagc accaccacct tctcagctgg ctcatgaggg agaagaagag  60
gcggaggctt tgatggacga gacagaggcg gtgggaactc acctggacac tgtactgaag  120
gtggacgccc gcaatatcat caccgtggag gtggacgccg ccgccgtaat tcagcagatc  180
agagagatct tccgaaccat ggcatcgcac ttcaactcta cgagagtggt gcgggatgaa  240
gccatcaagg gcattcgcga ccacttcagg gccgccgtcc ccactcgcaa cgtggtggtc  300
atccacactc aacacgtcca cacgctggtg gccgtggagc acagccatat ggtcttgcag  360
acgggcatct tcaagaaagt ccccgtcgac atctacgtct tcaagtctgg cgtgctcacc  420
aacctcggcg acggaggctt tatcaattgg gcatggggtg gctacgtcac cgaggttgtg  480
ggcaagcgcg ttcacttccg cctaccccc cgggcgctcc ct                      522

SEQ ID NO: 249         moltype = DNA  length = 522
FEATURE                Location/Qualifiers
source                 1..522
                       mol_type = other DNA
                       organism = Asplenium ebenoides
SEQUENCE: 249
atggccgaca aagcagcagc accaccacct tctcagctgg ctcatgaggg agaagaagag  60
gcggaggctt tgatggacga gacagaggcg gtgggaactc acctggacac tgtactgaag  120
gtggacgccc gcaatatcat caccgtggag gtggacgccg ccgccgtaat tcagcagatc  180
agagagatct tccgaaccat ggcatcgcac ttcaactcta cgagagtggt gcgggatgaa  240
gccatcaagg gcattcgcga ccacttcagg gccgccgtcc ccactcgcaa cgtggtggtc  300
atccacactc aacacgtcca cacgctggtg gccgtggagc acagccatat ggtcttgcag  360
acgggcatct tcaagaaagt ccccgtcgac atctacgtct tcaagtctgg cgtcctcacc  420
```

-continued

```
aacctcggcg acggaggctt tatcaattgg gcatggggtg gctacgtcac cgaggttgtg  480
ggcaagcgcg ttcacttccg cctacccccc ggggcgctcc ct                     522

SEQ ID NO: 250          moltype = DNA  length = 522
FEATURE                 Location/Qualifiers
source                  1..522
                        mol_type = other DNA
                        organism = Gymnocarpium dryopteris
SEQUENCE: 250
atggccgaca aagtagcagc agcgcctcct cctactagag aagcagaaga agaggtggag  60
gagacgatgg acgagactga ggcggtgggg acgcacctgg acttgatagc gcccctgagt  120
gtgcaacccc gcggcatcat caccgtggag gtggaccccg ccgccgtaat cgaacagatc  180
agagagatct tccaaaccct ggcacgtcat ttcaactcta cgagggtggt acgggatgaa  240
gccatcaagg gcattcgaga ccacttcagg gccgccatcc cgactcgcaa cgtggtggtc  300
attcacactc aacacgttca cacactggtg ggcttggagc atagccacct cgtcttgcag  360
accggcatat tcaaaaaggt ccccgttgac atctacgtct tcaagtccgg cgtgctcacg  420
aacctcggag acggaggctt catcaactgg gcatggggtg gcttcgtgac cgaggtcgtt  480
gggaagcgtg tccacttccg cttgcccccc ggggcgcttc ct                     522

SEQ ID NO: 251          moltype = DNA  length = 510
FEATURE                 Location/Qualifiers
source                  1..510
                        mol_type = other DNA
                        organism = Colysis pteropus
SEQUENCE: 251
atggcggaca aagtagcagc gggtcgacaa gctgaagaag aggtggagac gacgatggac  60
gagactgagg cggtggggac gcacctggac ttgttggcgg acgtgaaggt acaaccccgg  120
aacatcatta ccgtggaggt ggacgccgct gccgtaatcc agcagatcag agagatcttc  180
caaaccatgg cacgtcactt caactctacg agggtggtgc gggatgaagc catcaagggc  240
attcgagacc acttcttggc cgccgtcccg acccgcaacg tggtggtcgt tcacactcag  300
cacgttcaca ccttggtggg cctggagcac tcccacatgg tcttgcagac cggcgtcttc  360
aaaaaggtcc ccgtcgacat ctacgtcttc aagtccggcg tctttaccct cctcggagac  420
ggaggcttca tcaactgggc atggggcggc tacgtagacc aggtcgccgg taagcgtatc  480
cacttccgct tgccccccgg cgcgctccct                                   510

SEQ ID NO: 252          moltype = AA  length = 166
FEATURE                 Location/Qualifiers
source                  1..166
                        mol_type = protein
                        organism = Polystichum munitum
SEQUENCE: 252
MADNAKEEVE DMMDQTEAVG THLDVFAGLK VQPRSIITVE VDGAAVIQQI REIFTSLAAH  60
FNSTRVVRDE AIKGIRDHFR AAIPTRNVVV IHTQHVRTLV DVEHSHLVLQ TGLFKKVPVD  120
IYVFKSGVFT NLGDGGFINW AWGGFVSEVN GKRIHFVLPP GALPPN                 166

SEQ ID NO: 253          moltype = AA  length = 166
FEATURE                 Location/Qualifiers
source                  1..166
                        mol_type = protein
                        organism = Polystichum aculeatum
SEQUENCE: 253
MADKAKEEVE DTMDETEAVG THLDFFSGLK VQPRKVITVE VDAAAVIQQI REIFTSMAAH  60
FNSTRVVRDE AIKGIRDHFR AAIPTRNVVV IHTQHVHTLV DLEHSHLVLQ TGIFKKVPVD  120
IYVFKSGVFT NLGDGGFINW AWGGFVSEVN GKRIHFVLPP GALPPN                 166

SEQ ID NO: 254          moltype = AA  length = 166
FEATURE                 Location/Qualifiers
source                  1..166
                        mol_type = protein
                        organism = Polystichum aculeatum
SEQUENCE: 254
MADKAKEEVE DTMDETEAVG THLDFFSGLK VQPRKVITVE ADAAAVIQQI REIFTSMAAH  60
FNSTRVVRDE AIKGIRDHFR AAIPTRNVVV IHTQHVHTLV DLEHSHLVLQ TGIFKKVPVD  120
IYVFKSGVFT NLGDGGFINW AWGGFVSEVN GKRIHFVLPP GALPPN                 166

SEQ ID NO: 255          moltype = AA  length = 170
FEATURE                 Location/Qualifiers
source                  1..170
                        mol_type = protein
                        organism = Osmunda claytoniana
SEQUENCE: 255
MAEHHDVSQA ELQREEEEAL KPSLDETEEV GVQLSGINPR NIITIEVDAA AVIQQIRETF  60
RYLASIYNST RVQRDAAIKA IRDHFLVAIP TRNVVVIHTQ HVQTLVDAEH TSMKLKTGIF  120
TSTTVEVYVF KSGVLTNLGD GGFINWAWGG YTSSVVGKRV VFVNPPGALP             170

SEQ ID NO: 256          moltype = AA  length = 171
FEATURE                 Location/Qualifiers
source                  1..171
                        mol_type = protein
```

-continued

```
                        organism = Osmunda cinnamomea
SEQUENCE: 256
MAEHHGVSQA ELEREEEEAA LKPTLNETEE VGVQLSNIDP RRIITVEVDP AAVIQQIRET  60
FSDLARIYNS TRVQRDAAIK AIRDHFLVAI PTRNVVVIHT QHVRTLVAEE HTSLRLKTGI  120
FTTTTVQIYV FKSGVFTNLG DGGYINWAWG GYINSVNGKQ INFRNPPGAL P          171

SEQ ID NO: 257          moltype = AA  length = 171
FEATURE                 Location/Qualifiers
source                  1..171
                        mol_type = protein
                        organism = Osmunda cinnamomea
SEQUENCE: 257
MAEHHDVSQA ELEREEEEAA LKPTLNETEE VGVQLSNIDP RRIITVEVDP AAVIQQIRET  60
FSDLARIYNS TRVQRDAAIK AIRDHFLVAI PTRNVVVIHT QHVRTLVAEE HTSLRLKTGI  120
FTTTTVQIYV FKSGVFTNLG DGGYINWAWG GYINSVNGKQ INFRNPPGAL P          171

SEQ ID NO: 258          moltype = AA  length = 174
FEATURE                 Location/Qualifiers
source                  1..174
                        mol_type = protein
                        organism = Asplenium ebenoides
SEQUENCE: 258
MADKAAAPPP SQLAHEGEEE AEALMDETEA VGTHLDTVLK VDARNIITVE VDAAAVIQQI  60
REIFRTMASH FNSTRVVRDE AIKGIRDHFR AAVPTRNVVV IHTQHVHTLV AVEHSHMVLQ  120
TGIFKKVPVD IYVFKSGVLT NLGDGGFINW AWGGYVTEVV GKRVHFRLPP RALP       174

SEQ ID NO: 259          moltype = AA  length = 174
FEATURE                 Location/Qualifiers
source                  1..174
                        mol_type = protein
                        organism = Asplenium ebenoides
SEQUENCE: 259
MADKAAAPPP SQLAHEGEEE AEALMDETEA VGTHLDTVLK VDARNIITVE VDAAAVIQQI  60
REIFRTMASH FNSTRVVRDE AIKGIRDHFR AAVPTRNVVV IHTQHVHTLV AVEHSHMVLQ  120
TGIFKKVPVD IYVFKSGVLT NLGDGGFINW AWGGYVTEVV GKRVHFRLPP GALP       174

SEQ ID NO: 260          moltype = AA  length = 174
FEATURE                 Location/Qualifiers
source                  1..174
                        mol_type = protein
                        organism = Gymnocarpium dryopteris
SEQUENCE: 260
MADKVAAAPP PTREAEEEVE ETMDETEAVG THLDLIAPLS VQPRGIITVE VDPAAVIEQI  60
REIFQTLARH FNSTRVVRDE AIKGIRDHFR AAIPTRNVVV IHTQHVHTLV GLEHSHLVLQ  120
TGIFKKVPVD IYVFKSGVLT NLGDGGFINW AWGGFVTEVV GKRVHFRLPP GALP       174

SEQ ID NO: 261          moltype = AA  length = 170
FEATURE                 Location/Qualifiers
source                  1..170
                        mol_type = protein
                        organism = Colysis pteropus
SEQUENCE: 261
MADKVAAGRQ AEEEVETTMD ETEAVGTHLD LLADVKVQPR NIITVEVDAA AVIQQIREIF  60
QTMARHFNST RVVRDEAIKG IRDHFLAAVP TRNVVVVHTQ HVHTLVGLEH SHMVLQTGVF  120
KKVPVDIYVF KSGVFTLLGD GGFINWAWGG YVDQVAGKRI HFRLPPGALP            170
```